US010926006B2

(12) United States Patent
Schneiderman

(10) Patent No.: US 10,926,006 B2
(45) **Date of Patent: *Feb. 23, 2021**

(54) DRUG ELUTING STENT

(71) Applicant: Jacob Schneiderman, Kiryat Ono (IL)

(72) Inventor: Jacob Schneiderman, Kiryat Ono (IL)

(73) Assignee: REMODELESS CV LTD, Kiriat Ono (IL)

( * ) Notice: Subject to any disclaimer, the term of this patent is extended or adjusted under 35 U.S.C. 154(b) by 63 days.

This patent is subject to a terminal disclaimer.

(21) Appl. No.: 16/078,013

(22) PCT Filed: Feb. 15, 2017

(86) PCT No.: PCT/IL2017/050201

§ 371 (c)(1),
(2) Date: Aug. 15, 2018

(87) PCT Pub. No.: WO2017/141246

PCT Pub. Date: Aug. 24, 2017

(65) Prior Publication Data

US 2019/0022286 A1 Jan. 24, 2019

Related U.S. Application Data

(63) Continuation-in-part of application No. 15/000,062, filed on Jan. 19, 2016, now Pat. No. 10,143,780, which is a continuation-in-part of application No. PCT/IL2015/050866, filed on Aug. 27, 2015, and a continuation of application No. 14/730,282, filed on Jun. 4, 2015, now Pat. No. 10,105,469.

(60) Provisional application No. 62/295,178, filed on Feb. 15, 2016, provisional application No. 62/120,966, filed on Feb. 26, 2015, provisional application No. 62/188,676, filed on Jul. 5, 2015.

(51) Int. Cl.

| | |
|---|---|
| ***A61L 31/16*** | (2006.01) |
| ***A61K 38/22*** | (2006.01) |
| ***C08L 67/04*** | (2006.01) |
| ***A61L 31/08*** | (2006.01) |
| ***A61L 31/14*** | (2006.01) |
| ***A61L 31/04*** | (2006.01) |
| ***A61L 27/58*** | (2006.01) |
| ***A61L 27/54*** | (2006.01) |
| ***A61L 27/18*** | (2006.01) |
| ***A61L 31/06*** | (2006.01) |
| ***A61L 27/22*** | (2006.01) |
| ***A61L 31/10*** | (2006.01) |
| ***A61K 9/00*** | (2006.01) |
| ***A61L 27/34*** | (2006.01) |
| *A61K 9/06* | (2006.01) |
| *A61K 9/70* | (2006.01) |
| *A61K 47/34* | (2017.01) |

(52) U.S. Cl.
CPC ............ *A61L 31/16* (2013.01); *A61K 9/0024* (2013.01); *A61K 38/2264* (2013.01); *A61L 27/18* (2013.01); *A61L 27/227* (2013.01); *A61L 27/34* (2013.01); *A61L 27/54* (2013.01); *A61L 27/58* (2013.01); *A61L 31/047* (2013.01); *A61L 31/06* (2013.01); *A61L 31/08* (2013.01); *A61L 31/10* (2013.01); *A61L 31/148* (2013.01); *C08L 67/04* (2013.01); *A61K 9/0019* (2013.01); *A61K 9/06* (2013.01); *A61K 9/7007* (2013.01); *A61K 47/34* (2013.01); *A61L 2300/416* (2013.01); *A61L 2300/43* (2013.01); *A61L 2300/432* (2013.01); *A61L 2430/20* (2013.01)

(58) Field of Classification Search
None
See application file for complete search history.

(56) References Cited

U.S. PATENT DOCUMENTS

| | | | |
|---|---|---|---|
| 7,307,142 B2 | 12/2007 | Gertler | |
| 8,969,292 B2 | 3/2015 | Gertler | |
| 10,105,469 B2 | 10/2018 | Schneiderman | |
| 10,143,780 B2 | 12/2018 | Schneiderman | |
| 2005/0187607 A1 | 8/2005 | Akhtar et al. | |
| 2006/0229715 A1 | 10/2006 | Istephanous et al. | |
| 2009/0010987 A1 * | 1/2009 | Parker ..................... | A61F 2/915 424/423 |
| 2009/0274739 A1 | 11/2009 | Marks et al. | |
| 2011/0118827 A1 | 5/2011 | Wu | |
| 2015/0290428 A1 | 10/2015 | Tkebuchava | |

OTHER PUBLICATIONS

Deng et al. "Leptin relieves intestinal ischemia/reperfusion injury by promoting ERK1/2 phosphorylation and the NO signaling pathway". J Trauma, vol. 72, No. 1, pp. 143-149 (2012) (Year: 2012).*
Sagiroglu et al. "Effects of apelin and leptin on renal functions following renal ischemia/reperfusion: An experimental study". Experimental and Therapeutic Medicine 3: 908-914, 2012 (Year: 2012).*
(Continued)

*Primary Examiner* — Joanne Hama
*Assistant Examiner* — Scott T. Humbarger
(74) *Attorney, Agent, or Firm* — Soroker Agmon Nordman

(57) ABSTRACT

Devices and methods for treating ischemia and reperfusion injury (IRI) are configured for sustained-release of anti-proliferative drug into the wall of a blood vessel (to prevent in-stent stenosis), and for sustained-release of leptin antagonist into the lumen to be carried by the blood and be uptaken by tissue cells that were subjected to IRI.

9 Claims, 35 Drawing Sheets

Specification includes a Sequence Listing.

(56) References Cited

OTHER PUBLICATIONS

Sukhotnik et al. "The effect of leptin on intestinal recovery following ischemia-reperfusion injury in a rat" Pediatr Surg Int (2007) 23: 473-478 (Year: 2007).*

Zhang et al. "Leptin attenuates cerebral ischemia injury through the promotion of energy metabolism via the PI3K/Akt pathway". Journal of Cerebral Blood Flow & Metabolism (2013) 33, 567-574 (Year: 2013).*

Vendra, V.K., Wu, L. and Krishnan, S. (2011). Polymer Thin Films for Biomedical Applications. In Nanotechnologies for the Life Sciences, C.S.S.R. Kumar (Ed.). doi: 10.1002/9783527610419.ntls0179 (Year: 2011).

Tao, M. (2013). Locally applied leptin induces regional aortic wall degeneration preceding aneurysm formation in apolipoprotein E-deficient mice. Arteriosclerosis, thrombosis, and vascular biology, 33(2), 311-320. https://doi .org/10.1161 /ATVBAHA.112.300543 (Year: 2013).

Gong, C., Qi, T., Wei, X., Qu, Y., Wu, Q., Luo, F., & Qian, Z. (2013). Thermosensitive polymeric hydrogels as drug delivery systems, Current medicinal chemistry, 20(1), 79-94. (Year: 2013).

* cited by examiner

Histology of Leptin Treated Ascending Aorta

LA Moderates Elastic Lamellas' Fragmentation and αSMA Depletion

Leptin & Leptin Receptor in Human Normal Aortic Valve

Severe Aortic Stenosis

SEQUENCE LISTING

```
<160> NUMBER OF SEQ ID NOS: 72

<210> SEQ ID NO 1
<211> LENGTH: 167
<212> TYPE: PRT
<213> ORGANISM: Homo sapiens

<400> SEQUENCE: 1

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
```

-continued

```
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

<210> SEQ ID NO 2
<211> LENGTH: 3444
<212> TYPE: DNA
<213> ORGANISM: Homo sapiens

<400> SEQUENCE: 2

```
gtaggaatcg cagcgccagc ggttgcaagg cccaagaagc ccatcctggg aaggaaaatg      60

cattggggaa ccctgtgcgg attcttgtgg ctttggccct atcttttcta tgtccaagct     120

gtgcccatcc aaaaagtcca agatgacacc aaaaccctca tcaagacaat tgtcaccagg     180

atcaatgaca tttcacacac gcagtcagtc tcctccaaac agaaagtcac cggtttggac     240

ttcattcctg ggctccaccc catcctgacc ttatccaaga tggaccagac actggcagtc     300

taccaacaga tcctcaccag tatgccttcc agaaacgtga tccaaatatc caacgacctg     360

gagaacctcc gggatcttct tcacgtgctg gccttctcta agagctgcca cttgccctgg     420

gccagtggcc tggagacctt ggacagcctg gggggtgtcc tggaagcttc aggctactcc     480

acagaggtgg tggccctgag caggctgcag gggtctctgc aggacatgct gtggcagctg     540

gacctcagcc ctgggtgctg aggccttgaa ggtcactctt cctgcaagga ctacgttaag     600

ggaaggaact ctggcttcca ggtatctcca ggattgaaga gcattgcatg gacacccctt     660

atccaggact ctgtcaattt ccctgactcc tctaagccac tcttccaaag gcataagacc     720

ctaagcctcc ttttgcttga aaccaaagat atatacacag gatcctattc tcaccaggaa     780

gggggtccac ccagcaaaga gtgggctgca tctgggattc ccaccaaggt cttcagccat     840

caacaagagt tgtcttgtcc cctcttgacc catctccccc tcactgaatg cctcaatgtg     900

accaggggtg atttcagaga gggcagaggg gtaggcagag cctttggatg accagaacaa     960

ggttccctct gagaattcca aggagttcca tgaagaccac atccacacac gcaggaactc    1020

ccagcaacac aagctggaag cacatgttta tttattctgc attttattct ggatggattt    1080

gaagcaaagc accagcttct ccaggctctt tggggtcagc cagggccagg ggtctccctg    1140

gagtgcagtt tccaatccca tagatgggtc tggctgagct gaacccattt tgagtgactc    1200

gagggttggg ttcatctgag caagagctgg caaaggtggc tctccagtta gttctctcgt    1260

aactggtttc atttctactg tgactgatgt tacatcacag tgtttgcaat ggtgttgccc    1320

tgagtggatc tccaaggacc aggttatttt aaaaagattt gttttgtcaa gtgtcatatg    1380

taggtgtctg cacccagggg tggggaatgt ttgggcagaa gggagaagga tctagaatgt    1440

gttttctgaa taacatttgt gtggtgggtt ctttggaagg agtgagatca ttttcttatc    1500

ttctgcaatt gcttaggatg tttttcatga aaatagctct ttcagggggg ttgtgaggcc    1560

tggccaggca ccccctggag agaagtttct ggccctggct gaccccaaag agcctggaga    1620
```

```
agctgatgct ttgcttcaaa tccatccaga ataaaacgca aagggctgaa agccatttgt   1680

tggggcagtg gtaagctctg gctttctccg actgctaggg agtggtcttt cctatcatgg   1740

agtgacggtc ccacactggt gactgcgatc ttcagagcag gggtccttgg tgtgaccctc   1800

tgaatggtcc agggttgatc acactctggg tttattacat ggcagtgttc ctatttgggg   1860

cttgcatgcc aaattgtagt tcttgtctga ttggctcacc caagcaaggc caaaattacc   1920

aaaaatcttg gggggttttt actccagtgg tgaagaaaac tcctttagca ggtggtcctg   1980

agacctgaca agcactgcta ggcgagtgcc aggactcccc aggccaggcc accaggatgg   2040

cccttcccac tggaggtcac attcaggaag atgaaagagg aggtttgggg tctgccacca   2100

tcctgctgct gtgtttttgc tatcacacag tgggtggtgg atctgtccaa ggaaacttga   2160

atcaaagcag ttaactttaa gactgagcac ctgcttcatg ctcagccctg actggtgcta   2220

taggctggag aagctcaccc aataaacatt aagattgagg cctgccctca gggatcttgc   2280

attcccagtg gtcaaaccgc actcacccat gtgccaaggt ggggtattta ccacagcagc   2340

tgaacagcca aatgcatggt gcagttgaca gcaggtggga aatggtatga gctgaggggg   2400

gccgtgccca ggggcccaca gggaaccctg cttgcacttt gtaacatgtt tacttttcag   2460

ggcatcttag cttctattat agccacatcc ctttgaaaca agataactga gaatttaaaa   2520

ataagaaaat acataagacc ataacagcca acaggtggca ggaccaggac tatagcccag   2580

gtcctctgat acccagagca ttacgtgagc caggtaatga gggactggaa ccagggagac   2640

cgagcgcttt ctggaaaaga ggagtttcga ggtagagttt gaaggaggtg agggatgtga   2700

attgcctgca gagagaagcc tgttttgttg gaaggtttgg tgtgtggaga tgcagaggta   2760

aaagtgtgag cagtgagtta cagcgagagg cagagaaaga agagacagga gggcaagggc   2820

catgctgaag ggaccttgaa gggtaaagaa gtttgatatt aaaggagtta agagtagcaa   2880

gttctagaga agaggctggt gctgtggcca gggtgagagc tgctctggaa aatgtgaccc   2940

agatcctcac aaccacctaa tcaggctgag gtgtcttaag ccttttgctc acaaaacctg   3000

gcacaatggc taattcccag agtgtgaaac ttcctaagta taaatggttg tctgtttttg   3060

taacttaaaa aaaaaaaaaa aagtttggcc gggtgcggtg gctcacgcct gtaatcccag   3120

cactttggga ggccaaggtg gggggatcac aaggtcacta gatggcgagc atcctggcca   3180

acatggtgaa accccgtctc tactaaaaac acaaaagtta gctgagcgtg gtggcgggcg   3240

cctgtagtcc cagccactcg ggaggctgag acaggagaat cgcttaaacc tgggaggcgg   3300

agagtacagt gagccaagat cgcgccactg cactccggcc tgatgacaga gcgagattcc   3360

gtcttaaaaa aaaaaaaaaa aaagtttgtt tttaaaaaaa tctaaataaa ataactttgc   3420

cccctgcaaa aaaaaaaaaa aaaa                                         3444
```

```
<210> SEQ ID NO 3
<211> LENGTH: 146
<212> TYPE: PRT
<213> ORGANISM: Artificial Sequence
<220> FEATURE:
<223> OTHER INFORMATION: synthetic

<400> SEQUENCE: 3

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Ala Ala Phe Ile Pro Gly Leu His Pro Ile
```

```
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145


<210> SEQ ID NO 4
<211> LENGTH: 146
<212> TYPE: PRT
<213> ORGANISM: Artificial Sequence
<220> FEATURE:
<223> OTHER INFORMATION: synthetic

<400> SEQUENCE: 4

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Leu Asp Ala Ala Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145


<210> SEQ ID NO 5
<211> LENGTH: 146
<212> TYPE: PRT
<213> ORGANISM: Artificial Sequence
<220> FEATURE:
<223> OTHER INFORMATION: synthetic

<400> SEQUENCE: 5

Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30
```

```
Lys Gln Arg Val Thr Gly Ala Ala Phe Ile Pro Gly Leu His Pro Leu
        35                  40                  45

Leu Ser Leu Ser Lys Met Asp Gln Thr Leu Ala Ile Tyr Gln Gln Ile
    50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145


<210> SEQ ID NO 6
<211> LENGTH: 146
<212> TYPE: PRT
<213> ORGANISM: Artificial Sequence
<220> FEATURE:
<223> OTHER INFORMATION: synthetic

<400> SEQUENCE: 6

Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Leu Asp Ala Ala Pro Gly Leu His Pro Leu
        35                  40                  45

Leu Ser Leu Ser Lys Met Asp Gln Thr Leu Ala Ile Tyr Gln Gln Ile
    50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145


<210> SEQ ID NO 7
<211> LENGTH: 146
<212> TYPE: PRT
<213> ORGANISM: Artificial Sequence
<220> FEATURE:
<223> OTHER INFORMATION: synthetic

<400> SEQUENCE: 7

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30
```

Lys Gln Lys Val Thr Gly Ala Ala Ala Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 8
<211> LENGTH: 146
<212> TYPE: PRT
<213> ORGANISM: Artificial Sequence
<220> FEATURE:
<223> OTHER INFORMATION: synthetic

<400> SEQUENCE: 8

Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Ala Ala Ala Ile Pro Gly Leu His Pro Leu
        35                  40                  45

Leu Ser Leu Ser Lys Met Asp Gln Thr Leu Ala Ile Tyr Gln Gln Ile
    50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145

<210> SEQ ID NO 9
<211> LENGTH: 146
<212> TYPE: PRT
<213> ORGANISM: Artificial Sequence
<220> FEATURE:
<223> OTHER INFORMATION: synthetic

<400> SEQUENCE: 9

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser

```
            20                  25                  30

Lys Gln Lys Val Thr Gly Ala Ala Ala Ala Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145


<210> SEQ ID NO 10
<211> LENGTH: 146
<212> TYPE: PRT
<213> ORGANISM: Artificial Sequence
<220> FEATURE:
<223> OTHER INFORMATION: synthetic

<400> SEQUENCE: 10

Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Ala Ala Ala Ala Pro Gly Leu His Pro Leu
        35                  40                  45

Leu Ser Leu Ser Lys Met Asp Gln Thr Leu Ala Ile Tyr Gln Gln Ile
    50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145


<210> SEQ ID NO 11
<211> LENGTH: 438
<212> TYPE: DNA
<213> ORGANISM: Artificial Sequence
<220> FEATURE:
<223> OTHER INFORMATION: synthetic

<400> SEQUENCE: 11

gtgcccatcc aaaaagtcca agatgacacc aaaaccctca tcaagacaat tgtcaccagg      60

atcaatgaca tttcacacac gcagtcagtc tcctccaaac agaaagtcac tggtgcggct     120
```

-continued

```
ttcattcctg ggctccaccc catcctgacc ttatccaaga tggaccagac actggcagtc    180

taccaacaga tcctcaccag tatgccttcc agaaacgtga tccgaatatc caacgacctg    240

gagaacctcc gggatcttct tcacgtgctg gccttctcta agagctgcca cttgccctgg    300

gccagtggcc tggagacctt ggacagcctg gggggtgtcc tggaagcttc aggctactcc    360

acagaggtgg tggccctgag caggctgcag ggtctctgc aggacatgct gtggcagctg     420

gacctcagcc ctgggtgc                                                  438


<210> SEQ ID NO 12
<211> LENGTH: 438
<212> TYPE: DNA
<213> ORGANISM: Artificial Sequence
<220> FEATURE:
<223> OTHER INFORMATION: synthetic

<400> SEQUENCE: 12

gtgcccatcc aaaaagtcca agatgacacc aaaaccctca tcaagacaat tgtcaccagg     60

atcaatgaca tttcacacac gcagtcagtc tcctccaaac agaaagtcac tggtttggac    120

gccgctcctg ggctccaccc catcctgacc ttatccaaga tggaccagac actggcagtc    180

taccaacaga tcctcaccag tatgccttcc agaaacgtga tccgaatatc caacgacctg    240

gagaacctcc gggatcttct tcacgtgctg gccttctcta agagctgcca cttgccctgg    300

gccagtggcc tggagacctt ggacagcctg gggggtgtcc tggaagcttc aggctactcc    360

acagaggtgg tggccctgag caggctgcag ggtctctgc aggacatgct gtggcagctg     420

gacctcagcc ctgggtgc                                                  438


<210> SEQ ID NO 13
<211> LENGTH: 438
<212> TYPE: DNA
<213> ORGANISM: Artificial Sequence
<220> FEATURE:
<223> OTHER INFORMATION: synthetic

<400> SEQUENCE: 13

gtgtcgatcc gcaaggtcca ggatgacacc aaaaccctca tcaagacgat tgtcaccagg     60

atcaatgaca tctcacacac gcagtccgtc tcctccaaac agagggtcac cggtgctgct    120

ttcatccctg ggctccaccc tctcctgagt ttgtccaaga tggaccagac attggcaatc    180

taccaacaga tcctcgccag tctgccttcc agaaatgtga tccaaatatc taatgacctg    240

gagaacctcc gggaccttct ccacctgctg gccgcctcca agagctgccc cttgccgcag    300

gtcagggccc tagagagctt ggagagcctg ggcgtcgtcc tggaagcctc cctctactcc    360

accgaggtgg tggccctgag ccggctacag ggtctctac aggacatgtt gcggcagctg     420

gacctgagtc ccggctgc                                                  438


<210> SEQ ID NO 14
<211> LENGTH: 438
<212> TYPE: DNA
<213> ORGANISM: Artificial Sequence
<220> FEATURE:
<223> OTHER INFORMATION: synthetic

<400> SEQUENCE: 14

gtgtcgatcc gcaaggtcca ggatgacacc aaaaccctca tcaagacgat tgtcaccagg     60

atcaatgaca tctcacacac gcagtccgtc tcctccaaac agagggtcac cggtttggac    120
```

-continued gctgctcctg ggctccaccc tctcctgagt ttgtccaaga tggaccagac attggcaatc 180
taccaacaga tcctcgccag tctgccttcc agaaatgtga tccaaatatc taatgacctg 240
gagaacctcc gggaccttct ccacctgctg gccgcctcca agagctgccc cttgccgcag 300
gtcagggccc tagagagctt ggagagcctg ggcgtcgtcc tggaagcctc cctctactcc 360
accgaggtgg tggccctgag ccggctacag gggtctctac aggacatgtt gcggcagctg 420
gacctgagtc ccggctgc 438

<210> SEQ ID NO 15
<211> LENGTH: 438
<212> TYPE: DNA
<213> ORGANISM: Artificial Sequence
<220> FEATURE:
<223> OTHER INFORMATION: synthetic

<400> SEQUENCE: 15
gtgcccatcc aaaaagtcca agatgacacc aaaaccctca tcaagacaat tgtcaccagg 60
atcaatgaca tttcacacac gcagtcagtc tcctccaaac agaaagtcac tggtgcggct 120
gccattcctg ggctccaccc catcctgacc ttatccaaga tggaccagac actggcagtc 180
taccaacaga tcctcaccag tatgccttcc agaaacgtga tccgaatatc caacgacctg 240
gagaacctcc gggatcttct tcacgtgctg gccttctcta agagctgcca cttgccctgg 300
gccagtggcc tggagacctt ggacagcctg gggggtgtcc tggaagcttc aggctactcc 360
acagaggtgg tggccctgag caggctgcag gggtctctgc aggacatgct gtggcagctg 420
gacctcagcc ctgggtgc 438

<210> SEQ ID NO 16
<211> LENGTH: 438
<212> TYPE: DNA
<213> ORGANISM: Artificial Sequence
<220> FEATURE:
<223> OTHER INFORMATION: synthetic

<400> SEQUENCE: 16
gtgtcgatcc gcaaggtcca ggatgacacc aaaaccctca tcaagacgat tgtcaccagg 60
atcaatgaca tctcacacac gcagtccgtc tcctccaaac agagggtcac cggtgctgca 120
gctatccctg ggctccaccc tctcctgagt ttgtccaaga tggaccagac attggcaatc 180
taccaacaga tcctcgccag tctgccttcc agaaatgtga tccaaatatc taatgacctg 240
gagaacctcc gggaccttct ccacctgctg gccgcctcca agagctgccc cttgccgcag 300
gtcagggccc tagagagctt ggagagcctg ggcgtcgtcc tggaagcctc cctctactcc 360
accgaggtgg tggccctgag ccggctacag gggtctctac aggacatgtt gcggcagctg 420
gacctgagtc ccggctgc 438

<210> SEQ ID NO 17
<211> LENGTH: 438
<212> TYPE: DNA
<213> ORGANISM: Artificial Sequence
<220> FEATURE:
<223> OTHER INFORMATION: synthetic

<400> SEQUENCE: 17
gtgcccatcc aaaaagtcca agatgacacc aaaaccctca tcaagacaat tgtcaccagg 60
atcaatgaca tttcacacac gcagtcagtc tcctccaaac agaaagtcac tggtgcggct 120
gccgctcctg ggctccaccc catcctgacc ttatccaaga tggaccagac actggcagtc 180

```
taccaacaga tcctcaccag tatgccttcc agaaacgtga tccgaatatc caacgacctg    240

gagaacctcc gggatcttct tcacgtgctg gccttctcta agagctgcca cttgccctgg    300

gccagtggcc tggagacctt ggacagcctg gggggtgtcc tggaagcttc aggctactcc    360

acagaggtgg tggccctgag caggctgcag gggtctctgc aggacatgct gtggcagctg    420

gacctcagcc ctgggtgc                                                   438
```

<210> SEQ ID NO 18
<211> LENGTH: 438
<212> TYPE: DNA
<213> ORGANISM: Artificial Sequence
<220> FEATURE:
<223> OTHER INFORMATION: synthetic

<400> SEQUENCE: 18

```
gtgtcgatcc gcaaggtcca ggatgacacc aaaaccctca tcaagacgat tgtcaccagg     60

atcaatgaca tctcacacac gcagtccgtc tcctccaaac agagggtcac cggtgctgct    120

gctgctcctg ggctccaccc tctcctgagt ttgtccaaga tggaccagac attggcaatc    180

taccaacaga tcctcgccag tctgccttcc agaaatgtga tccaaatatc taatgacctg    240

gagaacctcc gggaccttct ccacctgctg gccgcctcca agagctgccc cttgccgcag    300

gtcagggccc tagagagctt ggagagcctg ggcgtcgtcc tggaagcctc cctctactcc    360

accgaggtgg tggccctgag ccggctacag gggtctctac aggacatgtt gcggcagctg    420

gacctgagtc ccggctgc                                                   438
```

<210> SEQ ID NO 19
<211> LENGTH: 41
<212> TYPE: DNA
<213> ORGANISM: Artificial Sequence
<220> FEATURE:
<223> OTHER INFORMATION: synthetic

<400> SEQUENCE: 19

```
ccaaacagaa agtcactggt gcggctttca ttcctgggct c                          41
```

<210> SEQ ID NO 20
<211> LENGTH: 41
<212> TYPE: DNA
<213> ORGANISM: Artificial Sequence
<220> FEATURE:
<223> OTHER INFORMATION: synthetic

<400> SEQUENCE: 20

```
gagcccagga atgaaagccg caccagtgac tttctgtttg g                          41
```

<210> SEQ ID NO 21
<211> LENGTH: 45
<212> TYPE: DNA
<213> ORGANISM: Artificial Sequence
<220> FEATURE:
<223> OTHER INFORMATION: synthetic

<400> SEQUENCE: 21

```
ccaaacagaa agtcactggt ttggacgccg ctcctgggct ccacc                      45
```

<210> SEQ ID NO 22
<211> LENGTH: 45
<212> TYPE: DNA
<213> ORGANISM: Artificial Sequence
<220> FEATURE:

-continued

<223> OTHER INFORMATION: synthetic

<400> SEQUENCE: 22
ggtggagccc aggagcggcg tccaaaccag tgactttctg tttgg 45

<210> SEQ ID NO 23
<211> LENGTH: 41
<212> TYPE: DNA
<213> ORGANISM: Artificial Sequence
<220> FEATURE:
<223> OTHER INFORMATION: synthetic

<400> SEQUENCE: 23
ccaaacagaa agtcactggt gcggccgcca ttcctgggct c 41

<210> SEQ ID NO 24
<211> LENGTH: 41
<212> TYPE: DNA
<213> ORGANISM: Artificial Sequence
<220> FEATURE:
<223> OTHER INFORMATION: synthetic

<400> SEQUENCE: 24
gagcccagga atggcggccg caccagtgac tttctgtttg g 41

<210> SEQ ID NO 25
<211> LENGTH: 45
<212> TYPE: DNA
<213> ORGANISM: Artificial Sequence
<220> FEATURE:
<223> OTHER INFORMATION: synthetic

<400> SEQUENCE: 25
ccaaacagaa agtcactggt gcggccgccg ctcctgggct ccacc 45

<210> SEQ ID NO 26
<211> LENGTH: 45
<212> TYPE: DNA
<213> ORGANISM: Artificial Sequence
<220> FEATURE:
<223> OTHER INFORMATION: synthetic

<400> SEQUENCE: 26
ggtggagccc aggagcggcg gccgcaccag tgactttctg tttgg 45

<210> SEQ ID NO 27
<211> LENGTH: 41
<212> TYPE: DNA
<213> ORGANISM: Artificial Sequence
<220> FEATURE:
<223> OTHER INFORMATION: synthetic

<400> SEQUENCE: 27
cagagggtca ccggtgctgc tttcatccct gggctccacc c 41

<210> SEQ ID NO 28
<211> LENGTH: 41
<212> TYPE: DNA
<213> ORGANISM: Artificial Sequence
<220> FEATURE:
<223> OTHER INFORMATION: synthetic

<400> SEQUENCE: 28
gggtggagcc cagggatgaa agcagcaccg gtgaccctct g 41

<210> SEQ ID NO 29
<211> LENGTH: 44
<212> TYPE: DNA
<213> ORGANISM: Artificial Sequence
<220> FEATURE:
<223> OTHER INFORMATION: synthetic

<400> SEQUENCE: 29
cctccaaaca gagggtcacc ggtttggacg ctgctcctgg gctc 44

<210> SEQ ID NO 30
<211> LENGTH: 44
<212> TYPE: DNA
<213> ORGANISM: Artificial Sequence
<220> FEATURE:
<223> OTHER INFORMATION: synthetic

<400> SEQUENCE: 30
gagcccagga gcagcgtcca aaccggtgac cctctgtttg gagg 44

<210> SEQ ID NO 31
<211> LENGTH: 46
<212> TYPE: DNA
<213> ORGANISM: Artificial Sequence
<220> FEATURE:
<223> OTHER INFORMATION: synthetic

<400> SEQUENCE: 31
tccaaacaga gggtcaccgg tgctgcagct atccctgggc tccacc 46

<210> SEQ ID NO 32
<211> LENGTH: 46
<212> TYPE: DNA
<213> ORGANISM: Artificial Sequence
<220> FEATURE:
<223> OTHER INFORMATION: synthetic

<400> SEQUENCE: 32
gggtggagcc cagggatagc tgcagcaccg gtgaccctct gtttgg 46

<210> SEQ ID NO 33
<211> LENGTH: 40
<212> TYPE: DNA
<213> ORGANISM: Artificial Sequence
<220> FEATURE:
<223> OTHER INFORMATION: synthetic

<400> SEQUENCE: 33
cagagggtca ccggtgctgc tgctgctccc gggctccacc 40

<210> SEQ ID NO 34
<211> LENGTH: 41
<212> TYPE: DNA
<213> ORGANISM: Artificial Sequence
<220> FEATURE:
<223> OTHER INFORMATION: synthetic

<400> SEQUENCE: 34
gggtggagcc cgggagcagc agcagcaccg gtgaccctct g 41

<210> SEQ ID NO 35
<211> LENGTH: 4
<212> TYPE: PRT
<213> ORGANISM: Artificial Sequence
<220> FEATURE:
<223> OTHER INFORMATION: synthetic

<400> SEQUENCE: 35

```
Leu Asp Phe Ile
1
```

<210> SEQ ID NO 36
<211> LENGTH: 147
<212> TYPE: PRT
<213> ORGANISM: Artificial Sequence
<220> FEATURE:
<223> OTHER INFORMATION: synthetic

<400> SEQUENCE: 36

```
Ala Val Pro Ile Gln Lys Val Gln Asp Asp Thr Lys Thr Leu Ile Lys
1               5                   10                  15

Thr Ile Val Thr Arg Ile Asn Leu Ile Ser His Thr Gln Ser Val Ser
            20                  25                  30

Ser Lys Gln Lys Val Thr Gly Ala Ala Ala Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Gln Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145
```

<210> SEQ ID NO 37
<211> LENGTH: 147
<212> TYPE: PRT
<213> ORGANISM: Homo sapiens

<400> SEQUENCE: 37

```
Ala Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Gln Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140
```

Pro Gly Cys
145

<210> SEQ ID NO 38
<211> LENGTH: 147
<212> TYPE: PRT
<213> ORGANISM: Artificial Sequence
<220> FEATURE:
<223> OTHER INFORMATION: synthetic

<400> SEQUENCE: 38

Ala Val Pro Ile Gln Lys Val Gln Asp Asp Thr Lys Thr Leu Ile Lys
1 5 10 15

Thr Leu Val Thr Arg Ile Asn Leu Ile Ser His Thr Gln Ser Val Ser
20 25 30

Ala Lys Gln Arg Val Thr Gly Ala Ala Ala Ile Pro Gly Leu His Pro
35 40 45

Ile Leu Ser Leu Ser Lys Met Asp Gln Thr Leu Ala Val Tyr Gln Gln
50 55 60

Val Leu Thr Ser Leu Pro Ser Gln Asn Val Leu Gln Ile Ala Asn Asp
65 70 75 80

Leu Glu Asn Leu Arg Asp Leu Leu His Leu Leu Ala Phe Ser Lys Ser
85 90 95

Cys Ser Leu Pro Gln Thr Ser Gly Leu Gln Lys Pro Glu Ser Leu Asp
100 105 110

Gly Val Leu Glu Ala Ser Leu Tyr Ser Thr Glu Val Val Ala Leu Ser
115 120 125

Arg Leu Gln Gly Ser Leu Gln Asp Ile Leu Gln Gln Val Asp Leu Ser
130 135 140

Pro Gly Cys
145

<210> SEQ ID NO 39
<211> LENGTH: 464
<212> TYPE: DNA
<213> ORGANISM: Artificial Sequence
<220> FEATURE:
<223> OTHER INFORMATION: synthetic

<400> SEQUENCE: 39
ccatggctgt tccgatccag aaagttcagg atgacaccaa aaccctgatc aaaaccatcg 60
ttacccgtat taatctgatc tctcataccc agtctgtttc tgctaagcag cgtgttaccg 120
gcgcggctgc aatcccgggc ctgcatccga tcctgtctct gtctaaaatg gaccagaccc 180
tggctgttta tcagcaggtt ctgacctctc tgccgtctca gaacgttctg cagatcgcta 240
acgacctgga aaacctgcgt gacctgctgc atctgctggc tttctctaaa tcttgctctc 300
tgccgcagac ctctggcctg cagaaaccgg aatctctgga cggcgttctg gaggcttctc 360
tgtattctac cgaagttgtt gctctgtctc gtctgcaggg ctctctgcag gacatcctgc 420
agcagttgga cgtttctccg gaatgctgat gaaagcttgg atcc 464

<210> SEQ ID NO 40
<211> LENGTH: 438
<212> TYPE: DNA
<213> ORGANISM: Artificial Sequence
<220> FEATURE:
<223> OTHER INFORMATION: synthetic

<400> SEQUENCE: 40
gtgcccatcc aaaaagtcca agatgacacc aaaaccctca tcaagacaat tgtcaccagg 60
atcaatgaca tttcacacac gcagtcagtc tcctccaaac agaaagtcac tggtgcggct 120
ttcattcctg ggctccaccc catcctgacc ttatccaaga tggaccagac actggcagtc 180
taccaacaga tcctcaccag tatgccttcc agaaacgtga tccgaatatc caacgacctg 240
gagaacctcc gggatcttct tcacgtgctg gccttctcta agagctgcca cttgccctgg 300
gccagtggcc tggagacctt ggacagcctg gggggtgtcc tggaagcttc aggctactcc 360
acagaggtgg tggccctgag caggctgcag gggtctctgc aggacatgct gtggcagctg 420
gacctcagcc ctgggtgc 438

<210> SEQ ID NO 41
<211> LENGTH: 438
<212> TYPE: DNA
<213> ORGANISM: Artificial Sequence
<220> FEATURE:
<223> OTHER INFORMATION: synthetic

<400> SEQUENCE: 41
gtgcccatcc aaaaagtcca agatgacacc aaaaccctca tcaagacaat tgtcaccagg 60
atcaatgaca tttcacacac gcagtcagtc tcctccaaac agaaagtcac tggtttggac 120
gccgctcctg ggctccaccc catcctgacc ttatccaaga tggaccagac actggcagtc 180
taccaacaga tcctcaccag tatgccttcc agaaacgtga tccgaatatc caacgacctg 240
gagaacctcc gggatcttct tcacgtgctg gccttctcta agagctgcca cttgccctgg 300
gccagtggcc tggagacctt ggacagcctg gggggtgtcc tggaagcttc aggctactcc 360
acagaggtgg tggccctgag caggctgcag gggtctctgc aggacatgct gtggcagctg 420
gacctcagcc ctgggtgc 438

<210> SEQ ID NO 42
<211> LENGTH: 438
<212> TYPE: DNA
<213> ORGANISM: Artificial Sequence
<220> FEATURE:
<223> OTHER INFORMATION: synthetic

<400> SEQUENCE: 42
gtgtcgatcc gcaaggtcca ggatgacacc aaaaccctca tcaagacgat tgtcaccagg 60
atcaatgaca tctcacacac gcagtccgtc tcctccaaac agagggtcac cggtgctgct 120
ttcatccctg ggctccaccc tctcctgagt ttgtccaaga tggaccagac attggcaatc 180
taccaacaga tcctcgccag tctgccttcc agaaatgtga tccaaatatc taatgacctg 240
gagaacctcc gggaccttct ccacctgctg gccgcctcca agagctgccc cttgccgcag 300
gtcagggccc tagagagctt ggagagcctg ggcgtcgtcc tggaagcctc cctctactcc 360
accgaggtgg tggccctgag ccggctacag gggtctctac aggacatgtt gcggcagctg 420
gacctgagtc ccggctgc 438

<210> SEQ ID NO 43
<211> LENGTH: 438
<212> TYPE: DNA
<213> ORGANISM: Artificial Sequence
<220> FEATURE:
<223> OTHER INFORMATION: synthetic

<400> SEQUENCE: 43

-continued gtgtcgatcc gcaaggtcca ggatgacacc aaaaccctca tcaagacgat tgtcaccagg 60
atcaatgaca tctcacacac gcagtccgtc tcctccaaac agagggtcac cggtttggac 120
gctgctcctg ggctccaccc tctcctgagt ttgtccaaga tggaccagac attggcaatc 180
taccaacaga tcctcgccag tctgccttcc agaaatgtga tccaaatatc taatgacctg 240
gagaacctcc gggaccttct ccacctgctg gccgcctcca agagctgccc cttgccgcag 300
gtcagggccc tagagagctt ggagagcctg ggcgtcgtcc tggaagcctc cctctactcc 360
accgaggtgg tggccctgag ccggctacag gggtctctac aggacatgtt gcggcagctg 420
gacctgagtc ccggctgc 438

<210> SEQ ID NO 44
<211> LENGTH: 438
<212> TYPE: DNA
<213> ORGANISM: Artificial Sequence
<220> FEATURE:
<223> OTHER INFORMATION: synthetic

<400> SEQUENCE: 44
gtgcccatcc aaaaagtcca agatgacacc aaaaccctca tcaagacaat tgtcaccagg 60
atcaatgaca tttcacacac gcagtcagtc tcctccaaac agaaagtcac tggtgcggct 120
gccattcctg ggctccaccc catcctgacc ttatccaaga tggaccagac actggcagtc 180
taccaacaga tcctcaccag tatgccttcc agaaacgtga tccgaatatc caacgacctg 240
gagaacctcc gggatcttct tcacgtgctg gccttctcta agagctgcca cttgccctgg 300
gccagtggcc tggagacctt ggacagcctg gggggtgtcc tggaagcttc aggctactcc 360
acagaggtgg tggccctgag caggctgcag gggtctctgc aggacatgct gtggcagctg 420
gacctcagcc ctgggtgc 438

<210> SEQ ID NO 45
<211> LENGTH: 438
<212> TYPE: DNA
<213> ORGANISM: Artificial Sequence
<220> FEATURE:
<223> OTHER INFORMATION: synthetic

<400> SEQUENCE: 45
gtgtcgatcc gcaaggtcca ggatgacacc aaaaccctca tcaagacgat tgtcaccagg 60
atcaatgaca tctcacacac gcagtccgtc tcctccaaac agagggtcac cggtgctgca 120
gctatccctg ggctccaccc tctcctgagt ttgtccaaga tggaccagac attggcaatc 180
taccaacaga tcctcgccag tctgccttcc agaaatgtga tccaaatatc taatgacctg 240
gagaacctcc gggaccttct ccacctgctg gccgcctcca agagctgccc cttgccgcag 300
gtcagggccc tagagagctt ggagagcctg ggcgtcgtcc tggaagcctc cctctactcc 360
accgaggtgg tggccctgag ccggctacag gggtctctac aggacatgtt gcggcagctg 420
gacctgagtc ccggctgc 438

<210> SEQ ID NO 46
<211> LENGTH: 438
<212> TYPE: DNA
<213> ORGANISM: Artificial Sequence
<220> FEATURE:
<223> OTHER INFORMATION: synthetic

<400> SEQUENCE: 46
gtgcccatcc aaaaagtcca agatgacacc aaaaccctca tcaagacaat tgtcaccagg 60

-continued atcaatgaca tttcacacac gcagtcagtc tcctccaaac agaaagtcac tggtgcggct 120
gccgctcctg ggctccaccc catcctgacc ttatccaaga tggaccagac actggcagtc 180
taccaacaga tcctcaccag tatgccttcc agaaacgtga tccgaatatc caacgacctg 240
gagaacctcc gggatcttct tcacgtgctg gccttctcta agagctgcca cttgccctgg 300
gccagtggcc tggagacctt ggacagcctg gggggtgtcc tggaagcttc aggctactcc 360
acagaggtgg tggccctgag caggctgcag gggtctctgc aggacatgct gtggcagctg 420
gacctcagcc ctgggtgc 438

<210> SEQ ID NO 47
<211> LENGTH: 438
<212> TYPE: DNA
<213> ORGANISM: Artificial Sequence
<220> FEATURE:
<223> OTHER INFORMATION: synthetic

<400> SEQUENCE: 47
gtgtcgatcc gcaaggtcca ggatgacacc aaaaccctca tcaagacgat tgtcaccagg 60
atcaatgaca tctcacacac gcagtccgtc tcctccaaac agagggtcac cggtgctgct 120
gctgctcctg ggctccaccc tctcctgagt ttgtccaaga tggaccagac attggcaatc 180
taccaacaga tcctcgccag tctgccttcc agaaatgtga tccaaatatc taatgacctg 240
gagaacctcc gggaccttct ccacctgctg gccgcctcca agagctgccc cttgccgcag 300
gtcagggccc tagagagctt ggagagcctg ggcgtcgtcc tggaagcctc cctctactcc 360
accgaggtgg tggccctgag ccggctacag gggtctctac aggacatgtt gcggcagctg 420
gacctgagtc ccggctgc 438

<210> SEQ ID NO 48
<211> LENGTH: 167
<212> TYPE: PRT
<213> ORGANISM: Rattus norvegicus

<400> SEQUENCE: 48

Met Cys Trp Arg Pro Leu Cys Arg Phe Leu Trp Leu Trp Ser Tyr Leu
1 5 10 15

Ser Tyr Val Gln Ala Val Pro Ile His Lys Val Gln Asp Asp Thr Lys
20 25 30

Thr Leu Ile Lys Thr Ile Val Thr Arg Ile Asn Asp Ile Ser His Thr
35 40 45

Gln Ser Val Ser Ala Arg Gln Arg Val Thr Gly Leu Asp Phe Ile Pro
50 55 60

Gly Leu His Pro Ile Leu Ser Leu Ser Lys Met Asp Gln Thr Leu Ala
65 70 75 80

Val Tyr Gln Gln Ile Leu Thr Ser Leu Pro Ser Gln Asn Val Leu Gln
85 90 95

Ile Ala His Asp Leu Glu Asn Leu Arg Asp Leu Leu His Leu Leu Ala
100 105 110

Phe Ser Lys Ser Cys Ser Leu Pro Gln Thr Arg Gly Leu Gln Lys Pro
115 120 125

Glu Ser Leu Asp Gly Val Leu Glu Ala Ser Leu Tyr Ser Thr Glu Val
130 135 140

Val Ala Leu Ser Arg Leu Gln Gly Ser Leu Gln Asp Ile Leu Gln Gln
145 150 155 160

Leu Asp Leu Ser Pro Glu Cys
165

<210> SEQ ID NO 49
<211> LENGTH: 576
<212> TYPE: DNA
<213> ORGANISM: Mus musculus

<400> SEQUENCE: 49
gtgggacagc gagctaatac ccagaactga gttgtgtcct gctaagtcct ctgccacgta 60
cccacgggat gaagaacctt tcatttcccc tccttttcct tttcttcctt gtccctgaac 120
tgctgggctc cagcatgcca ctgtgtccca tcgatgaagc catcgacaag aagatcaaac 180
aagacttcaa ctccctgttt ccaaatgcaa taaagaacat tggcttaaat tgctggacag 240
tctcctccag agggaagttg gcctcctgcc cagaaggcac agcagtcttg agctgctcct 300
gtggctctgc ctgtggctcg tgggacattc gtgaagaaaa agtgtgtcac tgccagtgtg 360
caaggataga ctggacagca gcccgctgct gtaagctgca ggtcgcttcc tgatgtcggg 420
gaagtgagcg tggtttccag cacagccacc cgttcctgta gctccagaga tgtctgatgt 480
cctccggtct ctacaggcac ctgcactcac gtgcgcgaat ccacacacaa gcacacatac 540
ttaaaaataa aacaaaacag gctggaaaaa aaaaaa 576

<210> SEQ ID NO 50
<211> LENGTH: 114
<212> TYPE: PRT
<213> ORGANISM: Mus musculus

<400> SEQUENCE: 50

Met Lys Asn Leu Ser Phe Pro Leu Leu Phe Leu Phe Phe Leu Val Pro
1 5 10 15

Glu Leu Leu Gly Ser Ser Met Pro Leu Cys Pro Ile Asp Glu Ala Ile
20 25 30

Asp Lys Lys Ile Lys Gln Asp Phe Asn Ser Leu Phe Pro Asn Ala Ile
35 40 45

Lys Asn Ile Gly Leu Asn Cys Trp Thr Val Ser Ser Arg Gly Lys Leu
50 55 60

Ala Ser Cys Pro Glu Gly Thr Ala Val Leu Ser Cys Ser Cys Gly Ser
65 70 75 80

Ala Cys Gly Ser Trp Asp Ile Arg Gly Gly Lys Val Cys His Cys Gln
85 90 95

Cys Ala Arg Ile Asp Trp Thr Ala Ala Arg Cys Cys Lys Leu Gln Val
100 105 110

Ala Ser

<210> SEQ ID NO 51
<211> LENGTH: 479
<212> TYPE: DNA
<213> ORGANISM: Homo sapiens
<220> FEATURE:
<221> NAME/KEY: misc_feature
<222> LOCATION: (140)..(140)
<223> OTHER INFORMATION: n is a, c, g, or t

<400> SEQUENCE: 51
gtgtgccgga tttggttagc tgagcccacc gagaggcgcc tgcaggatga aagctctctg 60
tctcctcctc ctccctgtcc tggggctgtt ggtgtctagc aagaccctgt gctccatgga 120
agaagccatc aatgagaggn tccaggaggt cgccggctcc ctaatattta gggcaataag 180

```
cagcattggc ctggagtgcc agagcgtcac ctccaggggg gacctggcta cttgcccccg    240

aggcttcgcc gtcaccggct gcacttgtgg ctccgcctgt ggctcgtggg atgtgcgcgc    300

cgagaccaca tgtcactgcc agtgcgcggg catggactgg accggagcgc gctgctgtcg    360

tgtgcagccc tgaggtcgcg cgcagcgcgt gcacagcgcg ggcggaggcg gctccaggtc    420

cggaggggtt gcgggggagc tggaaataaa cctggagatg atgatgatga tgatgatgg     479
```

<210> SEQ ID NO 52
<211> LENGTH: 107
<212> TYPE: PRT
<213> ORGANISM: Homo sapiens

<400> SEQUENCE: 52

```
Met Lys Ala Leu Cys Leu Leu Leu Leu Val Leu Gly Leu Leu Val Ser
1               5                   10                  15

Ser Lys Thr Leu Cys Ser Met Glu Glu Ala Ile Asn Glu Arg Ile Gln
            20                  25                  30

Glu Val Ala Gly Ser Leu Ile Phe Arg Ala Ile Ser Ser Ile Gly Leu
        35                  40                  45

Glu Cys Gln Ser Val Thr Ser Arg Gly Asp Leu Ala Thr Cys Pro Arg
    50                  55                  60

Gly Phe Ala Val Thr Gly Ser Thr Cys Gly Ser Ala Cys Gly Ser Trp
65                  70                  75                  80

Asp Val Arg Ala Glu Thr Thr Cys His Cys Gln Cys Ala Gly Met Asp
                85                  90                  95

Trp Thr Gly Ala Arg Cys Cys Arg Val Gln Pro
            100                 105
```

<210> SEQ ID NO 53
<211> LENGTH: 4420
<212> TYPE: DNA
<213> ORGANISM: Homo sapiens

<400> SEQUENCE: 53

```
aacctagcca acatggtgaa actccttctc tactaaaaat acaaaaatta gccaggtatg     60

gtggcgagcg cctgtagtcc cagctacgtg ggaggctgag gcaggagaat cgcttgaacc    120

caggaggcag aggcttgcgg tgagccgaga ttgcaccact gcactccagc ctgggcaaca    180

gagcgagacc ctgtctcaaa aaaaaaaaac ttggtttcgt gtggtgtatc ttcgcttgtt    240

tctgtgtgat ctgtgattgt ccttctgtcg tttcttggtt ttctcttatt ctcggcgtgt    300

tatgttgcgc tgtgcttcgt ttggttctac tgttttctgt ttccttcttt ctcgtttttg    360

tcagtcgtct tgtctgtctc cgcagcgcgc ttgtcactct ggtcgcgttg cctgtacgtc    420

attcgtcgtt ctgcctgctc gttatcgttc tcgcatgatt gttttcctcc gggatcgcat    480

ggctgctccc cttcttgtat gtcttcttgt ctcctgggct cgtcttctcc cgcttcttcg    540

tttgtctttc attctctctt ttcattcctc tttctttcac aattacattt cctctccgac    600

agtgagtcga ttgtctagtg tcaggggaag ggaagggaag aaacgaaacc ctgggggga     660

tctaggagca gacaagtccc ctgctctgtg ttttcataat ctagtatcca ggaaggggta    720

agcaccctgc gtgtatctgg ttgtaactaa ctactcacaa ctgcacttgc ctgtgtgaaa    780

acgtgagctt gtgatgatgc gtgacgtcag gtaggcgtcc ctgactctcc gtaacccaac    840

tttgcctgtg ccttggggat tcctccttgc aggtaggaag tgaggggtac aggttccagc    900

tctgggctga gacatgattc agggttccac cctgacctgg ggctcctgga gtcttggggc    960
```

-continued

```
cctggagggt cccgtccact gcccagactg acccaggtcc tcgatgaagc ctcattatga   1020
ggactggggg aaaaggaccc agccacttcc tggggaggtc ggagacccca gggtgagcgt   1080
caaggtagcc tcaaagatga gacgtcacct cttgaaggca gccatgagcc ttgggtgggg   1140
acgtcactag aggaagttca ggccctattt tcggaggaag cagttggaga ccccatagga   1200
ggaagggcga tggggcagta gaaagtcgcg gtgtccccgc cccctccagc agctacgcgc   1260
cccactctct tggagacgct agatcagtcc ctccgggcct actaaagaaa ccacgcaggg   1320
ctcagatccg ctccatcatc atcatcatca tcatcatcat catctccagg tttatttcca   1380
gctcccccgc aacccctccg gacctggagc cgcctccgcc cgcgctgtgc acgcgctgcg   1440
cgcgacctca gggctgcaca cgacagcagc gcgctccggt ccagtccatg cccgcgcact   1500
ggcagtgaca tgtggtctcg gcgcgcacat cccacgagcc acaggcggag ccacaagtgc   1560
agccggtgac ggcgaagcct gcagcccgga acacaggagc gtggactctg agctgggagg   1620
ctgagggtgg gagcgggagg ggggtgggga gcgcggaggg gggttggggg ggcgggggtg   1680
gggacgggga cggctggagg ctccaaccac tgaatgggca ctggaggcag ggagtgaggg   1740
tggacaccag tgtccagatg gtgggcggag aaggctggga gtcaggacca agatcctagg   1800
ggagtagagg ctggacacgg ggaacgtggc ggggaggggg cattcccagg ggacttggaa   1860
cagaaatggg cgcctggaca acagtctcct gcactcacct cgggggcaag tagccaggtc   1920
ccccctggag gtgacgctct ggcactccag gccaatgctg cttattgccc taaatactgg   1980
ggggcaggag gaaaggagac agggggagct gtgagaccaa acggtccctc cccatcctc    2040
ccctagccct gttggtttgg agctaggtcc ctgtgggcat aggagctcac tggcctccag   2100
gaccctgtct tgagttgggt gttttggagt aagggaaggt ttggagtgag agcggggatt   2160
gggtttggag ccgtggataa ggtggggaca gtcggagggg ttgggagtgg agttggggtt   2220
gaatttatga tctggttgga tttgaggatg agatttggtg agcgctgggg ctgggttgga   2280
gtcaggtctg tgccagggat cagtgaggtc tctgagaccc ttggggagct tgcccaagtg   2340
gggggtcctc acttagggag ccggcgacct cctggatcct ctcattgatg gcttcttcca   2400
tggagcacag ggtcttgcta gacaccaaca gccccaggac agggaggagg aggagacaga   2460
gagctttcat cctgcaggcg ctgaaagagg gaaccaagag acccacagct ggatcagccc   2520
tgccctgtgg ggaagatccg gcccatggag ggagtaggat ctgcccctgg acctggaccc   2580
ctgtcccccc atgtggggga cagggatgga ggctcagcct tgaccccagc ctccccgctg   2640
gtgccatggc aagcgcagga gcagctgtca cttaccctct cggtgggctc agctaaccaa   2700
atccggcaca cgaattcctg caccgcagct ctttctttga ggcctcttgg ggtggggctt   2760
cctggcttgg ctaataagtc cctgggcccc caaccctccg gtcccacatc cggggccaag   2820
aggaagcccc tgagcagaca gtaagggctg gaggaggaag ggagccttcc cacttccaac   2880
agggcctccg tcttcatgtc cagagactgg tcaggaggtg gtgccccagg gataatgcca   2940
ggggctgtgg tctgaggaac aggtagacaa gcagagtttt gcatgcaagg gtggctgatg   3000
caaacatgac aaaattaatg cctcttgcta ggcatggtgc ggacaagcac ttgtagtccc   3060
agctactaag gaggctgacg tgagagaatt gcttgagccc gggagttcga agctacagtg   3120
acttatgatc acagcactgc actccagtct gggcaacaga gcaagaccac ttctctaaaa   3180
tagtaataat aattatgtct ctgggtgaga atgacatacc acattcatac ccaaatgccc   3240
atgagcaata gaactggtaa ataaaatcat ggtttatggc cggtggctca cgcctgtaat   3300
```

```
cccagcactt tgggaggcca aggcgggcgg atcacttgag gtcaggagct tgagaccaac   3360

ctggccaaca tgatgaaacc ctgtctccat tagacataca aaaattaact gggcgtggtg   3420

gcgtgtgcct gtaatcccag ctacttggga ggctgaggtg ggagaatcac ttgaacccgg   3480

gatgtggagg ttgcagtgca ctgagatcgt gcccctgcac tccatcctgg atgactagct   3540

tgggcaccat agcaagactc catctcaaaa agaagaaaga aaaatcatgg tttattccat   3600

caatggcatc acctgcaaca gaagttggaa agccattgct catgggccaa ggtccagctc   3660

atgtttcttc ttggaccacc catgagcttg gaatggttat acatttttat ttgttctttg   3720

tttccagtac aacgggcctt tttgtggtaa aatacatata acatacaact taccattata   3780

acttactttt ttctgttttt gagacggaat cttgctctgt cgcccaggct ggagtgcagt   3840

ggcgcgatct cggctcacta caagctccgc ctcctgggtt cacgccattc tcctgcttca   3900

gcctcccaag tagctgggac tacaggcgcc tgccaccacg cccagctaat tttttgtatt   3960

tttttttttt tagtagagat ggagtttcac cgtgttagcc aggatggtct cgatcccctg   4020

accttgtgat ctgcccgcct tggcctccca aagtgctggg attacaggcg tgaaccaccg   4080

tgcccggcct tttttttttt ttttttgaga cggggtcttg ctatgttgcc caagctagtg   4140

tcagactcct ggcttcaagt aatcctccca ccttggactc cccagtagct gaagctacag   4200

gtatgcacca tcttgttcca ttttaaccat tgcttttgtt tgtttctttg tttcagagtc   4260

tcactcagtt gctcaggctg gagtacagtg gctcaatctt ggctcactgc aacctccacc   4320

tcctgggttc aagcaattct cctgcctcag cctcccgagt agctgggatt acaggcgtgc   4380

accaccatgc ccggctaatt ttttgtattt ttagtagaga                         4420

<210> SEQ ID NO 54
<211> LENGTH: 4420
<212> TYPE: DNA
<213> ORGANISM: Homo sapiens

<400> SEQUENCE: 54

tctctactaa aaatacaaaa aattagccgg gcatggtggt gcacgcctgt aatcccagct     60

actcgggagg ctgaggcagg agaattgctt gaacccagga ggtggaggtt gcagtgagcc    120

aagattgagc cactgtactc cagcctgagc aactgagtga gactctgaaa caaagaaaca    180

aacaaaagca atggttaaaa tggaacaaga tggtgcatac ctgtagcttc agctactggg    240

gagtccaagg tgggaggatt acttgaagcc aggagtctga cactagcttg ggcaacatag    300

caagaccccg tctcaaaaaa aaaaaaaaaa aggccgggca cggtggttca cgcctgtaat    360

cccagcactt tgggaggcca aggcgggcag atcacaaggt caggggatcg agaccatcct    420

ggctaacacg gtgaaactcc atctctacta aaaaaaaaaa aatacaaaaa attagctggg    480

cgtggtggca ggcgcctgta gtcccagcta cttgggaggc tgaagcagga gaatggcgtg    540

aacccaggag gcggagcttg tagtgagccg agatcgcgcc actgcactcc agcctgggcg    600

acagagcaag attccgtctc aaaaacagaa aaaagtaagt tataatggta agttgtatgt    660

tatatgtatt ttaccacaaa aaggcccgtt gtactggaaa caaagaacaa ataaaaatgt    720

ataaccattc caagctcatg ggtggtccaa gaagaaacat gagctggacc ttggcccatg    780

agcaatggct ttccaacttc tgttgcaggt gatgccattg atggaataaa ccatgatttt    840

tctttcttct ttttgagatg gagtcttgct atggtgccca agctagtcat ccaggatgga    900

gtgcaggggc acgatctcag tgcactgcaa cctccacatc ccgggttcaa gtgattctcc    960

cacctcagcc tcccaagtag ctgggattac aggcacacgc caccacgccc agttaatttt   1020
```

-continued

```
tgtatgtcta atggagacag ggtttcatca tgttggccag gttggtctca agctcctgac   1080
ctcaagtgat ccgcccgcct tggcctccca aagtgctggg attacaggcg tgagccaccg   1140
gccataaacc atgattttat ttaccagttc tattgctcat gggcatttgg gtatgaatgt   1200
ggtatgtcat tctcacccag agacataatt attattacta ttttagagaa gtggtcttgc   1260
tctgttgccc agactggagt gcagtgctgt gatcataagt cactgtagct tcgaactccc   1320
gggctcaagc aattctctca cgtcagcctc cttagtagct gggactacaa gtgcttgtcc   1380
gcaccatgcc tagcaagagg cattaatttt gtcatgtttg catcagccac ccttgcatgc   1440
aaaactctgc ttgtctacct gttcctcaga ccacagcccc tggcattatc cctggggcac   1500
cacctcctga ccagtctctg gacatgaaga cggaggccct gttggaagtg ggaaggctcc   1560
cttcctcctc cagcccttac tgtctgctca ggggcttcct cttggccccg gatgtgggac   1620
cggagggttg ggggcccagg gacttattag ccaagccagg aagccccacc ccaagaggcc   1680
tcaaagaaag agctgcggtg caggaattcg tgtgccggat ttggttagct gagcccaccg   1740
agagggtaag tgacagctgc tcctgcgctt gccatggcac cagcggggag gctggggtca   1800
aggctgagcc tccatccctg tcccccacat ggggggacag gggtccaggt ccaggggcag   1860
atcctactcc ctccatgggc cggatcttcc ccacagggca gggctgatcc agctgtgggt   1920
ctcttggttc cctctttcag cgcctgcagg atgaaagctc tctgtctcct cctcctccct   1980
gtcctggggc tgttggtgtc tagcaagacc ctgtgctcca tggaagaagc catcaatgag   2040
aggatccagg aggtcgccgg ctccctaagt gaggaccccc cacttgggca agctccccaa   2100
gggtctcaga gacctcactg atccctggca cagacctgac tccaacccag ccccagcgct   2160
caccaaatct catcctcaaa tccaaccaga tcataaattc aaccccaact ccactcccaa   2220
cccctccgac tgtccccacc ttatccacgg ctccaaaccc aatccccgct ctcactccaa   2280
accttccctt actccaaaac acccaactca agacagggtc ctggaggcca gtgagctcct   2340
atgcccacag ggacctagct ccaaaccaac agggctaggg gaggatgggg gagggaccgt   2400
ttggtctcac agctccccct gtctcctttc ctcctgcccc ccagtattta gggcaataag   2460
cagcattggc ctggagtgcc agagcgtcac ctccaggggg gacctggcta cttgcccccg   2520
aggtgagtgc aggagactgt tgtccaggcg cccatttctg ttccaagtcc cctgggaatg   2580
ccccctcccc gccacgttcc ccgtgtccag cctctactcc cctaggatct tggtcctgac   2640
tcccagcctt ctccgcccac catctggaca ctggtgtcca ccctcactcc ctgcctccag   2700
tgcccattca gtggttggag cctccagccg tccccgtccc cacccccgcc cccccaaccc   2760
ccctccgcgc tccccacccc cctcccgctc ccaccctcag cctcccagct cagagtccac   2820
gctcctgtgt tccgggctgc aggcttcgcc gtcaccggct gcacttgtgg ctccgcctgt   2880
ggctcgtggg atgtgcgcgc cgagaccaca tgtcactgcc agtgcgcggg catggactgg   2940
accggagcgc gctgctgtcg tgtgcagccc tgaggtcgcg cgcagcgcgt gcacagcgcg   3000
ggcggaggcg gctccaggtc cggaggggtt gcgggggagc tggaaataaa cctggagatg   3060
atgatgatga tgatgatgat gatgatggag cggatctgag ccctgcgtgg tttctttagt   3120
aggcccggag ggactgatct agcgtctcca agagagtggg gcgcgtagct gctggagggg   3180
gcggggacac cgcgactttc tactgcccca tcgcccttcc tcctatgggg tctccaactg   3240
cttcctccga aaatagggcc tgaacttcct ctagtgacgt ccccacccaa ggctcatggc   3300
tgccttcaag aggtgacgtc tcatctttga ggctaccttg acgctcaccc tggggtctcc   3360
```

-continued gacctcccca ggaagtggct gggtcctttt cccccagtcc tcataatgag gcttcatcga 3420
ggacctgggt cagtctgggc agtggacggg accctccagg gccccaagac tccaggagcc 3480
ccaggtcagg gtggaaccct gaatcatgtc tcagcccaga gctggaacct gtacccctca 3540
cttcctacct gcaaggagga atccccaagg cacaggcaaa gttgggttac ggagagtcag 3600
ggacgcctac ctgacgtcac gcatcatcac aagctcacgt tttcacacag gcaagtgcag 3660
ttgtgagtag ttagttacaa ccagatacac gcagggtgct taccccttcc tggatactag 3720
attatgaaaa cacagagcag gggacttgtc tgctcctaga tcccccccag ggtttcgttt 3780
cttcccttcc cttcccctga cactagacaa tcgactcact gtcggagagg aaatgtaatt 3840
gtgaaagaaa gaggaatgaa aagagagaat gaaagacaaa cgaagaagcg ggagaagacg 3900
agcccaggag acaagaagac atacaagaag gggagcagcc atgcgatccc ggaggaaaac 3960
aatcatgcga gaacgataac gagcaggcag aacgacgaat gacgtacagg caacgcgacc 4020
agagtgacaa gcgcgctgcg gagacagaca agacgactga caaaaacgag aaagaaggaa 4080
acagaaaaca gtagaaccaa acgaagcaca gcgcaacata acacgccgag aataagagaa 4140
aaccaagaaa cgacagaagg acaatcacag atcacacaga aacaagcgaa gatacaccac 4200
acgaaaccaa gttttttttt tttgagacag ggtctcgctc tgttgcccag gctggagtgc 4260
agtggtgcaa tctcggctca ccgcaagcct ctgcctcctg ggttcaagcg attctcctgc 4320
ctcagcctcc cacgtagctg ggactacagg cgctcgccac catacctggc taatttttgt 4380
atttttagta gagaaggagt ttcaccatgt tggctaggtt 4420

<210> SEQ ID NO 55
<211> LENGTH: 114
<212> TYPE: PRT
<213> ORGANISM: Artificial Sequence
<220> FEATURE:
<223> OTHER INFORMATION: consensus resistin sequence mouse/human
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid
<220> FEATURE:
<221> NAME/KEY: misc_feature
<222> LOCATION: (37)..(41)
<223> OTHER INFORMATION: Xaa can be any naturally occurring amino acid
<220> FEATURE:
<221> NAME/KEY: misc_feature
<222> LOCATION: (44)..(46)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(92)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(114)
<223> OTHER INFORMATION: Xaa can be any naturally occurring amino acid

<400> SEQUENCE: 55

```
Met Lys Xaa Leu Xaa Xaa Xaa Leu Leu Xaa Xaa Xaa Xaa Leu Xaa Xaa
1               5                   10                  15

Xaa Leu Leu Xaa Ser Ser Xaa Xaa Leu Cys Xaa Xaa Xaa Glu Ala Ile
```

```
            20                  25                  30

Xaa Xaa Xaa Ile Xaa Xaa Xaa Xaa Xaa Ser Leu Xaa Xaa Xaa Ala Ile
        35                  40                  45

Xaa Xaa Ile Gly Leu Xaa Cys Xaa Xaa Val Xaa Ser Arg Gly Xaa Leu
    50                  55                  60

Ala Xaa Cys Pro Xaa Gly Xaa Ala Val Xaa Xaa Cys Xaa Cys Gly Ser
65                  70                  75                  80

Ala Cys Gly Ser Trp Asp Xaa Arg Xaa Glu Xaa Xaa Cys His Cys Gln
                85                  90                  95

Cys Ala Xaa Xaa Asp Trp Thr Xaa Ala Arg Cys Cys Xaa Xaa Gln Xaa
            100                 105                 110

Xaa Xaa
```

<210> SEQ ID NO 56
<211> LENGTH: 5446
<212> TYPE: DNA
<213> ORGANISM: Artificial Sequence
<220> FEATURE:
<223> OTHER INFORMATION: Plasmid

<400> SEQUENCE: 56

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat ccactagtaa cggccgccag tgtgctggaa ttctgcagat atccatcaca    960
ctggcggccg ctcgagcatg catctagagg gccctattct atagtgtcac ctaaatgcta   1020
gagctcgctg atcagcctcg actgtgcctt ctagttgcca gccatctgtt gtttgcccct   1080
cccccgtgcc ttccttgacc ctggaaggtg ccactcccac tgtcctttcc taataaaatg   1140
aggaaattgc atcgcattgt ctgagtaggt gtcattctat tctggggggt ggggtggggc   1200
aggacagcaa gggggaggat tgggaagaca atagcaggca tgctggggat gcggtgggct   1260
ctatggcttc tgaggcggaa agaaccagct ggggctctag ggggtatccc cacgcgccct   1320
gtagcggcgc attaagcgcg gcgggtgtgg tggttacgcg cagcgtgacc gctacacttg   1380
ccagcgccct agcgcccgct cctttcgctt tcttcccttc ctttctcgcc acgttcgccg   1440
gctttccccg tcaagctcta aatcggggca tccctttagg gttccgattt agtgctttac   1500
```

ggcacctcga ccccaaaaaa cttgattagg gtgatggttc acgtagtggg ccatcgccct 1560
gatagacggt ttttcgccct ttgacgttgg agtccacgtt ctttaatagt ggactcttgt 1620
tccaaactgg aacaacactc aaccctatct cggtctattc ttttgattta taagggattt 1680
tggggatttc ggcctattgg ttaaaaaatg agctgattta acaaaaattt aacgcgaatt 1740
aattctgtgg aatgtgtgtc agttagggtg tggaaagtcc ccaggctccc caggcaggca 1800
gaagtatgca aagcatgcat ctcaattagt cagcaaccag gtgtggaaag tccccaggct 1860
ccccagcagg cagaagtatg caaagcatgc atctcaatta gtcagcaacc atagtcccgc 1920
ccctaactcc gcccatcccg cccctaactc cgcccagttc cgcccattct ccgccccatg 1980
gctgactaat tttttttatt tatgcagagg ccgaggccgc ctctgcctct gagctattcc 2040
agaagtagtg aggaggcttt tttggaggcc taggcttttg caaaaagctc ccgggagctt 2100
gtatatccat tttcggatct gatcaagaga caggatgagg atcgtttcgc atgattgaac 2160
aagatggatt gcacgcaggt tctccggccg cttgggtgga gaggctattc ggctatgact 2220
gggcacaaca gacaatcggc tgctctgatg ccgccgtgtt ccggctgtca gcgcaggggc 2280
gcccggttct ttttgtcaag accgacctgt ccggtgccct gaatgaactg caggacgagg 2340
cagcgcggct atcgtggctg gccacgacgg gcgttccttg cgcagctgtg ctcgacgttg 2400
tcactgaagc gggaagggac tggctgctat tgggcgaagt gccggggcag gatctcctgt 2460
catctcacct tgctcctgcc gagaaagtat ccatcatggc tgatgcaatg cggcggctgc 2520
atacgcttga tccggctacc tgcccattcg accaccaagc gaaacatcgc atcgagcgag 2580
cacgtactcg gatggaagcc ggtcttgtcg atcaggatga tctggacgaa gagcatcagg 2640
ggctcgcgcc agccgaactg ttcgccaggc tcaaggcgcg catgcccgac ggcgaggatc 2700
tcgtcgtgac ccatggcgat gcctgcttgc cgaatatcat ggtggaaaat ggccgctttt 2760
ctggattcat cgactgtggc cggctgggtg tggcggaccg ctatcaggac atagcgttgg 2820
ctacccgtga tattgctgaa gagcttggcg gcgaatgggc tgaccgcttc ctcgtgcttt 2880
acggtatcgc cgctcccgat tcgcagcgca tcgccttcta tcgccttctt gacgagttct 2940
tctgagcggg actctggggt tcgaaatgac cgaccaagcg acgcccaacc tgccatcacg 3000
agatttcgat tccaccgccg ccttctatga aaggttgggc ttcggaatcg ttttccggga 3060
cgccggctgg atgatcctcc agcgcgggga tctcatgctg gagttcttcg cccaccccaa 3120
cttgtttatt gcagcttata atggttacaa ataaagcaat agcatcacaa atttcacaaa 3180
taaagcattt ttttcactgc attctagttg tggtttgtcc aaactcatca atgtatctta 3240
tcatgtctgt ataccgtcga cctctagcta gagcttggcg taatcatggt catagctgtt 3300
tcctgtgtga aattgttatc cgctcacaat tccacacaac atacgagccg gaagcataaa 3360
gtgtaaagcc tggggtgcct aatgagtgag ctaactcaca ttaattgcgt tgcgctcact 3420
gcccgctttc cagtcgggaa acctgtcgtg ccagctgcat taatgaatcg gccaacgcgc 3480
ggggagaggc ggtttgcgta ttgggcgctc ttccgcttcc tcgctcactg actcgctgcg 3540
ctcggtcgtt cggctgcggc gagcggtatc agctcactca aaggcggtaa tacggttatc 3600
cacagaatca ggggataacg caggaaagaa catgtgagca aaaggccagc aaaaggccag 3660
gaaccgtaaa aaggccgcgt tgctggcgtt tttccatagg ctccgccccc ctgacgagca 3720
tcacaaaaat cgacgctcaa gtcagaggtg gcgaaacccg acaggactat aaagatacca 3780
ggcgtttccc cctggaagct ccctcgtgcg ctctcctgtt ccgaccctgc cgcttaccgg 3840
atacctgtcc gcctttctcc cttcgggaag cgtggcgctt tctcaatgct cacgctgtag 3900
gtatctcagt tcggtgtagg tcgttcgctc caagctgggc tgtgtgcacg aaccccccgt 3960
tcagcccgac cgctgcgcct tatccggtaa ctatcgtctt gagtccaacc cggtaagaca 4020
cgacttatcg ccactggcag cagccactgg taacaggatt agcagagcga ggtatgtagg 4080
cggtgctaca gagttcttga agtggtggcc taactacggc tacactagaa ggacagtatt 4140
tggtatctgc gctctgctga agccagttac cttcggaaaa agagttggta gctcttgatc 4200
cggcaaacaa accaccgctg gtagcggtgg tttttttgtt tgcaagcagc agattacgcg 4260
cagaaaaaaa ggatctcaag aagatccttt gatcttttct acggggtctg acgctcagtg 4320
gaacgaaaac tcacgttaag ggattttggt catgagatta tcaaaaagga tcttcaccta 4380
gatcctttta aattaaaaat gaagttttaa atcaatctaa agtatatatg agtaaacttg 4440
gtctgacagt taccaatgct taatcagtga ggcacctatc tcagcgatct gtctatttcg 4500
ttcatccata gttgcctgac tccccgtcgt gtagataact acgatacggg agggcttacc 4560
atctggcccc agtgctgcaa tgataccgcg agacccacgc tcaccggctc cagatttatc 4620
agcaataaac cagccagccg gaagggccga gcgcagaagt ggtcctgcaa ctttatccgc 4680
ctccatccag tctattaatt gttgccggga agctagagta agtagttcgc cagttaatag 4740
tttgcgcaac gttgttgcca ttgctacagg catcgtggtg tcacgctcgt cgtttggtat 4800
ggcttcattc agctccggtt cccaacgatc aaggcgagtt acatgatccc ccatgttgtg 4860
caaaaaagcg gttagctcct tcggtcctcc gatcgttgtc agaagtaagt tggccgcagt 4920
gttatcactc atggttatgg cagcactgca taattctctt actgtcatgc catccgtaag 4980
atgcttttct gtgactggtg agtactcaac caagtcattc tgagaatagt gtatgcggcg 5040
accgagttgc tcttgcccgg cgtcaatacg ggataatacc gcgccacata gcagaacttt 5100
aaaagtgctc atcattggaa aacgttcttc ggggcgaaaa ctctcaagga tcttaccgct 5160
gttgagatcc agttcgatgt aacccactcg tgcacccaac tgatcttcag catcttttac 5220
tttcaccagc gtttctgggt gagcaaaaac aggaaggcaa aatgccgcaa aaaagggaat 5280
aagggcgaca cggaaatgtt gaatactcat actcttcctt tttcaatatt attgaagcat 5340
ttatcagggt tattgtctca tgagcggata catatttgaa tgtatttaga aaaataaaca 5400
aataggggtt ccgcgcacat ttccccgaaa agtgccacct gacgtc 5446

<210> SEQ ID NO 57
<211> LENGTH: 5428
<212> TYPE: DNA
<213> ORGANISM: Artificial Sequence
<220> FEATURE:
<223> OTHER INFORMATION: plasmid

<400> SEQUENCE: 57
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480

-continued

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc ctttcctaat aaaatgagga aattgcatcg   1140
cattgtctga gtaggtgtca ttctattctg gggggtgggg tggggcagga cagcaagggg   1200
gaggattggg aagacaatag caggcatgct ggggatgcgg tgggctctat ggcttctgag   1260
gcggaaagaa ccagctgggg ctctaggggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacggca cctcgacccc   1500
aaaaaacttg attagggtga tggttcacgt agtgggccat cgccctgata gacggttttt   1560
cgccctttga cgttggagtc cacgttcttt aatagtggac tcttgttcca aactggaaca   1620
acactcaacc ctatctcggt ctattctttt gatttataag ggattttgcc gatttcggcc   1680
tattggttaa aaaatgagct gatttaacaa aaatttaacg cgaattaatt ctgtggaatg   1740
tgtgtcagtt agggtgtgga aagtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agagacagga tgaggatcgt ttcgcatgat tgaacaagat ggattgcacg   2160
caggttctcc ggccgcttgg gtggagaggc tattcggcta tgactgggca caacagacaa   2220
tcggctgctc tgatgccgcc gtgttccggc tgtcagcgca ggggcgcccg gttctttttg   2280
tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
gggactggct gctattgggc gaagtgccgg ggcaggatct cctgtcatct caccttgctc   2460
ctgccgagaa agtatccatc atggctgatg caatgcggcg gctgcatacg cttgatccgg   2520
ctacctgccc attcgaccac caagcgaaac atcgcatcga gcgagcacgt actcggatgg   2580
aagccggtct tgtcgatcag gatgatctgg acgaagagca tcaggggctc gcgccagccg   2640
aactgttcgc caggctcaag gcgcgcatgc ccgacggcga ggatctcgtc gtgacccatg   2700
gcgatgcctg cttgccgaat atcatggtgg aaaatggccg cttttctgga ttcatcgact   2760
gtggccggct gggtgtggcg gaccgctatc aggacatagc gttggctacc cgtgatattg   2820
ctgaagagct tggcggcgaa tggctgaccg cttcctcgt gctttacggt atcgccgctc   2880
```

ccgattcgca gcgcatcgcc ttctatcgcc ttcttgacga gttcttctga gcgggactct 2940
ggggttcgaa atgaccgacc aagcgacgcc caacctgcca tcacgagatt tcgattccac 3000
cgccgccttc tatgaaaggt tgggcttcgg aatcgttttc cgggacgccg gctggatgat 3060
cctccagcgc ggggatctca tgctggagtt cttcgcccac cccaacttgt ttattgcagc 3120
ttataatggt tacaaataaa gcaatagcat cacaaatttc acaaataaag catttttttc 3180
actgcattct agttgtggtt tgtccaaact catcaatgta tcttatcatg tctgtatacc 3240
gtcgacctct agctagagct tggcgtaatc atggtcatag ctgtttcctg tgtgaaattg 3300
ttatccgctc acaattccac acaacatacg agccggaagc ataaagtgta aagcctgggg 3360
tgcctaatga gtgagctaac tcacattaat tgcgttgcgc tcactgcccg ctttccagtc 3420
gggaaacctg tcgtgccagc tgcattaatg aatcggccaa cgcgcgggga gaggcggttt 3480
gcgtattggg cgctcttccg cttcctcgct cactgactcg ctgcgctcgg tcgttcggct 3540
gcggcgagcg gtatcagctc actcaaaggc ggtaatacgg ttatccacag aatcagggga 3600
taacgcagga aagaacatgt gagcaaaagg ccagcaaaag gccaggaacc gtaaaaaggc 3660
cgcgttgctg gcgtttttcc ataggctccg cccccctgac gagcatcaca aaaatcgacg 3720
ctcaagtcag aggtggcgaa acccgacagg actataaaga taccaggcgt ttccccctgg 3780
aagctccctc gtgcgctctc ctgttccgac cctgccgctt accggatacc tgtccgcctt 3840
tctcccttcg ggaagcgtgg cgctttctca tagctcacgc tgtaggtatc tcagttcggt 3900
gtaggtcgtt cgctccaagc tgggctgtgt gcacgaaccc cccgttcagc ccgaccgctg 3960
cgccttatcc ggtaactatc gtcttgagtc caacccggta agacacgact tatcgccact 4020
ggcagcagcc actggtaaca ggattagcag agcgaggtat gtaggcggtg ctacagagtt 4080
cttgaagtgg tggcctaact acggctacac tagaagaaca gtatttggta tctgcgctct 4140
gctgaagcca gttaccttcg gaaaaagagt tggtagctct tgatccggca aacaaaccac 4200
cgctggtagc ggtttttttg tttgcaagca gcagattacg cgcagaaaaa aaggatctca 4260
agaagatcct ttgatctttt ctacggggtc tgacgctcag tggaacgaaa actcacgtta 4320
agggattttg gtcatgagat tatcaaaaag gatcttcacc tagatccttt taaattaaaa 4380
atgaagtttt aaatcaatct aaagtatata tgagtaaact tggtctgaca gttaccaatg 4440
cttaatcagt gaggcaccta tctcagcgat ctgtctattt cgttcatcca tagttgcctg 4500
actccccgtc gtgtagataa ctacgatacg ggagggctta ccatctggcc ccagtgctgc 4560
aatgataccg cgagacccac gctcaccggc tccagattta tcagcaataa accagccagc 4620
cggaagggcc gagcgcagaa gtggtcctgc aactttatcc gcctccatcc agtctattaa 4680
ttgttgccgg gaagctagag taagtagttc gccagttaat agtttgcgca acgttgttgc 4740
cattgctaca ggcatcgtgg tgtcacgctc gtcgtttggt atggcttcat tcagctccgg 4800
ttcccaacga tcaaggcgag ttacatgatc ccccatgttg tgcaaaaaag cggttagctc 4860
cttcggtcct ccgatcgttg tcagaagtaa gttggccgca gtgttatcac tcatggttat 4920
ggcagcactg cataattctc ttactgtcat gccatccgta agatgctttt ctgtgactgg 4980
tgagtactca accaagtcat tctgagaata gtgtatgcgg cgaccgagtt gctcttgccc 5040
ggcgtcaata cgggataata ccgcgccaca tagcagaact ttaaaagtgc tcatcattgg 5100
aaaacgttct tcggggcgaa aactctcaag gatcttaccg ctgttgagat ccagttcgat 5160
gtaacccact cgtgcaccca actgatcttc agcatctttt actttcacca gcgtttctgg 5220

```
gtgagcaaaa acaggaaggc aaaatgccgc aaaaaaggga ataagggcga cacggaaatg   5280

ttgaatactc atactcttcc tttttcaata ttattgaagc atttatcagg gttattgtct   5340

catgagcgga tacatatttg aatgtattta gaaaaataaa caaatagggg ttccgcgcac   5400

atttccccga aaagtgccac ctgacgtc                                      5428
```

<210> SEQ ID NO 58
<211> LENGTH: 5427
<212> TYPE: DNA
<213> ORGANISM: Artificial Sequence
<220> FEATURE:
<223> OTHER INFORMATION: plasmid

<400> SEQUENCE: 58

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaacgg gccctctaga ctcgagcggc cgccactgtg ctggatatct gcagaattcc    960

accacactgg actagtggat ccgagctcgg taccaagctt aagtttaaac cgctgatcag   1020

cctcgactgt gccttctagt tgccagccat ctgttgtttg cccctccccc gtgccttcct   1080

tgaccctgga aggtgccact cccactgtcc tttcctaata aaatgaggaa attgcatcgc   1140

attgtctgag taggtgtcat tctattctgg ggggtggggt ggggcaggac agcaaggggg   1200

aggattggga agacaatagc aggcatgctg gggatgcggt gggctctatg gcttctgagg   1260

cggaaagaac cagctggggc tctagggggt atccccacgc gccctgtagc ggcgcattaa   1320

gcgcggcggg tgtggtggtt acgcgcagcg tgaccgctac acttgccagc gccctagcgc   1380

ccgctccttt cgctttcttc ccttcctttc tcgccacgtt cgccggcttt ccccgtcaag   1440

ctctaaatcg ggggctccct ttagggttcc gatttagtgc tttacggcac ctcgacccca   1500

aaaaacttga ttagggtgat ggttcacgta gtgggccatc gccctgatag acggtttttc   1560

gccctttgac gttggagtcc acgttcttta atagtggact cttgttccaa actggaacaa   1620

cactcaaccc tatctcggtc tattcttttg atttataagg gattttgccg atttcggcct   1680

attggttaaa aaatgagctg atttaacaaa aatttaacgc gaattaattc tgtggaatgt   1740

gtgtcagtta gggtgtggaa agtccccagg ctccccagca ggcagaagta tgcaaagcat   1800

gcatctcaat tagtcagcaa ccaggtgtgg aaagtcccca ggctccccag caggcagaag   1860
```

```
tatgcaaagc atgcatctca attagtcagc aaccatagtc ccgcccctaa ctccgcccat   1920
cccgccccta actccgccca gttccgccca ttctccgccc catggctgac taattttttt   1980
tatttatgca gaggccgagg ccgcctctgc ctctgagcta ttccagaagt agtgaggagg   2040
cttttttgga ggcctaggct tttgcaaaaa gctcccggga gcttgtatat ccattttcgg   2100
atctgatcaa gagacaggat gaggatcgtt tcgcatgatt gaacaagatg gattgcacgc   2160
aggttctccg gccgcttggg tggagaggct attcggctat gactgggcac aacagacaat   2220
cggctgctct gatgccgccg tgttccggct gtcagcgcag gggcgcccgg ttctttttgt   2280
caagaccgac ctgtccggtg ccctgaatga actgcaggac gaggcagcgc ggctatcgtg   2340
gctggccacg acgggcgttc cttgcgcagc tgtgctcgac gttgtcactg aagcgggaag   2400
ggactggctg ctattgggcg aagtgccggg gcaggatctc ctgtcatctc accttgctcc   2460
tgccgagaaa gtatccatca tggctgatgc aatgcggcgg ctgcatacgc ttgatccggc   2520
tacctgccca ttcgaccacc aagcgaaaca tcgcatcgag cgagcacgta ctcggatgga   2580
agccggtctt gtcgatcagg atgatctgga cgaagagcat caggggctcg cgccagccga   2640
actgttcgcc aggctcaagg cgcgcatgcc cgacggcgag gatctcgtcg tgacccatgg   2700
cgatgcctgc ttgccgaata tcatggtgga aaatggccgc ttttctggat tcatcgactg   2760
tggccggctg ggtgtggcgg accgctatca ggacatagcg ttggctaccc gtgatattgc   2820
tgaagagctt ggcggcgaat gggctgaccg cttcctcgtg ctttacggta tcgccgctcc   2880
cgattcgcag cgcatcgcct tctatcgcct tcttgacgag ttcttctgag cgggactctg   2940
gggttcgaaa tgaccgacca agcgacgccc aacctgccat cacgagattt cgattccacc   3000
gccgccttct atgaaaggtt gggcttcgga atcgttttcc gggacgccgg ctggatgatc   3060
ctccagcgcg gggatctcat gctggagttc ttcgcccacc ccaacttgtt tattgcagct   3120
tataatggtt acaaataaag caatagcatc acaaatttca caaataaagc atttttttca   3180
ctgcattcta gttgtggttt gtccaaactc atcaatgtat cttatcatgt ctgtataccg   3240
tcgacctcta gctagagctt ggcgtaatca tggtcatagc tgtttcctgt gtgaaattgt   3300
tatccgctca caattccaca caacatacga gccggaagca taaagtgtaa agcctggggt   3360
gcctaatgag tgagctaact cacattaatt gcgttgcgct cactgcccgc tttccagtcg   3420
ggaaacctgt cgtgccagct gcattaatga atcggccaac gcgcggggag aggcggtttg   3480
cgtattgggc gctcttccgc ttcctcgctc actgactcgc tgcgctcggt cgttcggctg   3540
cggcgagcgg tatcagctca ctcaaaggcg gtaatacggt tatccacaga atcaggggat   3600
aacgcaggaa agaacatgtg agcaaaaggc cagcaaaagg ccaggaaccg taaaaaggcc   3660
gcgttgctgg cgtttttcca taggctccgc ccccctgacg agcatcacaa aaatcgacgc   3720
tcaagtcaga ggtggcgaaa cccgacagga ctataaagat accaggcgtt tccccctgga   3780
agctccctcg tgcgctctcc tgttccgacc ctgccgctta ccggatacct gtccgccttt   3840
ctcccttcgg gaagcgtggc gctttctcat agctcacgct gtaggtatct cagttcggtg   3900
taggtcgttc gctccaagct gggctgtgtg cacgaacccc ccgttcagcc cgaccgctgc   3960
gccttatccg gtaactatcg tcttgagtcc aacccggtaa gacacgactt atcgccactg   4020
gcagcagcca ctggtaacag gattagcaga gcgaggtatg taggcggtgc tacagagttc   4080
ttgaagtggt ggcctaacta cggctacact agaagaacag tatttggtat ctgcgctctg   4140
ctgaagccag ttaccttcgg aaaaagagtt ggtagctctt gatccggcaa acaaaccacc   4200
```

```
gctggtagcg gtttttttgt ttgcaagcag cagattacgc gcagaaaaaa aggatctcaa   4260
gaagatcctt tgatcttttc tacggggtct gacgctcagt ggaacgaaaa ctcacgttaa   4320
gggattttgg tcatgagatt atcaaaaagg atcttcacct agatcctttt aaattaaaaa   4380
tgaagtttta aatcaatcta aagtatatat gagtaaactt ggtctgacag ttaccaatgc   4440
ttaatcagtg aggcacctat ctcagcgatc tgtctatttc gttcatccat agttgcctga   4500
ctccccgtcg tgtagataac tacgatacgg gagggcttac catctggccc cagtgctgca   4560
atgataccgc gagacccacg ctcaccggct ccagatttat cagcaataaa ccagccagcc   4620
ggaagggccg agcgcagaag tggtcctgca actttatccg cctccatcca gtctattaat   4680
tgttgccggg aagctagagt aagtagttcg ccagttaata gtttgcgcaa cgttgttgcc   4740
attgctacag gcatcgtggt gtcacgctcg tcgtttggta tggcttcatt cagctccggt   4800
tcccaacgat caaggcgagt tacatgatcc cccatgttgt gcaaaaaagc ggttagctcc   4860
ttcggtcctc cgatcgttgt cagaagtaag ttggccgcag tgttatcact catggttatg   4920
gcagcactgc ataattctct tactgtcatg ccatccgtaa gatgcttttc tgtgactggt   4980
gagtactcaa ccaagtcatt ctgagaatag tgtatgcggc gaccgagttg ctcttgcccg   5040
gcgtcaatac gggataatac cgcgccacat agcagaactt taaaagtgct catcattgga   5100
aaacgttctt cggggcgaaa actctcaagg atcttaccgc tgttgagatc cagttcgatg   5160
taacccactc gtgcacccaa ctgatcttca gcatctttta ctttcaccag cgtttctggg   5220
tgagcaaaaa caggaaggca aaatgccgca aaaaagggaa taagggcgac acggaaatgt   5280
tgaatactca tactcttcct ttttcaatat tattgaagca tttatcaggg ttattgtctc   5340
atgagcggat acatatttga atgtatttag aaaaataaac aaataggggt tccgcgcaca   5400
tttccccgaa aagtgccacc tgacgtc                                       5427
```

<210> SEQ ID NO 59
<211> LENGTH: 4818
<212> TYPE: DNA
<213> ORGANISM: Artificial Sequence
<220> FEATURE:
<223> OTHER INFORMATION: plasmid

<400> SEQUENCE: 59

```
ggtaccgagc tcttacgcgt gctagcccgg gctcgagatc tgcgatctaa gtaagcttgg     60
cattccggta ctgttggtaa agccaccatg gaagacgcca aaaacataaa gaaaggcccg    120
gcgccattct atccgctgga agatggaacc gctggagagc aactgcataa ggctatgaag    180
agatacgccc tggttcctgg aacaattgct tttacagatg cacatatcga ggtggacatc    240
acttacgctg agtacttcga aatgtccgtt cggttggcag aagctatgaa acgatatggg    300
ctgaatacaa atcacagaat cgtcgtatgc agtgaaaact ctcttcaatt ctttatgccg    360
gtgttgggcg cgttatttat cggagttgca gttgcgcccg cgaacgacat ttataatgaa    420
cgtgaattgc tcaacagtat gggcatttcg cagcctaccg tggtgttcgt ttccaaaaag    480
gggttgcaaa aaattttgaa cgtgcaaaaa aagctcccaa tcatccaaaa aattattatc    540
atggattcta aaacggatta ccagggattt cagtcgatgt acacgttcgt cacatctcat    600
ctacctcccg gttttaatga atacgatttt gtgccagagt ccttcgatag ggacaagaca    660
attgcactga tcatgaactc ctctggatct actggtctgc ctaaaggtgt cgctctgcct    720
catagaactg cctgcgtgag attctcgcat gccagagatc ctatttttgg caatcaaatc    780
attccggata ctgcgatttt aagtgttgtt ccattccatc acggttttgg aatgtttact    840
```

-continued

```
acactcggat atttgatatg tggatttcga gtcgtcttaa tgtatagatt tgaagaagag    900
ctgtttctga ggagccttca ggattacaag attcaaagtg cgctgctggt gccaacccta    960
ttctccttct tcgccaaaag cactctgatt gacaaatacg atttatctaa tttacacgaa   1020
attgcttctg gtggcgctcc cctctctaag gaagtcgggg aagcggttgc caagaggttc   1080
catctgccag gtatcaggca aggatatggg ctcactgaga ctacatcagc tattctgatt   1140
acacccgagg gggatgataa accgggcgcg gtcggtaaag ttgttccatt ttttgaagcg   1200
aaggttgtgg atctggatac cgggaaaacg ctgggcgtta atcaaagagg cgaactgtgt   1260
gtgagaggtc ctatgattat gtccggttat gtaaacaatc cggaagcgac caacgccttg   1320
attgacaagg atggatggct acattctgga gacatagctt actgggacga agacgaacac   1380
ttcttcatcg ttgaccgcct gaagtctctg attaagtaca aaggctatca ggtggctccc   1440
gctgaattgg aatccatctt gctccaacac cccaacatct tcgacgcagg tgtcgcaggt   1500
cttcccgacg atgacgccgg tgaacttccc gccgccgttg ttgttttgga gcacggaaag   1560
acgatgacgg aaaaagagat cgtggattac gtcgccagtc aagtaacaac cgcgaaaaag   1620
ttgcgcggag gagttgtgtt tgtggacgaa gtaccgaaag gtcttaccgg aaaactcgac   1680
gcaagaaaaa tcagagagat cctcataaag gccaagaagg gcggaaagat cgccgtgtaa   1740
ttctagagtc ggggcggccg gccgcttcga gcagacatga taagatacat tgatgagttt   1800
ggacaaacca caactagaat gcagtgaaaa aaatgcttta tttgtgaaat ttgtgatgct   1860
attgctttat ttgtaaccat tataagctgc aataaacaag ttaacaacaa caattgcatt   1920
cattttatgt ttcaggttca gggggaggtg tgggaggttt tttaaagcaa gtaaaacctc   1980
tacaaatgtg gtaaaatcga taaggatccg tcgaccgatg cccttgagag ccttcaaccc   2040
agtcagctcc ttccggtggg cgcggggcat gactatcgtc gccgcactta tgactgtctt   2100
ctttatcatg caactcgtag gacaggtgcc ggcagcgctc ttccgcttcc tcgctcactg   2160
actcgctgcg ctcggtcgtt cggctgcggc gagcggtatc agctcactca aaggcggtaa   2220
tacggttatc cacagaatca ggggataacg caggaaagaa catgtgagca aaaggccagc   2280
aaaaggccag gaaccgtaaa aaggccgcgt tgctggcgtt tttccatagg ctccgccccc   2340
ctgacgagca tcacaaaaat cgacgctcaa gtcagaggtg gcgaaacccg acaggactat   2400
aaagatacca ggcgtttccc cctggaagct ccctcgtgcg ctctcctgtt ccgaccctgc   2460
cgcttaccgg atacctgtcc gcctttctcc cttcgggaag cgtggcgctt tctcaatgct   2520
cacgctgtag gtatctcagt tcggtgtagg tcgttcgctc caagctgggc tgtgtgcacg   2580
aaccccccgt tcagcccgac cgctgcgcct tatccggtaa ctatcgtctt gagtccaacc   2640
cggtaagaca cgacttatcg ccactggcag cagccactgg taacaggatt agcagagcga   2700
ggtatgtagg cggtgctaca gagttcttga agtggtggcc taactacggc tacactagaa   2760
ggacagtatt tggtatctgc gctctgctga agccagttac cttcggaaaa agagttggta   2820
gctcttgatc cggcaaacaa accaccgctg gtagcggtgg tttttttgtt tgcaagcagc   2880
agattacgcg cagaaaaaaa ggatctcaag aagatccttt gatcttttct acggggtctg   2940
acgctcagtg gaacgaaaac tcacgttaag ggattttggt catgagatta tcaaaaagga   3000
tcttcaccta gatcctttta aattaaaaat gaagttttaa atcaatctaa agtatatatg   3060
agtaaacttg gtctgacagt taccaatgct taatcagtga ggcacctatc tcagcgatct   3120
gtctatttcg ttcatccata gttgcctgac tccccgtcgt gtagataact acgatacggg   3180
```

```
agggcttacc atctggcccc agtgctgcaa tgataccgcg agacccacgc tcaccggctc   3240
cagatttatc agcaataaac cagccagccg gaagggccga gcgcagaagt ggtcctgcaa   3300
ctttatccgc ctccatccag tctattaatt gttgccggga agctagagta agtagttcgc   3360
cagttaatag tttgcgcaac gttgttgcca ttgctacagg catcgtggtg tcacgctcgt   3420
cgtttggtat ggcttcattc agctccggtt cccaacgatc aaggcgagtt acatgatccc   3480
ccatgttgtg caaaaaagcg gttagctcct tcggtcctcc gatcgttgtc agaagtaagt   3540
tggccgcagt gttatcactc atggttatgg cagcactgca taattctctt actgtcatgc   3600
catccgtaag atgcttttct gtgactggtg agtactcaac caagtcattc tgagaatagt   3660
gtatgcggcg accgagttgc tcttgcccgg cgtcaatacg ggataatacc gcgccacata   3720
gcagaacttt aaaagtgctc atcattggaa aacgttcttc ggggcgaaaa ctctcaagga   3780
tcttaccgct gttgagatcc agttcgatgt aacccactcg tgcacccaac tgatcttcag   3840
catcttttac tttcaccagc gtttctgggt gagcaaaaac aggaaggcaa aatgccgcaa   3900
aaaagggaat aagggcgaca cggaaatgtt gaatactcat actcttcctt tttcaatatt   3960
attgaagcat ttatcagggt tattgtctca tgagcggata catatttgaa tgtatttaga   4020
aaaataaaca aataggggtt ccgcgcacat ttccccgaaa agtgccacct gacgcgccct   4080
gtagcggcgc attaagcgcg gcgggtgtgg tggttacgcg cagcgtgacc gctacacttg   4140
ccagcgccct agcgcccgct cctttcgctt tcttcccttc ctttctcgcc acgttcgccg   4200
gctttccccg tcaagctcta aatcgggggc tccctttagg gttccgattt agtgctttac   4260
ggcacctcga ccccaaaaaa cttgattagg gtgatggttc acgtagtggg ccatcgccct   4320
gatagacggt ttttcgccct ttgacgttgg agtccacgtt ctttaatagt ggactcttgt   4380
tccaaactgg aacaacactc aaccctatct cggtctattc ttttgattta taagggattt   4440
tgccgatttc ggcctattgg ttaaaaaatg agctgattta acaaaaattt aacgcgaatt   4500
ttaacaaaat attaacgttt acaatttccc attcgccatt caggctgcgc aactgttggg   4560
aagggcgatc ggtgcgggcc tcttcgctat tacgccagcc caagctacca tgataagtaa   4620
gtaatattaa ggtacgggag gtacttggag cggccgcaat aaaatatctt tattttcatt   4680
acatctgtgt gttggttttt tgtgtgaatc gatagtacta acatacgctc tccatcaaaa   4740
caaaacgaaa caaaacaaac tagcaaaata ggctgtcccc agtgcaagtg caggtgccag   4800
aacatttctc tatcgata                                                 4818
```

<210> SEQ ID NO 60
<211> LENGTH: 3451
<212> TYPE: DNA
<213> ORGANISM: Artificial Sequence
<220> FEATURE:
<223> OTHER INFORMATION: plasmid

<400> SEQUENCE: 60

```
ggatccgctg tggaatgtgt gtcagttagg gtgtggaaag tccccaggct ccccagcagg     60
cagaagtatg caaagcatgc atctcaatta gtcagcaacc aggtgtggaa agtccccagg    120
ctccccagca ggcagaagta tgcaaagcat gcatctcaat tagtcagcaa ccatagtccc    180
gcccctaact ccgcccatcc cgcccctaac tccgcccagt tccgcccatt ctccgcccca    240
tggctgacta atttttttta tttatgcaga ggccgaggcc gcctcggcct ctgagctatt    300
ccagaagtag tgaggaggct tttttggagg cctaggcttt tgcaaaaagc ttattaaccc    360
tcactaaagg gagtactagt accggtacct cgagaattcg aacgcgtgat cagctgttct    420
```

-continued

```
atagtgtcac ctaaatagct tcgaggtcga cctcgaaact tgtttattgc agcttataat    480
ggttacaaat aaagcaatag catcacaaat ttcacaaata aagcattttt ttcactgcat    540
tctagttgtg gtttgtccaa actcatcaat gtatcttatc atgtctggat ccctcggaga    600
tctgggccca tgcggccgcg gatcgatgct cactcaaagg cggtaatacg gttatccaca    660
gaatcagggg ataacgcagg aaagaacatg tgagcaaaag gccagcaaaa ggccaggaac    720
cgtaaaaagg ccgcgttgct ggcgtttttc cataggctcc gcccccctga cgagcatcac    780
aaaaatcgac gctcaagtca gaggtggcga aacccgacag gactataaag ataccaggcg    840
tttccccctg gaagctccct cgtgcgctct cctgttccga ccctgccgct taccggatac    900
ctgtccgcct ttctcccttc gggaagcgtg gcgctttctc aatgctcacg ctgtaggtat    960
ctcagttcgg tgtaggtcgt tcgctccaag ctgggctgtg tgcacgaacc ccccgttcag   1020
cccgaccgct gcgccttatc cggtaactat cgtcttgagt ccaacccggt aagacacgac   1080
ttatcgccac tggcagcagc cactggtaac aggattagca gagcgaggta tgtaggcggt   1140
gctacagagt tcttgaagtg gtggcctaac tacggctaca ctagaaggac agtatttggt   1200
atctgcgctc tgctgaagcc agttaccttc ggaaaaagag ttggtagctc ttgatccggc   1260
aaacaaacca ccgctggtag cggtggtttt tttgtttgca agcagcagat tacgcgcaga   1320
aaaaaaggat ctcaagaaga tcctttgatc ttttctacgg ggtctgacgc tcagtggaac   1380
gaaaactcac gttaagggat tttggtcatg acattaacct ataaaaatag gcgtatcacg   1440
aggccctttc gtctcgcgcg tttcggtgat gacggtgaaa acctctgaca catgcagctc   1500
ccggagacgg tcacagcttg tctgtaagcg gatgccggga gcagacaagc ccgtcagggc   1560
gcgtcagcgg gtgttggcgg gtgtcggggc tggcttaact atgcggcatc agagcagatt   1620
gtactgagag tgcaccatat gcggtgtgaa ataccgcaca gatgcgtaag gagaaaatac   1680
cgcatcaggc gacgcgccct gtagcggcgc attaagcgcg gcgggtgtgg tggttacgcg   1740
cagcgtgacc gctacacttg ccagcgccct agcgcccgct cctttcgctt tcttcccttc   1800
ctttctcgcc acgttcgccg gctttccccg tcaagctcta aatcgggggc tccctttagg   1860
gttccgattt agagctttac ggcacctcga ccgcaaaaaa cttgatttgg gtgatggttc   1920
acgtagtggg ccatcgccct gatagacggt ttttcgccct ttgacgttgg agtccacgtt   1980
ctttaatagt ggactcttgt tccaaactgg aacaacactc aaccctatct cggtctattc   2040
ttttgattta taagggattt tgccgatttc ggcctattgg ttaaaaaatg agctgattta   2100
acaaatattt aacgcgaatt ttaacaaaat attaacgttt acaatttcca ttcgccattc   2160
aggctgcaac tagatctaga gtccgttaca taacttacgg taaatggccc gcctggctga   2220
ccgcccaacg acccccgccc attgacgtca ataatgacgt atgttcccat agtaacgcca   2280
atagggactt tccattgacg tcaatgggtg gagtatttac ggtaaactgc ccacttggca   2340
gtacatcaag tgtatcatat gccaagtacg ccccctattg acgtcaatga cggtaaatgg   2400
cccgcctggc attatgccca gtacatgacc ttatgggact ttcctacttg gcagtacatc   2460
tacgtattag tcatcgctat taccatggtg atgcggtttt ggcagtacat caatgggcgt   2520
ggatagcggt ttgactcacg gggatttcca agtctccacc ccattgacgt caatgggagt   2580
ttgttttggc accaaaatca acgggacttt ccaaaatgtc gtaacaactc cgccccattg   2640
acgcaaatgg gcggtaggcg tgtacggtgg gaggtctata taagcagagc tcgtttagtg   2700
aaccgtcaga tcgcctggag acgccatcca cgctgttttg acctccatag aagacaccgg   2760
```

-continued

```
gaccgatcca gcctccgcgg ccgggaacgg tgcattggaa cggacctgca gcacgtgttg   2820

acaattaatc atcggcatag tatatcggca tagtataata cgactcacta taggagggcc   2880

accatggcca agttgaccag tgccgttccg gtgctcaccg cgcgcgacgt cgccggagcg   2940

gtcgagttct ggaccgaccg gctcgggttc tcccgggact tcgtggagga cgacttcgcc   3000

ggtgtggtcc gggacgacgt gaccctgttc atcagcgcgg tccaggacca ggtggtgccg   3060

gacaacaccc tggcctgggt gtgggtgcgc ggcctggacg agctgtacgc cgagtggtcg   3120

gaggtcgtgt ccacgaactt ccgggacgcc tccgggccgg ccatgaccga gatcggcgag   3180

cagccgtggg ggcgggagtt cgccctgcgc gacccggccg gcaactgcgt gcacttcgtg   3240

gccgaggagc aggactgacc gacgccgacc aacaccgccg gtccgacggc ggcccacggg   3300

tcccaggggg gtcgacctcg aaacttgttt attgcagctt ataatggtta caaataaagc   3360

aatagcatca caaatttcac aaataaagca tttttttcac tgcattctag ttgtggtttg   3420

tccaaactca tcaatgtatc ttatcatgtc t                                 3451
```

<210> SEQ ID NO 61
<211> LENGTH: 5163
<212> TYPE: DNA
<213> ORGANISM: Artificial Sequence
<220> FEATURE:
<223> OTHER INFORMATION: plasmid

<400> SEQUENCE: 61

```
gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggac tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

caccatggag acagacacac tcctgctatg ggtactgctg ctctgggttc caggttccac    960

tggtgacgcg gcccagccgg ccaggcgcgc gcgccgtacg aagcttggta ccgagctcgg   1020

atccactcca gtgtggtgga attctgcaga tatccagcac agtggcggcc gctcgaggag   1080

ggcccgaaca aaaactcatc tcagaagagg atctgaatag cgccgtcgac catcatcatc   1140

atcatcattg agtttaaacc cgctgatcag cctcgactgt gccttctagt tgccagccat   1200

ctgttgtttg cccctccccc gtgccttcct tgaccctgga aggtgccact cccactgtcc   1260

tttcctaata aaatgaggaa attgcatcgc attgtctgag taggtgtcat tctattctgg   1320

ggggtggggt ggggcaggac agcaaggggg aggattggga agacaatagc aggcatgctg   1380
```

```
gggatgcggt gggctctatg gcttctgagg cggaaagaac cagctggggc tctagggggt   1440
atccccacgc gccctgtagc ggcgcattaa gcgcggcggg tgtggtggtt acgcgcagcg   1500
tgaccgctac acttgccagc gccctagcgc ccgctccttt cgctttcttc ccttcctttc   1560
tcgccacgtt cgccggcttt ccccgtcaag ctctaaatcg ggcatccct ttagggttcc   1620
gatttagtgc tttacggcac ctcgacccca aaaaacttga ttagggtgat ggttcacgta   1680
gtgggccatc gccctgatag acggtttttc gccctttgac gttggagtcc acgttcttta   1740
atagtggact cttgttccaa actggaacaa cactcaaccc tatctcggtc tattcttttg   1800
atttataagg gattttgggg atttcggcct attggttaaa aaatgagctg atttaacaaa   1860
aatttaacgc gaattaattc tgtggaatgt gtgtcagtta gggtgtggaa agtccccagg   1920
ctccccagca ggcagaagta tgcaaagcat gcatctcaat tagtcagcaa ccaggtgtgg   1980
aaagtcccca ggctccccag caggcagaag tatgcaaagc atgcatctca attagtcagc   2040
aaccatagtc ccgcccctaa ctccgcccat cccgccccta actccgccca gttccgccca   2100
ttctccgccc catggctgac taattttttt tatttatgca gaggccgagg ccgcctctgc   2160
ctctgagcta ttccagaagt agtgaggagg cttttttgga ggcctaggct tttgcaaaaa   2220
gctcccggga gcttgtatat ccattttcgg atctgatcag cacgtgttga caattaatca   2280
tcggcatagt atatcggcat agtataatac gacaaggtga ggaactaaac catggccaag   2340
ttgaccagtg ccgttccggt gctcaccgcg cgcgacgtcg ccggagcggt cgagttctgg   2400
accgaccggc tcgggttctc ccgggacttc gtggaggacg acttcgccgg tgtggtccgg   2460
gacgacgtga ccctgttcat cagcgcggtc caggaccagg tggtgccgga caacaccctg   2520
gcctgggtgt gggtgcgcgg cctggacgag ctgtacgccg agtggtcgga ggtcgtgtcc   2580
acgaacttcc gggacgcctc cgggccggcc atgaccgaga tcggcgagca gccgtggggg   2640
cgggagttcg ccctgcgcga cccggccggc aactgcgtgc acttcgtggc cgaggagcag   2700
gactgacacg tgctacgaga tttcgattcc accgccgcct tctatgaaag gttgggcttc   2760
ggaatcgttt tccgggacgc cggctggatg atcctccagc gcggggatct catgctggag   2820
ttcttcgccc accccaactt gtttattgca gcttataatg gttacaaata aagcaatagc   2880
atcacaaatt tcacaaataa agcatttttt tcactgcatt ctagttgtgg tttgtccaaa   2940
ctcatcaatg tatcttatca tgtctgtata ccgtcgacct ctagctagag cttggcgtaa   3000
tcatggtcat agctgtttcc tgtgtgaaat tgttatccgc tcacaattcc acacaacata   3060
cgagccggaa gcataaagtg taaagcctgg ggtgcctaat gagtgagcta actcacatta   3120
attgcgttgc gctcactgcc cgctttccag tcgggaaacc tgtcgtgcca gctgcattaa   3180
tgaatcggcc aacgcgcggg gagaggcggt ttgcgtattg ggcgctcttc cgcttcctcg   3240
ctcactgact cgctgcgctc ggtcgttcgg ctgcggcgag cggtatcagc tcactcaaag   3300
gcggtaatac ggttatccac agaatcaggg gataacgcag gaaagaacat gtgagcaaaa   3360
ggccagcaaa aggccaggaa ccgtaaaaag gccgcgttgc tggcgttttt ccataggctc   3420
cgcccccctg acgagcatca caaaaatcga cgctcaagtc agaggtggcg aaacccgaca   3480
ggactataaa gataccaggc gtttccccct ggaagctccc tcgtgcgctc tcctgttccg   3540
accctgccgc ttaccggata cctgtccgcc tttctccctt cgggaagcgt ggcgctttct   3600
caatgctcac gctgtaggta tctcagttcg gtgtaggtcg ttcgctccaa gctgggctgt   3660
gtgcacgaac cccccgttca gcccgaccgc tgcgccttat ccggtaacta tcgtcttgag   3720
```

```
tccaacccgg taagacacga cttatcgcca ctggcagcag ccactggtaa caggattagc   3780

agagcgaggt atgtaggcgg tgctacagag ttcttgaagt ggtggcctaa ctacggctac   3840

actagaagga cagtatttgg tatctgcgct ctgctgaagc cagttacctt cggaaaaaga   3900

gttggtagct cttgatccgg caaacaaacc accgctggta gcggtggttt ttttgtttgc   3960

aagcagcaga ttacgcgcag aaaaaaagga tctcaagaag atcctttgat cttttctacg   4020

gggtctgacg ctcagtggaa cgaaaactca cgttaaggga ttttggtcat gagattatca   4080

aaaaggatct tcacctagat ccttttaaat taaaaatgaa gttttaaatc aatctaaagt   4140

atatatgagt aaacttggtc tgacagttac caatgcttaa tcagtgaggc acctatctca   4200

gcgatctgtc tatttcgttc atccatagtt gcctgactcc ccgtcgtgta gataactacg   4260

atacgggagg gcttaccatc tggccccagt gctgcaatga taccgcgaga cccacgctca   4320

ccggctccag atttatcagc aataaaccag ccagccggaa gggccgagcg cagaagtggt   4380

cctgcaactt tatccgcctc catccagtct attaattgtt gccgggaagc tagagtaagt   4440

agttcgccag ttaatagttt gcgcaacgtt gttgccattg ctacaggcat cgtggtgtca   4500

cgctcgtcgt ttggtatggc ttcattcagc tccggttccc aacgatcaag gcgagttaca   4560

tgatccccca tgttgtgcaa aaaagcggtt agctccttcg gtcctccgat cgttgtcaga   4620

agtaagttgg ccgcagtgtt atcactcatg gttatggcag cactgcataa ttctcttact   4680

gtcatgccat ccgtaagatg cttttctgtg actggtgagt actcaaccaa gtcattctga   4740

gaatagtgta tgcggcgacc gagttgctct tgcccggcgt caatacggga taataccgcg   4800

ccacatagca gaactttaaa agtgctcatc attggaaaac gttcttcggg gcgaaaactc   4860

tcaaggatct taccgctgtt gagatccagt tcgatgtaac ccactcgtgc acccaactga   4920

tcttcagcat cttttacttt caccagcgtt tctgggtgag caaaaacagg aaggcaaaat   4980

gccgcaaaaa agggaataag ggcgacacgg aaatgttgaa tactcatact cttccttttt   5040

caatattatt gaagcattta tcagggttat tgtctcatga gcggatacat atttgaatgt   5100

atttagaaaa ataaacaaat aggggttccg cgcacatttc cccgaaaagt gccacctgac   5160

gtc                                                                 5163
```

<210> SEQ ID NO 62
<211> LENGTH: 5325
<212> TYPE: DNA
<213> ORGANISM: Artificial Sequence
<220> FEATURE:
<223> OTHER INFORMATION: plasmid

<400> SEQUENCE: 62

```
gcgcgcgttg acattgatta ttgactagtt attaatagta atcaattacg gggtcattag     60

ttcatagccc atatatggag ttccgcgtta cataacttac ggtaaatggc ccgcctggct    120

gaccgcccaa cgacccccgc ccattgacgt caataatgac gtatgttccc atagtaacgc    180

caatagggac tttccattga cgtcaatggg tggactattt acggtaaact gcccacttgg    240

cagtacatca agtgtatcat atgccaagta cgccccctat tgacgtcaat gacggtaaat    300

ggcccgcctg gcattatgcc cagtacatga ccttatggga ctttcctact tggcagtaca    360

tctacgtatt agtcatcgct attaccatgg tgatgcggtt ttggcagtac atcaatgggc    420

gtggatagcg gtttgactca cggggatttc caagtctcca ccccattgac gtcaatggga    480

gtttgttttg gcaccaaaat caacgggact ttccaaaatg tcgtaacaac tccgccccat    540

tgacgcaaat gggcggtagg cgtgtacggt gggaggtcta tataagcaga gctctctggc    600
```

-continued

```
taactagaga acccactgct tactggctta tcgaaattaa tacgactcac tatagggaga    660
cccaagcttg gtaccgagct cggatccact agtaacggcc gccagtgtgc tggaattcgg    720
cttggggata tccaccatgg agacagacac actcctgcta tgggtactgc tgctctgggt    780
tccaggttcc actggtgact atccatatga tgttccagat tatgctgggg cccagccggc    840
cagatctccc gggatccgcg gctgcaggtc gacgaacaaa aactcatctc agaagaggat    900
ctgaatgctg tgggccagga cacgcaggag gtcatcgtgg tgccacactc cttgcccttt    960
aaggtggtgg tgatctcagc catcctggcc ctggtggtgc tcaccatcat ctcccttatc   1020
atcctcatca tgctttggca gaagaagcca cgttaggcgg ccgctcgaga tcagcctcga   1080
ctgtgccttc tagttgccag ccatctgttg tttgcccctc ccccgtgcct tccttgaccc   1140
tggaaggtgc cactcccact gtcctttcct aataaaatga ggaaattgca tcgcattgtc   1200
tgagtaggtg tcattctatt ctggggggtg gggtggggca ggacagcaag ggggaggatt   1260
gggaagacaa tagcaggcat gctggggatg cggtgggctc tatggcttct gaggcggaaa   1320
gaaccagtgg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gcccccctga cgagcatcac aaaaatcgac gctcaagtca gaggtggcga   1500
aacccgacag gactataaag ataccaggcg tttccccctg gaagctccct cgtgcgctct   1560
cctgttccga ccctgccgct taccggatac ctgtccgcct ttctcccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
tttgtttgca agcagcagat tacgcgcaga aaaaaaggat ctcaagaaga tcctttgatc   2040
ttttctacgg ggtctgacgc tcagtggaac gaaaactcac gttaagggat tttggtcatg   2100
agattatcaa aaaggatctt cacctagatc cttttaaatt aaaaatgaag ttttaaatca   2160
atctaaagta tatatgagta acctgaggct atggcagggc ctgccgcccc gacgttggct   2220
gcgagccctg ggccttcacc cgaacttggg ggtggggtg gggaaaagga agaaacgcgg   2280
gcgtattggc cccaatgggg tctcggtggg gtatcgacag agtgccagcc ctgggaccga   2340
accccgcgtt tatgaacaaa cgacccaaca ccgtgcgttt tattctgtct ttttattgcc   2400
gtcatagcgc gggttccttc cggtattgtc tccttccgtg tttcagttag cctcccccta   2460
gggtgggcga agaactccag catgagatcc ccgcgctgga ggatcatcca gccggcgtcc   2520
cggaaaacga ttccgaagcc caacctttca tagaaggcgg cggtggaatc gaaatctcgt   2580
gatggcaggt tgggcgtcgc ttggtcggtc atttcgaacc ccagagtccc gctcagaaga   2640
actcgtcaag aaggcgatag aaggcgatgc gctgcgaatc gggagcggcg ataccgtaaa   2700
gcacgaggaa gcggtcagcc cattcgccgc caagctcttc agcaatatca cgggtagcca   2760
acgctatgtc ctgatagcgg tccgccacac ccagccggcc acagtcgatg aatccagaaa   2820
agcggccatt ttccaccatg atattcggca agcaggcatc gccatgggtc acgacgagat   2880
cctcgccgtc gggcatgctc gccttgagcc tggcgaacag ttcggctggc gcgagcccct   2940
```

-continued gatgctcttg atcatcctga tcgacaagac cggcttccat ccgagtacgt gctcgctcga 3000
tgcgatgttt cgcttggtgg tcgaatgggc aggtagccgg atcaagcgta tgcagccgcc 3060
gcattgcatc agccatgatg gatactttct cggcaggagc aaggtgagat gacaggagat 3120
cctgccccgg cacttcgccc aatagcagcc agtcccttcc cgcttcagtg acaacgtcga 3180
gcacagctgc gcaaggaacg cccgtcgtgg ccagccacga tagccgcgct gcctcgtctt 3240
gcagttcatt cagggcaccg gacaggtcgg tcttgacaaa aagaaccggg cgcccctgcg 3300
ctgacagccg gaacacggcg gcatcagagc agccgattgt ctgttgtgcc cagtcatagc 3360
cgaatagcct ctccacccaa gcggccggag aacctgcgtg caatccatct tgttcaatca 3420
tgcgaaacga tcctcatcct gtctcttgat cgatctttgc aaaagcctag gcctccaaaa 3480
aagcctcctc actacttctg gaatagctca gaggccgagg aggcggcctc ggcctctgca 3540
taaataaaaa aaattagtca gccatggggc ggagaatggg cggaactggg cggagttagg 3600
ggcgggatgg gcggagttag gggcgggact atggttgctg actaattgag atgcatgctt 3660
tgcatacttc tgcctgctgg ggagcctggg gactttccac acctggttgc tgactaattg 3720
agatgcatgc tttgcatact tctgcctgct ggggagcctg gggactttcc acaccctaac 3780
tgacacacat tccacagctg gttctttccg cctcaggact cttccttttt caataaatca 3840
atctaaagta tatatgagta aacttggtct gacagttacc aatgcttaat cagtgaggca 3900
cctatctcag cgatctgtct atttcgttca tccatagttg cctgactccc cgtcgtgtag 3960
ataactacga tacgggaggg cttaccatct ggccccagtg ctgcaatgat accgcgagac 4020
ccacgctcac cggctccaga tttatcagca ataaaccagc cagccggaag ggccgagcgc 4080
agaagtggtc ctgcaacttt atccgcctcc atccagtcta ttaattgttg ccgggaagct 4140
agagtaagta gttcgccagt taatagtttg cgcaacgttg ttgccattgc tacaggcatc 4200
gtggtgtcac gctcgtcgtt tggtatggct tcattcagct ccggttccca acgatcaagg 4260
cgagttacat gatcccccat gttgtgcaaa aaagcggtta gctccttcgg tcctccgatc 4320
gttgtcagaa gtaagttggc cgcagtgtta tcactcatgg ttatggcagc actgcataat 4380
tctcttactg tcatgccatc cgtaagatgc ttttctgtga ctggtgagta ctcaaccaag 4440
tcattctgag aatagtgtat gcggcgaccg agttgctctt gcccggcgtc aatacgggat 4500
aataccgcgc cacatagcag aactttaaaa gtgctcatca ttggaaaacg ttcttcgggg 4560
cgaaaactct caaggatctt accgctgttg agatccagtt cgatgtaacc cactcgtgca 4620
cccaactgat cttcagcatc ttttactttc accagcgttt ctgggtgagc aaaaacagga 4680
aggcaaaatg ccgcaaaaaa gggaataagg gcgacacgga aatgttgaat actcatactc 4740
ttcctttttc aatattattg aagcatttat cagggttatt gtctcatgag cggatacata 4800
tttgaatgta tttagaaaaa taaacaaata ggggttccgc gcacatttcc ccgaaaagtg 4860
ccacctgacg cgccctgtag cggcgcatta agcgcggcgg gtgtggtggt tacgcgcagc 4920
gtgaccgcta cacttgccag cgccctagcg cccgctcctt tcgctttctt cccttccttt 4980
ctcgccacgt tcgccggctt tccccgtcaa gctctaaatc gggggctccc tttagggttc 5040
cgatttagtg ctttacggca cctcgacccc aaaaaacttg attagggtga tggttcacgt 5100
agtgggccat cgccctgata gacggttttt cgccctttga cgttggagtc cacgttcttt 5160
aatagtggac tcttgttcca aactggaaca acactcaacc ctatctcggt ctattctttt 5220
gatttataag ggattttgcc gatttcggcc tattggttaa aaaatgagct gatttaacaa 5280
aaatttaacg cgaattttaa caaaatatta acgcttacaa tttac 5325

<210> SEQ ID NO 63
<211> LENGTH: 5452
<212> TYPE: DNA
<213> ORGANISM: Artificial Sequence
<220> FEATURE:
<223> OTHER INFORMATION: plasmid

<400> SEQUENCE: 63
gtaccgaatt caagcttcgt gaggctccgg tgcccgtcag tgggcagagc gcacatcgcc 60
cacagtcccc gagaagttgg ggggaggggt cggcaattga accggtgcct agagaaggtg 120
gcgcggggta aactgggaaa gtgatgtcgt gtactggctc cgcctttttc ccgagggtgg 180
gggagaaccg tatataagtg cagtagtcgc cgtgaacgtt ctttttcgca acgggtttgc 240
cgccagaaca caggtaagtg ccgtgtgtgg ttcccgcggg cctggcctct ttacgggtta 300
tggcccttgc gtgccttgaa ttacttccac ctggctccag tacgtgattc ttgatcccga 360
gctggagcca ggggcgggcc ttgcgcttta ggagcccctt cgcctcgtgc ttgagttgag 420
gcctggcctg ggcgctgggg ccgccgcgtg cgaatctggt ggcaccttcg cgcctgtctc 480
gctgctttcg ataagtctct agccatttaa aatttttgat gacctgctgc gacgcttttt 540
ttctggcaag atagtcttgt aaatgcgggc caggatctgc acactggtat ttcggttttt 600
gggcccgcgg ccggcgacgg ggcccgtgcg tcccagcgca catgttcggc gaggcggggc 660
ctgcgagcgc ggccaccgag aatcggacgg gggtagtctc aagctggccg gcctgctctg 720
gtgcctggcc tcgcgccgcc gtgtatcgcc ccgccctggg cggcaaggct ggcccggtcg 780
gcaccagttg cgtgagcgga aagatggccg cttcccggcc ctgctccagg gggctcaaaa 840
tggaggacgc ggcgctcggg agagcgggcg ggtgagtcac ccacacaaag gaaaagggcc 900
tttccgtcct cagccgtcgc ttcatgtgac tccacggagt accgggcgcc gtccaggcac 960
ctcgattagt tctggagctt ttggagtacg tcgtctttag gttgggggga ggggttttat 1020
gcgatggagt ttccccacac tgagtgggtg gagactgaag ttaggccagc ttggcacttg 1080
atgtaattct ccttggaatt tggccttttt gagtttggat cttggttcat tctcaagcct 1140
cagacagtgg ttcaaagttt ttttcttcca tttcaggtgt cgtgaacacg tggccaccat 1200
ggcccaggtg cagctgcagg tcgacctcga gatcaaacgg gcggccgcag aacaaaaact 1260
catctcagaa gaggatctga atggggccgc atagtctaga agctcgctga tcagcctcga 1320
ctgtgccttc tagttgccag ccatctgttg tttgcccctc ccccgtgcct tccttgaccc 1380
tggaaggtgc cactcccact gtcctttcct aataaaatga ggaaattgca tcgcattgtc 1440
tgagtaggtg tcattctatt ctggggggtg gggtggggca ggacagcaag ggggaggatt 1500
gggaagacaa tagcaggcat gctggggatg gcccgggctc tatggcttct gaggcggaaa 1560
gaaccagctg gggctctagg gggtatcccc acgcgccctg tagcggcgca ttaagcgcgg 1620
cgggtgtggt ggttacgcgc agcgtgaccg ctacacttgc cagcgcccta gcgcccgctc 1680
ctttcgcttt cttcccttcc tttctcgcca cgttcgccgg ctttccccgt caagctctaa 1740
atcggggcat ccctttaggg ttccgattta gtgctttacg gcacctcgac cccaaaaaac 1800
ttgattaggg tgatggttca cgtagtgggc catcgccctg atagacggtt tttcgccctt 1860
tgacgttgga gtccacgttc tttaatagtg gactcttgtt ccaaactgga acaacactca 1920
accctatctc ggtctattct tttgatttat aagggatttt ggggatttcg gcctattggt 1980
taaaaaatga gctgatttaa caaaaattta acgcgaatta attctgtgga atgtgtgtca 2040

-continued

```
gttagggtgt ggaaagtccc caggctcccc aggcaggcag aagtatgcaa agcatgcatc   2100
tcaattagtc agcaaccagg tgtggaaagt ccccaggctc cccagcaggc agaagtatgc   2160
aaagcatgca tctcaattag tcagcaacca tagtcccgcc cctaactccg cccatcccgc   2220
ccctaactcc gcccagttcc gcccattctc cgccccatgg ctgactaatt ttttttattt   2280
atgcagaggc cgaggccgcc tctgcctctg agctattcca gaagtagtga ggaggctttt   2340
ttggaggcct aggcttttgc aaaaagctcc cgggaggtcc acaatgattg aacaagatgg   2400
attgcacgca ggttctccgg ccgcttgggt ggagaggcta ttcggctatg actgggcaca   2460
acagacaatc ggctgctctg atgccgccgt gttccggctg tcagcgcagg ggcgcccggt   2520
tctttttgtc aagaccgacc tgtccggtgc cctgaatgaa ctccaggacg aggcagcgcg   2580
gctatcgtgg ctggccacga cgggcgttcc ttgcgcagct gtgctcgacg ttgtcactga   2640
agcgggaagg gactggctgc tattgggcga agtgccgggg caggatctcc tgtcatctca   2700
ccttgctcct gccgagaaag tatccatcat ggctgatgca atgcggcggc tgcatacgct   2760
tgatccggct acctgcccat tcgaccacca agcgaaacat cgcatcgagc gagcacgtac   2820
tcggatggaa gccggtcttg tcgatcagga tgatctggac gaagagcatc aggggctcgc   2880
gccagccgaa ctgttcgcca ggctcaaggc gcgtatgccc gacggcgagg atctcgtcgt   2940
gactcatggc gatgcctgct tgccgaatat catggtggaa aatggccgct tttctggatt   3000
catcgactgt ggccggctgg gtgtggcgga ccgctatcag gacatagcgt tggctacccg   3060
tgatattgct gaagagcttg gcggcgaatg ggctgaccgc ttcctcgtgc tttacggtat   3120
cgccgctccc gattcgcagc gcatcgcctt ctatcgcctt cttgacgagt tcttctgagc   3180
gggactctgg ggttcgaaat gaccgaccaa gcgacgccca acctgccatc acgagatttc   3240
gattccaccg ccgccttcta tgaaaggttg ggcttcggaa tcgttttccg ggacgccggc   3300
tggatgatcc tccagcgcgg ggatctcatg ctggagttct tcgcccaccc caacttgttt   3360
attgcagctt ataatggtta caaataaagc aatagcatca caaatttcac aaataaagca   3420
tttttttcac tgcattctag ttgtggtttg tccaaactca tcaatgtatc ttatcatgtc   3480
tgtataccgg atctttccgc ttcctcgctc actgactcgc tgcgctcggt cgttcggctg   3540
cggcgagcgg tatcagctca ctcaaaggcg gtaatacggt tatccacaga atcaggggat   3600
aacgcaggaa agaacatgtg agcaaaaggc cagcaaaagg ccaggaaccg taaaaaggcc   3660
gcgttgctgg cgtttttcca taggctccgc ccccctgacg agcatcacaa aaatcgacgc   3720
tcaagtcaga ggtggcgaaa cccgacagga ctataaagat accaggcgtt tccccctgga   3780
agctccctcg tgcgctctcc tgttccgacc ctgccgctta ccggatacct gtccgccttt   3840
ctcccttcgg gaagcgtggc gctttctcaa tgctcacgct gtaggtatct cagttcggtg   3900
taggtcgttc gctccaagct gggctgtgtg cacgaacccc ccgttcagcc cgaccgctgc   3960
gccttatccg gtaactatcg tcttgagtcc aacccggtaa gacacgactt atcgccactg   4020
gcagcagcca ctggtaacag gattagcaga gcgaggtatg taggcggtgc tacagagttc   4080
ttgaagtggt ggcctaacta cggctacact agaaggacag tatttggtat ctgcgctctg   4140
ctgaagccag ttaccttcgg aaaaagagtt ggtagctctt gatccggcaa acaaaccacc   4200
gctggtagcg gtggtttttt tgtttgcaag cagcagatta cgcgcagaaa aaaaggatct   4260
caagaagatc ctttgatctt ttctacgggg tctgacgctc agtggaacga aaactcacgt   4320
taagggattt tggtcatgag attatcaaaa aggatcttca cctagatcct tttaaattaa   4380
aaatgaagtt ttaaatcaat ctaaagtata tatgagtaaa cttggtctga cagttaccaa   4440
```

tgcttaatca gtgaggcacc tatctcagcg atctgtctat ttcgttcatc catagttgcc 4500
tgactccccg tcgtgtagat aactacgata cgggagggct taccatctgg ccccagtgct 4560
gcaatgatac cgcgagaccc acgctcaccg gctccagatt tatcagcaat aaaccagcca 4620
gccggaaggg ccgagcgcag aagtggtcct gcaactttat ccgcctccat ccagtctatt 4680
aattgttgcc gggaagctag agtaagtagt tcgccagtta atagtttgcg caacgttgtt 4740
gccattgcta caggcatcgt ggtgtcacgc tcgtcgtttg gtatggcttc attcagctcc 4800
ggttcccaac gatcaaggcg agttacatga tcccccatgt tgtgcaaaaa agcggttagc 4860
tccttcggtc ctccgatcgt tgtcagaagt aagttggccg cagtgttatc actcatggtt 4920
atggcagcac tgcataattc tcttactgtc atgccatccg taagatgctt ttctgtgact 4980
ggtgagtact caaccaagtc attctgagaa tagtgtatgc ggcgaccgag ttgctcttgc 5040
ccggcgtcaa tacgggataa taccgcgcca catagcagaa ctttaaaagt gctcatcatt 5100
ggaaaacgtt cttcggggcg aaaactctca aggatcttac cgctgttgag atccagttcg 5160
atgtaaccca ctcgtgcacc caactgatct tcagcatctt ttactttcac cagcgtttct 5220
gggtgagcaa aaacaggaag gcaaaatgcc gcaaaaaagg gaataagggc gacacggaaa 5280
tgttgaatac tcatactctt cctttttcaa tattattgaa gcatttatca gggttattgt 5340
ctcatgagcg gatacatatt tgaatgtatt tagaaaaata aacaaatagg ggttccgcgc 5400
acatttcccc gaaaagtgcc acctgacgtc agatcgacgg atcgggagat cg 5452

<210> SEQ ID NO 64
<211> LENGTH: 4883
<212> TYPE: DNA
<213> ORGANISM: Artificial Sequence
<220> FEATURE:
<223> OTHER INFORMATION: plasmid

<400> SEQUENCE: 64
gtaccgaatt cacattgatt attgagtagt tattaatagt aatcaattac ggggtcatta 60
gttcatagcc catatatgga gttccgcgtt acataactta cggtaaatgg cccgcctggc 120
tgaccgccca acgacccccg cccattgacg tcaataatga cgtatgttcc catagtaacg 180
ccaataggga ctttccattg acgtcaatgg gtggagtatt tacggtaaac tgcccacttg 240
gcagtacatc aagtgtatca tatgccaagt acgcccccta ttgacgtcaa tgacggtaaa 300
tggcccgcct ggcattatgc ccagtacatg accttatggg actttcctac ttggcagtac 360
atctacggtt agtcatcgct attaccatag tgatgcggtt ttggcagtac atcaatgggc 420
gtggatagcg gtttgactca cggggatttc caagtctcca ccccattgac gtcaatggga 480
gtttgttttg gcaccaaaat caacgggact ttccaaaatg tcgtaacaac tccgccccat 540
tgacgcaaat gggcggtagg cgtgtacggt gggaggtcta tataagcaga gctttctggc 600
taactagaga acccgtggcc accatggccc aggtgcagct gcaggtcgac ctcgagatca 660
aacgggcggc cgcagaacaa aaactcatct cagaagagga tctgaatggg gccgcatagt 720
ctagaagctc gctgatcagc ctcgactgtg ccttctagtt gccagccatc tgttgtttgc 780
ccctcccccg tgccttcctt gaccctggaa ggtgccactc ccactgtcct ttcctaataa 840
aatgaggaaa ttgcatcgca ttgtctgagt aggtgtcatt ctattctggg gggtggggtg 900
gggcaggaca gcaaggggga ggattgggaa gacaatagca ggcatgctgg ggatggcccg 960
ggctctatgg cttctgaggc ggaaagaacc agctggggct ctagggggta tccccacgcg 1020

-continued

```
ccctgtagcg gcgcattaag cgcggcgggt gtggtggtta cgcgcagcgt gaccgctaca   1080
cttgccagcg ccctagcgcc cgctcctttc gctttcttcc cttcctttct cgccacgttc   1140
gccggctttc cccgtcaagc tctaaatcgg gggctccctt tagggttccg atttagtgct   1200
ttacggcacc tctccccaa aaaacttgat tagggtgatg gttcacgtag tgggccatcg   1260
ccctgataga cggtttttcg ccctttgacg ttggagtcca cgttctttaa tagtggactc   1320
ttgttccaaa ctggaacaac actcaaccct atctcggtct attcttttga tttataaggg   1380
attttgccga tttcggccta ttggttaaaa aatgagctga tttaacaaaa atttaacgcg   1440
aattaattct gtggaatgtg tgtcagttag ggtgtggaaa gtccccaggc tccccagcag   1500
gcagaagtat gcaaagcatg catctcaatt agtcagcaac caggtgtgga aagtccccag   1560
gctccccagc aggcagaagt atgcaaagca tgcatctcaa ttagtcagca accatagtcc   1620
cgcccctaac tccgcccatc ccgcccctaa ctccgcccag ttccgcccat tctccgcccc   1680
taggctgact aattttttt atttatgcag aggccgaggc cgcctctgcc tctgagctat   1740
tccagaagta gtgaggaggc ttttttggag gcctaggctt ttgcaaaaag ctccccccc   1800
gggaggtcca caatggttga acaagatgga ttgcacgcag gttctccggc cgcttgggtg   1860
gagaggctat tcggctatga ctgggcacaa cagacaatcg gctgctctga tgccgccgtg   1920
ttccggctgt cagcgcaggg gcgcccggtt ctttttgtca agaccgacct gtccggtgcc   1980
ctgaatgaac tccaggacga ggcagcgcgg ctatcgtggc tggccacgac gggcgttcct   2040
tgcgcagctg tgctcgacgt tgtcactgaa gcgggaaggg actggctgct attgggcgaa   2100
gtgccggggc aggatctcct gtcatctcac cttgctcctg ccgagaaagt atccatcatg   2160
gctgatgcaa tgcggcggct gcatacgctt gatccggcta cctgcccatt cgaccaccaa   2220
gcgaaacatc gcatcgagcg agcacgtact cggatggaag ccggtcttgt cgatcaggat   2280
gatctggacg aagagcatca ggggctcgcg ccagccgaac tgttcgccag gctcaaggcg   2340
cgtatgcccg acggcgagga tctcgtcgtg actcatggcg atgcctgctt gccgaatatc   2400
atggtggaaa atggccgctt ttctggattc atcgactgtg gccggctggg tgtggcggac   2460
cgctatcagg acatagcgtt ggctacccgt gatattgctg aagagcttgg cggcgaatgg   2520
gctgaccgct tcctcgtgct ttacggtatc gccgctcccg attcgcagcg catcgccttc   2580
tatcgccttc ttgacgagtt cttctgagcg ggactctggg gttcgaaatg accgaccaag   2640
cgacgcccaa cctgccatca cgagatttcg attccaccgc cgccttctat gaaaggttgg   2700
gcttcggaat cgttttccgg gacgccggct ggatgatcct ccagcgcggg gatctcatgc   2760
tggagttctt cgcccacccc aacttgttta ttgcagctta taatggttac aaataaagca   2820
atagcatcac aaatttcaca aataaagcat ttttttcact gcattctagt tgtggtttgt   2880
ccaaactcat caatgtatct tatcatgtct gtataccgtc gatctttccg cttcctcgct   2940
cactgactcg ctgcgctcgg tcgttcggct gcggcgagcg gtatcagctc actcaaaggc   3000
ggtaatacgg ttatccacag aatcagggga taacgcagga aagaacatgt gagcaaaagg   3060
ccagcaaaag gccaggaacc gtaaaaaggc cgcgttgctg gcgtttttcc ataggctccg   3120
cccccctgac gagcatcaca aaaatcgacg ctcaagtcag aggtggcgaa acccgacagg   3180
actataaaga taccaggcgt ttccccctgg aagctccctc gtgcgctctc ctgttccgac   3240
cctgccgctt accggatacc tgtccgcctt tctcccttcg ggaagcgtgg cgctttctca   3300
tagctcacgc tgtaggtatc tcagttcggt gtaggtcgtt cgctccaagc tgggctgtat   3360
gcacgaaccc cccgttcagc ccgaccgctg cgccttatcc ggtaactatc gtcttgagtc   3420
```

caacccggta agacacgact tatcgccact ggcagcagcc actggtaaca ggattagcag 3480
agcgaggtat gtaggcggtg ctacagagtt cttgaagtgg tggcctaact acggctacac 3540
tagaagaaca gtatttggta tctgcgctct gctgaagcca gttaccttcg gaaaaagagt 3600
tggtagctct tgatccggca aacaaaccac cgctggtagc ggtggttttt ttgtttgcaa 3660
gcagcagatt acgcgcagaa aaaaaggatc tcaagaagat cctttgatct tttctacggg 3720
gtctgacgct cagtggaacg aaaactcacg ttaagggatt ttggtcatga gattatcaaa 3780
aaggatcttc acctagatcc ttttaaatta aaaatgaagt tttaaatcaa tctaaagtat 3840
atatgagtaa acttggtctg acagttacca atgcttaatc agtgaggcac ctatctcagc 3900
gatctgtcta tttcgttcat ccatagttgc ctgactcccc gtcgtgtaga taactacgat 3960
acgggagggc ttaccatctg gccccagtgc tgcaatgata ccgcgagacc cacgctcacc 4020
ggctccagat ttatcagcaa taaaccagcc agccggaagg gccgagcgca gaagtggtcc 4080
tgcaacttta tccgcctcca tccagtctat taattgttgc cgggaagcta gagtaagtag 4140
ttcgccagtt aatagtttgc gcaacgttgt tgccattgct acaggcatcg tggtgtcacg 4200
ctcgtcgttt ggtatggctt cattcagctc cggttcccaa cgatcaaggc gagttacatg 4260
atcccccatg ttgtgcaaaa aagcggttag ctccttcggt cctccgatcg ttgtcagaag 4320
taagttggcc gcagtgttat cactcatggt tatggcagca ctgcataatt ctcttactgt 4380
catgccatcc gtaagatgct tttctgtgac tggtgagtac tcaaccaagt cattctgaga 4440
atagtgtatg cggcgaccga gttgctcttg cccggcgtca atacgggata ataccgcgcc 4500
acatagcaga actttaaaag tgctcatcat tggaaaacgt tcttcggggc gaaaactctc 4560
aaggatctta ccgctgttga gatccagttc gatgtaaccc actcgggcac ccaactgatc 4620
ttcagcatct tttactttca ccagcgtttc tgggtgagca aaaacaggaa ggcaaaatgc 4680
cgcaaaaaag ggaataaggg cgacacggaa atgttgaata ctcatactct tcctttttca 4740
atattattga agcatttatc agggttattg tctcatgagc ggatacatat ttgaatgtat 4800
ttagaaaaat aaacaaatag gggttccgcg cacatttccc cgaaaagtgc cacctgacgt 4860
cagatcgacg gatcgggaga tcg 4883

<210> SEQ ID NO 65
<211> LENGTH: 5060
<212> TYPE: DNA
<213> ORGANISM: Artificial Sequence
<220> FEATURE:
<223> OTHER INFORMATION: plasmid

<400> SEQUENCE: 65
gcgcgcgttg acattgatta ttgactagtt attaatagta atcaattacg gggtcattag 60
ttcatagccc atatatggag ttccgcgtta cataacttac ggtaaatggc ccgcctggct 120
gaccgcccaa cgacccccgc ccattgacgt caataatgac gtatgttccc atagtaacgc 180
caatagggac tttccattga cgtcaatggg tggactattt acggtaaact gcccacttgg 240
cagtacatca agtgtatcat atgccaagta cgccccctat tgacgtcaat gacggtaaat 300
ggcccgcctg gcattatgcc cagtacatga ccttatggga ctttcctact tggcagtaca 360
tctacgtatt agtcatcgct attaccatgg tgatgcggtt ttggcagtac atcaatgggc 420
gtggatagcg gtttgactca cggggatttc caagtctcca ccccattgac gtcaatggga 480
gtttgttttg gcaccaaaat caacgggact ttccaaaatg tcgtaacaac tccgccccat 540

-continued

```
tgacgcaaat gggcggtagg cgtgtacggt gggaggtcta tataagcaga gctctctggc    600
taactagaga acccactgct tactggctta tcgaaattaa tacgactcac tatagggaga    660
cccaagctgg ctagcgttta aacttaagct tggtaccgag ctcggatcca ctagtccagt    720
gtggtggaat tcggcttaag ccgaattctg cagatatcca gcacagtggc ggccgctcga    780
gtctagaggg cccgtttaaa cccgctgatc agcctcgact gtgccttcta gttgccagcc    840
atctgttgtt tgcccctccc ccgtgccttc cttgaccctg gaaggtgcca ctcccactgt    900
cctttcctaa taaaatgagg aaattgcatc gcattgtctg agtaggtgtc attctattct    960
ggggggtggg gtggggcagg acagcaaggg ggaggattgg gaagacaata gcaggcatgc   1020
tggggatgcg gtgggctcta tggcttctga ggcggaaaga accagtggcg gtaatacggt   1080
tatccacaga atcaggggat aacgcaggaa agaacatgtg agcaaaaggc cagcaaaagg   1140
ccaggaaccg taaaaaggcc gcgttgctgg cgtttttcca taggctccgc ccccctgacg   1200
agcatcacaa aaatcgacgc tcaagtcaga ggtggcgaaa cccgacagga ctataaagat   1260
accaggcgtt tccccctgga agctccctcg tgcgctctcc tgttccgacc ctgccgctta   1320
ccggatacct gtccgccttt ctcccttcgg gaagcgtggc gctttctcat agctcacgct   1380
gtaggtatct cagttcggtg taggtcgttc gctccaagct gggctgtgtg cacgaacccc   1440
ccgttcagcc cgaccgctgc gccttatccg gtaactatcg tcttgagtcc aacccggtaa   1500
gacacgactt atcgccactg gcagcagcca ctggtaacag gattagcaga gcgaggtatg   1560
taggcggtgc tacagagttc ttgaagtggt ggcctaacta cggctacact agaaggacag   1620
tatttggtat ctgcgctctg ctgaagccag ttaccttcgg aaaaagagtt ggtagctctt   1680
gatccggcaa acaaaccacc gctggtagcg gtggtttttt tgtttgcaag cagcagatta   1740
cgcgcagaaa aaaaggatct caagaagatc ctttgatctt ttctacgggg tctgacgctc   1800
agtggaacga aaactcacgt taagggattt tggtcatgag attatcaaaa aggatcttca   1860
cctagatcct tttaaattaa aaatgaagtt ttaaatcaat ctaaagtata tatgagtaac   1920
ctgaggctat ggcagggcct gccgccccga cgttggctgc gagccctggg ccttcacccg   1980
aacttggggg gtggggtggg gaaaaggaag aaacgcgggc gtattggccc caatggggtc   2040
tcggtggggt atcgacagag tgccagccct gggaccgaac cccgcgttta tgaacaaacg   2100
acccaacacc gtgcgtttta ttctgtcttt ttattgccgt catagcgcgg gttccttccg   2160
gtattgtctc cttccgtgtt tcagttagcc tccccctagg gtgggcgaag aactccagca   2220
tgagatcccc gcgctggagg atcatccagc cggcgtcccg gaaaacgatt ccgaagccca   2280
acctttcata gaaggcggcg gtggaatcga aatctcgtga tggcaggttg ggcgtcgctt   2340
ggtcggtcat ttcgaacccc agagtcccgc tcagaagaac tcgtcaagaa ggcgatagaa   2400
ggcgatgcgc tgcgaatcgg gagcggcgat accgtaaagc acgaggaagc ggtcagccca   2460
ttcgccgcca agctcttcag caatatcacg ggtagccaac gctatgtcct gatagcggtc   2520
cgccacaccc agccggccac agtcgatgaa tccagaaaag cggccatttt ccaccatgat   2580
attcggcaag caggcatcgc catgggtcac gacgagatcc tcgccgtcgg gcatgctcgc   2640
cttgagcctg gcgaacagtt cggctggcgc gagcccctga tgctcttgat catcctgatc   2700
gacaagaccg gcttccatcc gagtacgtgc tcgctcgatg cgatgtttcg cttggtggtc   2760
gaatgggcag gtagccggat caagcgtatg cagccgccgc attgcatcag ccatgatgga   2820
tactttctcg gcaggagcaa ggtgagatga caggagatcc tgccccggca cttcgcccaa   2880
tagcagccag tcccttcccg cttcagtgac aacgtcgagc acagctgcgc aaggaacgcc   2940
```

cgtcgtggcc agccacgata gccgcgctgc ctcgtcttgc agttcattca gggcaccgga 3000
caggtcggtc ttgacaaaaa gaaccgggcg cccctgcgct gacagccgga acacggcggc 3060
atcagagcag ccgattgtct gttgtgccca gtcatagccg aatagcctct ccacccaagc 3120
ggccggagaa cctgcgtgca atccatcttg ttcaatcatg cgaaacgatc ctcatcctgt 3180
ctcttgatcg atctttgcaa aagcctaggc ctccaaaaaa gcctcctcac tacttctgga 3240
atagctcaga ggccgaggcg gcctcggcct ctgcataaat aaaaaaaatt agtcagccat 3300
ggggcggaga atgggcggaa ctgggcggag ttaggggcgg gatgggcgga gttaggggcg 3360
ggactatggt tgctgactaa ttgagatgca tgctttgcat acttctgcct gctggggagc 3420
ctggggactt tccacacctg gttgctgact aattgagatg catgctttgc atacttctgc 3480
ctgctgggga gcctggggac tttccacacc ctaactgaca cacattccac agctggttct 3540
ttccgcctca ggactcttcc tttttcaata aatcaatcta aagtatatat gagtaaactt 3600
ggtctgacag ttaccaatgc ttaatcagtg aggcacctat ctcagcgatc tgtctatttc 3660
gttcatccat agttgcctga ctccccgtcg tgtagataac tacgatacgg gagggcttac 3720
catctggccc cagtgctgca atgataccgc gagacccacg ctcaccggct ccagatttat 3780
cagcaataaa ccagccagcc ggaagggccg agcgcagaag tggtcctgca actttatccg 3840
cctccatcca gtctattaat tgttgccggg aagctagagt aagtagttcg ccagttaata 3900
gtttgcgcaa cgttgttgcc attgctacag gcatcgtggt gtcacgctcg tcgtttggta 3960
tggcttcatt cagctccggt tcccaacgat caaggcgagt tacatgatcc cccatgttgt 4020
gcaaaaaagc ggttagctcc ttcggtcctc cgatcgttgt cagaagtaag ttggccgcag 4080
tgttatcact catggttatg gcagcactgc ataattctct tactgtcatg ccatccgtaa 4140
gatgcttttc tgtgactggt gagtactcaa ccaagtcatt ctgagaatag tgtatgcggc 4200
gaccgagttg ctcttgcccg gcgtcaatac gggataatac cgcgccacat agcagaactt 4260
taaaagtgct catcattgga aaacgttctt cggggcgaaa actctcaagg atcttaccgc 4320
tgttgagatc cagttcgatg taacccactc gtgcacccaa ctgatcttca gcatctttta 4380
ctttcaccag cgtttctggg tgagcaaaaa caggaaggca aaatgccgca aaaaagggaa 4440
taagggcgac acggaaatgt tgaatactca tactcttcct ttttcaatat tattgaagca 4500
tttatcaggg ttattgtctc atgagcggat acatatttga atgtatttag aaaaataaac 4560
aaataggggt tccgcgcaca tttccccgaa aagtgccacc tgacgcgccc tgtagcggcg 4620
cattaagcgc ggcgggtgtg gtggttacgc gcagcgtgac cgctacactt gccagcgccc 4680
tagcgcccgc tcctttcgct ttcttccctt cctttctcgc cacgttcgcc ggctttcccc 4740
gtcaagctct aaatcggggg ctccctttag ggttccgatt tagtgcttta cggcacctcg 4800
accccaaaaa acttgattag ggtgatggtt cacgtagtgg gccatcgccc tgatagacgg 4860
tttttcgccc tttgacgttg gagtccacgt tctttaatag tggactcttg ttccaaactg 4920
gaacaacact caaccctatc tcggtctatt cttttgattt ataagggatt ttgccgattt 4980
cggcctattg gttaaaaaat gagctgattt aacaaaaatt taacgcgaat tttaacaaaa 5040
tattaacgct tacaatttac 5060

<210> SEQ ID NO 66
<211> LENGTH: 13905
<212> TYPE: DNA
<213> ORGANISM: Artificial Sequence
<220> FEATURE:

<223> OTHER INFORMATION: plasmid

<400> SEQUENCE: 66

```
atggctgcgt gagacacacg tagcctacca gtttcttact gctctactct gcaaagcaag     60
agattaataa cccatcatgg attctgtgta cgtggacata gacgctgaca gcgccttttt    120
gaaggccctg caacgtgcgt accccatgtt tgaggtggaa cctaggcagg tcacatcgaa    180
tgaccatgct aatgctagag cgttctcgca tctagccata aaactaatag agcaggaaat    240
tgatcccgac tcaaccatcc tggatatagg tagtgcgcca gcaaggagga tgatgtcgga    300
caggaagtac cactgcgttt gcccgatgcg cagcgcagaa gatcccgaga gactcgctaa    360
ttatgcgaga aagctcgcat ctgccgcagg aaaagtcctg gacagaaaca tttctggaaa    420
gatcggggac ttacaagcgg tgatggccgt gccagacacg gagacgccaa cattttgctt    480
acacacagat gtctcatgta gacagagagc agacgtcgcg atataccaag acgtctatgc    540
tgtacacgca cccacgtcgc tataccacca ggcgattaaa ggagtccgag tggcgtactg    600
ggtagggttc gacacaaccc cgttcatgta caacgctatg gcgggtgcct acccctcata    660
ctcgacaaat tgggcggatg agcaggtact gaaggctaag aacataggat tatgttcaac    720
agacctgacg gaaggtagac gaggcaaatt gtctatcatg agagggaaaa agctaaaacc    780
gtgcgaccgt gtgctgttct cagtagggtc aacgctttac ccggaaagcc gcacgctact    840
taagagctgg cacctaccat cggtgttcca tctaaagggc aagcttagct tcacatgccg    900
ctgtgacaca gtggtttcgt gtgagggcta cgtcgttaag agaataacga tgagcccagg    960
cctttatgga aaaaccatag ggtatgcggt aacccaccac gcagacggat tcttgatgtg   1020
caagactacc gacacggttg acggcgaaag agtgtcattc tcggtgtgca cgtacgtgcc   1080
ggcgaccatt tgtgatcaaa tgaccggcat ccttgctaca gaagtcacgc cggaggatgc   1140
acagaagctg ttggtggggc tgaaccagag gatagtggtt aacggcagaa cgcaacggaa   1200
cacgaacacc atgaagaact acctacttcc cgtggtcgcc caggccttca gtaagtgggc   1260
aaaggagtgc cggaaggaca tggaagatga gaagcttctg gggggtcagag aaagaacact   1320
aacctgctgc tgtctatggg catttaagaa gcagaaaaca cacacggtct acaagaggcc   1380
tgatacccag tcaatccaga aggttcaggc cgaatttgac agctttgtag taccgggcct   1440
gtggtcgtcc gggttgtcaa tcccgttgag gactagaatc aagtggttgt tacgcaaggt   1500
gccgaaaaca gacctgatcc catacagcgg gaatgcccaa gaagcccagg atgcagaaaa   1560
agaagcagag gaagaacgag aagcagaact gactcatgag gctctaccac ccctacaggc   1620
agcacaggaa gatgtccagg tcgaaatcga cgtggaacag cttgaggata gagctggtgc   1680
tggaataata gagactccga gaggcgctat caaagttact gcccaactaa cagaccacgt   1740
cgtgggggag tacctggtac tttccccgca gaccgtacta cgcagccaga agctcagcct   1800
gatccacgct ttagcggagc aagtgaagac gtgtacgcac agcggacgag cagggaggta   1860
tgcggtcgaa gcgtacgatg gccgagtcct agtgccctca ggctatgcaa tttcgcctga   1920
agacttccag agtctaagcg aaagcgcaac gatggtgtac aacgaaagag agttcgtaaa   1980
cagaaagtta caccacattg cgatgcacgg accagccctg aacactgacg aagagtcgta   2040
tgagctggtg agggcagaga ggacagaaca cgagtacgtc tacgacgtgg accagagaag   2100
atgctgtaag aaggaagaag ctgcaggact ggtactggtg ggcgacttga ctaatccgcc   2160
ctaccacgaa ttcgcatacg aagggctaaa aattcgcccc gcctgcccat acaaaattgc   2220
agtcatagga gtcttcgggg taccaggatc tggcaagtca gccattatca agaacctagt   2280
```

-continued

```
taccaggcaa gacctggtga ctagcggaaa gaaagaaaac tgccaagaaa tcagcaccga   2340
cgtgatgaga cagagaggtc tagagatatc tgcacgtacg gtagattcgc tgctcttgaa   2400
tggatgcaac agaccagtcg acgtgttgta cgtagacgag gcgtttgcgt gccactctgg   2460
aacgttactt gctttgatcg ccttggtgag accaagacag aaagttgtac tttgtggtga   2520
cccgaagcag tgcggcttct tcaatatgat gcagatgaaa gtcaactaca atcataacat   2580
ctgcacccaa gtgtaccaca aaagtatctc caggcggtgt acactgcctg tgactgccat   2640
tgtgtcatcg ttgcattacg aaggcaaaat gcgcactacg aatgagtaca acatgccgat   2700
tgtagtggac actacaggct caacgaaacc tgaccctgga gacctcgtgt taacgtgctt   2760
cagagggtgg gttaaacaac tgcaaattga ctatcgtgga cacgaggtca tgacagcagc   2820
cgcatcccaa gggttaacta gaaaaggagt ttacgcagtt aggcaaaaag ttaacgaaaa   2880
cccactctat gcatcaacat cagagcacgt caacgtactc ctaacgcgta cggaaggtaa   2940
actggtatgg aagacactct ctggtgaccc gtggataaag acgctgcaga acccaccgaa   3000
aggaaacttc aaagcaacta ttaaggagtg ggaggtggag cacgcatcga taatggcggg   3060
catctgcagt caccaagtga cctttgacac attccaaaac aaagccaacg tttgctgggc   3120
taagagcttg gtccctatcc tcgaaacagc ggggataaaa ctaaatgata ggcagtggtc   3180
ccagataatt caagccttca aagaagacaa agcatactca cccgaagtag ccctgaatga   3240
aatatgcacg cgcatgtatg gggtggatct agacagtggg ctattctcta aaccgttggt   3300
atctgtgtat tacgcggata accattggga taataggccg ggaggaaaga tgttcggatt   3360
caaccctgag gcagcgtcca ttctagaaag aaagtaccca tttacaaaag gaaagtggaa   3420
catcaacaag cagatctgcg tgactaccag gaggatagaa gacttcaacc ctaccaccaa   3480
cattataccg gtcaacagga gactaccaca ctcattagtg gccgaacacc gcccagtaaa   3540
aggggaaaga atggaatggc tggttaacaa gataaacgga caccacgtac tcctggttag   3600
cggctataac cttgcactgc ctactaagag agtcacctgg gtagcgccac taggtgtccg   3660
cggagcggac tatacataca acctagagct gggtctacca gcaacacttg gtaggtatga   3720
cctagtggtc ataaacatcc acacaccttt tcgcatacac cattaccaac agtgcgtaga   3780
tcacgcaatg aaactgcaaa tgctaggggg tgactcactg agactgctca aaccgggtgg   3840
ctctctattg atcagagcat acggttacgc agatagaacc agtgaacgag tcatctgcgt   3900
actgggacgc aagtttagat cgtctagagc attgaaacca ccatgtgtca ccagtaatac   3960
tgagatgttt ttcctattta gcaattttga caatggcaga aggaatttta caacgcatgt   4020
catgaacaat caactgaatg cagcctttgt aggacaggcc acccgagcag gatgtgcacc   4080
atcgtaccgg gtaaaacgca tggacatcgc gaagaacgat gaagagtgcg tggttaacgc   4140
cgccaaccct cgcgggttac caggtgacgg tgtttgcaag gcagtatata aaaagtggcc   4200
ggagtccttt aaaaacagtg caacaccagt aggaaccgca aaaacagtta tgtgcggtac   4260
gtatccagta atccacgccg taggaccaaa cttctcaaat tattcggagt ctgaagggga   4320
ccgggaattg gcggctgcct atcgagaagt cgcaaaggaa gtaactagac tgggagtaaa   4380
tagcgtagct atacctctcc tctccacagg tgtatactca ggagggaaag acaggctaac   4440
ccagtcactg aaccacctct ttacagccat ggactcgacg gatgcagacg tggtcatcta   4500
ctgccgagac aaggaatggg agaagaaaat atctgaggcc atacagatgc ggacccaagt   4560
ggagctgctg gatgagcaca tctccataga ctgcgatgtc attcgcgtgc accctgacag   4620
```

-continued

```
tagcttggca ggcagaaaag gatacagcac cacggaaggc gcactgtatt catatctaga   4680
agggacacgt tttcaccaga cggcagtgga tatggcagag atatacacta tgtggccaaa   4740
gcaaacagag gccaatgagc aagtctgcct atatgccctg ggggaaagta ttgaatcaat   4800
caggcagaaa tgcccggtgg atgatgcaga cgcatcatct cccccgaaaa ctgtcccgtg   4860
tctttgccgg tatgccatga ctcctgaacg cgtcacccga cttcgcatga accatgtcac   4920
aaatataatt gtgtgttctt catttcccct tccaaagtac aagatagaag gagtgcaaaa   4980
agtcaaatgc tccaaggtaa tgttattcga tcacaatgtg ccatcgcgcg taagtccaag   5040
ggaatacaga tcttcccagg agtctgtaca ggaagtgagt acgacaacgt cattgacgca   5100
tagccagttt gatctaagcg ccgatggcga gacactgcct gtcccgtcag acctggatgc   5160
tgacgcccca gccctagaac cggccctaga cgacggggcg gtacatacat taccaaccat   5220
aatcggaaac cttgcggccg tgtctgactg ggtaatgagc accgtacctg tcgcgccgcc   5280
tagaagaagg agagggagaa acctgactgt gacatgtgac gagagagaag ggaatataac   5340
acccatggct agcgtccgat tctttagagc agagctgtgt ccggccgtac aagaaacagc   5400
ggagacgcgt gacacagcta tttcccttca ggcaccgcca agtaccacca tggaactgag   5460
ccatccaccg atctccttcg gagcaccaag cgagacgttc cccatcacat ttggggactt   5520
cgacgaagga gaaatcgaaa gcttgtcttc tgagctacta actttcggag acttcctacc   5580
cggtgaagtg gatgatctga cagatagcga ctggtccacg tgcccagaca cggacgacga   5640
gttatgacta gacagggcag gtgggtatat attctcgtcg gacactggtc caggccattt   5700
acaacagaag tcggtacgcc agtcagtgct gccggtaaac accctggagg aagtccacga   5760
ggagaagtgt tacccaccta agctggatga attaaaggag caactactac ttaagaaact   5820
ccaggagagt gcgtccatgg ccaatagaag caggtatcag tcacgcaaag tggaaaatat   5880
gaaagcaaca atcatccaga gactaaagag aggctgtaaa ctgtatttaa tggcagagac   5940
cccgaaagtc ccgacttatc ggaccatata cccggcgcct gtgtactcgc ctccgatcaa   6000
tgtccgattg tccaaccccg agtccgcagt ggcagcatgt aatgagttct tagctagaaa   6060
ctacccaact gtttcatcat accaaatcac cgacgagtat gatgcatatc tagacatggt   6120
ggacgggtcg gagagttgct tggaccgagc gacattcaat ccgtcaaaac ttaggagcta   6180
cccgaaacaa catgcttatc acgcgccttc tatcagaagc gctgtacctt ccccattcca   6240
gaacacacta cagaatgtac tggcagcagc cacgaaaagg aactgcaacg tcacacagat   6300
gagggaatta cccactttgg actcagcagt attcaacgtg gagtgtttta aaaaattcgc   6360
atgtaaccga gaatactggg aagaatttgc agccagccct atcaggataa caactgagaa   6420
tctaacaacc tatgtcacta aactaaaggg gccaaaagca gcagcgctgt ttgcaaaaac   6480
ccataatctg ctgccactgc aggatgtacc aatggatagg ttcacagtag atatgaaaag   6540
ggatgtgaag gtaactcctg gtacaaagca tacagaggaa agacctaagg tgcaggttat   6600
acaggcggct gaacccttgg caacagcgta cctatgtgga attcacagag aactggttag   6660
gagattgaac gccgtcctcc tacccaatgt gcatacacta tttgacatgt ctgccgagga   6720
cttcgatgcc attatagccg cacacttcaa gccaggagac gctgttttag aaacggacat   6780
agcctccttt gataagagcc aagatgattc acttgcgctt accgccttaa tgctgttaga   6840
agatttggga gtggatcact ccctgttgga cttgatagag gctgctttcg gagagatttc   6900
cagctgtcat ctgccgacag gtacgcgctt caagttcggc gctatgatga aatccggtat   6960
gttcctaact ctgttcgtca acacgttgtt aaatatcacc atcgctagcc gggtgttgga   7020
```

-continued

```
agatcgtctg acaaaatccg catgcgcggc cttcatcggc gacgacaaca taatacatgg   7080
tgtcgtctcc gatgaattga tggcagccag atgcgctact tggatgaaca tggaagtgaa   7140
gatcatagat gcagttgtat cccagaaagc tccttacttt tgtggagggt ttatactgca   7200
tgatactgtg acaggaacag cttgcagagt ggcggacccg ctaaaaaggt tatttaaatt   7260
gggcaaaccg ttagcggcag gtgacgaaca agatgaagac agaagacggg cgctggctga   7320
tgaagtaatc agatggcaac gaacagggct aatagatgag ctggagaaag cggtgtactc   7380
taggtacgaa gtgcagggta tatcagttgc ggtaatgtcc atggccacct ttgcaagctc   7440
cagatccaac ttcgagaagc tcagaggacc cgtcataact ttgtacggcg gtcctaaata   7500
ggtacgcact acagctacct attttgcaga agccgacagc aggtacctaa ataccaatca   7560
gccataatgg agtttatccc aacccaaact ttctacaata ggaggtacca gcctcgacct   7620
tggactccgc gccctactat ccaagttatc agacccagac cgcgtccgca aaggaaagcc   7680
gggcaacttg cccagctgat ctcagcagtt aataaactga caatgcgcgc ggtacctcaa   7740
cagaagccgc gcaagaatcg gaagaataag aagcaaaagc aaaagcagca ggcgccacga   7800
aacaacatga atcaaaagaa gcagcccccct aaaaagaaac cggctcaaaa gaaaaagaag   7860
ccgggccgta gagagagaat gtgcatgaaa atcgaaaatg attgcatctt cgaagtcaag   7920
catgaaggta aggtaacagg ttacgcgtgc ttggtagggg acaaagtaat gaagccagca   7980
cacgtaaagg ggaccatcga taatgcggac ctggccaaat tggccttcaa gcggtcatct   8040
aagtacgacc ttgaatgcgc gcagataccc gtgcacatga agtccgacgc ttcgaagttc   8100
acccatgaga aaccggaggg gtactacaac tggcaccacg gagcagtaca gtactcagga   8160
ggccggttca ccatccctac aggtgcgggc aaaccagggg acagcggtag accgatcttc   8220
gacaacaagg ggcgcgtggt ggccatagtt ttaggaggag ctaatgaagg agcccgtaca   8280
gccctctcgg tggtgacctg gaacaaagac atcgtcacga aaatcacccc tgagggggcc   8340
gaagagtgga gtcttgccat tccagttatg tgcctgctgg caaataccac gttcccctgc   8400
tcccagcccc cttgcacacc ctgctgctac gaaaaagagc cggagaaaac cctgcgcatg   8460
ctagaagaca acgtcatgag ccccgggtac tatcagctgc tacaagcatc cttaacatgt   8520
tctccccgcc gccagcgacg cagtattaag gacaacttca atgtctataa agccataaga   8580
ccgtacctag ctcactgtcc cgactgtgga gaagggcact cgtgccatag tcccgtagcg   8640
ctagaacgca tcagaaacga agcgacagac gggacgctga aaatccaggt ttccttgcaa   8700
atcggaataa agacggatga tagccatgat tggaccaagc tgcgttacat ggacaatcat   8760
atgccagcag acgcagagag ggccaggcta tttgtaagaa cgtcagcacc gtgcacgatt   8820
actggaacaa tgggacactt catcctggcc cgatgtccga aaggagaaac tctgacggtg   8880
ggattcactg acggtaggaa gatcagtcac tcatgtacgc acccatttca ccacgaccct   8940
cctgtgatag gccgggaaaa atttcattcc cgaccgcagc acggtagaga actaccttgc   9000
agcacgtacg cgcagagcac cgctgcaact gccgaggaga tagaggtaca tatgccccca   9060
gacaccccag atcgcacatt gatgtcacaa cagtccggta atgtaaagat cacagtcaat   9120
agtcagacgg tgcggtacaa gtgtaattgc ggtgactcaa atgaaggact aaccactaca   9180
gacaaagtga ttaataactg caaggttgat caatgccatg ccgcggtcac caatcacaaa   9240
aaatggcagt ataattcccc tctggtcccg cgtaatgctg aactcgggga ccgaaaagga   9300
aaagttcaca ttccgtttcc tctggcaaat gtgacatgca gggtgcctaa ggcaaggaac   9360
```

-continued

```
cccaccgtga cgtacggaaa aaaccaagtc atcatgctgc tgtatcctga ccacccaacg   9420
ctcctgtcct accggaatat gggagaagaa ccaaactatc aagaagagtg ggtgacgcat   9480
aagaaggaga tcaggttaac cgtgccgact gaagggctcg aggtcacgtg gggcaacaac   9540
gagccgtaca agtattggcc gcagttatcc acaaacggta cagcccacgg ccacccgcat   9600
gagataattt tgtattatta tgagctgtac cctactatga ctgtggtagt tgtgtcagtg   9660
gcctcgttcg tactcctgtc gatggtgggt gtggcagtgg ggatgtgcat gtgtgcacga   9720
cgcagatgca ttacaccgta cgaactgaca ccaggagcta ccgtcccttt cctgcttagc   9780
ctaatatgct gcattagaac agctaaagcg gccacatacc aagaggctgc ggtatacctg   9840
tggaacgagc agcagccttt gttttggctg caagccctta ttccgctggc agccctgatt   9900
gtcctatgca actgtctgag actcttacca tgcttttgta aaacgttgac tttttagcc    9960
gtaatgagcg tcggtgccca cactgtgagc gcgtacgaac acgtaacagt gatcccgaac  10020
acggtgggag taccgtataa gactctagtc aacagaccgg gctacagccc catggtactg  10080
gagatggagc ttctgtcagt cactttggag ccaacgctat cgcttgatta catcacgtgc  10140
gagtataaaa ccgtcatccc gtctccgtac gtgaaatgct gcggtacagc agagtgcaag  10200
gacaagagcc tacctgatta cagctgtaag gtcttcaccg gcgtctaccc attcatgtgg  10260
ggcggcgcct actgcttctg cgacactgaa aatacgcaat tgagcgaagc acatgtggag  10320
aagtccgaat catgcaaaac agaatttgca tcagcatata gggctcatac cgcatccgca  10380
tcagctaagc tccgcgtcct ttaccaagga aataatgtta ctgtatctgc ttatgcaaac  10440
ggcgatcatg ccgtcacagt taaggacgct aaattcattg tggggccaat gtcttcagcc  10500
tggacacctt ttgacaataa aatcgtggtg tacaaaggcg acgtctacaa catggactac  10560
ccgcccttcg gcgcaggaag accaggacaa tttggcgaca tccaaagtcg cacgcctgag  10620
agcgaagacg tctatgctaa cacacaactg gtactgcaga gaccgtccgc gggtacggtg  10680
cacgtgccgt actctcaggc accatctggc ttcaagtatt ggctaaaaga acgaggggcg  10740
tcgctgcagc acacagcacc atttggctgt caaatagcaa caaacccggt aagagcgatg  10800
aactgcgccg tagggaacat gcctatctcc atcgacatac cggacgcggc cttcactagg  10860
gtcgtcgacg cgccatcttt aacggacatg tcgtgtgagg taccagcctg cacccactcc  10920
tcagactttg gggcgtagc catcattaaa tatgcagcca gcaagaaagg caagtgtgcg   10980
gtgcattcga tgactaacgc cgtcactatt cgggaagctg aaatagaagt agaagggaac  11040
tctcagttgc aaatctcttt ttcgacggcc ctagccagcg ccgaattccg cgtacaagtc  11100
tgttctacac aagtacactg tgcagccgag tgccatccac cgaaagacca tatagtcaat  11160
tacccggcgt cacacaccac cctcggggtc caagacattt ccgttacggc gatgtcatgg  11220
gtgcagaaga tcacgggagg tgtgggactg gttgtcgctg ttgcagcact gatcctaatc  11280
gtggtgctat gcgtgtcgtt tagcaggcac taacttgaca actaggtacg aaggtatatg  11340
tgtcccctaa gagacacacc acatatagct aagaatcaat agataagtat agatcaaagg  11400
gctgaacaac ccctgaatag taacaaaata taaaaatcaa caaaaatcat aaaatagaaa  11460
accagaaaca gaagtaggta agaaggtata tgtgtcccct aagagacaca ccatatatag  11520
ctaagaatca atagataagt atagatcaaa gggctgaata acccctgaat aataacaaaa  11580
tataaaaatc aataaaaatc ataaaataga aaaccataaa cagaagtagt tcaaagggct  11640
ataaaacccc tgaaaagtaa caaaacataa aactaataaa aatcaaatga ataccataat  11700
tggcaatcgg aagagatgta ggtacttaag cttcctaaaa gcagccgaac tcgctttgag  11760
```

atgtaggcgt agcacaccga actcttccat aattctccga acccacaggg acgtaggaga 11820
tgttcaaagt ggctataaaa ccctgaacag taataaaaca taaaattaat aaggatcaaa 11880
tgagtaccat aattggcaaa cggaagagat gtaggtactt aagcttccta aaagcagccg 11940
aactcacttt gagatgtagg catagcatac cgaactcttc cacaattctc cgtacccata 12000
gggacgtagg agatgttatt ttgtttttaa tatttcaaaa aaaaaaaaaa aaaaaaaaaa 12060
aaagcggccg cttaattaat cgaggggaat taattcttga agacgaaagg gccaggtggc 12120
acttttcggg gaaatgtgcg cggaacccct atttgtttat ttttctaaat acattcaaat 12180
atgtatccgc tcatgagaca ataaccctga taaatgcttc aataatattg aaaaaggaag 12240
agtatgagta ttcaacattt ccgtgtcgcc cttattccct tttttgcggc attttgcctt 12300
cctgtttttg ctcacccaga aacgctggtg aaagtaaaag atgctgaaga tcagttgggt 12360
gcacgagtgg gttacatcga actggatctc aacagcggta agatccttga gagttttcgc 12420
cccgaagaac gttttccaat gatgagcact tttaaagttc tgctatgtgg cgcggtatta 12480
tcccgtgttg acgccgggca agagcaactc ggtcgccgca tacactattc tcagaatgac 12540
ttggttgagt actcaccagt cacagaaaag catcttacgg atggcatgac agtaagagaa 12600
ttatgcagtg ctgccataac catgagtgat aacactgcgg ccaacttact tctgacaacg 12660
atcggaggac cgaaggagct aaccgctttt ttgcacaaca tgggggatca tgtaactcgc 12720
cttgatcgtt gggaaccgga gctgaatgaa gccataccaa acgacgagcg tgacaccacg 12780
atgcctgtag caatggcaac aacgttgcgc aaactattaa ctggcgaact acttactcta 12840
gcttcccggc aacaattaat agactggatg gaggcggata aagttgcagg accacttctg 12900
cgctcggccc ttccggctgg ctggtttatt gctgataaat ctggagccgg tgagcgtggg 12960
tctcgcggta tcattgcagc actggggcca gatggtaagc cctcccgtat cgtagttatc 13020
tacacgacgg ggagtcaggc aactatggat gaacgaaata gacagatcgc tgagataggt 13080
gcctcactga ttaagcattg gtaactgtca gaccaagttt actcatatat actttagatt 13140
gatttaaaac ttcattttta atttaaaagg atctaggtga agatcctttt tgataatctc 13200
atgaccaaaa tcccttaacg tgagttttcg ttccactgag cgtcagaccc cgtagaaaag 13260
atcaaaggat cttcttgaga tccttttttt ctgcgcgtaa tctgctgctt gcaaacaaaa 13320
aaaccaccgc taccagcggt ggtttgtttg ccggatcaag agctaccaac tctttttccg 13380
aaggtaactg gcttcagcag agcgcagata ccaaatactg tccttctagt gtagccgtag 13440
ttaggccacc acttcaagaa ctctgtagca ccgcctacat acctcgctct gctaatcctg 13500
ttaccagtgg ctgctgccag tggcgataag tcgtgtctta ccgggttgga ctcaagacga 13560
tagttaccgg ataaggcgca gcggtcgggc tgaacggggg gttcgtgcac acagcccagc 13620
ttggagcgaa cgacctacac cgaactgaga tacctacagc gtgagctatg agaaagcgcc 13680
acgcttcccg aagggagaaa ggcggacagg tatccggtaa gcggcagggt cggaacagga 13740
gagcgcacga gggagcttcc agggggaaac gcctggtatc tttatagtcc tgtcgggttt 13800
cgccacctct gacttgagcg tcgatttttg tgatgctcgt caggggggcg gagcctatgg 13860
aaaaacgcca gcaacgcgag ctcctggatt taggtgacac tatag 13905

<210> SEQ ID NO 67
<211> LENGTH: 4006
<212> TYPE: DNA
<213> ORGANISM: Artificial Sequence
<220> FEATURE:

<223> OTHER INFORMATION: plasmid

<400> SEQUENCE: 67

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tcgtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt acttaatacg actcactata ggctagcctc gagaattcac gcgtggtacc   1080
tctagagtcg acccgggcgg ccgcttcgag cagacatgat aagatacatt gatgagtttg   1140
gacaaaccac aactagaatg cagtgaaaaa aatgctttat ttgtgaaatt tgtgatgcta   1200
ttgctttatt tgtaaccatt ataagctgca ataaacaagt taacaacaac aattgcattc   1260
attttatgtt tcaggttcag ggggagatgt gggaggtttt ttaaagcaag taaaacctct   1320
acaaatgtgg taaaatcgat aaggatccgg gctggcgtaa tagcgaagag gcccgcaccg   1380
atcgcccttc ccaacagttg cgcagcctga atggcgaatg gacgcgccct gtagcggcgc   1440
attaagcgcg gcgggtgtgg tggttacgcg cagcgtgacc gctacacttg ccagcgccct   1500
agcgcccgct cctttcgctt tcttcccttc ctttctcgcc acgttcgccg gctttccccg   1560
tcaagctcta aatcgggggc tccctttagg gttccgattt agtgctttac ggcacctcga   1620
ccccaaaaaa cttgattagg gtgatggttc acgtagtggg ccatcgccct gatagacggt   1680
ttttcgccct ttgacgttgg agtccacgtt ctttaatagt ggactcttgt tccaaactgg   1740
aacaacactc aaccctatct cggtctattc ttttgattta taagggattt tgccgatttc   1800
ggcctattgg ttaaaaaatg agctgattta acaaaaattt aacgcgaatt ttaacaaaat   1860
attaacgctt acaatttcct gatgcggtat tttctcctta cgcatctgtg cggtatttca   1920
caccgcatat ggtgcactct cagtacaatc tgctctgatg ccgcatagtt aagccagccc   1980
cgacacccgc caacacccgc tgacgcgccc tgacgggctt gtctgctccc ggcatccgct   2040
tacagacaag ctgtgaccgt ctccgggagc tgcatgtgtc agaggttttc accgtcatca   2100
ccgaaacgcg cgagacgaaa gggcctcgtg atacgcctat ttttataggt taatgtcatg   2160
ataataatgg tttcttagac gtcaggtggc acttttcggg gaaatgtgcg cggaacccct   2220
atttgtttat ttttctaaat acattcaaat atgtatccgc tcatgagaca ataaccctga   2280
```

taaatgcttc aataatattg aaaaaggaag agtatgagta ttcaacattt ccgtgtcgcc 2340
cttattccct tttttgcggc attttgcctt cctgtttttg ctcacccaga aacgctggtg 2400
aaagtaaaag atgctgaaga tcagttgggt gcacgagtgg gttacatcga actggatctc 2460
aacagcggta agatccttga gagttttcgc cccgaagaac gttttccaat gatgagcact 2520
tttaaagttc tgctatgtgg cgcggtatta tcccgtattg acgccgggca agagcaactc 2580
ggtcgccgca tacactattc tcagaatgac ttggttgagt actcaccagt cacagaaaag 2640
catcttacgg atggcatgac agtaagagaa ttatgcagtg ctgccataac catgagtgat 2700
aacactgcgg ccaacttact tctgacaacg atcggaggac cgaaggagct aaccgctttt 2760
ttgcacaaca tgggggatca tgtaactcgc cttgatcgtt gggaaccgga gctgaatgaa 2820
gccataccaa acgacgagcg tgacaccacg atgcctgtag caatggcaac aacgttgcgc 2880
aaactattaa ctggcgaact acttactcta gcttcccggc aacaattaat agactggatg 2940
gaggcggata aagttgcagg accacttctg cgctcggccc ttccggctgg ctggtttatt 3000
gctgataaat ctggagccgg tgagcgtggg tctcgcggta tcattgcagc actggggcca 3060
gatggtaagc cctcccgtat cgtagttatc tacacgacgg ggagtcaggc aactatggat 3120
gaacgaaata gacagatcgc tgagataggt gcctcactga ttaagcattg gtaactgtca 3180
gaccaagttt actcatatat actttagatt gatttaaaac ttcattttta atttaaaagg 3240
atctaggtga agatcctttt tgataatctc atgaccaaaa tcccttaacg tgagttttcg 3300
ttccactgag cgtcagaccc cgtagaaaag atcaaaggat cttcttgaga tccttttttt 3360
ctgcgcgtaa tctgctgctt gcaaacaaaa aaaccaccgc taccagcggt ggtttgtttg 3420
ccggatcaag agctaccaac tctttttccg aaggtaactg gcttcagcag agcgcagata 3480
ccaaatactg ttcttctagt gtagccgtag ttaggccacc acttcaagaa ctctgtagca 3540
ccgcctacat acctcgctct gctaatcctg ttaccagtgg ctgctgccag tggcgataag 3600
tcgtgtctta ccgggttgga ctcaagacga tagttaccgg ataaggcgca gcggtcgggc 3660
tgaacggggg gttcgtgcac acagcccagc ttggagcgaa cgacctacac cgaactgaga 3720
tacctacagc gtgagctatg agaaagcgcc acgcttcccg aagggagaaa ggcggacagg 3780
tatccggtaa gcggcagggt cggaacagga gagcgcacga gggagcttcc agggggaaac 3840
gcctggtatc tttatagtcc tgtcgggttt cgccacctct gacttgagcg tcgatttttg 3900
tgatgctcgt caggggggcg gagcctatgg aaaaacgcca gcaacgcggc ctttttacgg 3960
ttcctggcct tttgctggcc ttttgctcac atggctcgac agatct 4006

<210> SEQ ID NO 68
<211> LENGTH: 14011
<212> TYPE: DNA
<213> ORGANISM: Artificial Sequence
<220> FEATURE:
<223> OTHER INFORMATION: plasmid

<400> SEQUENCE: 68
tactcgtaaa gcgagttgaa ggatcatatt tagttgcgtt tatgagataa gattgaaagc 60
acgtgtaaaa tgtttcccgc gcgttggcac aactatttac aatgcggcca agttataaaa 120
gattctaatc tgatatgttt taaaacacct ttgcggcccg agttgtttgc gtacgtgact 180
agcgaagaag atgtgtggac cgcagaacag atagtaaaac aaaaccctag tattggagca 240
ataatcgatt taaccaacac gtctaaatat tatgatggtg tgcatttttt gcgggcgggc 300

```
ctgttataca aaaaaattca agtacctggc cagactttgc cgcctgaaag catagttcaa        360

gaatttattg acacggtaaa agaatttaca gaaaagtgtc ccggcatgtt ggtgggcgtg        420

cactgcacac acggtattaa tcgcaccggt tacatggtgt gcagatattt aatgcacacc        480

ctgggtattg cgccgcagga agccatagat agattcgaaa aagccagagg tcacaaaatt        540

gaaagacaaa attacgttca agatttatta atttaattaa tattatttgc attctttaac        600

aaatacttta tcctattttc aaattgttgc gcttcttcca gcgaaccaaa actatgcttc        660

gcttgctccg tttagcttgt agccgatcag tggcgttgtt ccaatcgacg gtaggattag        720

gccggatatt ctccaccaca atgttggcaa cgttgatgtt acgtttatgc ttttggtttt        780

ccacgtacgt cttttggccg gtaatagccg taaacgtagt gccgtcgcgc gtcacgcaca        840

acaccggatg tttgcgcttg tccgcggggt attgaaccgc gcgatccgac aaatccacca        900

cttttggcaac taaatcggtg acctgcgcgt cttttttctg cattatttcg tctttctttt        960

gcatggtttc ctggaagccg gtgtacatgc ggtttagatc agtcatgacg cgcgtgacct       1020

gcaaatcttt ggcctcgatc tgcttgtcct tgatggcaac gatgcgttca ataaactctt       1080

gttttttaac aagttcctcg gttttttgcg ccaccaccgc ttgcagcgcg tttgtgtgct       1140

cggtgaatgt cgcaatcagc ttagtcacca actgtttgct ctcctcctcc cgttgtttga       1200

tcgcgggatc gtacttgccg gtgcagagca cttgaggaat tacttcttct aaaagccatt       1260

cttgtaattc tatggcgtaa ggcaatttgg acttcataat cagctgaatc acgccggatt       1320

tagtaatgag cactgtatgc ggctgcaaat acagcgggtc gccccttttc acgacgctgt       1380

tagaggtagg gccccccattt tggatggtct gctcaaataa cgatttgtat ttattgtcta       1440

catgaacacg tatagcttta tcacaaactg tatattttaa actgttagcg acgtccttgg       1500

ccacgaaccg gacctgttgg tcgcgctcta gcacgtaccg caggttgaac gtatcttctc       1560

caaatttaaa ttctccaatt ttaacgcgag ccattttgat acacgtgtgt cgattttgca       1620

acaactattg ttttttaacg caaactaaac ttattgtggt aagcaataat taaatatggg       1680

ggaacatgcg ccgctacaac actcgtcgtt atgaacgcag acggcgccgg tctcggcgca       1740

agcggctaaa acgtgttgcg cgttcaacgc ggcaaacatc gcaaaagcca atagtacagt       1800

tttgatttgc atattaacgg cgatttttta aattatctta tttaataaat agttatgacg       1860

cctacaactc cccgcccgcg ttgactcgct gcacctcgag cagttcgttg acgccttcct       1920

ccgtgtggcc gaacacgtcg agcgggtggt cgatgaccag cggcgtgccg cacgcgacgc       1980

acaagtatct gtacaccgaa tgatcgtcgg gcgaaggcac gtcggcctcc aagtggcaat       2040

attggcaaat tcgaaaatat atacagttgg gttgtttgcg catatctatc gtggcgttgg       2100

gcatgtacgt ccgaacgttg atttgcatgc aagccgaaat taaatcattg cgattagtgc       2160

gattaaaacg ttgtacatcc tcgcttttaa tcatgccgtc gattaaatcg cgcaatcgag       2220

tcaagtgatc aaagtgtgga ataatgtttt ctttgtattc ccgagtcaag cgcagcgcgt       2280

atttttaacaa actagccatc ttgtaagtta gtttcattta atgcaacttt atccaataat       2340

atattatgta tcgcacgtca agaattaaca atgcgcccgt tgtcgcatct caacacgact       2400

atgatagaga tcaaataaag cgcgaattaa atagcttgcg acgcaacgtg cacgatctgt       2460

gcacgcgttc cggcacgagc tttgattgta ataagttttt acgaagcgat gacatgaccc       2520

ccgtagtgac aacgatcacg cccaaaagaa ctgccgacta caaaattacc gagtatgtcg       2580

gtgacgttaa aactattaag ccatccaatc gaccgttagt cgaatcagga ccgctggtgc       2640

gagaagccgc gaagtatggc gaatgcatcg tataacgtgt ggagtccgct cattagagcg       2700
```

-continued

```
tcatgtttag acaagaaagc tacatattta attgatcccg atgattttat tgataaattg   2760
accctaactc catacacggt attctacaat ggcggggttt tggtcaaaat ttccggactg   2820
cgattgtaca tgctgttaac ggctccgccc actattaatg aaattaaaaa ttccaatttt   2880
aaaaaacgca gcaagagaaa catttgtatg aaagaatgcg tagaaggaaa gaaaaatgtc   2940
gtcgacatgc tgaacaacaa gattaatatg cctccgtgta taaaaaaaat attgaacgat   3000
ttgaaagaaa acaatgtacc gcgcggcggt atgtacagga agaggtttat actaaactgt   3060
tacattgcaa acgtggtttc gtgtgccaag tgtgaaaacc gatgtttaat caaggctctg   3120
acgcatttct acaaccacga ctccaagtgt gtgggtgaag tcatgcatct tttaatcaaa   3180
tcccaagatg tgtataaacc accaaactgc caaaaaatga aaactgtcga caagctctgt   3240
ccgtttgctg gcaactgcaa gggtctcaat cctatttgta attattgaat aataaaacaa   3300
ttataaatgc taaatttgtt ttttattaac gatacaaacc aaacgcaaca agaacatttg   3360
tagtattatc tataattgaa aacgcgtagt tataatcgct gaggtaatat ttaaaatcat   3420
tttcaaatga ttcacagtta atttgcgaca atataatttt attttcacat aaactagacg   3480
ccttgtcgtc ttcttcttcg tattccttct ctttttcatt tttctcctca taaaaattaa   3540
catagttatt atcgtatcca tatatgtatc tatcgtatag agtaaatttt ttgttgtcat   3600
aaatatatat gtctttttta atggggtgta tagtaccgct gcgcatagtt tttctgtaat   3660
ttacaacagt gctattttct ggtagttctt cggagtgtgt tgctttaatt attaaattta   3720
tataatcaat gaatttggga tcgtcggttt tgtacaatat gttgccggca tagtacgcag   3780
cttcttctag ttcaattaca ccattttttta gcagcaccgg attaacataa ctttccaaaa   3840
tgttgtacga accgttaaac aaaaacagtt cacctccctt ttctatacta ttgtctgcga   3900
gcagttgttt gttgttaaaa ataacagcca ttgtaatgag acgcacaaac taatatcaca   3960
aactggaaat gtctatcaat atatagttgc tgatatcaga tccagacatg ataagataca   4020
ttgatgagtt tggacaaacc acaactagaa tgcagtgaaa aaaatgcttt atttgtgaaa   4080
tttgtgatgc tattgcttta tttgtaacca ttataagctg caataaacaa gttaacaaca   4140
acaattgcat tcattttatg tttcaggttc agggggaggt gtgggaggtt ttttaaagca   4200
agtaaaacct ctacaaatgt ggtatggctg attatgatcc tctagagtcg agatcccccct   4260
cgcccggtta ttattatttt tgacaccaga ccaactggta atggtagcga ccggcgctca   4320
gctggaattc cgccgatact gacgggctcc aggagtcgtc gccaccaatc cccatatgga   4380
aaccgtcgat attcagccat gtgccttctt ccgcgtgcag cagatggcga tggctggttt   4440
ccatcagttg ctgttgactg tagcggctga tgttgaactg gaagtcgccg cgccactggt   4500
gtgggccata attcaattcg cgcgtcccgc agcgcagacc gttttcgctc gggaagacgt   4560
acggggtata catgtctgac aatggcagat cccagcggtc aaaacaggcg gcagtaaggc   4620
ggtcgggata gttttcttgc ggccctaatc cgagccagtt tacccgctct gctacctgcg   4680
ccagctggca gttcaggcca atccgcgccg gatgcggtgt atcgctcgcc acttcaacat   4740
caacggtaat cgccatttga ccactaccat caatccggta ggttttccgg ctgataaata   4800
aggttttccc ctgatgctgc cacgcgtgag cggtcgtaat cagcaccgca tcagcaagtg   4860
tatctgccgt gcactgcaac aacgctgctt cggcctggta atggcccgcc gccttccagc   4920
gttcgaccca ggcgttaggg tcaatgcggg tcgcttcact tacgccaatg tcgttatcca   4980
gcggtgcacg ggtgaactga tcgcgcagcg gcgtcagcag ttgtttttta tcgccaatcc   5040
```

acatctgtga aagaaagcct gactggcggt taaattgcca acgcttatta cccagctcga 5100
tgcaaaaatc catttcgctg gtggtcagat gcgggatggc gtgggacgcg gcggggagcg 5160
tcacactgag gttttccgcc agacgccact gctgccaggc gctgatgtgc ccggcttctg 5220
accatgcggt cgcgttcggt tgcactacgc gtactgtgag ccagagttgc ccggcgctct 5280
ccggctgcgg tagttcaggc agttcaatca actgtttacc ttgtggagcg acatccagag 5340
gcacttcacc gcttgccagc ggcttaccat ccagcgccac catccagtgc aggagctcgt 5400
tatcgctatg acggaacagg tattcgctgg tcacttcgat ggtttgcccg gataaacgga 5460
actggaaaaa ctgctgctgg tgttttgctt ccgtcagcgc tggatgcggc gtgcggtcgg 5520
caaagaccag accgttcata cagaactggc gatcgttcgg cgtatcgcca aaatcaccgc 5580
cgtaagccga ccacgggttg ccgttttcat catatttaat cagcgactga tccacccagt 5640
cccagacgaa gccgccctgt aaacggggat actgacgaaa cgcctgccag tatttagcga 5700
aaccgccaag actgttaccc atcgcgtggg cgtattcgca aaggatcagc gggcgcgtct 5760
ctccaggtag cgaaagccat tttttgatgg accatttcgg cacagccggg aagggctggt 5820
cttcatccac gcgcgcgtac atcgggcaaa taatatcggt ggccgtggtg tcggctccgc 5880
cgccttcata ctgcaccggg cgggaaggat cgacagattt gatccagcga tacagcgcgt 5940
cgtgattagc gccgtggcct gattcattcc ccagcgacca gatgatcaca ctcgggtgat 6000
tacgatcgcg ctgcaccatt cgcgttacgc gttcgctcat cgccggtagc cagcgcggat 6060
catcggtcag acgattcatt ggcaccatgc cgtgggtttc aatattggct tcatccacca 6120
catacaggcc gtagcggtcg cacagcgtgt accacagcgg atggttcgga taatgcgaac 6180
agcgcacggc gttaaagttg ttctgcttca tcagcaggat atcctgcacc atcgtctgct 6240
catccatgac ctgaccatgc agaggatgat gctcgtgacg gttaacgcct cgaatcagca 6300
acggcttgcc gttcagcagc agcagaccat tttcaatccg cacctcgcgg aaaccgacat 6360
cgcaggcttc tgcttcaatc agcgtgccgt cggcggtgtg cagttcaacc accgcacgat 6420
agagattcgg gatttcggcg ctccacagtt tcgggttttc gacgttcaga cgtagtgtga 6480
cgcgatcggc ataaccacca cgctcatcga taatttcacc gccgaaaggc gcggtgccgc 6540
tggcgacctg cgtttcaccc tgccataaag aaactgttac ccgtaggtag tcacgcaact 6600
cgccgcacat ctgaacttca gcctccagta cagcgcggct gaaatcatca ttaaagcgag 6660
tggcaacatg gaaatcgctg atttgtgtag tcggtttatg cagcaacgag acgtcacgga 6720
aaatgccgct catccgccac atatcctgat cttccagata actgccgtca ctccaacgca 6780
gcaccatcac cgcgaggcgg ttttctccgg cgcgtaaaaa tgcgctcagg tcaaattcag 6840
acggcaaacg actgtcctgg ccgtaaccga cccagcgccc gttgcaccac agatgaaacg 6900
ccgagttaac gccatcaaaa ataattcgcg tctggccttc ctgtagccag ctttcatcaa 6960
cattaaatgt gagcgagtaa caacccgtcg gattctccgt gggaacaaac ggcggattga 7020
ccgtaatggg ataggttacg ttggtgtaga tgggcgcatc gtaaccgtgc atctgccagt 7080
ttgaggggac gacgacagta tcggcctcag gaagatcgca ctccagccag ctttccggca 7140
ccgcttctgg tgccggaaac caggcaaagc gccattcgcc attcaggctg cgcaactgtt 7200
gggaagggcg atcggtgcgg gcctcttcgc tattacgcca gctggcgaaa gggggatgtg 7260
ctgcaaggcg attaagttgg gtaacgccag ggttttccca gtcacgacgt tgtaaaacga 7320
cgggatctat catgattgta aataaaatgt aatttacagt atagtatttt aattaatata 7380
caaatgattt gataataatt cttatttaac tataatatat tgtgttgggt tgaattaaag 7440

-continued

```
gtcccggcat cctcaaatgc ataatttcat agtccccctt gttgtaagtg atgcgtattt   7500
ctgaatcttt gtaaaatagc acacaagact ccaacgcgtt tggcgtttta ttttcttgct   7560
cgaggatatc atggagataa ttaaaatgat aaccatctcg caaataaata agtattttac   7620
tgttttcgta acagttttgt aataaaaaaa cctataaata ttccggatta ttcataccgt   7680
cccaccatcg ggcgtgctag catcatgaaa ttcttagtca acgttgccct tgtttttatg   7740
gtcgtgtaca tttcttacat ctatgcggac ccaagcccgg gcggccgcta ctaggatcct   7800
ttcctgggac ccggcaagaa ccaaaaactc actctcttca aggaaatccg taatgttaaa   7860
cccgacacga tgaagcttgt cgttggatgg aaaggaaaag agttctacag ggaaacttgg   7920
acccgcttca tggaagacag cttccccatt gttaacgacc aagaagtgat ggatgttttc   7980
cttgttgtca acatgcgtcc cactagaccc aaccgttgtt acaaattcct ggcccaacac   8040
gctctgcgtt gcgaccccga ctatgtacct catgacgtga ttaggatcgt cgagccttca   8100
tgggtgggca gcaacaacga gtaccgcatc agcctggcta agaagggcgg cggctgccca   8160
ataatgaacc ttcactctga gtacaccaac tcgttcgaac agttcatcga tcgtgtcatc   8220
tgggagaact tctacaagcc catcgtttac atcggtaccg actctgctga agaggaggaa   8280
attctccttg aagtttccct ggtgttcaaa gtaaaggagt ttgcaccaga cgcacctctg   8340
ttcactggtc cggcgtatta aaacacgata cattgttatt agtacattta ttaagcgcta   8400
gattctgtgc gttgttgatt tacagacaat tgttgtacgt attttaataa ttcattaaat   8460
ttataatctt tagggtggta tgttagagcg aaaatcaaat gattttcagc gtctttatat   8520
ctgaatttaa atattaaatc ctcaatagat ttgtaaaata ggtttcgatt agtttcaaac   8580
aagggttgtt tttccgaacc gatggctgga ctatctaatg gattttcgct caacgccaca   8640
aaacttgcca aatcttgtag cagcaatcta gctttgtcga tattcgtttg tgttttgttt   8700
tgtaataaag gttcgacgtc gttcaaaata ttatgcgctt ttgtatttct ttcatcactg   8760
tcgttagtgt acaattgact cgacgtaaac acgttaaata aagcttggac atatttaaca   8820
tcgggcgtgt tagctttatt aggccgatta tcgtcgtcgt cccaaccctc gtcgttagaa   8880
gttgcttccg aagacgattt tgccatagcc acacgacgcc tattaattgt gtcggctaac   8940
acgtccgcga tcaaatttgt agttgagctt tttggaatta tttctgattg cgggcgtttt   9000
tgggcgggtt tcaatctaac tgtgcccgat tttaattcag acaacacgtt agaaagcgat   9060
ggtgcaggcg gtggtaacat ttcagacggc aaatctacta atggcggcgg tggtggagct   9120
gatgataaat ctaccatcgg tggaggcgca ggcggggctg gcggcggagg cggaggcgga   9180
ggtggtggcg gtgatgcaga cggcggttta ggctcaaatg tctctttagg caacacagtc   9240
ggcacctcaa ctattgtact ggtttcgggc gccgtttttg gtttgaccgg tctgagacga   9300
gtgcgatttt tttcgtttct aatagcttcc aacaattgtt gtctgtcgtc taaaggtgca   9360
gcgggttgag gttccgtcgg cattggtgga gcgggcggca attcagacat cgatggtggt   9420
ggtggtggtg gaggcgctgg aatgttaggc acgggagaag gtggtggcgg cggtgccgcc   9480
ggtataattt gttctggttt agtttgttcg cgcacgattg tgggcaccgg cgcaggcgcc   9540
gctggctgca caacggaagg tcgtctgctt cgaggcagcg cttggggtgg tggcaattca   9600
atattataat tggaatacaa atcgtaaaaa tctgctataa gcattgtaat ttcgctatcg   9660
tttaccgtgc cgatatttaa caaccgctca atgtaagcaa ttgtattgta aagagattgt   9720
ctcaagctcc gcacgccgat aacaagcctt ttcattttta ctacagcatt gtagtggcga   9780
```

```
gacacttcgc tgtcgtcgac gtacatgtat gctttgttgt caaaaacgtc gttggcaagc   9840
tttaaaatat ttaaaagaac atctctgttc agcaccactg tgttgtcgta aatgttgttt   9900
ttgataattt gcgcttccgc agtatcgaca cgttcaaaaa attgatgcgc atcaattttg   9960
ttgttcctat tattgaataa ataagattgt acagattcat atctacgatt cgtcatggcc  10020
accacaaatg ctacgctgca aacgctggta caattttacg aaaactgcaa aaacgtcaaa  10080
actcggtata aaataatcaa cgggcgcttt ggcaaaatat ctattttatc gcacaagccc  10140
actagcaaat tgtatttgca gaaaacaatt tcggcgcaca attttaacgc tgacgaaata  10200
aaagttcacc agttaatgag cgaccaccca aattttataa aaatctattt taatcacggt  10260
tccatcaaca accaagtgat cgtgatggac tacattgact gtcccgattt atttgaaaca  10320
ctacaaatta aaggcgagct ttcgtaccaa cttgttagca atattattag acagctgtgt  10380
gaagcgctca acgatttgca caagcacaat ttcatacaca acgacataaa actcgaaaat  10440
gtcttatatt tcgaagcact tgatcgcgtg tatgtttgcg attacggatt gtgcaaacac  10500
gaaaactcac ttagcgtgca cgacggcacg ttggagtatt ttagtccgga aaaaattcga  10560
cacacaacta tgcacgtttc gtttgactgg tacgcggcgt gttaacatac aagttgctaa  10620
ccggcggccg acacccattt gaaaaaaagcg aagacgaaat gttggacttg aatagcatga  10680
agcgtcgtca gcaatacaat gacattggcg ttttaaaaca cgttcgtaac gttaacgctc  10740
gtgactttgt gtactgccta acaagataca acatagattg tagactcaca aattacaaac  10800
aaattataaa acatgagttt ttgtcgtaaa aatgccactt gttttacgag tagaattacg  10860
cgccctgtag cggcgcatta agcgcggcgg gtgtggtggt tacgcgcagc gtgaccgcta  10920
cacttgccag cgccctagcg cccgctcctt tcgctttctt cccttccttt ctcgccacgt  10980
tcgccggctt tccccgtcaa gctctaaatc gggggctccc tttagggttc cgatttagtg  11040
ctttacggca cctcgacccc aaaaaacttg attagggtga tggttcacgt agtgggccat  11100
cgccctgata gacggttttt cgccctttga cgttggagtc cacgttcttt aatagtggac  11160
tcttgttcca aactggaaca acactcaacc ctatctcggt ctattctttt gatttataag  11220
ggattttgcc gatttcggcc tattggttaa aaaatgagct gatttaacaa aaatttaacg  11280
cgaattttaa caaaatatta acgtttacaa tttaaatatt tgcttataca atcttcctgt  11340
ttttggggct tttctgatta tcaaccgggg taattcgtaa tcatggtcat agctgtttcc  11400
tgtgtgaaat tgttatccgc tcacaattcc acacaacata cgagccggaa gcataaagtg  11460
taaagcctgg ggtgcctaat gagtgagcta actcacatta attgcgttgc gctcactgcc  11520
cgctttccag tcgggaaacc tgtcgtgcca gctgcattaa tgaatcggcc aacgcgcggg  11580
gagaggcggt ttgcgtattg ggcgctcttc cgcttcctcg ctcactgact cgctgcgctc  11640
ggtcgttcgg ctgcggcgag cggtatcagc tcactcaaag gcggtaatac ggttatccac  11700
agaatcaggg gataacgcag gaaagaacat gtgagcaaaa ggccagcaaa aggccaggaa  11760
ccgtaaaaag gccgcgttgc tggcgttttt ccataggctc cgcccccctg acgagcatca  11820
caaaaatcga cgctcaagtc agaggtggcg aaacccgaca ggactataaa gataccaggc  11880
gtttccccct ggaagctccc tcgtgcgctc tcctgttccg accctgccgc ttaccggata  11940
cctgtccgcc tttctccctt cgggaagcgt ggcgctttct catagctcac gctgtaggta  12000
tctcagttcg gtgtaggtcg ttcgctccaa gctgggctgt gtgcacgaac cccccgttca  12060
gcccgaccgc tgcgccttat ccggtaacta tcgtcttgag tccaacccgg taagacacga  12120
cttatcgcca ctggcagcag ccactggtaa caggattagc agagcgaggt atgtaggcgg  12180
```

tgctacagag ttcttgaagt ggtggcctaa ctacggctac actagaagga cagtatttgg 12240
tatctgcgct ctgctgaagc cagttacctt cggaaaaaga gttggtagct cttgatccgg 12300
caaacaaacc accgctggta gcggtggttt ttttgtttgc aagcagcaga ttacgcgcag 12360
aaaaaaagga tctcaagaag atcctttgat cttttctacg gggtctgacg ctcagtggaa 12420
cgaaaactca cgttaaggga ttttggtcat gagattatca aaaaggatct tcacctagat 12480
ccttttaaat taaaaatgaa gttttaaatc aatctaaagt atatatgagt aaacttggtc 12540
tgacagttac caatgcttaa tcagtgaggc acctatctca gcgatctgtc tatttcgttc 12600
atccatagtt gcctgactcc ccgtcgtgta gataactacg atacgggagg gcttaccatc 12660
tggccccagt gctgcaatga taccgcgaga cccacgctca ccggctccag atttatcagc 12720
aataaaccag ccagccggaa gggccgagcg cagaagtggt cctgcaactt tatccgcctc 12780
catccagtct attaattgtt gccgggaagc tagagtaagt agttcgccag ttaatagttt 12840
gcgcaacgtt gttgccattg ctacaggcat cgtggtgtca cgctcgtcgt ttggtatggc 12900
ttcattcagc tccggttccc aacgatcaag gcgagttaca tgatccccca tgttgtgcaa 12960
aaaagcggtt agctccttcg gtcctccgat cgttgtcaga agtaagttgg ccgcagtgtt 13020
atcactcatg gttatggcag cactgcataa ttctcttact gtcatgccat ccgtaagatg 13080
cttttctgtg actggtgagt actcaaccaa gtcattctga gaatagtgta tgcggcgacc 13140
gagttgctct tgcccggcgt caatacggga taataccgcg ccacatagca gaactttaaa 13200
agtgctcatc attggaaaac gttcttcggg gcgaaaactc tcaaggatct taccgctgtt 13260
gagatccagt tcgatgtaac ccactcgtgc acccaactga tcttcagcat cttttacttt 13320
caccagcgtt tctgggtgag caaaaacagg aaggcaaaat gccgcaaaaa agggaataag 13380
ggcgacacgg aaatgttgaa tactcatact cttccttttt caatattatt gaagcattta 13440
tcagggttat tgtctcatga gcggatacat atttgaatgt atttagaaaa ataaacaaat 13500
aggggttccg cgcacatttc cccgaaaagt gccacctgac gtctaagaaa ccattattat 13560
catgacatta acctataaaa ataggcgtat cacgaggccc tttcgtctcg cgcgtttcgg 13620
tgatgacggt gaaaacctct gacacatgca gctcccggag acggtcacag cttgtctgta 13680
agcggatgcc gggagcagac aagcccgtca gggcgcgtca gcgggtgttg gcgggtgtcg 13740
gggctggctt aactatgcgg catcagagca gattgtactg agagtgcacc atatgcggtg 13800
tgaaataccg cacagatgcg taaggagaaa ataccgcatc aggcgccatt cgccattcag 13860
gctgcgcaac tgttgggaag ggcgatcggt gcgggcctct tcgctattac gccagctggc 13920
gaaaggggga tgtgctgcaa ggcgattaag ttgggtaacg ccagggtttt cccagtcacg 13980
acgttgtaaa acgacggcca gtgccaagct t 14011

<210> SEQ ID NO 69
<211> LENGTH: 14180
<212> TYPE: DNA
<213> ORGANISM: Artificial Sequence
<220> FEATURE:
<223> OTHER INFORMATION: plasmid

<400> SEQUENCE: 69
tactcgtaaa gcgagttgaa ggatcatatt tagttgcgtt tatgagataa gattgaaagc 60
acgtgtaaaa tgtttcccgc gcgttggcac aactatttac aatgcggcca agttataaaa 120
gattctaatc tgatatgttt taaaacacct ttgcggcccg agttgtttgc gtacgtgact 180

```
agcgaagaag atgtgtggac cgcagaacag atagtaaaac aaaaccctag tattggagca    240
ataatcgatt taaccaacac gtctaaatat tatgatggtg tgcatttttt gcgggcgggc    300
ctgttataca aaaaaattca agtacctggc cagactttgc cgcctgaaag catagttcaa    360
gaatttattg acacggtaaa agaatttaca gaaaagtgtc ccggcatgtt ggtgggcgtg    420
cactgcacac acggtattaa tcgcaccggt tacatggtgt gcagatattt aatgcacacc    480
ctgggtattg cgccgcagga agccatagat agattcgaaa aagccagagg tcacaaaatt    540
gaaagacaaa attacgttca agatttatta atttaattaa tattatttgc attctttaac    600
aaatacttta tcctattttc aaattgttgc gcttcttcca gcgaaccaaa actatgcttc    660
gcttgctccg tttagcttgt agccgatcag tggcgttgtt ccaatcgacg gtaggattag    720
gccggatatt ctccaccaca atgttggcaa cgttgatgtt acgtttatgc ttttggtttt    780
ccacgtacgt cttttggccg gtaatagccg taaacgtagt gccgtcgcgc gtcacgcaca    840
acaccggatg tttgcgcttg tccgcggggt attgaaccgc gcgatccgac aaatccacca    900
ctttggcaac taaatcggtg acctgcgcgt ctttttttctg cattatttcg tctttctttt    960
gcatggtttc ctggaagccg gtgtacatgc ggtttagatc agtcatgacg cgcgtgacct   1020
gcaaatcttt ggcctcgatc tgcttgtcct tgatggcaac gatgcgttca ataaactctt   1080
gtttttttaac aagttcctcg gtttttttgcg ccaccaccgc ttgcagcgcg tttgtgtgct   1140
cggtgaatgt cgcaatcagc ttagtcacca actgtttgct ctcctcctcc cgttgtttga   1200
tcgcgggatc gtacttgccg gtgcagagca cttgaggaat tacttcttct aaaagccatt   1260
cttgtaattc tatggcgtaa ggcaatttgg acttcataat cagctgaatc acgccggatt   1320
tagtaatgag cactgtatgc ggctgcaaat acagcgggtc gccccttttc acgacgctgt   1380
tagaggtagg gcccccattt tggatggtct gctcaaataa cgatttgtat ttattgtcta   1440
catgaacacg tatagcttta tcacaaactg tatattttaa actgttagcg acgtccttgg   1500
ccacgaaccg gacctgttgg tcgcgctcta gcacgtaccg caggttgaac gtatcttctc   1560
caaatttaaa ttctccaatt ttaacgcgag ccattttgat acacgtgtgt cgattttgca   1620
acaactattg ttttttaacg caaactaaac ttattgtggt aagcaataat taaatatggg   1680
ggaacatgcg ccgctacaac actcgtcgtt atgaacgcag acggcgccgg tctcggcgca   1740
agcggctaaa acgtgttgcg cgttcaacgc ggcaaacatc gcaaaagcca atagtacagt   1800
tttgatttgc atattaacgg cgattttttta aattatctta tttaataaat agttatgacg   1860
cctacaactc cccgcccgcg ttgactcgct gcacctcgag cagttcgttg acgccttcct   1920
ccgtgtggcc gaacacgtcg agcgggtggt cgatgaccag cggcgtgccg cacgcgacgc   1980
acaagtatct gtacaccgaa tgatcgtcgg gcgaaggcac gtcggcctcc aagtggcaat   2040
attggcaaat tcgaaaatat atacagttgg gttgtttgcg catatctatc gtggcgttgg   2100
gcatgtacgt ccgaacgttg atttgcatgc aagccgaaat taaatcattg cgattagtgc   2160
gattaaaacg ttgtacatcc tcgcttttaa tcatgccgtc gattaaatcg cgcaatcgag   2220
tcaagtgatc aaagtgtgga ataatgtttt ctttgtattc ccgagtcaag cgcagcgcgt   2280
attttaacaa actagccatc ttgtaagtta gtttcattta atgcaacttt atccaataat   2340
atattatgta tcgcacgtca agaattaaca atgcgcccgt tgtcgcatct caacacgact   2400
atgatagaga tcaaataaag cgcgaattaa atagcttgcg acgcaacgtg cacgatctgt   2460
gcacgcgttc cggcacgagc tttgattgta ataagttttt acgaagcgat gacatgaccc   2520
ccgtagtgac aacgatcacg cccaaaagaa ctgccgacta caaaattacc gagtatgtcg   2580
```

-continued

```
gtgacgttaa aactattaag ccatccaatc gaccgttagt cgaatcagga ccgctggtgc   2640
gagaagccgc gaagtatggc gaatgcatcg tataacgtgt ggagtccgct cattagagcg   2700
tcatgtttag acaagaaagc tacatattta attgatcccg atgattttat tgataaattg   2760
accctaactc catacacggt attctacaat ggcggggttt tggtcaaaat ttccggactg   2820
cgattgtaca tgctgttaac ggctccgccc actattaatg aaattaaaaa ttccaatttt   2880
aaaaaacgca gcaagagaaa catttgtatg aaagaatgcg tagaaggaaa gaaaaatgtc   2940
gtcgacatgc tgaacaacaa gattaatatg cctccgtgta taaaaaaaat attgaacgat   3000
ttgaaagaaa acaatgtacc gcgcggcggt atgtacagga agaggtttat actaaactgt   3060
tacattgcaa acgtggtttc gtgtgccaag tgtgaaaacc gatgtttaat caaggctctg   3120
acgcatttct acaaccacga ctccaagtgt gtgggtgaag tcatgcatct tttaatcaaa   3180
tcccaagatg tgtataaacc accaaactgc caaaaaatga aaactgtcga caagctctgt   3240
ccgtttgctg gcaactgcaa gggtctcaat cctatttgta attattgaat aataaaacaa   3300
ttataaatgc taaatttgtt ttttattaac gatacaaacc aaacgcaaca agaacatttg   3360
tagtattatc tataattgaa aacgcgtagt tataatcgct gaggtaatat ttaaaatcat   3420
tttcaaatga ttcacagtta atttgcgaca atataatttt attttcacat aaactagacg   3480
ccttgtcgtc ttcttcttcg tattccttct ctttttcatt tttctcctca taaaaattaa   3540
catagttatt atcgtatcca tatatgtatc tatcgtatag agtaaatttt ttgttgtcat   3600
aaatatatat gtcttttttta atggggtgta tagtaccgct gcgcatagtt tttctgtaat   3660
ttacaacagt gctattttct ggtagttctt cggagtgtgt tgctttaatt attaaattta   3720
tataatcaat gaatttggga tcgtcggttt tgtacaatat gttgccggca tagtacgcag   3780
cttcttctag ttcaattaca ccattttttta gcagcaccgg attaacataa ctttccaaaa   3840
tgttgtacga accgttaaac aaaaacagtt cacctccctt ttctatacta ttgtctgcga   3900
gcagttgttt gttgttaaaa ataacagcca ttgtaatgag acgcacaaac taatatcaca   3960
aactggaaat gtctatcaat atatagttgc tgatatcaga tccagacatg ataagataca   4020
ttgatgagtt tggacaaacc acaactagaa tgcagtgaaa aaaatgcttt atttgtgaaa   4080
tttgtgatgc tattgcttta tttgtaacca ttataagctg caataaacaa gttaacaaca   4140
acaattgcat tcattttatg tttcaggttc agggggaggt gtgggaggtt ttttaaagca   4200
agtaaaacct ctacaaatgt ggtatggctg attatgatcc tctagagtcg agatcccccct   4260
cgcccggtta ttattatttt tgacaccaga ccaactggta atggtagcga ccggcgctca   4320
gctggaattc cgccgatact gacgggctcc aggagtcgtc gccaccaatc cccatatgga   4380
aaccgtcgat attcagccat gtgccttctt ccgcgtgcag cagatggcga tggctggttt   4440
ccatcagttg ctgttgactg tagcggctga tgttgaactg gaagtcgccg cgccactggt   4500
gtgggccata attcaattcg cgcgtcccgc agcgcagacc gttttcgctc gggaagacgt   4560
acggggtata catgtctgac aatggcagat cccagcggtc aaaacaggcg gcagtaaggc   4620
ggtcgggata gttttcttgc ggccctaatc cgagccagtt tacccgctct gctacctgcg   4680
ccagctggca gttcaggcca atccgcgccg gatgcggtgt atcgctcgcc acttcaacat   4740
caacggtaat cgccatttga ccactaccat caatccggta ggttttccgg ctgataaata   4800
aggttttccc ctgatgctgc cacgcgtgag cggtcgtaat cagcaccgca tcagcaagtg   4860
tatctgccgt gcactgcaac aacgctgctt cggcctggta atggcccgcc gccttccagc   4920
```

-continued

```
gttcgaccca ggcgttaggg tcaatgcggg tcgcttcact tacgccaatg tcgttatcca   4980
gcggtgcacg ggtgaactga tcgcgcagcg gcgtcagcag ttgtttttta tcgccaatcc   5040
acatctgtga aagaaagcct gactggcggt taaattgcca acgcttatta cccagctcga   5100
tgcaaaaatc catttcgctg gtggtcagat gcgggatggc gtgggacgcg gcggggagcg   5160
tcacactgag gttttccgcc agacgccact gctgccaggc gctgatgtgc ccggcttctg   5220
accatgcggt cgcgttcggt tgcactacgc gtactgtgag ccagagttgc ccggcgctct   5280
ccggctgcgg tagttcaggc agttcaatca actgtttacc ttgtggagcg acatccagag   5340
gcacttcacc gcttgccagc ggcttaccat ccagcgccac catccagtgc aggagctcgt   5400
tatcgctatg acggaacagg tattcgctgg tcacttcgat ggtttgcccg gataaacgga   5460
actggaaaaa ctgctgctgg tgttttgctt ccgtcagcgc tggatgcggc gtgcggtcgg   5520
caaagaccag accgttcata cagaactggc gatcgttcgg cgtatcgcca aaatcaccgc   5580
cgtaagccga ccacgggttg ccgttttcat catatttaat cagcgactga tccacccagt   5640
cccagacgaa gccgccctgt aaacggggat actgacgaaa cgcctgccag tatttagcga   5700
aaccgccaag actgttaccc atcgcgtggg cgtattcgca aaggatcagc gggcgcgtct   5760
ctccaggtag cgaaagccat tttttgatgg accatttcgg cacagccggg aagggctggt   5820
cttcatccac gcgcgcgtac atcgggcaaa taatatcggt ggccgtggtg tcggctccgc   5880
cgccttcata ctgcaccggg cgggaaggat cgacagattt gatccagcga tacagcgcgt   5940
cgtgattagc gccgtggcct gattcattcc ccagcgacca gatgatcaca ctcgggtgat   6000
tacgatcgcg ctgcaccatt cgcgttacgc gttcgctcat cgccggtagc cagcgcggat   6060
catcggtcag acgattcatt ggcaccatgc cgtgggtttc aatattggct tcatccacca   6120
catacaggcc gtagcggtcg cacagcgtgt accacagcgg atggttcgga taatgcgaac   6180
agcgcacggc gttaaagttg ttctgcttca tcagcaggat atcctgcacc atcgtctgct   6240
catccatgac ctgaccatgc agaggatgat gctcgtgacg gttaacgcct cgaatcagca   6300
acggcttgcc gttcagcagc agcagaccat tttcaatccg cacctcgcgg aaaccgacat   6360
cgcaggcttc tgcttcaatc agcgtgccgt cggcggtgtg cagttcaacc accgcacgat   6420
agagattcgg gatttcggcg ctccacagtt tcgggttttc gacgttcaga cgtagtgtga   6480
cgcgatcggc ataaccacca cgctcatcga taatttcacc gccgaaaggc gcggtgccgc   6540
tggcgacctg cgtttcaccc tgccataaag aaactgttac ccgtaggtag tcacgcaact   6600
cgccgcacat ctgaacttca gcctccagta cagcgcggct gaaatcatca ttaaagcgag   6660
tggcaacatg gaaatcgctg atttgtgtag tcggtttatg cagcaacgag acgtcacgga   6720
aaatgccgct catccgccac atatcctgat cttccagata actgccgtca ctccaacgca   6780
gcaccatcac cgcgaggcgg ttttctccgg cgcgtaaaaa tgcgctcagg tcaaattcag   6840
acggcaaacg actgtcctgg ccgtaaccga cccagcgccc gttgcaccac agatgaaacg   6900
ccgagttaac gccatcaaaa ataattcgcg tctggccttc ctgtagccag ctttcatcaa   6960
cattaaatgt gagcgagtaa caacccgtcg gattctccgt gggaacaaac ggcggattga   7020
ccgtaatggg ataggttacg ttggtgtaga tgggcgcatc gtaaccgtgc atctgccagt   7080
ttgaggggac gacgacagta tcggcctcag gaagatcgca ctccagccag ctttccggca   7140
ccgcttctgg tgccggaaac caggcaaagc gccattcgcc attcaggctg cgcaactgtt   7200
gggaagggcg atcggtgcgg gcctcttcgc tattacgcca gctggcgaaa gggggatgtg   7260
ctgcaaggcg attaagttgg gtaacgccag ggttttccca gtcacgacgt tgtaaaacga   7320
```

```
cgggatctat catgattgta aataaaatgt aatttacagt atagtatttt aattaatata   7380
caaatgattt gataataatt cttatttaac tataatatat tgtgttgggt tgaattaaag   7440
gtcccggcat cctcaaatgc ataatttcat agtcccccctt gttgtaagtg atgcgtattt   7500
ctgaatcttt gtaaaatagc acacaagact ccaacgcgtt tggcgtttta ttttcttgct   7560
cgaggatatc atggagataa ttaaaatgat aaccatctcg caaataaata agtattttac   7620
tgttttcgta acagttttgt aataaaaaaa cctataaata ttccggatta ttcataccgt   7680
cccaccatcg ggcgtgctag catcatggtg ggccctgca tgctgctgct gctgctgctg   7740
ctgggcctga ggctacagct ctccctgggc atcatcccag ttgaggagga gaacccggga   7800
aatagtgact ctgaatgtcc cctgtcccac gatgggtact gcctccatga tggtgtgtgc   7860
atgtatattg aagcattgga caagtatgca tgcaactgtg ttgttggtta catcggggag   7920
cgatgtcagt accgagacct gaagtggtgg gaactgcgct gaggatcctt tcctgggacc   7980
cggcaagaac caaaaactca ctctcttcaa ggaaatccgt aatgttaaac ccgacacgat   8040
gaagcttgtc gttggatgga aaggaaaaga gttctacagg gaaacttgga cccgcttcat   8100
ggaagacagc ttccccattg ttaacgacca agaagtgatg gatgttttcc ttgttgtcaa   8160
catgcgtccc actagaccca accgttgtta caaattcctg gcccaacacg ctctgcgttg   8220
cgaccccgac tatgtacctc atgacgtgat taggatcgtc gagccttcat gggtgggcag   8280
caacaacgag taccgcatca gcctggctaa gaagggcggc ggctgcccaa taatgaacct   8340
tcactctgag tacaccaact cgttcgaaca gttcatcgat cgtgtcatct gggagaactt   8400
ctacaagccc atcgtttaca tcggtaccga ctctgctgaa gaggaggaaa ttctccttga   8460
agtttccctg gtgttcaaag taaaggagtt tgcaccagac gcacctctgt tcactggtcc   8520
ggcgtattaa aacacgatac attgttatta gtacatttat taagcgctag attctgtgcg   8580
ttgttgattt acagacaatt gttgtacgta ttttaataat tcattaaatt tataatcttt   8640
agggtggtat gttagagcga aaatcaaatg attttcagcg tctttatatc tgaatttaaa   8700
tattaaatcc tcaatagatt tgtaaaatag gtttcgatta gtttcaaaca agggttgttt   8760
ttccgaaccg atggctggac tatctaatgg attttcgctc aacgccacaa aacttgccaa   8820
atcttgtagc agcaatctag ctttgtcgat attcgtttgt gttttgtttt gtaataaagg   8880
ttcgacgtcg ttcaaaatat tatgcgcttt tgtatttctt tcatcactgt cgttagtgta   8940
caattgactc gacgtaaaca cgttaaataa agcttggaca tatttaacat cgggcgtgtt   9000
agctttatta ggccgattat cgtcgtcgtc ccaaccctcg tcgttagaag ttgcttccga   9060
agacgatttt gccatagcca cacgacgcct attaattgtg tcggctaaca cgtccgcgat   9120
caaatttgta gttgagcttt ttggaattat ttctgattgc gggcgttttt gggcgggttt   9180
caatctaact gtgcccgatt ttaattcaga caacacgtta gaaagcgatg gtgcaggcgg   9240
tggtaacatt tcagacggca aatctactaa tggcggcggt ggtggagctg atgataaatc   9300
taccatcggt ggaggcgcag gcggggctgg cggcggaggc ggaggcggag gtggtggcgg   9360
tgatgcagac ggcggtttag gctcaaatgt ctctttaggc aacacagtcg gcacctcaac   9420
tattgtactg gtttcgggcg ccgtttttgg tttgaccggt ctgagacgag tgcgattttt   9480
ttcgtttcta atagcttcca acaattgttg tctgtcgtct aaaggtgcag cgggttgagg   9540
ttccgtcggc attggtggag cgggcggcaa ttcagacatc gatggtggtg gtggtggtgg   9600
aggcgctgga atgttaggca cgggagaagg tggtggcggc ggtgccgccg gtataatttg   9660
```

-continued

```
ttctggttta gtttgttcgc gcacgattgt gggcaccggc gcaggcgccg ctggctgcac   9720
aacggaaggt cgtctgcttc gaggcagcgc ttggggtggt ggcaattcaa tattataatt   9780
ggaatacaaa tcgtaaaaat ctgctataag cattgtaatt tcgctatcgt ttaccgtgcc   9840
gatatttaac aaccgctcaa tgtaagcaat tgtattgtaa agagattgtc tcaagctccg   9900
cacgccgata acaagccttt tcatttttac tacagcattg tagtggcgag acacttcgct   9960
gtcgtcgacg tacatgtatg ctttgttgtc aaaaacgtcg ttggcaagct ttaaaatatt  10020
taaaagaaca tctctgttca gcaccactgt gttgtcgtaa atgttgtttt tgataatttg  10080
cgcttccgca gtatcgacac gttcaaaaaa ttgatgcgca tcaattttgt tgttcctatt  10140
attgaataaa taagattgta cagattcata tctacgattc gtcatggcca ccacaaatgc  10200
tacgctgcaa acgctggtac aattttacga aaactgcaaa aacgtcaaaa ctcggtataa  10260
aataatcaac gggcgctttg gcaaaatatc tattttatcg cacaagccca ctagcaaatt  10320
gtatttgcag aaaacaattt cggcgcacaa ttttaacgct gacgaaataa aagttcacca  10380
gttaatgagc gaccacccaa attttataaa aatctatttt aatcacggtt ccatcaacaa  10440
ccaagtgatc gtgatggact acattgactg tcccgattta tttgaaacac tacaaattaa  10500
aggcgagctt tcgtaccaac ttgttagcaa tattattaga cagctgtgtg aagcgctcaa  10560
cgatttgcac aagcacaatt tcatacacaa cgacataaaa ctcgaaaatg tcttatattt  10620
cgaagcactt gatcgcgtgt atgtttgcga ttacggattg tgcaaacacg aaaactcact  10680
tagcgtgcac gacggcacgt tggagtattt tagtccggaa aaaattcgac acacaactat  10740
gcacgtttcg tttgactggt acgcggcgtg ttaacataca agttgctaac cggcggccga  10800
cacccatttg aaaaaagcga agacgaaatg ttggacttga atagcatgaa gcgtcgtcag  10860
caatacaatg acattggcgt tttaaaacac gttcgtaacg ttaacgctcg tgactttgtg  10920
tactgcctaa caagatacaa catagattgt agactcacaa attacaaaca aattataaaa  10980
catgagtttt tgtcgtaaaa atgccacttg ttttacgagt agaattacgc gccctgtagc  11040
ggcgcattaa gcgcggcggg tgtggtggtt acgcgcagcg tgaccgctac acttgccagc  11100
gccctagcgc ccgctccttt cgctttcttc ccttcctttc tcgccacgtt cgccggcttt  11160
ccccgtcaag ctctaaatcg ggggctccct ttagggttcc gatttagtgc tttacggcac  11220
ctcgacccca aaaaacttga ttagggtgat ggttcacgta gtgggccatc gccctgatag  11280
acggtttttc gccctttgac gttggagtcc acgttcttta atagtggact cttgttccaa  11340
actggaacaa cactcaaccc tatctcggtc tattcttttg atttataagg gattttgccg  11400
atttcggcct attggttaaa aaatgagctg atttaacaaa aatttaacgc gaattttaac  11460
aaaatattaa cgtttacaat ttaaatattt gcttatacaa tcttcctgtt tttggggctt  11520
ttctgattat caaccggggt aattcgtaat catggtcata gctgtttcct gtgtgaaatt  11580
gttatccgct cacaattcca cacaacatac gagccggaag cataaagtgt aaagcctggg  11640
gtgcctaatg agtgagctaa ctcacattaa ttgcgttgcg ctcactgccc gctttccagt  11700
cgggaaacct gtcgtgccag ctgcattaat gaatcggcca acgcgcgggg agaggcggtt  11760
tgcgtattgg gcgctcttcc gcttcctcgc tcactgactc gctgcgctcg gtcgttcggc  11820
tgcggcgagc ggtatcagct cactcaaagg cggtaatacg gttatccaca gaatcagggg  11880
ataacgcagg aaagaacatg tgagcaaaag gccagcaaaa ggccaggaac cgtaaaaagg  11940
ccgcgttgct ggcgtttttc cataggctcc gcccccctga cgagcatcac aaaaatcgac  12000
gctcaagtca gaggtggcga aacccgacag gactataaag ataccaggcg tttccccctg  12060
```

gaagctccct cgtgcgctct cctgttccga ccctgccgct taccggatac ctgtccgcct 12120
ttctcccttc gggaagcgtg gcgctttctc atagctcacg ctgtaggtat ctcagttcgg 12180
tgtaggtcgt tcgctccaag ctgggctgtg tgcacgaacc ccccgttcag cccgaccgct 12240
gcgccttatc cggtaactat cgtcttgagt ccaacccggt aagacacgac ttatcgccac 12300
tggcagcagc cactggtaac aggattagca gagcgaggta tgtaggcggt gctacagagt 12360
tcttgaagtg gtggcctaac tacggctaca ctagaaggac agtatttggt atctgcgctc 12420
tgctgaagcc agttaccttc ggaaaaagag ttggtagctc ttgatccggc aaacaaacca 12480
ccgctggtag cggtggtttt tttgtttgca agcagcagat tacgcgcaga aaaaaaggat 12540
ctcaagaaga tcctttgatc ttttctacgg ggtctgacgc tcagtggaac gaaaactcac 12600
gttaagggat tttggtcatg agattatcaa aaaggatctt cacctagatc cttttaaatt 12660
aaaaatgaag ttttaaatca atctaaagta tatatgagta aacttggtct gacagttacc 12720
aatgcttaat cagtgaggca cctatctcag cgatctgtct atttcgttca tccatagttg 12780
cctgactccc cgtcgtgtag ataactacga tacgggaggg cttaccatct ggccccagtg 12840
ctgcaatgat accgcgagac ccacgctcac cggctccaga tttatcagca ataaaccagc 12900
cagccggaag ggccgagcgc agaagtggtc ctgcaacttt atccgcctcc atccagtcta 12960
ttaattgttg ccgggaagct agagtaagta gttcgccagt taatagtttg cgcaacgttg 13020
ttgccattgc tacaggcatc gtggtgtcac gctcgtcgtt tggtatggct tcattcagct 13080
ccggttccca acgatcaagg cgagttacat gatcccccat gttgtgcaaa aaagcggtta 13140
gctccttcgg tcctccgatc gttgtcagaa gtaagttggc cgcagtgtta tcactcatgg 13200
ttatggcagc actgcataat tctcttactg tcatgccatc cgtaagatgc ttttctgtga 13260
ctggtgagta ctcaaccaag tcattctgag aatagtgtat gcggcgaccg agttgctctt 13320
gcccggcgtc aatacgggat aataccgcgc cacatagcag aactttaaaa gtgctcatca 13380
ttggaaaacg ttcttcgggg cgaaaactct caaggatctt accgctgttg agatccagtt 13440
cgatgtaacc cactcgtgca cccaactgat cttcagcatc ttttactttc accagcgttt 13500
ctgggtgagc aaaaacagga aggcaaaatg ccgcaaaaaa gggaataagg gcgacacgga 13560
aatgttgaat actcatactc ttcctttttc aatattattg aagcatttat cagggttatt 13620
gtctcatgag cggatacata tttgaatgta tttagaaaaa taaacaaata ggggttccgc 13680
gcacatttcc ccgaaaagtg ccacctgacg tctaagaaac cattattatc atgacattaa 13740
cctataaaaa taggcgtatc acgaggccct ttcgtctcgc gcgtttcggt gatgacggtg 13800
aaaacctctg acacatgcag ctcccggaga cggtcacagc ttgtctgtaa gcggatgccg 13860
ggagcagaca agcccgtcag ggcgcgtcag cgggtgttgg cgggtgtcgg ggctggctta 13920
actatgcggc atcagagcag attgtactga gagtgcacca tatgcggtgt gaaataccgc 13980
acagatgcgt aaggagaaaa taccgcatca ggcgccattc gccattcagg ctgcgcaact 14040
gttgggaagg gcgatcggtg cgggcctctt cgctattacg ccagctggcg aaagggggat 14100
gtgctgcaag gcgattaagt tgggtaacgc cagggttttc ccagtcacga cgttgtaaaa 14160
cgacggccag tgccaagctt 14180

<210> SEQ ID NO 70
<211> LENGTH: 4452
<212> TYPE: DNA
<213> ORGANISM: Artificial Sequence
<220> FEATURE:

<223> OTHER INFORMATION: plasmid

<400> SEQUENCE: 70

```
cacctgacgc gccctgtagc ggcgcattaa gcgcggcggg tgtggtggtt acgcgcagcg     60
tgaccgctac acttgccagc gccctagcgc ccgctccttt cgctttcttc ccttcctttc    120
tcgccacgtt cgccggcttt ccccgtcaag ctctaaatcg ggggctccct ttagggttcc    180
gatttagtgc tttacggcac ctcgacccca aaaaacttga ttagggtgat ggttcacgta    240
gtgggccatc gccctgatag acggtttttc gccctttgac gttggagtcc acgttcttta    300
atagtggact cttgttccaa actggaacaa cactcaaccc tatctcggtc tattcttttg    360
atttataagg gattttgccg atttcggcct attggttaaa aaatgagctg atttaacaaa    420
aatttaacgc gaattttaac aaaatattaa cgcttacaat ttacgcgtta agatacattg    480
atgagtttgg acaaaccaca actagaatgc agtgaaaaaa atgctttatt tgtgaaattt    540
gtgatgctat tgctttattt gtaaccatta taagctgcaa taaacaagtt aacaacaaca    600
attgcattca ttttatgttt caggttcagg gggaggtgtg ggaggttttt taaagcaagt    660
aaaacctcta caaatgtggt atggctgatt atgatcatga acagactgtg aggactgagg    720
ggcctgaaat gagccttggg actgtgaatc taaaatacac aaacaattag aatcagtagt    780
ttaacacatt atacacttaa aaattggatc tccattcgcc attcaggctg cgcaactgtt    840
gggaagggcg atcggtgcgg gcctcttcgc tattacgcca gctggcgaaa gggggatgtg    900
ctgcaaggcg attaagttgg gtaacgccag ggttttccca gtcacgacgt tgtaaaacga    960
cggccagtga attgtaatac gactcactat agggcgaatt gggtacactt acctggtacc   1020
ccacccgggt ggaaaatcga tgggcccgcg gccgctctag aagtactctc gagaagcttt   1080
ttgaattctt tggatccact agtgtcgacc tgcaggcgcg cgagctccag cttttgttcc   1140
ctttagtgag ggttaatttc gagcttggcg taatcaaggt catagctgtt tcctgtgtga   1200
aattgttatc cgctcacaat tccacacaat atacgagccg gaagtataaa gtgtaaagcc   1260
tggggtgcct aatgagtgag ctaactcaca gtaattgcgg ctagccaggt gcacaccaat   1320
gtggtgaatg gtcaaatggc gtttattgta tcgagctagg cacttaaata caattatctc   1380
tgcaatgcgg tattcagtgg ttcgtccaat ccatgtcaga cccgtctgtt gccttcctaa   1440
taaggcacga tcgtaccacc ttacttccac caatcggcat gcacggtgct tttctctcc    1500
ttgtaaggca tgttgctaac tcatcgttac catgttgcaa gactacaaga gtattgcata   1560
agactacatt tccccctccc tatgcaaaag cgaaactact atatcctgag gggactccta   1620
accgcgtaca accgaagccc cgcttttcgc ctaaacacac cctagtcccc tcagatacgc   1680
gtatatctgg cccgtacatc gcgaagcagc gcaaaacgcc taaccctaag cagattcttc   1740
atgcaattgt cggtcaagcc ttgccttgtt gtagcttaaa ttttgctcgc gcactactca   1800
gcgacctcca acacacaagc agggagcaga tgcatggcgg taatacggtt atccacagaa   1860
tcaggggata acgcaggaaa gaacatgtga gcaaaaggcc agcaaaaggc caggaaccgt   1920
aaaaaggccg cgttgctggc gtttttccat aggctccgcc cccctgacga gcatcacaaa   1980
aatcgacgct caagtcagag gtggcgaaac ccgacaggac tataaagata ccaggcgttt   2040
ccccctggaa gctccctcgt gcgctctcct gttccgaccc tgccgcttac cggatacctg   2100
tccgcctttc tcccttcggg aagcgtggcg ctttctcata gctcacgctg taggtatctc   2160
agttcggtgt aggtcgttcg ctccaagctg ggctgtgtgc acgaaccccc cgttcagccc   2220
gaccgctgcg ccttatccgg taactatcgt cttgagtcca acccggtaag acacgactta   2280
```

```
tcgccactgg cagcagccac tggtaacagg attagcagag cgaggtatgt aggcggtgct   2340
acagagttct tgaagtggtg gcctaactac ggctacacta gaaggacagt atttggtatc   2400
tgcgctctgc tgaagccagt taccttcgga aaaagagttg gtagctcttg atccggcaaa   2460
caaaccaccg ctggtagcgg tggttttttt gtttgcaagc agcagattac gcgcagaaaa   2520
aaaggatctc aagaagatcc tttgatcttt tctacggggt ctgacgctca gtggaacgaa   2580
aactcacgtt aagggatttt ggtcatgaga ttatcaaaaa ggatcttcac ctagatcctt   2640
ttaaattaaa aatgaagttt taaatcaatc taaagtatat atgagtaacc tgaggctatg   2700
gcagggcctg ccgccccgac gttggctgcg agccctgggc cttcacccga acttgggggg   2760
tggggtgggg aaaaggaaga aacgcgggcg tattggcccc aatggggtct cggtggggta   2820
tcgacagagt gccagccctg ggaccgaacc ccgcgtttat gaacaaacga cccaacaccg   2880
tgcgttttat tctgtctttt tattgccgtc atagcgcggg ttccttccgg tattgtctcc   2940
ttccgtgttt cagttagcct cccccctaggg tgggcgaaga actccagcat gagatccccg   3000
cgctggagga tcatccagcc ggcgtcccgg aaaacgattc cgaagcccaa cctttcatag   3060
aaggcggcgg tggaatcgaa atctcgtgat ggcaggttgg gcgtcgcttg gtcggtcatt   3120
tcgaacccca gagtcccgct cagaagaact cgtcaagaag gcgatagaag gcgatgcgct   3180
gcgaatcggg agcggcgata ccgtaaagca cgaggaagcg gtcagcccat tcgccgccaa   3240
gctcttcagc aatatcacgg gtagccaacg ctatgtcctg atagcggtcc gccacaccca   3300
gccggccaca gtcgatgaat ccagaaaagc ggccattttc caccatgata ttcggcaagc   3360
aggcatcgcc atgggtcacg acgagatcct cgccgtcggg catgctcgcc ttgagcctgg   3420
cgaacagttc ggctggcgcg agcccctgat gctcttcgtc cagatcatcc tgatcgacaa   3480
gaccggcttc catccgagta cgtgctcgct cgatgcgatg tttcgcttgg tggtcgaatg   3540
ggcaggtagc cggatcaagc gtatgcagcc gccgcattgc atcagccatg atggatactt   3600
tctcggcagg agcaaggtga gatgacagga gatcctgccc cggcacttcg cccaatagca   3660
gccagtccct tcccgcttca gtgacaacgt cgagcacagc tgcgcaagga acgcccgtcg   3720
tggccagcca cgatagccgc gctgcctcgt cttgcagttc attcagggca ccggacaggt   3780
cggtcttgac aaaaagaacc gggcgcccct gcgctgacag ccggaacacg gcggcatcag   3840
agcagccgat tgtctgttgt gcccagtcat agccgaatag cctctccacc caagcggccg   3900
gagaacctgc gtgcaatcca tcttgttcaa tcatgcgaaa cgatcctcat cctgtctctt   3960
gatcgatctt tgcaaaagcc taggcctcca aaaaagcctc ctcactactt ctggaatagc   4020
tcagaggccg aggcggcctc ggcctctgca taaataaaaa aaattagtca gccatggggc   4080
ggagaatggg cggaactggg cggagttagg ggcgggatgg gcggagttag gggcgggact   4140
atggttgctg actaattgag atgcatgctt tgcatacttc tgcctgctgg ggagcctggg   4200
gactttccac acctggttgc tgactaattg agatgcatgc tttgcatact tctgcctgct   4260
ggggagcctg ggactttcc acaccctaac tgacacacat tccacagctg gttctttccg   4320
cctcaggact cttccttttt caatattatt gaagcattta tcagggttat tgtctcatga   4380
gcggatacat atttgaatgt atttagaaaa ataaacaaat aggggttccg cgcacatttc   4440
cccgaaaagt gc                                                        4452
```

<210> SEQ ID NO 71
<211> LENGTH: 4518
<212> TYPE: DNA

```
<213> ORGANISM: Artificial Sequence
<220> FEATURE:
<223> OTHER INFORMATION: plasmid

<400> SEQUENCE: 71

cacctgacgc gccctgtagc ggcgcattaa gcgcggcggg tgtggtggtt acgcgcagcg     60

tgaccgctac acttgccagc gccctagcgc ccgctccttt cgctttcttc ccttcctttc    120

tcgccacgtt cgccggcttt ccccgtcaag ctctaaatcg ggggctccct ttagggttcc    180

gatttagtgc tttacggcac ctcgacccca aaaaacttga ttagggtgat ggttcacgta    240

gtgggccatc gccctgatag acggtttttc gccctttgac gttggagtcc acgttcttta    300

atagtggact cttgttccaa actggaacaa cactcaaccc tatctcggtc tattcttttg    360

atttataagg gattttgccg atttcggcct attggttaaa aaatgagctg atttaacaaa    420

aatttaacgc gaattttaac aaaatattaa cgcttacaat ttacgcgtta agatacattg    480

atgagtttgg acaaaccaca actagaatgc agtgaaaaaa atgctttatt tgtgaaattt    540

gtgatgctat tgctttattt gtaaccatta taagctgcaa taaacaagtt aacaacaaca    600

attgcattca ttttatgttt caggttcagg gggaggtgtg ggaggttttt taaagcaagt    660

aaaacctcta caaatgtggt atggctgatt atgatcatga acagactgtg aggactgagg    720

ggcctgaaat gagccttggg actgtgaatc taaaatacac aaacaattag aatcagtagt    780

ttaacacatt atacacttaa aaattggatc tccattcgcc attcaggctg cgcaactgtt    840

gggaagggcg atcggtgcgg gcctcttcgc tattacgcca gctggcgaaa gggggatgtg    900

ctgcaaggcg attaagttgg gtaacgccag ggttttccca gtcacgacgt tgtaaaacga    960

cggccagtga attgtaatac gactcactat agggcgaatt gggtacactt acctggtacc   1020

ccacccgggt ggaaaatcga tgggcccgcg gccgctctag aagtactctc gagaagcttt   1080

ttgaattctt tggatccact agtgtcgacc tgcaggcgcg cgagctccag cttttgttcc   1140

ctttagtgag ggttaatttc gagcttggcg taatcaaggt catagctgtt tcctgtgtga   1200

aattgttatc cgctcacaat tccacacaat atacgagccg gaagtataaa gtgtaaagcc   1260

tggggtgcct aatgagtgag ctaactcaca gtaattgcgg ctagcggatc tgacggttca   1320

ctaaaccagc tctgcttata tagacctccc accgtacacg cctaccgccc atttgcgtca   1380

atggggcgga gttgttacga cattttggaa agtcccgttg attttggtgc caaaacaaac   1440

tcccattgac gtcaatgggg tggagacttg gaaatccccg tgagtcaaac cgctatccac   1500

gcccattgat gtactgccaa aaccgcatca ccatggtaat agcgatgact aatacgtaga   1560

tgtactgcca agtaggaaag tcccataagg tcatgtactg ggcataatgc caggcgggcc   1620

atttaccgtc attgacgtca atagggggcg tacttggcat atgatacact tgatgtactg   1680

ccaagtgggc agtttaccgt aaatactcca cccattgacg tcaatggaaa gtccctattg   1740

gcgttactat gggaacatac gtcattattg acgtcaatgg gcgggggtcg ttgggcggtc   1800

agccaggcgg gccatttacc gtaagttatg taacgcggaa ctccatatat gggctatgaa   1860

ctaatgaccc cgtaattgat tactattaat aactaatgca tggcggtaat acggttatcc   1920

acagaatcag gggataacgc aggaaagaac atgtgagcaa aaggccagca aaaggccagg   1980

aaccgtaaaa aggccgcgtt gctggcgttt ttccataggc tccgcccccc tgacgagcat   2040

cacaaaaatc gacgctcaag tcagaggtgg cgaaacccga caggactata aagataccag   2100

gcgtttcccc ctggaagctc cctcgtgcgc tctcctgttc cgaccctgcc gcttaccgga   2160

tacctgtccg cctttctccc ttcgggaagc gtggcgcttt ctcatagctc acgctgtagg   2220
```

```
tatctcagtt cggtgtaggt cgttcgctcc aagctgggct gtgtgcacga acccccgtt   2280
cagcccgacc gctgcgcctt atccggtaac tatcgtcttg agtccaaccc ggtaagacac   2340
gacttatcgc cactggcagc agccactggt aacaggatta gcagagcgag gtatgtaggc   2400
ggtgctacag agttcttgaa gtggtggcct aactacggct acactagaag gacagtattt   2460
ggtatctgcg ctctgctgaa gccagttacc ttcggaaaaa gagttggtag ctcttgatcc   2520
ggcaaacaaa ccaccgctgg tagcggtggt ttttttgttt gcaagcagca gattacgcgc   2580
agaaaaaaag gatctcaaga agatcctttg atcttttcta cggggtctga cgctcagtgg   2640
aacgaaaact cacgttaagg gattttggtc atgagattat caaaaaggat cttcacctag   2700
atccttttaa attaaaaatg aagttttaaa tcaatctaaa gtatatatga gtaacctgag   2760
gctatggcag ggcctgccgc cccgacgttg gctgcgagcc ctgggccttc acccgaactt   2820
gggggggtggg gtggggaaaa ggaagaaacg cgggcgtatt ggccccaatg gggtctcggt   2880
ggggtatcga cagagtgcca gccctgggac cgaaccccgc gtttatgaac aaacgaccca   2940
acaccgtgcg ttttattctg tctttttatt gccgtcatag cgcgggttcc ttccggtatt   3000
gtctccttcc gtgtttcagt tagcctcccc ctagggtggg cgaagaactc cagcatgaga   3060
tccccgcgct ggaggatcat ccagccggcg tcccggaaaa cgattccgaa gcccaacctt   3120
tcatagaagg cggcggtgga atcgaaatct cgtgatggca ggttgggcgt cgcttggtcg   3180
gtcatttcga accccagagt cccgctcaga agaactcgtc aagaaggcga tagaaggcga   3240
tgcgctgcga atcgggagcg gcgataccgt aaagcacgag gaagcggtca gcccattcgc   3300
cgccaagctc ttcagcaata tcacgggtag ccaacgctat gtcctgatag cggtccgcca   3360
cacccagccg gccacagtcg atgaatccag aaaagcggcc attttccacc atgatattcg   3420
gcaagcaggc atcgccatgg gtcacgacga gatcctcgcc gtcgggcatg ctcgccttga   3480
gcctggcgaa cagttcggct ggcgcgagcc cctgatgctc ttcgtccaga tcatcctgat   3540
cgacaagacc ggcttccatc cgagtacgtg ctcgctcgat gcgatgtttc gcttggtggt   3600
cgaatgggca ggtagccgga tcaagcgtat gcagccgccg cattgcatca gccatgatgg   3660
atactttctc ggcaggagca aggtgagatg acaggagatc ctgccccggc acttcgccca   3720
atagcagcca gtcccttccc gcttcagtga caacgtcgag cacagctgcg caaggaacgc   3780
ccgtcgtggc cagccacgat agccgcgctg cctcgtcttg cagttcattc agggcaccgg   3840
acaggtcggt cttgacaaaa agaaccgggc gcccctgcgc tgacagccgg aacacggcgg   3900
catcagagca gccgattgtc tgttgtgccc agtcatagcc gaatagcctc tccacccaag   3960
cggccggaga acctgcgtgc aatccatctt gttcaatcat gcgaaacgat cctcatcctg   4020
tctcttgatc gatctttgca aaagcctagg cctccaaaaa agcctcctca ctacttctgg   4080
aatagctcag aggccgaggc ggcctcggcc tctgcataaa taaaaaaaat tagtcagcca   4140
tggggcggag aatgggcgga actgggcgga gttaggggcg ggatgggcgg agttaggggc   4200
gggactatgg ttgctgacta attgagatgc atgctttgca tacttctgcc tgctggggag   4260
cctggggact ttccacacct ggttgctgac taattgagat gcatgctttg catacttctg   4320
cctgctgggg agcctgggga ctttccacac cctaactgac acacattcca cagctggttc   4380
tttccgcctc aggactcttc ctttttcaat attattgaag catttatcag ggttattgtc   4440
tcatgagcgg atacatattt gaatgtattt agaaaaataa acaaataggg gttccgcgca   4500
catttccccg aaaagtgc                                                  4518
```

<210> SEQ ID NO 72
<211> LENGTH: 4974
<212> TYPE: DNA
<213> ORGANISM: Artificial Sequence
<220> FEATURE:
<223> OTHER INFORMATION: plasmid

<400> SEQUENCE: 72
aagctttttg caaaagccta ggcctccaaa aaagcctcct cactacttct ggaatagctc 60
agaggccgag gcggcctcgg cctctgcata aataaaaaaa attagtcagc catggggcgg 120
agaatgggcg gaactgggcg gagttagggg cgggatgggc ggagttaggg gcgggactat 180
ggttgctgac taattgagat gcatgctttg catacttctg cctgctgggg agcctgggga 240
ctttccacac ctggttgctg actaattgag atgcatgctt tgcatacttc tgcctgctgg 300
ggagcctggg gactttccac accctaactg acacacattc cacaggatcc ggtcgcgcga 360
atttcgagcg gtgttccgcg gtcctcctcg tatagaaact cggaccactc tgagacgaag 420
gctcgcgtcc aggccagcac gaaggaggct aagtgggagg ggtagcggtc gttgtccact 480
agggggtcca ctcgctccag ggtgtgaaga cacatgtcgc cctcttcggc atcaaggaag 540
gtgattggtt tataggtgta ggccacgtga ccgggtgttc ctgaaggggg gctataaaag 600
ggggtggggg cgcgttcgtc ctcactctct tccgcatcgc tgtctgcgag ggccagctgt 660
tgggctcgcg gttgaggaca aactcttcgc ggtctttcca gtactcttgg atcggaaacc 720
cgtcggcctc cgaacggtac tccgccaccg agggacctga gcgagtccgc atcgaccgga 780
tcggaaaacc tctcgactgt tggggtgagt actccctctc aaaagcgggc atgacttctg 840
cgctaagatt gtcagtttcc aaaaacgagg aggatttgat attcacctgg cccgcggtga 900
tgcctttgag ggtggccgcg tccatctggt cagaaaagac aatctttttg ttgtcaagct 960
tgaggtgtgg caggcttgag atctggccat acacttgagt gacaatgaca tccactttgc 1020
ctttctctcc acaggtgtcc actcccaggt ccaactgcag gcgagcctga attcgggggg 1080
gggggggggg gggacagctc agggctgcga tttcgcgcca aacttgacgg caatcctagc 1140
gtgaaggctg gtaggatttt atccccgctg ccatcatggt tcgaccattg aactgcatcg 1200
tcgccgtgtc ccaaaatatg gggattggca agaacggaga cctaccctgg cctccgctca 1260
ggaacgagtt caagtacttc caaagaatga ccacaacctc ttcagtggaa ggtaaacaga 1320
atctggtgat tatgggtagg aaaacctggt tctccattcc tgagaagaat cgacctttaa 1380
aggacagaat taatatagtt ctcagtagag aactcaaaga accaccacga ggagctcatt 1440
ttcttgccaa aagtttggat gatgccttaa gacttattga acaaccggaa ttggcaagta 1500
aagtagacat ggttggatag tcggaggcag ttctgtttac caggaagcca tgaatcaacc 1560
aggccacctc agactctttg tgacaaggat catgcaggaa tttgaaagtg acacgttttt 1620
cccagaaatt gatttgggga aatataaact tctcccagaa tacccaggcg tcctctctga 1680
ggtccaggag gaaaaaggca tcaagtataa gtttgaagtc tacgagaaga aagactaaca 1740
ggaagatgct ttcaagttct ctgctcccct cctaaagcta tgcattttta taagaccatg 1800
ggacttttgc tggctttaga tcataatcag ccataccaca tttgtagagg ttttacttgc 1860
tttaaaaaac ctcccacacc tccccctgaa cctgaaacat aaaatgaatg caattgttgt 1920
tgttaacttg tttattgcag cttataatgg ttacaaataa agcaatagca tcacaaattt 1980
cacaaataaa gcattttttt cactgcattc tagttgtggt ttgtccaaac tcatcaatgt 2040
atcttatcat gtctggatcc ccggccaacg gtctggtgac ccggctgcga gagctcggtg 2100

```
tacctgagac gcgagtaagc ccttgagtca aagacgtagt cgttgcaagt ccgcaccagg   2160
tactgatatc ccaccaaaaa gtgcggcggc ggctggcggt agaggggcca gcgtagggtg   2220
gccggggctc cgggggcgag gtcttccaac ataaggcgat gatcatcgat gctagaccgt   2280
gcaaaaggag agcctgtaag cgggcactct tccgtggtct ggtggataaa ttcgcaaggg   2340
tatcatggcg gacgaccggg gttcgaaccc cggatccggc cgtccgccgt gatccatgcg   2400
gttaccgccc gcgtgtcgaa cccaggtgtg cgacgtcaga caacggggga gcgctccttt   2460
tggcttcctt ccaggcgcgg cggctgctgc gctagctttt ttggcgagct cgaattaatt   2520
ctgcattaat gaatcggcca acgcgcgggg agaggcggtt tgcgtattgg gcgctcttcc   2580
gcttcctcgc tcactgactc gctgcgctcg gtcgttcggc tgcggcgagc ggtatcagct   2640
cactcaaagg cggtaatacg gttatccaca gaatcagggg ataacgcagg aaagaacatg   2700
tgagcaaaag gccagcaaaa ggccaggaac cgtaaaaagg ccgcgttgct ggcgtttttc   2760
cataggctcc gcccccctga cgagcatcac aaaaatcgac gctcaagtca gaggtggcga   2820
aacccgacag gactataaag ataccaggcg tttccccctg gaagctccct cgtgcgctct   2880
cctgttccga ccctgccgct taccggatac ctgtccgcct ttctcccttc gggaagcgtg   2940
gcgctttctc atagctcacg ctgtaggtat ctcagttcgg tgtaggtcgt tcgctccaag   3000
ctgggctgtg tgcacgaacc ccccgttcag cccgaccgct gcgccttatc cggtaactat   3060
cgtcttgagt ccaacccggt aagacacgac ttatcgccac tggcagcagc cactggtaac   3120
aggattagca gagcgaggta tgtaggcggt gctacagagt tcttgaagtg gtggcctaac   3180
tacggctaca ctagaagaac agtatttggt atctgcgctc tgctgaagcc agttaccttc   3240
ggaaaaagag ttggtagctc ttgatccggc aaacaaacca ccgctggtag cggtggtttt   3300
tttgtttgca agcagcagat tacgcgcaga aaaaaaggat ctcaagaaga tcctttgatc   3360
ttttctacgg ggtctgacgc tcagtggaac gaaaactcac gttaagggat tttggtcatg   3420
agattatcaa aaaggatctt cacctagatc cttttaaatt aaaaatgaag ttttaaatca   3480
atctaaagta tatatgagta aacttggtct gacagttacc aatgcttaat cagtgaggca   3540
cctatctcag cgatctgtct atttcgttca tccatagttg cctgactccc cgtcgtgtag   3600
ataactacga tacgggaggg cttaccatct ggccccagtg ctgcaatgat accgcgagac   3660
ccacgctcac cggctccaga tttatcagca ataaaccagc cagccggaag ggccgagcgc   3720
agaagtggtc ctgcaacttt atccgcctcc atccagtcta ttaattgttg ccgggaagct   3780
agagtaagta gttcgccagt taatagtttg cgcaacgttg ttgccattgc tacaggcatc   3840
gtggtgtcac gctcgtcgtt tggtatggct tcattcagct ccggttccca acgatcaagg   3900
cgagttacat gatcccccat gttgtgcaaa aaagcggtta gctccttcgg tcctccgatc   3960
gttgtcagaa gtaagttggc cgcagtgtta tcactcatgg ttatggcagc actgcataat   4020
tctcttactg tcatgccatc cgtaagatgc ttttctgtga ctggtgagta ctcaaccaag   4080
tcattctgag aatagtgtat gcggcgaccg agttgctctt gcccggcgtc aatacgggat   4140
aataccgcgc cacatagcag aactttaaaa gtgctcatca ttggaaaacg ttcttcgggg   4200
cgaaaactct caaggatctt accgctgttg agatccagtt cgatgtaacc cactcgtgca   4260
cccaactgat cttcagcatc ttttactttc accagcgttt ctgggtgagc aaaaacagga   4320
aggcaaaatg ccgcaaaaaa gggaataagg gcgacacgga aatgttgaat actcatactc   4380
ttcctttttc aatattattg aagcatttat cagggttatt gtctcatgag cggatacata   4440
```

-continued

```
tttgaatgta tttagaaaaa taaacaaata ggggttccgc gcacatttcc ccgaaaagtg   4500

ccacctgacg tctaagaaac cattattatc atgacattaa cctataaaaa taggcgtatc   4560

acgaggccct ttcgtctcgc gcgtttcggt gatgacggtg aaaacctctg acacatgcag   4620

ctcccggaga cggtcacagc ttgtctgtaa gcggatgccg ggagcagaca agcccgtcag   4680

ggcgcgtcag cgggtgttgg cgggtgtcgg ggctggctta actatgcggc atcagagcag   4740

attgtactga gagtgcacca tatgcggtgt gaaataccgc acagatgcgt aaggagaaaa   4800

taccgcatca ggcgccattc gccattcagg ctgcgcaact gttgggaagg gcgatcggtg   4860

cgggcctctt cgctattacg ccagctggcg aaagggggat gtgctgcaag gcgattaagt   4920

tgggtaacgc cagggttttc ccagtcacga cgttgtaaaa cgacggccag tgcc         4974
```

DRUG ELUTING STENT

FIELD OF THE INVENTION

The present invention relates to the field of medicine, and in some embodiments to devices and compositions comprising a leptin antagonist formulated for localized release of a leptin antagonist at the site of treatment, specifically the treatment of ischemia and reperfusion injury.

BACKGROUND OF THE INVENTION

Cardiovascular disease (CVD) is a class of diseases that involve the heart and/or the blood vessels. Several studies have related inflammatory markers to cardiovascular disease (CVD) and several assays for inflammatory markers are commercially available. For example, C-reactive protein (CRP), a common inflammatory marker, has been found to be present in increased levels in patients who are at risk for cardiovascular disease [Karakas and Koenig, 2009 Herz 34 (8): 607-13] while osteoprotegerin, which is involved with regulation of NF-κB, has been found to be a risk factor for cardiovascular disease and mortality [Venuraju et al., 2010 J. Am. Coll. Cardiol. 55 (19): 2049-61].

As a result of these findings, the number of inflammatory marker tests ordered by clinicians for CVD risk prediction has grown rapidly. However, to date there is no consensus among professionals as to how these markers of inflammation should be used as a basis for clinical treatment.

Although it has been shown that some cardiovascular disorders can benefit from suppression of inflammation-related processes and cellular proliferation as part of a remodeling response (e.g. use of locally released cytotoxic drugs such as paclitaxel or sirolimus in preventing restenosis or use of doxycycline in treatment of abdominal aortic aneurysm (AAA)), to date, there is no evidence to suggest that cardiovascular disease can benefit from anti-inflammatory treatment.

Cardiovascular diseases are very often associated with ischemia/reperfusion injury (IRI). IRI is caused by critical reduction of blood supply to an organ followed by renewal of blood flow and re-oxygenation. Tissue damage is driven by activation of inflammatory processes, including synthesis of cytokines, chemokines and reactive oxygen species (ROS). Chemokines mediate inflammation and regulate pro-inflammatory cytokine, adhesion molecule expression, leukocyte infiltration and activation. During IRI, excessive production of ROS cause oxidative stress, which impacts mitochondrial oxidative phosphorylation, causing ATP depletion, increase intracellular calcium and activation of membrane phospholipids proteases. Reperfusion and oxygenation produce oxygen free radicals, which promote lipid peroxidation and tissue damage by free radicals. Notably, the mechanisms involved in IRI tissue damage as mentioned above apply to all tissues. However, cellular damage correlates with the magnitude of ischemia, and cell type. For instance, kidney and brain cells are extremely sensitive to ischemic damage, which is further exacerbated by reperfusion injury.

Leptin is a naturally occurring pleiotropic molecule that regulates food intake as well as metabolic and endocrine functions. Leptin also plays a regulatory role in immunity, inflammation, and hematopoiesis.

The human leptin precursor is a linear polypeptide 167 amino acid residues long represented by NCBI Reference Sequence NP_000221.1 (SEQ ID NO 1) encoded by the mRNA having the nucleotide sequence NCBI Reference Sequence NM_000230. Residues 1-21 of the sequence constitute the signal peptide while residues 22-167 constitute the mature hormone.

Leptin antagonists are also known, see for example, U.S. Pat. Nos. 7,307,142 and 8,969,292.

SUMMARY OF THE INVENTION

The invention, in some embodiments, relates to the field of medicine, and more particularly to methods and devices that use leptin antagonists. In some embodiments, the invention relates to compositions comprising a leptin antagonist formulated for localized release of a leptin antagonist to inhibit activity of leptin at the site of treatment as well as methods of using such compositions for treating disorders, including cardiovascular disorders.

According to an aspect of some embodiments of the invention, there is provided a method of treatment comprising: exposing in vivo tissue of a subject in need thereof to local administration of a pharmaceutically-effective amount of leptin antagonist, thereby providing a therapeutic effect to the tissue. In some embodiments, the tissue is substantially continuously exposed to a pharmaceutically-effective amount of leptin antagonist for a period of not less than three days, not less than 5 days, not less than 8 days and even not less than 14 days.

According to an aspect of some embodiments of the invention, there is also provided a method of treatment comprising implanting in contact with tissue in the body of a subject in need thereof a composition configured for in vivo local administration of leptin antagonist, thereby providing a therapeutic effect to the tissue. In some embodiments, the configuration for the in vivo release is such that when the composition is implanted in vivo, leptin antagonist is released from the composition in a pharmaceutically-effective amount for a period of not less than three days, not less than 5 days, not less than 8 days and even not less than 14 days.

In some embodiments of the methods, the need is that the subject suffers from at least one pathology selected from the group consisting of: cardiovascular disease; remodeling of stable athersclerotic plaque into an unstable lesion; ascending aortic aneurysm-associated hypertension, hypercholesterolemia or diabetes mellitus; bicuspid aortic valve; Takayasu disease; rheumatoid arteritis; Marfan's syndrome; ankylosing spondylitis; giant cell arteritis; inflammatory aortic aneurysm; pulmonary artery aneurysm in Marfan's syndrome; aortic dissection in an aortic or peripheral large artery; angiogenesis; cancer; local discrete lesion therapy; and arteriovenous malformation.

In some embodiments, the need is that the subject suffers from a cardiovascular disorder, wherein the therapeutic effect is down-regulation of an expression or activity of leptin in a cardiovascular tissue.

In some embodiments, the cardiovascular tissue is aortic and/or mitral heart valve leaflet tissue. In some embodiments, the local administration is effected by positioning a carrier capable of releasing the leptin antagonist on an outer wall (e.g., tunica externa) or the inner wall (e.g., tunica intima) of an aorta.

In some embodiments, the cardiovascular tissue is arterial or venous wall tissue. In some embodiments, the local administration is effected by positioning a carrier capable of releasing the leptin antagonist on an outer wall (e.g., tunica externa) or the inner wall (e.g., tunica intima) of the arterial or venous wall tissue.

In some embodiments, the cardiovascular disorder is a vascular aneurysm. In some embodiments, the cardiovascular disorder is an aortic vascular disorder. In some embodiments, the cardiovascular disorder is left ventricular remodeling.

In some embodiments, the local administration is effected via an intravascular catheter. In some embodiments, the local administration is effected via direct injection.

According to an aspect of some embodiments of the invention, there is also provided a method for treatment of athersclerotic plaque, comprising: administering a pharmaceutically-effective amount of a leptin antagonist to athersclerotic plaque accumulated in the inner walls of an artery, thereby at least one of: (a) reducing the rate and (b) reducing the incidence, of conversion of a stable athersclerotic plaque to an unstable lesion.

According to an aspect of some embodiments of the invention, there is also provided a composition comprising a leptin antagonist and a carrier, for use in treating a disorder selected from the group consisting of: cardiovascular disease; remodeling of stable athersclerotic plaque into an unstable lesion; ascending aortic aneurysm-associated hypertension, hypercholesterolemia or diabetes mellitus; bicuspid aortic valve; Takayasu disease; rheumatoid arteritis; Marfan's syndrome; ankylosing spondylitis; giant cell arteritis; inflammatory aortic aneurysm; pulmonary artery aneurysm in Marfan's syndrome; aortic dissection in an aortic or peripheral large artery; site of arterial anastomosis, angiogenesis; cancer; local neoplastic discrete lesion therapy; and arteriovenous malformation, wherein the carrier is configured for localized administration of the leptin antagonist.

In some embodiments, the carrier is a biodegradable support. In some embodiments, the biodegradable support is composed of a polymer selected from the group consisting of a hydrogel, poly glycolic acid (PGA), poly lactic co-glycolic acid (PLGA), polylactide (PLA), and poly (L-lactide) (PLLA), and combinations thereof.

In some embodiments, the carrier is a hydrogel. In some embodiments, the carrier is configured as a film. In some embodiments, the carrier is a device selected from the group consisting of a mesh, a balloon and a vascular graft. In some embodiments, the carrier is a depot-forming injectable composition.

In some embodiments, the disorder is a cardiovascular disorder, wherein the leptin antagonist effects down-regulation of an expression or activity of leptin in a cardiovascular tissue. In some embodiments, the cardiovascular disorder is a vascular disorder. In some such embodiments, the vascular disorder is an aortic vascular disorder. In some embodiments, the cardiovascular disorder is left ventricular remodeling.

In some such embodiments, the cardiovascular tissue is aortic and/or mitral heart valve leaflet tissue. In some such embodiments, the cardiovascular tissue is arterial or venous wall tissue.

In some embodiments, the local administration is effected by positioning a carrier capable of releasing the leptin antagonist on a location selected from the group consisting of: an outer wall of an aorta, an outer wall of an artery, an outer wall of an vein, a luminal surface of an aorta, a luminal surface of an artery and a luminal surface of an vein. In some such embodiments, the local administration is effected by positioning a carrier capable of releasing the leptin antagonist on an outer wall (e.g., tunica externa) or the inner wall (e.g., tunica intima) of the arterial or venous wall tissue. In some embodiments, the localized administration is to be effected via an intravascular catheter. In some embodiments, the localized administration is to be effected via direct injection.

According to an aspect of some embodiments of the invention, there is also provided a method of treating a condition in a subject in need thereof, the method comprising administering intracavitarily to inner walls of a fluid-filled bodily cavity of the subject a composition comprising a leptin antagonist.

According to an aspect of some embodiments of the invention, there is also provided a composition comprising: a leptin antagonist for use in treating a condition, wherein the composition is configured for intracavitary administration to inner walls of a fluid-filled bodily cavity of a subject.

According to an aspect of some embodiments of the invention, there is also provided an intracavitarily-implantable medical device, comprising: at least one solid functional device part configured for deploying the device in a fluid-filled bodily cavity of a subject; and functionally associated with at least one the device component, a leptin antagonist.

According to an aspect of some embodiments of the invention, there is also provided a surgical connecting device, comprising: a solid device body made of a material; and functionally associated with the device body, a pharmaceutically-effective amount of leptin antagonist. In some embodiments, the device body is in the form selected from the group consisting of surgical suture thread and a surgical staple.

According to an aspect of the invention, there is provided a method for treating ischemia and reperfusion injury (IRI) by administrating leptin antagonist upon reperfusion and maintaining sustained administration of the leptin antagonist into the vessel undergoing the reperfusion procedure, for delivering the leptin antagonist by the blood flow into the damaged cells of the tissue injured by the IRI via bolus intra-arterial injection, or sustained release from a drug eluting stent.

According to an aspect of some embodiments of the invention, there is provided a double function drug eluting stent (df-DES) configured to enable sustained release of anti-proliferative drug into the wall of a blood vessel and to enable sustained release of leptin antagonist (LA) into the lumen, so that the leptin antagonist is carried by the blood stream to be uptaken by tissue cells that sustained ischemia and reperfusion injury.

Any suitable leptin antagonist may be used for implementing the teachings herein. Various types and specific suitable leptin antagonists are listed in the description herein. In some embodiments, the leptin antagonist is capable of binding a leptin receptor. In some embodiments, the leptin antagonist is incapable of dimerization. In some embodiments, the leptin antagonist comprises a polypeptide portion. In some embodiments, the leptin antagonist is selected from the group consisting of a polypeptide, a salt, and/or an ester thereof. In some embodiments, the leptin antagonist is a modified leptin polypeptide.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS

Figure 1B:
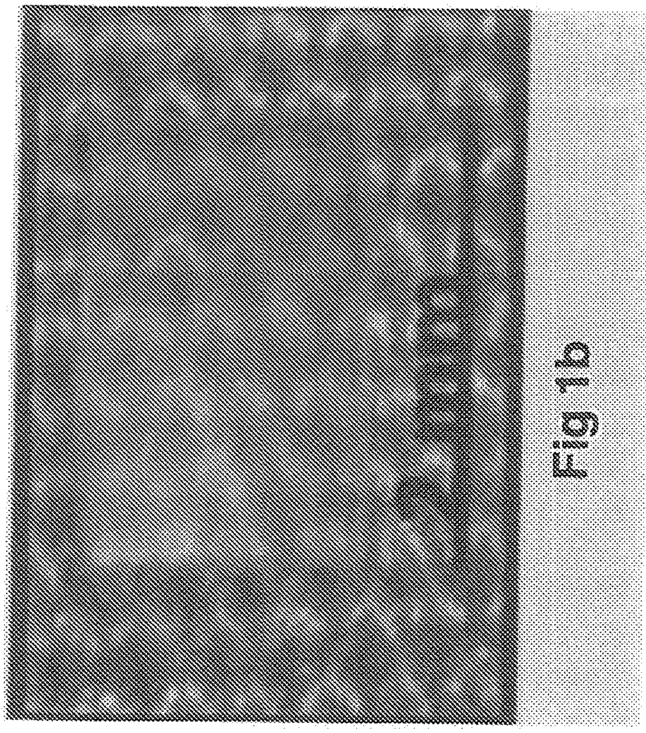
FIG. 1*a-c* illustrate a gel (FIG. 1*a*), film (FIG. 1*b*) and mesh (FIG. 1*c*) for local release of a leptin antagonist.

The invention, in some embodiments, relates to the field of medicine, and more particularly to methods and devices that use leptin antagonists. In some embodiments, the invention relates to compositions comprising a leptin antagonist formulated for localized release of a leptin antagonist at the site of treatment as well as methods of using such compositions for treating disorders, including cardiovascular disorders. In some embodiments, the compositions comprising a leptin antagonist can be used for localized suppression of leptin-related conditions, including tissue remodeling processes.

Although it has been proposed that leptin might play a role in vascular inflammation, oxidative stress, and vascular smooth muscle hypertrophy that may contribute to coronary heart disease among other pathologies, to date no one has conclusively shown that localized down-regulation of leptin activity can be used to treat cardiovascular disorders characterized by remodeling of cardiovascular tissue such as cardiac, arterial or valve tissue.

The present inventor set out to elucidate the role of leptin in disorders, such as cardiovascular disorders by employing a leptin antagonist in a localized manner. Experiments conducted by the present inventor (see Examples section hereinbelow) demonstrate that localized release of leptin in cardiovascular tissue can lead to cardiovascular tissue remodeling while localized down-regulation of leptin activity can lead to suppression and even reversal of cardiovascular tissue (arterial wall tissue, heart muscle tissue and valve leaflet tissue) remodeling induced by angiotensin II. Thus, the present inventor has shown for the first time that a locally administered leptin antagonist can be used to treat cardiovascular disorders characterized by tissue remodeling.

While reducing the present invention to practice, the present inventor has shown that down-regulation of leptin activity at specific sites in the cardiovascular system can lead to suppression and reversal of pathological tissue remodeling and thereby establishing localized leptin down-regulation as a suitable approach for treating various cardiovascular disorders, such as cardiovascular disorders characterized by pathological tissue remodeling.

The present inventor has discovered an unexpected pharmaceutical efficacy of locally administered leptin antagonists, especially leptin antagonists administered by sustained release.

Particularly, the present inventor has found that in vivo implantation of a composition configured for sustained-release of leptin antagonist can have a desirable pharmaceutical effect on tissue in proximity of the implanted composition with limited or no substantial side-effects, for example, no discernible hormonal or immunological effects.

The present inventor has also found that such in vivo administration (e.g., by implantation) inside a fluid-filled cavity of the body (for example of the cardiovascular system such as blood vessels or cardiac chambers) can have a desirable pharmaceutical effect on tissue in proximity of the implanted composition with limited or no substantial side-effects: leptin antagonist from the composition has not been found to be washed away by the fluid and, instead, has been found to interact with the tissue providing a desirable pharmaceutical effect. Presumably, leptin antagonist released from the composition passes into and through the cavity walls (e.g., tunica intima) in pharmaceutically-effective amounts. This is particularly surprising in cavities of the cardiovascular system (e.g., veins, arteries and cardiac chambers) where the large volumes of blood passing through such cavities are expected to wash away released leptin antagonist and where it is expected that the cardiovascular intima is relatively non-permeable to passage of compounds, especially proteins.

Without wishing to be held to any one theory, it is currently believed that the success of some embodiments of the teachings herein is at least partially attributable to the serendipitous increased permeability of cardiovascular intima during inflammation. It may be that the intima of healthy cardiovascular intima is relatively impermeable to leptin antagonist released from the composition, so that there is little or no passage of leptin antagonist into and through the endothelium and underlying tissue, thereby avoiding substantial negative side-effects. In contrast, it seems that the permeability of the cardiovascular intima during inflammation increases sufficiently to allow passage of a therapeutically-effective amount of leptin antagonist released from the composition into the tissue. It is currently believed that this effect is self-regulating. A higher degree of inflammation leads to a higher degree of intima permeability allowing passage of more leptin antagonist leading to a relatively high dose of leptin antagonist in the more pathological tissue. As inflammation decreases (inter alia, due to the pharmaceutical effect of the administered leptin antagonist), intima permeability decreases thereby decreasing the dose of leptin antagonist actually in the tissue that is still sufficient to exercise a desired pharmaceutical effect but with a reduced incidence of substantial negative side effects.

In some embodiments, the present invention includes local administration of leptin antagonist to treat and attenuate expansion of ascending aortic aneurysm, and corresponding cardiac sequelae (driven by the aorto-ventricular coupling), including left ventricular hypertrophy, as well as hyperplasia of left heart valve leaflets.

In some embodiments, the present invention includes treatment of peripheral vascular disorders such as the progression of arterial or venous aneurysms while minimizing systemic exposure to the administered leptin antagonist.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Thus, according to one aspect of the present invention there is provided a composition comprising a leptin antagonist and a carrier configured for localized administration, for treating disorders such as cardiovascular disorders. As used herein, “cardiovascular disorders” refer to disorders of the cardiovascular system, i.e. the heart and central, cranial and peripheral vasculature. Examples of such disorders include, but are not limited to valve stenosis, aneurysms, vessel response to vascular injury, cardiomyopathy and the like.

The carrier can be a solid, gel or liquid carrier, while the leptin antagonist can be any agent capable of down-regulating leptin activity in the target tissue. Examples of a leptin antagonist include agents capable of binding and/or degrading leptin or leptin receptors as well as agents capable of down-regulating leptin expression (at the DNA or RNA levels, i.e., agents capable of blocking transcription or translation). For example, the leptin antagonist known as SMLA (Shpilman et al., J Biol Chem. 2011; 286:4429-4442) has a 60 fold higher affinity to the leptin receptor compared to the endogenous leptin. Therefore, it binds to the leptin receptors in the treated tissue/organ, leaving no leptin receptors available to complex with the endogenous leptin. The complex leptin receptor-leptin antagonist is inactive and can’t exert any damage to the tissue, locally. Specific preferred leptin antagonists are listed hereinbelow.

One example of a leptin antagonist that is an agent capable of down-regulating leptin is an antibody or antibody fragment capable of specifically binding leptin or a leptin receptor. Preferably, the antibody specifically binds at least one epitope of leptin, e.g., an epitope defined amino acids 26-59 of mammalian leptin (e.g. rat leptin—SEQ ID NO 48). As used herein, the term “epitope” refers to any antigenic determinant on an antigen to which the paratope of an antibody binds.

As used herein, the term “antibody” refers to a substantially intact antibody molecule.

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote R J. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

In cases where target antigens are too small to elicit an adequate immunogenic response, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art. (See, for example, Harlow, E. and Lane, D. (1988). Antibodies: A Laboratory Manual, Cold Spring Harbor Laboratory, New York.) For example, antibody fragments according to the present invention can be prepared by proteolytic hydrolysis of the antibody or by expression in *E. coli* or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an $(Fab')_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). The hydrolysis of rabbit γ-globulin and antibodies with crystalline papain. Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Localization of antibody-combining sites within the variable portions of heavy and light chains. Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as *E. coli*. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of *Escherichia coli*. Biotechnology (N.Y.) 11(11), 1271-1277; and U.S. Pat. No. 4,946,778).

Isolated complementarity-determining region peptides can be obtained by constructing genes encoding the CDR of an antibody of interest. Such genes may be prepared, for example, by RT-PCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

It will be appreciated that for human therapy, humanized antibodies are preferred. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody (see, for example: Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed essentially as described (see, for example: Jones et al. (1986); Riechmann et al. (1988); Verhoeyen, M. et al. (1988). Reshaping human antibodies: grafting an antilysozyme activity. Science 239, 1534-1536; and U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species. In practice, humanized antibodies may be typically human antibodies in which some CDR residues and possibly some framework residues are substituted by residues from analogous sites in rodent antibodies.

Human antibodies can also be produced using various additional techniques known in the art, including phage-display libraries (Hoogenboom, H. R. and Winter, G. (1991). By-passing immunization. Human antibodies from synthetic repertoires of germline VH gene segments rearranged in vitro. J Mol Biol 227, 381-388; Marks, J. D. et al. (1991). By-passing immunization. Human antibodies from V-gene libraries displayed on phage. J Mol Biol 222, 581-597; Cole et al. (1985), Monoclonal Antibodies and Cancer Therapy, Alan R. Liss, Inc., pp. 77-96; and Boemer, P. et al. (1991). Production of antigen-specific human monoclonal antibodies from in vitro-primed human splenocytes. J Immunol 147, 86-95). Humanized antibodies can also be created by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807; 5,545,806; 5,569,825; 5,625,126; 5,633,425; and 5,661,016; Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93).

After antibodies have been obtained, they may be tested for activity, for example via enzyme-linked immunosorbent assay (ELISA).

Anti-leptin antibodies as well as epitope sequences suitable for generating antibodies and antibody fragments are described in US20070104708 (SEQ ID NOs 49-55) which is incorporated herein by reference as if fully set-forth herein.

Leptin peptide antagonists can also be used with the present invention. One leptin antagonist, a modified mammalian leptin polypeptide termed superactive leptin mutein is disclosed in U.S. Pat. No. 8,969,292 which is incorporated by reference as if fully set-forth herein.

The term "peptide" as used herein encompass native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, $CH_2$—S, $CH_2$—S═O, O═C—NH, $CH_2$—O, $CH_2$—$CH_2$, S═C—NH, CH═CH, and CF═CH; backbone modifications; and residue modifications. Methods for preparing peptidomimetic compounds are well known in the art and are specified, for example, in Ramsden, C. A., ed. (1992), Quantitative Drug Design, Chapter 17.2, F. Choplin Pergamon Press, which is incorporated by reference as if fully set forth herein. Further details in this respect are provided hereinbelow.

Peptide bonds (—CO—NH—) within the peptide may be substituted, for example, by N-methylated bonds (—N(CH3)—CO—); ester bonds (—C(R)H—C—O—O—C(R)—N—); ketomethylene bonds (—CO—CH2-); a_-aza bonds (—NH—N(R)—CO—), wherein R is any alkyl group, e.g., methyl; carba bonds (~CH2-NH—); hydroxyethylene bonds (—CH(OH)—CH2-); thioamide bonds (—CS—NH—); olefinic double bonds (—CH═CH—); retro amide bonds (—NH—CO—); and peptide derivatives (—N(R)—CH2-CO—), wherein R is the "normal" side chain, naturally presented on the carbon atom. These modifications can occur at any of the bonds along the peptide chain and even at several (2-3) at the same time.

Natural aromatic amino acids, Trp, Tyr, and Phe, may be substituted for synthetic non-natural acids such as, for instance, tetrahydroisoquinoline-3-carboxylic acid (TIC), naphthylelanine (Nol), ring-methylated derivatives of Phe, halogenated derivatives of Phe, and o-methyl-Tyr.

In addition to the above, the peptides of the present invention may also include one or more modified amino acids or one or more non-amino acid monomers (e.g., fatty acids, complex carbohydrates, etc.).

The term "amino acid" or "amino acids" is understood to include the 20 naturally occurring amino acids; those amino acids often modified post-translationally in vivo, including, for example, hydroxyproline, phosphoserine, and phosphothreonine; and other less common amino acids, including but not limited to 2-aminoadipic acid, hydroxylysine, isodesmosine, nor-valine, nor-leucine, and ornithine. Furthermore, the term "amino acid" includes both D- and L-amino acids.

Amino acids are referred to by the standard three letter code. Amino acids are L amino acids unless otherwise noted, for example, by addition of the prefix "D". For example, the code Trp refers to L-tryptophan, while the codes D-Trp and DTrp refers to D-tryptophan. The code Aib refers to 2-aminoisobutyric acid. The code Orn refers to ornithine. The code Lys-Ac refers to acetyllysine. The code HomoLys refers to homolysine. The code H-Cys refers to homocysteine.

In some embodiments, peptidic leptin antagonists used to implement the teachings herein are utilized in a linear form, although in some embodiments, cyclic forms thereof are used.

In some embodiments, peptidic leptin antagonists used to implement the teachings herein are synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York).

In general, peptide synthesis methods comprise the sequential addition of one or more amino acids or suitably protected amino acids to a growing peptide chain. Normally, either the amino or the carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth.

Further description of peptide synthesis is disclosed in U.S. Pat. No. 6,472,505. A preferred method of preparing the peptide compounds of the present invention involves solid-phase peptide synthesis, utilizing a solid support.

In some embodiments, peptidic leptin antagonists used to implement the teachings herein are generated using cell expression approaches by utilizing expression vectors for prokaryotic or eukaryotic expression or alternatively, the peptide can be expressed in-situ by delivering a suitable expression construct to cardiovascular tissue.

To express the peptide sequence in cardiovascular cells, a polynucleotide sequence encoding the peptide (see, for example, US20130133089) is preferably ligated into a nucleic acid construct suitable for mammalian cell expression. Such a nucleic acid construct includes a promoter sequence for directing transcription of the polynucleotide sequence in the cell in a constitutive or inducible manner.

Constitutive promoters suitable for use with the present invention are promoter sequences that are active under most environmental conditions and most types of cells, such as the cytomegalovirus (CMV) and Rous sarcoma virus (RSV).

Polyadenylation sequences can also be added to the expression vector in order to increase the efficiency of mRNA translation. Two distinct sequence elements are required for accurate and efficient polyadenylation: GU- or U-rich sequences located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression vector of the present invention may or may not include a eukaryotic replicon. If a eukaryotic replicon is present, the vector is capable of amplification in eukaryotic cells using the appropriate selectable marker. If the vector does not comprise a eukaryotic replicon, no episomal amplification is possible.

Examples for mammalian expression vectors include, but are not limited to, pcDNA3 (SEQ ID NO 56), pcDNA3.1 (+/−)(SEQ ID NO 57-58), pGL3 (SEQ ID NO 59), pZeoSV2 (+/−) (SEQ ID NO 60), pSecTag2 (SEQ ID NO 61), pDisplay (SEQ ID NO 62), pEF/myc/cyto (SEQ ID NO 63), pCMV/myc/cyto (SEQ ID NO 64), pCR3.1 (SEQ ID NO 65), pSinRep5 (SEQ ID NO 66), DH26S, DHBB, pNMT1, pNMT41, and pNMT81, which are available from Invitrogen, pCI (SEQ ID NO 67) which is available from Promega, pMbac (SEQ ID NO 68), pPbac (SEQ ID NO 69), pBK-RSV (SEQ ID NO 70) and pBK-CMV (SEQ ID NO 71), which are available from Strategene, pTRES which is available from Clontech, and their derivatives.

Expression vectors containing regulatory elements from eukaryotic viruses such as retroviruses can be also used. SV40 vectors include pSVT7 and pMT2 (SEQ ID NO 72), for instance. Vectors derived from bovine papilloma virus include pBV-1MTHA, and vectors derived from Epstein-Barr virus include pHEBO and p2O5. Other exemplary vectors include pMSG, pAV009/$A^+$, pMTO10/$A^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein. For example, bone marrow cells can be targeted using the human T-cell leukemia virus type I (HTLV-I) and kidney cells may be targeted using the heterologous promoter present in the baculovirus *Autographa californica* multiple nucleopolyhedrovirus (AcMNPV), as described by Liang, C. Y. et al. (2004). High efficiency gene transfer into mammalian kidney cells using baculovirus vectors. Arch Virol 149, 51-60.

Recombinant viral vectors are useful for in vivo expression of a leptin peptide since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Figure 1A:
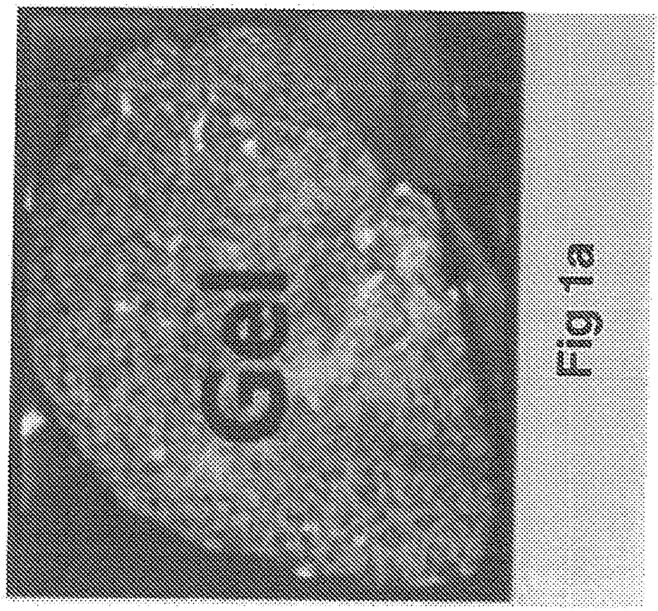
Figure 1C:
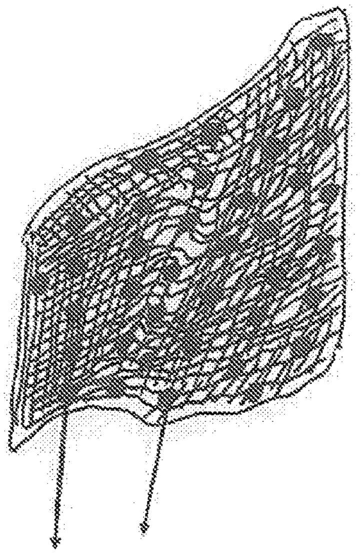
Figure 3:
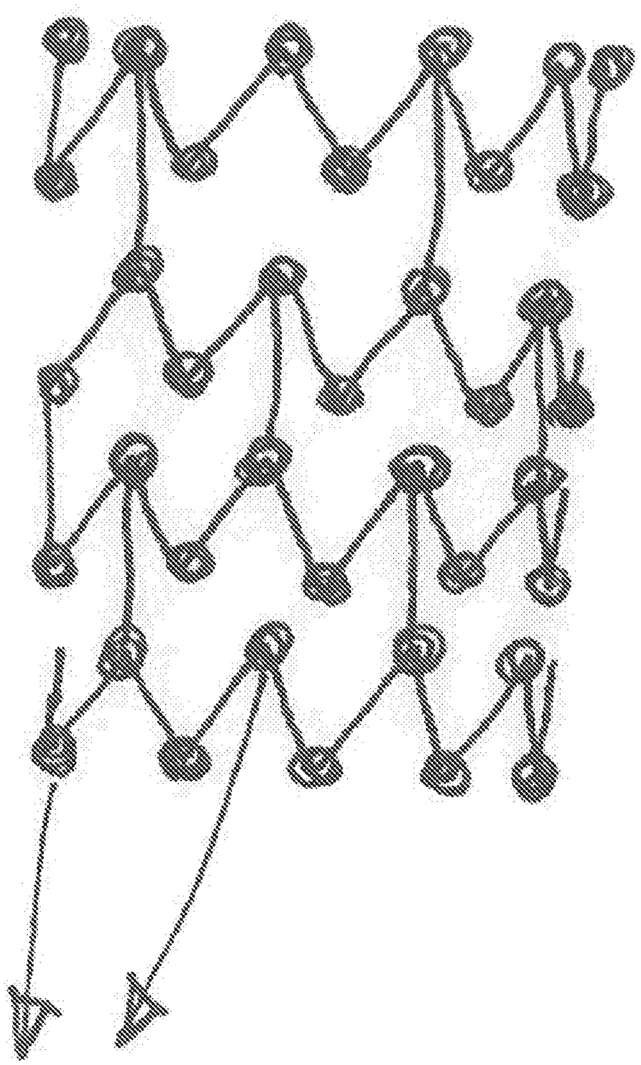
FIG. 3 illustrates a slow release leptin eluted from a scaffold.

As is mentioned hereinabove, compositions (also called, compositions-of-matter) according to the teachings herein also includes a carrier for local delivery of the leptin antagonist. Such a carrier can be a mesh (FIG. 1*c*) an injectable gel (e.g. in-situ forming depot) (FIG. 1*a*), a thin (preferably biodegradable) film (FIG. 1*b*), a scaffold (FIG. 3). In some embodiments, the composition is a coating on a medical device (FIG. 27A). In some embodiments, a medical device is impregnated with the composition (FIG. 27B). In some embodiments, the composition is in the form of a sheet (such as the film of FIG. 1*b* or the mesh of FIG. 1*c*) that constitutes a portion of a medical device such as a stent cover (FIG. 27C) or graft of a graft-stent assembly (FIG. 27D). In some embodiments, the composition constitutes a medical device (FIG. 27E).

Figure 2:
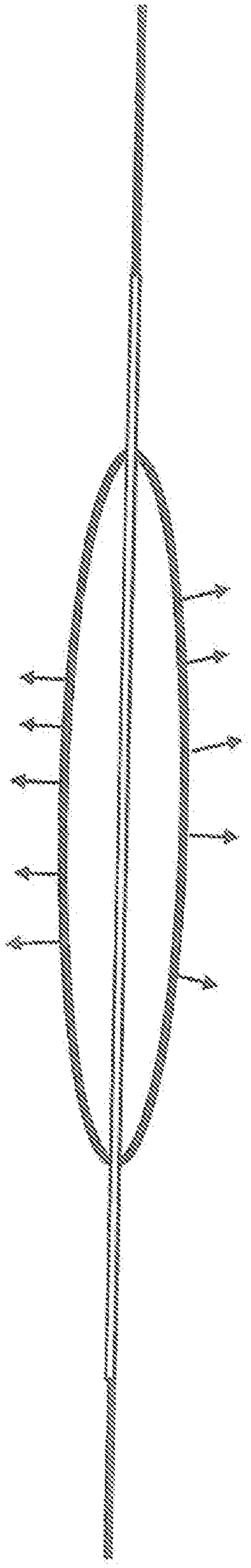
FIG. 2 illustrates a balloon catheter configured for local release of a leptin antagonist (drug release indicated by arrows).

In some embodiments a carrier of a composition is a balloon catheter, or a composition is delivered locally using a drug-eluting balloon catheter (FIG. 2). The manufacture and use of drug-eluting balloons for localized delivery of active-pharmaceutical ingredients are well known in the art (especially to the walls of fluid-filled bodily cavities, such as of the cardiovascular system), for example, the In.Pact Admiral® DCB drug-coated balloon by Medtronic (Dublin, Ireland) and Lutonix® 035 by C. R. Bard, Inc. (Murray Hill, N.J., USA).

Examples of in-situ formed depots (ISFD) include semi-solid polymers which can be injected as a melt and form a depot upon cooling to body temperature or two part systems which gel upon mixing (FIG. 3*a*). Depending on the embodiments, such compositions can be injected into or in contact with bodily tissue that is to be treated The requirements for a semi-solid ISFDs include low melting or glass transition temperatures in the range of 25-65° C. and an intrinsic viscosity in the range of 0.05-0.8 dl/g [12-14]. Below the viscosity threshold of 0.05 dl/g no delayed diffusion could be observed, whereas above 0.8 dl/g the ISFD was no longer injectable using a needle. At injection temperatures above 37° C. but below 65° C. these polymers behave like viscous fluids which solidify to highly viscous depots. Drugs are incorporated into the molten polymer by mixing without the application of solvents. In the art, it is known to use thermoplastic pastes (TP) can be used to generate a subcutaneous drug reservoir from which diffusion occurs into the systemic circulation. In contrast, in some embodiments of the teachings herein, a thermoplastic paste is used to generate a composition for the sustained release of leptin antagonist from which diffusion occurs into tissue in contact with the composition, thereby effecting sustained-release local administration of the leptin antagonist.

In situ cross-linked polymer systems utilize a cross-linked polymer network to control the diffusion of bioactive agents (e.g., leptin antagonists for implementing the teachings herein) over a prolonged period of time, thereby allowing implementation of sustained release compositions comprising leptin antagonists for use in local administration thereof. Use of in situ cross-linking implants necessitate protection of the bioactive agents during the cross-linking reaction. This could be achieved by encapsulation into fast degrading gelatin micro-particles.

An ISFD can also be based on polymer precipitation. A water-insoluble and biodegradable polymer is dissolved in a biocompatible organic solvent to which leptin antagonist is added forming a solution or suspension after mixing that constitutes a composition according to the teachings herein. When this composition is injected into the body of a subject in need thereof the water miscible organic solvent dissipates and water penetrates into the organic phase. This leads to phase separation and precipitation of the polymer forming a depot at the site of injection. One example of such a system is Atrigele™ (ARTIX Laboratories). The thus-formed depot is a composition for the sustained release of leptin antagonist from which diffusion occurs into tissue in contact with the composition, thereby effecting sustained-release local administration of the leptin antagonist.

Thermally induced gelling systems can also be used as ISFDs. Numerous polymers show abrupt changes in solubility as a function of environmental temperature. The prototypic thermosensitive polymer is poly(N-isopropyl acryl amide), poly-NIPAAM, which exhibits a rather sharp lower critical solution temperature.

Thermoplastic pastes such as the new generation of poly(ortho-esters) developed by AP Pharma can also be used for depot drug delivery. Such pastes include polymers that are semi-solid at room temperature, hence heating for drug incorporation and injection is no longer necessary. Injection is possible through needles no larger than 22 gauge. The leptin antagonist is mixed into the systems in a dry and, therefore, stabilized state. Shrinkage or swelling upon injection is thought to be marginal and, therefore, the initial drug burst is expected to be lower than in the other types of ISFD. An additional advantage is afforded by the self-catalyzed degradation by surface erosion. As noted above, IFSD compositions are suitable for effecting sustained-release local administration of the leptin antagonist. In some embodiments, an IFSD composition can be formulated for sustained-release (SR), extended-release (ER, XR, or XL), time-release or timed-release, controlled-release (CR), or continuous-release.

Examples of thin films (FIG. 3*b*) suitable for release of a leptin antagonist (or polynucleotide encoding same) include polymeric films (for a review of thin films, see Zelikin ACS Nano, 2010, 4 (5), pp 2494-2509; Venkat et al. 2010, Polymer Thin Films for Biomedical Applications, Wiley VCH Verlag GmbH & Co. KGaA, Weinheim). Such thin film carriers can be biodegradable or dissolvable over time.

Biodegradable microspheres fabricated from, for example, PGA, PLGA, PLA, or PLLA can also be used for local delivery of a leptin antagonist. Such microspheres can be produced as described by Kim and Park (J Control Release. 2004 Jul. 23; 98(1): 115-25).

A balloon such as an angioplasty balloon (FIG. 2) can also be used to deliver a leptin antagonist to a vascular wall or an inner wall of a heart chamber. Approach for coating/loading a balloon with a peptide are described in EP2643030; U.S. Pat. Nos. 8,617,136; 8,617,104; 8,617,114; WO1997017099; US20110166547 and US20120150142. As noted above, such drug-eluting balloons for use for localized delivery of active-pharmaceutical ingredients are well known in the art, for example, the In.Pact Admiral® drug-coated balloon by Medtronic (Dublin, Ireland) and Lutonix® 035 by C. R. Bard, Inc. (Murray Hill, N.J., USA). It is important to note that such drug-eluting balloons are known to administer extended release compositions of active pharmaceutical ingredients, e.g., In.Pact Admiral delivers a composition that provides extended release of a continuous therapeutic dose of Paclitaxel for over 180 days.

Although delivery of leptin or leptin receptor binding agents such as those described above (or expression thereof in cardiovascular cells), is presently preferred, downregulation of leptin activity at specific tissues can also be effected at the transcript level using a variety of molecules that interfere with transcription and/or translation (e.g., antisense, siRNA, Ribozyme, or DNAzyme).

RNA interference can be used to downregulate endogenous leptin via a small interfering RNA (siRNA) molecule. RNAi is a two-step process, in the first, the initiation step, input double-stranded (dsRNA) is digested into 21- to 23-nucleotide (nt) small interfering RNAs (siRNAs), probably by the action of Dicer, a member of the RNase III family of dsRNA-specific ribonucleases, which processes (cleaves) dsRNA (introduced directly or by means of a transgene or a virus) in an ATP-dependent manner. Successive cleavage events degrade the RNA to 19- to 21-bp duplexes (the siRNA), each with 2-nucleotide 3' overhangs (Hutvagner, G. and Zamore. P. D. (2002). RNAi: Nature abhors a double-strand. Curr Opin Gen Dev 12, 225-232; and Bernstein, E. (2001). Role for a bidentate ribonuclease in the initiation step of RNA interference. Nature 409, 363-366).

In the second step, termed the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base-pairing interactions and cleaves the mRNA into 12-nucleotide fragments from the 3' terminus of the siRNA (Hutvagner and Zamore (2002); Hammond et al. (2001) Nat. Rev. Gen. 2:110-119 (2001); and Sharp, P. A. (2001). RNA interference. Genes Dev 15, 485-490). Although the mechanism of cleavage remains to be elucidated, research indicates that each RISC contains a single siRNA and an RNase (Hutvagner and Zamore (2002)).

Synthesis of RNAi molecules suitable for use with the present invention can be effected as follows. First, the leptin mRNA sequence (SEQ ID NO 2) is scanned downstream of the AUG start codon for AA-dinucleotide sequences. Occurrence of each AA and the 19 3'-adjacent nucleotides is recorded as a potential siRNA target site. Preferably, siRNA target sites are selected from the open reading frame (ORF), as untranslated regions (UTRs) are richer in regulatory protein binding sites. UTR-binding proteins and/or translation initiation complexes may interfere with binding of the siRNA endonuclease complex (Tuschl (2001)). It will be appreciated, however, that siRNAs directed at untranslated regions may also be effective, as demonstrated for GAPDH, wherein siRNA directed at the 5' UTR mediated about a 90% decrease in cellular GAPDH mRNA and completely abolished protein levels (wwwdotambiondotcom/techlib/tn/91/912dothtml).

Second, potential target sites are compared to an appropriate genomic database (e.g., human, mouse, rat, etc.) using any sequence alignment software, such as the BlastN software available from the NCBI server (wwwdotncbidotnlmdotnihdotgov/BLAST/). Putative target sites that exhibit significant homology to other coding sequences are filtered out.

Qualifying target sequences are selected as templates for siRNA synthesis. Preferred sequences are those including low G/C content, as these have proven to be more effective in mediating gene silencing as compared with sequences including G/C content higher than 55%. Several target sites are preferably selected along the length of the target gene for evaluation. For better evaluation of the selected siRNAs, a negative control is preferably used in conjunction. Negative-control siRNAs preferably include the same nucleotide composition as the siRNAs but lack significant homology to the genome. Thus, a scrambled nucleotide sequence of the siRNA is preferably used, provided it does not display any significant homology to any other gene.

Another agent capable of downregulating leptin is a DNAzyme molecule, which is capable of specifically cleaving an mRNA transcript or a DNA sequence of the leptin. DNAzymes are single-stranded polynucleotides that are capable of cleaving both single- and double-stranded target sequences (Breaker, R. R. and Joyce, G. F. (1995). A DNA enzyme with $Mg^{2+}$-dependent RNA phosphoesterase activity. Curr Biol 2, 655-660; Santoro, S. W. and Joyce, G. F. (1997). A general purpose RNA-cleaving DNA enzyme. Proc Natl Acad Sci USA 94, 4262-4266). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro and Joyce (1997)); for review of DNAzymes, see: Khachigian, L. M. (2002). DNAzymes: cutting a path to a new class of therapeutics. Curr Opin Mol Ther 4, 119-121.

Examples of construction and amplification of synthetic, engineered DNAzymes recognizing single- and double-stranded target cleavage sites are disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh, T. et al., Abstract 409, American Society of Gene Therapy 5th Annual Meeting (wwwdotasgtdotorg), Jun. 5-9, 2002, Boston, Mass. USA.). In another application, DNAzymes complementary to bcr-abl oncogenes were successful in inhibiting the oncogene's expression in leukemia cells, and in reducing relapse rates in autologous bone marrow transplants in cases of Chronic Myelogenous Leukemia (CML) and Acute Lymphoblastic Leukemia (ALL).

Downregulation of leptin can also be effected by using an antisense polynucleotide capable of specifically hybridizing with an mRNA transcript encoding leptin.

Design of antisense molecules that can be used to efficiently downregulate a leptin must be effected while considering two aspects important to the antisense approach. The first aspect is delivery of the oligonucleotide into the cytoplasm of the appropriate cells, while the second aspect is design of an oligonucleotide that specifically binds the designated mRNA within cells in a manner inhibiting the translation thereof.

The prior art teaches of a number of delivery strategies which can be used to efficiently deliver oligonucleotides into a wide variety of cell types (see, for example: Luft, F. C. (1998). Making sense out of antisense oligodeoxynucleotide delivery: getting there is half the fun. J Mol Med 76(2), 75-76 (1998); Kronenwett et al. (1998). Oligodeoxyribonucleotide uptake in primary human hematopoietic cells is enhanced by cationic lipids and depends on the hematopoietic cell subset. Blood 91, 852-862; Rajur, S. B. et al. (1997). Covalent protein-oligonucleotide conjugates for efficient delivery of antisense molecules. Bioconjug Chem 8, 935-940; Lavigne et al. Biochem Biophys Res Commun 237: 566-71 (1997); and Aoki, M. et al. (1997). In vivo transfer efficiency of antisense oligonucleotides into the myocardium using HVJ-liposome method. Biochem Biophys Res Commun 231, 540-545).

In addition, also available are algorithms for identifying those sequences with the highest predicted binding affinity for their target mRNA based on a thermodynamic cycle that accounts for the energetics of structural alterations in both the target mRNA and the oligonucleotide (see, for example, Walton, S. P. et al. (1999). Prediction of antisense oligonucleotide binding affinity to a structured RNA target. Biotechnol Bioeng 65, 1-9).

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF-alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiencies of specific oligonucleotides using an in vitro system were also published (Matveeva, O. et al. (1998). Prediction of antisense oligonucleotide efficacy by in vitro methods. Nature Biotechnology 16, 1374-1375).

Another agent capable of down-regulating leptin is a ribozyme molecule capable of specifically cleaving an mRNA transcript encoding leptin. Ribozymes increasingly are being used for the sequence-specific inhibition of gene expression by the cleavage of mRNAs encoding proteins of interest (Welch, P. J. et al. (1998). Expression of ribozymes in gene transfer systems to modulate target RNA levels. Curr Opin Biotechnol 9, 486-496).

An additional method of regulating the expression of leptin in cardiovascular cells is via triplex-forming oligonucleotides (TFOs). Recent studies show that TFOs can be designed to recognize and bind to polypurine or polypirimidine regions in double-stranded helical DNA in a sequence-specific manner. These recognition rules are outlined in: Maher III, L. J., et al. (1989). Inhibition of DNA binding proteins by oligonucleotide-directed triple helix formation. Science 245, 725-730; Moser, H. E., et al. (1987). Sequence-specific cleavage of double helical DNA by triple helix formation. Science 238, 645-650; Beal, P. A. and Dervan, P. B. (1991). Second structural motif for recognition of DNA by oligonucleotide-directed triple-helix formation. Science 251, 1360-1363; Cooney, M., et al. (1988). Science 241, 456-459; and Hogan, M. E., et al., EP Publication 375408. Modifications of the oligonucleotides, such as the introduction of intercalators and backbone substitutions, and optimization of binding conditions (e.g., pH and cation concentration) have aided in overcoming inherent obstacles to TFO activity such as charge repulsion and instability, and it was recently shown that synthetic oligonucleotides can be targeted to specific sequences (for a recent review, see Seidman, M. M. and Glazer, P. M. (2003). The potential for gene repair via triple helix formation J Clin Invest 112, 487-494).

As is described hereinabove, the present invention can be used to treat cardiovascular disorders affecting heart or vascular tissue. The following describes several option for local delivery of a leptin antagonist to tissue, for example heart and other cardiovascular tissue, specifically muscle and valve tissue.

(i) Arterial catheterization can be used to inject as a bolus, or to deploy a medical device such as a mesh, a thin film, a biodegradable scaffold, a stent cover, a stent, a graft assembly, a coil, a stent, a ring or a prosthetic cardiac valve loaded with a leptin antagonist against a luminal wall of an ascending aorta distal to the orifice of the coronary arteries. In case of aneurysm at another location along the aorta, a visceral artery, or small tributary; the same intra-arterial approach can be used for local application.

(ii) An IFSD (for example, as described above, e.g., a gel) loaded with a leptin antagonist can be delivered via a balloon or needle to the aortic wall.

(iii) A composition such as a pliable non-degradable or biodegradable mesh or film loaded with the leptin antagonist that is placed in contact with an outer surface of tissue or an organ to be treated, e.g., by surgical delivery via open surgery or thorascopy, for example surgically delivered to the peri-aortic region (above the aortic root level). In case of small aneurysm in the abdominal aorta the leptin antagonist extended release film or mesh can be applied via open surgery or minimally invasive laparoscopy.

Method of Treatment

According to an aspect of some embodiments of the invention, there is also provided a method of treatment comprising: exposing in vivo tissue of a subject in need thereof to a pharmaceutically-effective amount of leptin antagonist thereby providing a therapeutic effect to the tissue. For example, in some such embodiments, a composition comprising leptin antagonist is administered (e.g., by injection) locally and selectively via intra-vascular approach, or directly into the tissue. In some embodiments, the exposing of the in vivo tissue to the leptin antagonist is substantially continuously for a period of not less than three days. In some embodiments, the period is not less than five days, not less than 8 days and even not less than 14 days. For example, in some such embodiments, an extended release composition comprising leptin antagonist (e.g., a medical device impregnated with, coated with or made from a leptin antagonist is placed directly in contact with the tissue.

According to an aspect of some embodiments of the invention, there is also provided a method of treatment comprising implanting in contact with tissue in need thereof in the body of a subject a composition configured for the in vivo release of leptin antagonist, thereby providing a therapeutic effect to the tissue. In some embodiments, the composition is configured for sustained release of the leptin antagonist. In some embodiments, the implanting is intracavitary implanting within a fluid-filled bodily cavity of the subject. In some embodiments, by sustained release is meant that, when the composition is implanted in vivo, leptin antagonist is released from the composition in pharmaceutically effective amounts for a period of not less than three days, in some embodiments not less than five days, not less than 8 days and even not less than 14 days.

The subject in need thereof is any suitable mammalian subject. In some embodiments, the subject is a non-human animal. In some embodiments, the subject is a human.

The need is any suitable need. In some embodiments, the need is at least one need selected from the group consisting of: attenuating a pathology; reducing the chance of developing a pathology; reducing the rate of development a pathology; and mitigating the effect of a pathology.

The pathology is any pathology that can be treated by local administration of leptin antagonist, and in some embodiments, substantial continuous local exposure to leptin antagonist. In some embodiments, the pathology is at least one pathology selected from the group consisting of:

cardiovascular disease;

remodeling of stable athersclerotic plaque into an unstable lesion (vulnerable plaque or rupture-prone plaque);

ascending aortic aneurysm, in some embodiments ascending aortic aneurysm associated with at least one member of the group consisting of hypertension, dyslipidemia, hypercholesterolemia, obesity, diabetes mellitus and bicuspid aortic valve (BAV);

thoracic aortic aneurysm (e.g., to prevent rupture or dissection thereof);

Takayasu disease (e.g., to attenuate cellular proliferative response, and aortic wall remodeling in some embodiments, by administration or implantation of a leptin antagonist composition to an inner or outer vessel wall in the vicinity of a vascular lesion);

Rheumatoid arteritis (e.g., to attenuate aortic wall remodeling, in some embodiments, by administration or implantation of a leptin antagonist composition to an inner or outer vessel wall in the vicinity of a vascular lesion);

Marfan's syndrome (by mitigation or prevention of ascending aortic aneurysms or pulmonary artery aneurysms, in some embodiments, by perivascular administration or deployment of a leptin antagonist composition to the outer or inner wall of the ascending aorta); giant cell arteritis; ankylosing spondylitis; inflammatory aortic aneurysm; peripheral arterial or venous aneurysms; prevention of arterial dilatation at site of anchorage of bridging stent grafts ("landing zone") applied for EVAR (in the abdominal or thoracic aorta), visceral or peripheral arteries; prevention of myointimal hyperplasia at sites of vascular injury; prevention of restenosis following PTA or PTCA (peripheral or cardiac balloon angioplasty); angiogenesis; cancer; and arteriovenous malformation (e.g., administration of leptin antagonist composition directly into a malformation or into the feeding artery).

Depending on the embodiment, any pathology, including any pathology listed above, may be treated in accordance with the teachings herein by local administration of leptin antagonist. For example, in some embodiments, administration is local administration of a dose (optionally repeated) of leptin antagonist, for example by direct intravascular injection into the affected tissue or tissue proximal to the affected tissue or with the use of a drug-eluting balloon. For example, in some embodiments, administration is local administration by a sustained release composition (that releases a pharmaceutically-effective amount of leptin antagonist for a period of not less than three days) placed in contact with an outer surface of tissue (e.g., with tunica externa), inside the tissue (e.g., injection of a IFSD as described above into the tissue) or with a composition placed in contact with an inner surface of a tissue (e.g. with tunica intima).

The tissue is any suitable tissue. In some embodiments the tissue is part of the cardiovascular system. In some such embodiments, the tissue is selected from the group consisting of arteries, coronary arteries, ascending aorta, abdominal aorta, pulmonary artery mitral valve, aortic valve and pulmonary valve. In some embodiments, the tissue is cardiovascular tissue with accumulated plaque, for example, an artery with accumulated plaque. In some embodiments, the tissue is a tumor, especially a cancerous tumor that grows or spreads in a process that includes angiogenesis. In some embodiments, the tissue is an arteriovenous malformation.

In some embodiments, the leptin antagonist composition is locally administered during or post surgery, e.g., following carotid thrombendartrectomy or after ablation of atherosclerotic occlusion from a vessel.

In some embodiments, the leptin antagonist is locally administered by contact to the outside of tissue to be treated, e.g., in contact with tunica externa.

In some embodiments, the leptin antagonist is locally administered inside tissue, for example, is injected or implanted inside tissue such as a tumor or the site of arteriovenous malformation.

In some embodiments, the leptin antagonist is locally administered intraluminally, e.g., a leptin antagonist composition is deployed in contact with a tunica intima, inside a fluid-filled bodily cavity such as inside the lumen of a blood vessel e.g., using an intraluminal catheter, for example, in conjunction with a stent or prosthetic cardiac valve.

It should be noted that in some embodiments, local administration of a leptin antagonist in accordance with the teachings herein at the ascending aorta may be effective in attenuating ascending aortic aneurysms, as well as moderating left ventricular hypertrophy, and left heart valve thickness (aortic and mitral). Administration of leptin antagonist at arterial aneurysms in other locations is anticipated to achieve a similar outcome, attenuating aneurysm expansion.

Accordingly, embodiments of the teachings herein are used to treat cardiovascular disorders such as heart valve stenosis, arterial or venous aneurysms, or left ventricular remodeling by enabling localized release of a leptin antagonist at the site of treatment.

Pharmaceutical Composition and Method of Making Pharmaceutical Composition

According to an aspect of some embodiments of the teachings herein, there is also provided a pharmaceutical composition, comprising: as an active ingredient a leptin antagonist; and a pharmaceutically acceptable carrier configured for in vivo sustained release of the leptin antagonist.

According to an aspect of some embodiments of the teachings herein, there is also provided a method of making a pharmaceutical composition, comprising: combining a leptin antagonist; and a pharmaceutically acceptable carrier configured for in vivo sustained release of the leptin antagonist.

In some embodiments, by sustained release is meant that, when the composition is implanted in vivo, leptin antagonist is released from the composition in pharmaceutically effective amounts for a period of not less than three days, in some embodiments not less than five days, not less than 8 days and even not less than 14 days.

In some embodiments, the in vivo implantation is in a human subject. The in vivo implantation is in any suitable location. In some embodiments, the in vivo implantation is contacting an organ through a serous tissue layer or adventitia (tunica externa) layer covering the organ, e.g., is placed contacting a blood vessel such as the aorta from the outside of the blood vessel. In some embodiments, the in vivo implantation is outside an organ directly contacting tissue of the organ (for organs covered with serous tissue, the composition is implanted underneath the serous tissue). In some embodiments, the in vivo implantation is into an organ. In some embodiments, the implantation is from inside a hollow defined by the organ, for example, inside a blood vessel lumen contacting the endothelium thereof.

In some embodiments, the composition is in the form of a leptin antagonist containing sheet, in some such embodiments configured to be contacted with in vivo tissue, for example, by suturing, with the use of biological adhesive, or pressed against the tissue, for example with the help of a stent or such component, e.g., the sheet is used as a stent cover for a balloon-expandable or self-expanding stent.

In some embodiments, the composition is configured to coat or be supported by an implantable medical device, e.g., is used as a coating for, is adsorbed or absorbed into or onto a stent (thereby constituting a drug-eluting balloon expandable or self-expanding stent), prosthetic valve (e.g., cardiac valve), implantable spike or rod.

In some embodiments, the composition is formed into the shape of an implantable medical device, e.g., a bioresorbable stent, a bioresorbable spike or rod.

In some embodiments, the composition is injectable, e.g., is a viscous fluid or a fluid that subsequent to injection solidifies or gels, e.g., a hydrogel.

Any suitable pharmaceutically-acceptable carrier that can be configured for in vivo sustained release of the leptin antagonist can be used. In some embodiments the carrier comprises a biodegradable polymer. In some such embodiments, the carrier comprises a polymer selected from the group consisting of a hydrogel, poly glycolic acid (PGA), poly lactic co-glycolic acid (PLGA), polylactide (PLA), and poly (L-lactide) (PLLA), and combinations thereof.

The pharmaceutical composition and methods of making such a composition are in accordance with those known in the art of pharmacology, using any suitable method or combination of methods as known in the art such as described in "Remington's Pharmaceutical Sciences," Mack Publishing Co., Easton, Pa., latest edition, which is incorporated herein by reference. Such methods include conventional mixing, curing, polymerizing, dissolving, granulating, dragee-making, levigating, emulsifying, encapsulating, entrapping or lyophilizing. Pharmaceutical compositions may be formulated in conventional manner using one or more physiologically acceptable carriers, diluents, excipients or auxiliaries which facilitate processing of the leptin antagonist into a pharmaceutical composition.

Use of Leptin Antagonist

According to an aspect of some embodiments of the teachings herein, there is also provided a use of a leptin antagonist according to the teachings herein for the localized treatment of tissue of a living organism, comprising, implanting a composition comprising a leptin antagonist in vivo to contact tissue in need thereof so that the tissue is exposed to a pharmaceutically effective amount of leptin antagonist, thereby providing a therapeutic effect to the tissue. In some embodiments, the composition and the implanting is such that the tissue is exposed to a pharmaceutically effective amount of leptin antagonist substantially continuously for a period of at least three days. In some embodiments, the period is not less than five days, not less than 8 days and even not less than 14 days.

In some embodiments, an above administration is periodically repeated. For example, in some embodiments, administration of leptin antagonist is repeated. For example, in some embodiments, administration of leptin antagonist is repeated after at least a period, the period selected from the group consisting of 1 week, 2 weeks, 3 weeks, 4 weeks, 1 month, 2 months and 3 months.

Treatment of Athersclerotic Plaque

It is known that stable athersclerotic plaque accumulates in the inner walls of mammalian arteries. In some instances, the stable plaque transforms into an unstable lesion such as vulnerable plaque or rupture-prone plaque. Fragment from the unstable lesion may disintegrate, forming emboli.

An aspect of the teachings herein is based on the Inventor's discovery that locally synthesized leptin within the carotid atherosclerotic plaque, which characterize unstable plaques (rupture prone), correlates with brain emboli. Therefore, the Inventor believes that a leptin antagonist administered to a stable athersclerotic plaque should reduce the rate and/or incidence of the conversion of a stable athersclerotic plaque to an unstable lesion.

According to an aspect of some embodiments of the teachings herein, there is provided a method for treatment of athersclerotic plaque, comprising: administering a pharmaceutically-effective amount of a leptin antagonist to athersclerotic plaque accumulated in the inner walls of an artery, thereby at least one of: (a) reducing the rate and (b) reducing the incidence, of conversion of a stable athersclerotic plaque to an unstable lesion.

Administration of the leptin antagonist is any suitable administration. In some embodiments, the administration is by sustained-release of the leptin antagonist directly to an inner wall in which plaque is accumulated, from a leptin antagonist containing composition. In some embodiments, such sustained release is substantial continuous release of a pharmaceutically-effective amount of leptin antagonist for a period of not less than three days, not less than 5 days, not less than 8 days and even not less than 14 days. In some such embodiments, the composition is in direct contact with the surface of the plaque to be treated. In some embodiments, the composition is in contact with the inner walls of a blood vessel with accumulated plaque.

Surgical Connecting Devices

It is know that trauma to a blood vessel may lead to myointimal hyperplasia (MIH), One type of trauma that may cause MIH is caused by surgical connecting devices such as surgical staples and suture threads that are applied to blood vessels, for example, during surgery for example surgical anastomosis. It has been found that in some instances, local administration of leptin antagonist to such wounds may be able to mitigate or prevent MIH.

Thus, according to an aspect of some embodiments of the invention, there is also provided a surgical connecting device, comprising: a solid device body made of a material; and functionally associated with the device body, a pharmaceutically-effective amount of leptin antagonist. In some embodiments, the device body is in the form selected from the group consisting of surgical suture thread and a surgical staple.

Figure 27:
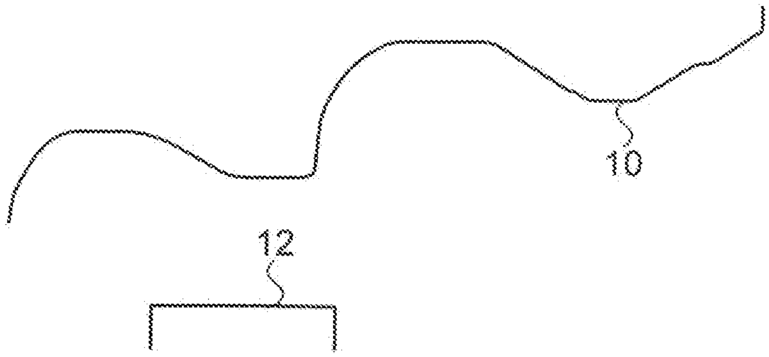
FIG. 27 schematically depicts embodiments of surgical connecting devices according to the teachings herein.

An embodiment of a suture thread 10 and of a surgical staple 12 in accordance with the teachings herein are schematically depicted in FIG. 27.

In some embodiments, the device body, e.g., of thread 10 or staple 12, is absorbable (i.e., bioresorbable).

The device body, e.g., of thread 10 or staple 12, is made of any suitable material. In some embodiments, the device body is made of a material comprises a polymer selected from the group consisting of poly glycolic acid (PGA), poly lactic co-glycolic acid (PLGA), polylactide (PLA), and poly (L-lactide) (PLLA), and combinations thereof.

The leptin antagonist is functionally associated with the device body, e.g., of thread 10 or staple 12, in any suitable manner.

In some embodiments, the functional association of the leptin antagonist with the device body is that a composition comprising the leptin antagonist coats the device body. For example, in some such embodiments thread 10 or staple 12 are made of PGA, and coated with a coating of PLGA that includes a pharmaceutically effective amount of leptin antagonist.

In some embodiments, the functional association of the leptin antagonist with the device body is that a composition comprising the leptin antagonist impregantes the device body. For example, in some such embodiments thread 10 is made of silk and impregnated with a composition that includes a pharmaceutically effective amount of leptin antagonist.

In some embodiments, the functional association of the leptin antagonist with the device body is that the material from which the device body is made is a composition comprising the leptin antagonist. For example, in some such embodiments thread 10 or staple 12 are made of PGA that includes a pharmaceutically effective amount of leptin antagonist.

Administration of Leptin Antagonist in Fluid-Filled Cavities

As noted above, the present inventor has found that in vivo implantation inside a fluid-filled cavity of the body (for example of the cardiovascular system such as blood vessels or cardiac chambers) can have a desirable pharmaceutical effect on tissue in proximity of the implanted composition with limited or no substantial side-effects:

Method of Treatment in a Fluid-Filled Bodily Cavity

Thus, according to an aspect of some embodiments of the invention, there is also provided a method of treating a condition in a subject in need thereof, the method comprising administering intracavitarily to inner walls of a fluid-filled bodily cavity of the subject a composition comprising a leptin antagonist. In some embodiments of the method, the subject is human. In some embodiments of the method, the subject is a non-human animal.

In some embodiments of the method, the intracavitary administration exposes in vivo tissue to a pharmaceutically-effective amount of the leptin antagonist and thereby provides a therapeutic effect to the in vivo tissue.

In some embodiments of the method, the in vivo tissue comprises tissue of the inner walls of the cavity (e.g., tunica intima).

In some embodiments of the method, the administration is local administration. In some such embodiments, the in vivo tissue exposed to the pharmaceutically-effective amount of the leptin antagonist is exclusively tissue in physical proximity to the administered composition. In some such embodiments, the in vivo tissue exposed to the pharmaceutically-effective amount of the leptin antagonist is exclusively tissue in physical contact with the administered composition.

In some embodiments of the method, exposing of the in vivo tissue to a pharmaceutically-effective amount of the leptin antagonist is substantially continuously for a period of at least three days, at least five days, at least eight days and in some embodiments, even at least fourteen days.

In some embodiments of the method, the composition is a sustained-release composition, configured for sustained release of a pharmaceutically-effective amount of the leptin antagonist when located inside a bodily cavity. In some embodiments, the sustained release comprises release of a pharmaceutically-effective amount of the leptin antagonist over a period of at least three days, at least five days, at least eight days and in some embodiments, even at least fourteen days.

In some embodiments of the method, the intracavitary administering comprises implantation of the composition within the cavity in contact with the inner walls of the cavity.

In some embodiments of the method, the intracavitary administering comprises deploying an intracavitarily-implantable medical device in the cavity. In some such embodiments, the medical device is deployed in contact with the inner walls of the cavity. In some such embodiments, the leptin antagonist is functionally associated with the deployed intracavitarily-implantable medical device. In some preferred such embodiments, the leptin antagonist is functionally associated with a portion of the deployed intracavitarily-implantable medical device that contacts bodily tissue when the medical device is deployed. In some such embodiments, the intracavitarily implantable medical device is selected from the group consisting of: a stent cover, a graft assembly, a coil (e.g., aneurysm coil), a stent (e.g., expandable stent, self-expanding stent, covered stent, partially covered stent, not covered stent), a ring (e.g, a graft anchor), a suture, a staple and a prosthetic cardiac valve. Although the teachings herein are applicable to any prosthetic cardiac valve, the teachings are particularly advantageous for implementing with catheter-deployed prosthetic cardiac valves (e.g., TAMVI, TAVI): since these valves are typically held in place without sutures so that myointimal hyperplasia that potentially develops as a result of trauma caused during deployment may lead to leakage.

Composition for Treatment in a Fluid-Filled Bodily Cavity

According to an aspect of some embodiments of the invention, there is also provided a composition comprising: a leptin antagonist for use in treating a condition, wherein the composition is configured for intracavitary administration to inner walls of a fluid-filled bodily cavity of a subject.

In some embodiments of the composition, the subject is human. In some embodiments of the composition, the subject is a non-human animal.

In some embodiments, the intracavitary administration of the composition exposes in vivo tissue to a pharmaceutically-effective amount of the leptin antagonist, thereby providing a therapeutic effect to the in vivo tissue. In some embodiments, such in vivo tissue comprises tissue of inner walls of a the cavity.

In some embodiments, the administration is local administration. In some such embodiments, the in vivo tissue exposed to the pharmaceutically-effective amount of the leptin antagonist is exclusively tissue in physical proximity to the administered composition. In some such embodiments, the in vivo tissue exposed to the pharmaceutically-effective amount of the leptin antagonist is exclusively tissue in physical contact with the administered composition.

In some embodiments of the composition, exposing of the in vivo tissue to a pharmaceutically-effective amount of the leptin antagonist is substantially continuously for a period of at least three days, at least five days, at least eight days and in some embodiments, even at least fourteen days.

In some embodiments, the composition is a sustained-release composition, configured for sustained release of a pharmaceutically-effective amount of the leptin antagonist when located inside a bodily cavity. In some embodiments, the sustained release comprises release of a pharmaceutically-effective amount of the leptin antagonist over a period of at least three days, at least five days, at least eight days and in some embodiments, even at least fourteen days.

In some embodiments of the composition, the configuration for intracavitary administration comprises configuration for implantation of the composition within the cavity in contact with the inner walls of the cavity.

In some embodiments of the composition, the configuration for intracavitary administration comprises configuration for deploying with an intracavitarily-implantable medical device in the cavity. In some such embodiments, the medical device is configured for deployment in contact with the inner walls of the cavity. In some such embodiments, the leptin antagonist is functionally associated with the intracavitarily-implantable medical device. In some preferred such embodiments, the leptin antagonist is functionally associated with a portion of the intracavitarily-implantable medical device that contacts bodily tissue when the medical device is deployed. In some such embodiments, the intracavitarily implantable medical device is selected from the group consisting of: a stent cover, a graft assembly, a coil (e.g., aneurysm coil), a stent (e.g., expandable stent, self-expanding stent, covered stent, partially covered stent, not covered stent), a ring (e.g, a graft anchor), a suture, a staple and a prosthetic cardiac valve. As noted above, although the teachings herein are applicable to any prosthetic cardiac valve, the teachings are particularly advantageous for implementing with catheter-deployed prosthetic cardiac valves (e.g., TAMVI, TAVI).

In some embodiments of the method or composition, the condition is a pathological cardiovascular condition. In some embodiments of the method or composition, the condition is a cardiovascular condition selected from the group consisting of atherosclerosis, valve stenosis, aneurysms, vessel response to vascular injury, and cardiomyopathy. In some embodiments of the method or composition, the administration of the leptin antagonist is to athersclerotic plaque accumulated in the inner walls of an artery, thereby at least one of: (a) reducing the rate and (b) reducing the incidence, of conversion of a stable athersclerotic plaque to an unstable lesion. In some embodiments of the method or composition, the administration of the leptin antagonist is to bodily tissue in order to prevent or mitigate the development of myointimal hyperplasia, for example, myointimal hyperplasia that potentially develops as a result of trauma caused during deployment of a medical device in a the body of a living subject.

In some embodiments of the method or composition, the composition constitutes a coating of an intracavitarily implantable medical device. In some embodiments of the method or composition, the composition is impregnated in an intracavitarily implantable medical device. In some such embodiments of the method or composition, the composition comprises, in addition to the leptin antagonist, a polymer selected from the group consisting of a hydrogel, poly glycolic acid (PGA), poly lactic co-glycolic acid (PLGA), polylactide (PLA), and poly (L-lactide) (PLLA), and combinations thereof.

In some embodiments of the method or composition, the composition is in the form selected from the group consisting of a sheet and a tube constituting a portion of an intracavitarily implantable medical device comprising the leptin antagonist. In some such embodiments of the method or composition, the composition comprises, in addition to the leptin antagonist, a polymer selected from the group consisting of a hydrogel, poly glycolic acid (PGA), poly lactic co-glycolic acid (PLGA), polylactide (PLA), and poly (L-lactide) (PLLA), and combinations thereof. In some such embodiments of the method or composition, the intracavitarily implantable medical device comprises a stent and the composition constitutes a stent cover (e.g., a partial or complete stent cover, a balloon-expandable or a self-expanding stent). In some such embodiments of the method or composition, the intracavitarily implantable medical device comprises a graft-assembly (e.g., a stent-graft or ring-graft assembly) and the composition constitutes a graft portion thereof. For example, some embodiments are configured to function as a stent-graft assembly for treatment of AAA, like the Endurant® II by Medtronic (Dublin, Ireland).

In some embodiments of the method or composition, the composition constitutes at least a portion of an intracavitarily implantable medical device, and in some embodiments, the composition constitutes substantially an entire intracavitarily implantable medical device. As noted above, in some such embodiments of the method or composition, the intracavitarily implantable medical device is selected from the group consisting of a stent cover, a graft assembly, a coil (e.g., aneurysm coil), a stent (e.g., expandable stent, self-expanding stent, covered stent, partially covered stent, not covered stent), a ring (e.g, a graft anchor), a suture, a staple and a prosthetic cardiac valve. In some such embodiments of the method or composition, the composition comprises, in addition to the leptin antagonist, a polymer selected from the group consisting of a hydrogel, poly glycolic acid (PGA), poly lactic co-glycolic acid (PLGA), polylactide (PLA), and poly (L-lactide) (PLLA), and combinations thereof.

Medical Device for Treatment in a Fluid-Filled Bodily Cavity

According to an aspect of some embodiments of the invention, there is also provided an intracavitarily-implantable medical device, comprising:

at least one solid functional device part configured for deploying the device in a fluid-filled bodily cavity of a subject; and functionally associated with at least one the device component, a leptin antagonist.

In some embodiments of the medical device, the leptin antagonist is functionally associated with the at least one the device part as a component of a pharmaceutical composition comprising the leptin antagonist.

In some embodiments of the medical device, the pharmaceutical composition is a sustained-release composition, configured for sustained release of a pharmaceutically-effective amount of the leptin antagonist when located inside a bodily cavity.

In some embodiments of the medical device, sustained release comprises release of a pharmaceutically-effective amount of the leptin antagonist over a period of at least three days, at least five days, at least eight days and in some embodiments, even at least fourteen days.

In some embodiments of the medical device, the pharmaceutically-acceptable carrier further comprises a polymer selected from the group consisting of a hydrogel, poly glycolic acid (PGA), poly lactic co-glycolic acid (PLGA), polylactide (PLA), and poly (L-lactide) (PLLA), and combinations thereof.

In some embodiments of the medical device, the functional association is at least one device component having a coating comprising the pharmaceutical composition. In some embodiments of the medical device, the functional association is at least one device component being impregnated with the pharmaceutical composition. In some embodiments of the medical device, the functional association is at least one device component being fashioned of the pharmaceutical composition.

In some embodiments of the medical device, the medical device is selected from the group consisting of a stent cover, a graft assembly, a coil (e.g., aneurysm coil), a stent (e.g., expandable stent, self-expanding stent, covered stent, partially covered stent, not covered stent), a ring (e.g, a graft anchor), a suture, a staple and a prosthetic cardiac valve (as noted above, preferably catheter-deployed prosthetic cardiac valves.

In some embodiments of the method, composition and device, the fluid-filled bodily cavity is a bodily cavity of the cardiovascular system. In some such embodiments, the cavity is selected from the group consisting of a cardiac chamber, an artery and a vein. In some such embodiments, the cardiac chamber is selected from the group consisting of left ventricle, right ventricle, left atrium and right atrium. In some such embodiments, the artery is selected from the group consisting of a systemic artery, a coronary artery and a pulmonary artery. In some such embodiments, the systemic artery is an aorta, for example selected from the group consisting of an ascending aorta, aortic arch, descending aorta and an abdominal aorta.

Figure 28:
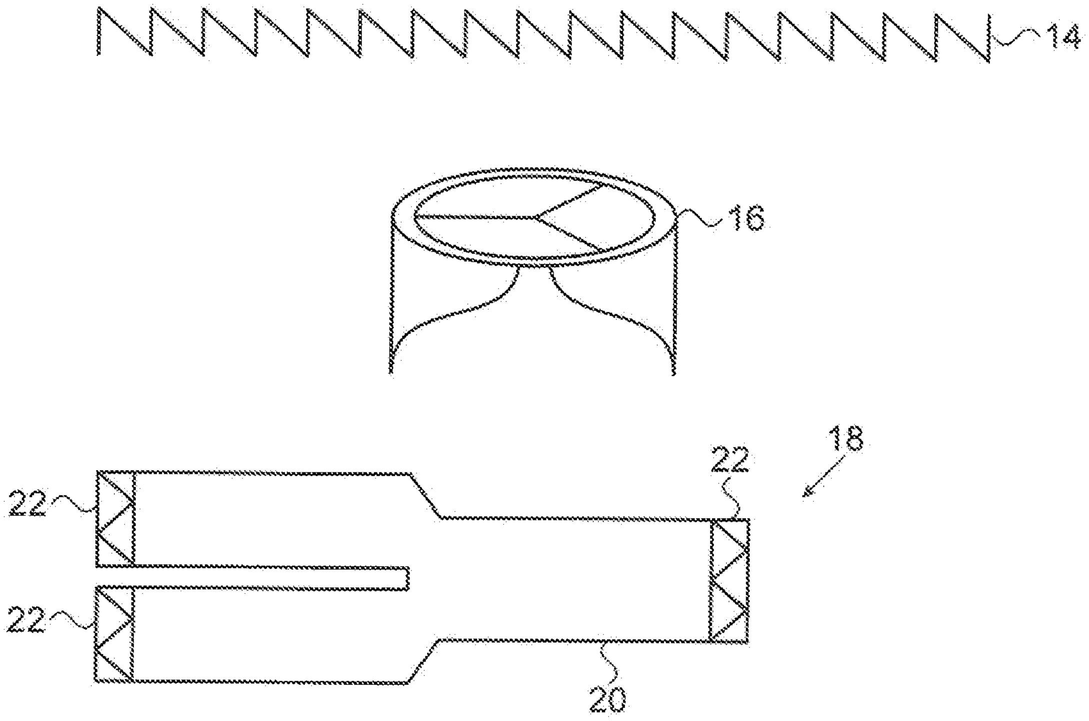
FIG. 28 schematically depicts embodiments of the teachings herein suitable for intracavitary administration of leptin antagonist.

In FIG. 28, an aneurysm coil 14 according to the teachings herein is schematically depicted. Aneurysm coil 14 is substantially similar to known aneurysm coils except by being functionally associated with a pharmaceutically-effective amount of leptin antagonist, is made in substantially the same way, and is used in substantially the same way. Depending on the embodiment, a given aneurysm coil 14 may include one or more of the additional features detailed hereinabove. For example, in some embodiments, coil 14 is made of platinum, and coated with a coating of a hydrogel that includes a pharmaceutically effective amount of leptin antagonist. For example, in some embodiments, coil 14 is made of a material such as platinum or a polymer textured with micrometer dimension features such as valleys and pores, where inside the features is held a composition (e.g., a gel such as of Example 11) that comprises leptin antagonist. For example, in some embodiments, coil 14 is made of a composition comprising the leptin antagonist, e.g., is made of PGA that includes a pharmaceutically effective amount of leptin antagonist.

In FIG. 28, a prosthetic cardiac valve 16 according to the teachings herein is schematically depicted. Prosthetic cardiac valve 16 is substantially similar to known prosthetic cardiac valves except by being functionally associated with a pharmaceutically-effective amount of leptin antagonist, is made in substantially the same way, and is used in substantially the same way. Specifically, prosthetic cardiac valve 16 has at least one component that is functionally associated with a pharmaceutically-effective amount of leptin antagonist. Depending on the embodiment, a given prosthetic cardiac valve 16 according to the teachings herein may include one or more components, each having one or more of the additional features detailed hereinabove. For example, in some embodiments, the retainer ring of prosthetic cardiac valve 16 is made of a cobalt chromium ring with a polyester cloth cover, the ring and cloth cover both coated with a coating of a hydrogel that includes a pharmaceutically effective amount of leptin antagonist. For example, in some embodiments, the leaflets of prosthetic cardiac valve 16 are made of a material such as porcine or bovine tissue (e.g., cardiac leaflets, pericardium) that has been soaked in and is therefore impregnated with a composition (e.g., a gel such as of Example 11) that comprises leptin antagonist.

In FIG. 28, a graft assembly 18 according to the teachings herein is schematically depicted. Graft assembly 18 is a ring-graft assembly suitable for treatment of abdominal aorta aneurysms and includes a flexible graft 20 that defines a conduit for blood flow and three expandable anchoring rings 22 as graft anchors. Each anchoring ring 22 is a radially expandable device that is substantially a single 360° ring of material. As known in the art, some embodiments of graft assemblies are stent-graft assemblies where one or more of the anchors are radially expandable stents, that are longer in the axial direction and/or describe more than a 360° degree rotation and/or comprise more than a single ring of material. Stents are preferred as anchors as these typically also provide support for the vessel in which deployed and provide greater anchoring of the graft to a vessel in which deployed. Graft assembly 18 is substantially similar to known graft assemblies except by being functionally associated with a pharmaceutically-effective amount of leptin antagonist, is made in substantially the same way, and is used in substantially the same way. Specifically, graft assembly 18 has at least one component that is functionally associated with a pharmaceutically-effective amount of leptin antagonist. Depending on the embodiment, a given graft assembly 18 according to the teachings herein may include one or more components, each having one or more of the additional features detailed hereinabove.

For example, in some embodiments, graft 20 is substantially a tube made of a high-density multifilament polyester cloth coated with a coating of a hydrogel that includes a pharmaceutically effective amount of leptin antagonist. In some embodiments, the coating is on the entire outer surface of graft 20. In some embodiments, the coating is on the outer surface of the termini of the three legs of graft 20 (e.g., a 5 cm length from each terminus.

For example, in some embodiments, graft 20 is made of a high-density multifilament polyester cloth coat that has been soaked in and is therefore impregnated with a composition (e.g., a gel such as of Example 11) that comprises leptin antagonist. In some embodiments, the entire graft 20 is impregnated with leptin antagonist composition. In some embodiments, only the termini of the three legs of graft 20

(e.g., a 5 cm length from each terminus) is impregnated with leptin antagonist composition.

For example, in some embodiments, rings 22 are made of nitinol, and coated with a coating of a hydrogel that includes a pharmaceutically effective amount of leptin antagonist. For example, in some embodiments, rings 22 are made of a material such as nitinol textured with micrometer dimension features such as valleys and pores, where inside the features is held a composition (e.g., a gel such as of Example 11) that comprises leptin antagonist.

Figure 29:
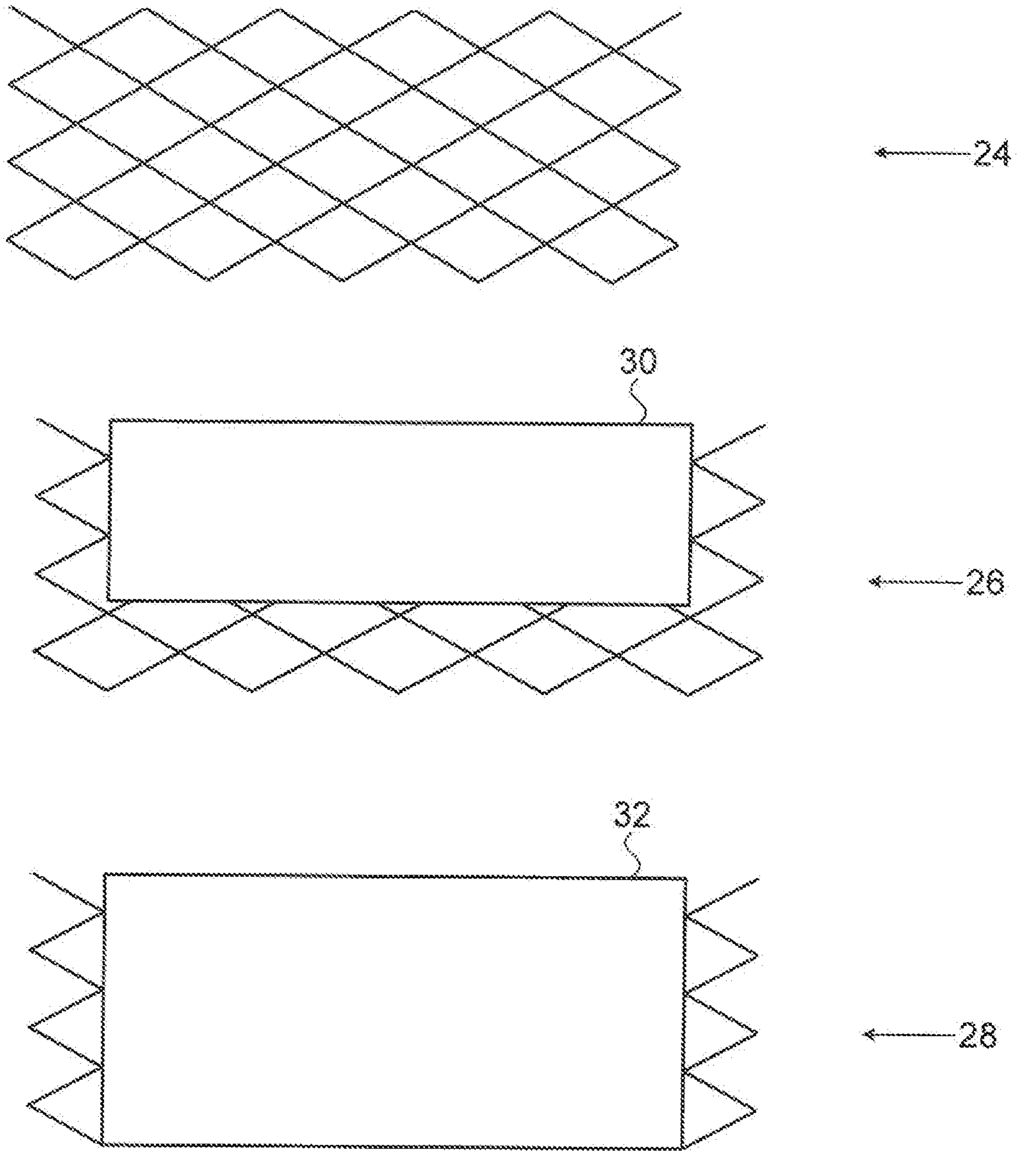
FIG. 29 schematically depicts further embodiments of the teachings herein suitable for intracavitary administration of leptin antagonist.

In FIG. 29, stents 24, 26 and 28 according to the teachings herein are schematically depicted. Stents 24, 26 and 28 are all elongated, tubular, outwardly radially-expandable frameworks that are known in the art. Stent 24 is a coverless stent without a cover. Stent 26 is a partially-covered stent with a partial cover 30. Partial cover 30 is a sheet secured to the framework of stent 26 in the usual way, e.g., with sutures. Stent 28 is a covered stent with a full cover 32. Full cover 32 is a tube secured to the framework of stent 28 in the usual way, e.g., with sutures or by tension.

Stents 24, 26 and 28 are substantially similar to known stents except by being functionally associated with a pharmaceutically-effective amount of leptin antagonist, are made in substantially the same way, and are used in substantially the same way. Specifically, each one of stents 24, 26 and 28 has at least one component that is functionally associated with a pharmaceutically-effective amount of leptin antagonist. Depending on the embodiment, a given stent 24, 26 and 28 according to the teachings herein may include one or more components, each having one or more of the additional features detailed hereinabove. Embodiments of any one of stents 24, 26 and 28 are self-expanding stents. Embodiments of any one of stents 24, 26 and 28 are balloon-expandable stents.

For example, in some embodiments, a cover 30 or a cover 32 is made of a high-density multifilament polyester cloth coated with a coating of a hydrogel that includes a pharmaceutically effective amount of leptin antagonist, typically on the outer surface of the cover.

For example, in some embodiments, a cover 30 or a cover 32 is made of a high-density multifilament polyester cloth coated that has been soaked in and is therefore impregnated with a composition (e.g., a gel such as of Example 11) that comprises leptin antagonist.

For example, in some embodiments, a cover 30 or a cover 32 is made of a material that is a composition comprising leptin antagonist, e.g., a PLGA sheet of example 4.

For example, in some embodiments, a framework of any one of stents 24, 26 and 28 is made of cobalt chromium coated with a coating of a hydrogel that includes a pharmaceutically effective amount of leptin antagonist.

For example, in some embodiments, a framework of any one of stents 24, 26 and 28 is made of a material such as nitinol or a polymer textured with micrometer dimension features such as valleys and pores, where inside the features is held a composition (e.g., a gel such as of Example 11) that comprises leptin antagonist.

For example, in some embodiments, a framework of any one of stents 24, 26 and 28 is made of a material that is a composition comprising leptin antagonist, e.g., PLA or PLLA comprising a pharmaceutically-effective amount of leptin antagonist.

Treatment of Ischemia and Reperfusion Injury (IRI)

Activated renin-angiotensin aldosterone system (RAAS) and angiotensin II (AngII) in ischemia/reperfusion injury IRI contribute to tissue damage through various pathways. It the myocardium AngII has been shown to induce cardiac cell hypertrophy and left ventricular dysfunction through the induction of leptin in cardiomyocytes. Subsequently, experimental data provide evidence that both, cardiomyocyte hypertrophy and the resulting heart failure can be mitigated by inhibiting leptin synthesis or activity. In the kidney angiotensin II causes cell injury through constriction of renal vessels, enhancement of vascular sensitivity to sympathetic nerve stimulation, increased oxidative stress and induced apoptosis. Also recruitment of macrophages and neutrophil activation in the injured kidney may be driven by angiotensin II and its mediator, leptin. Studies have demonstrated that angiotensin converting enzyme inhibitors (ACEIs) and angiotensin receptor blockers have protective effects on IRI in the kidney.

The present invention relates to the use of leptin antagonist not only in the treatment of a cardiovascular tissue but also in the treatment of an organ injured by ischemia and reperfusion injury (IRI) for alleviating tissue damage and preserving the organ function.

According to an aspect of the invention, there is provided a method for treating ischemia and reperfusion injury (IRI) by administrating leptin antagonist upon reperfusion and maintaining sustained administration of the leptin antagonist into the vessel undergoing the reperfusion procedure for delivering the leptin antagonist by the blood flow into the damaged cells of the tissue injured by the IRI.

According to some embodiments of the invention, the method is implemented by implanting an intracavitarily-implantable drug delivery device configured for sustained delivering the leptin antagonist. In particular the drug delivery device is a drug eluting stent that is used both to restore the flow of blood in an occluded vessel and to deliver leptin antagonist locally to the specific tissue perfused by the treated vessel. When the drug delivering device is a drug eluting stent, the stent is also configured to deliver an anti-proliferative drug to the wall of the vessel for preventing restenosis. The anti-proliferative drug may be any known anti-proliferative drug such as rapamycin or paclitaxel. The total dose of leptin antagonist in the stent may be released into the lumen over a period of at least 3 days, preferably between 10 to 14 days, and even for a longer period. The release rate is determined, inter alia, by the choice of the sustained release material. For example, PLGA (Poly lactic-co-glycolic acid) 65:35 MW 45000-75000 Da was tested in a mouse model and was found suitable to establish this timeframe. The kinetics of drug release for the anti-proliferative drug may be designed based parameters known in the art. The stent may be used as a stand alone device, or as a supplement to support an intra-arterial bolus treatment with leptin antagonist, depending on the specific clinical circumstances.

According to some embodiments of the present invention, the method of treating IRI is applicable to isolated tissue sections that function as an end organ (i.e., are supplied by a single blood vessel), and that were exposed to a period of non-fatal ischemia and underwent reperfusion via thrombo-slysis or intravascular angioplasty.

According to some embodiments of the present invention, the method of treating IRI is applicable for the treatment of a cardiac left ventricular tissue after acute MI at the time of primary revascularization for moderation of cellular damage in cardiac cells (cardiomyocytes) that were subjected to ischemia and reperfusion injury and for preserving cardiac function.

According to some embodiments of the present invention, the method of treating IRI is applicable for treating IRI in any in other end organs, for example, the kidney, intestine or brain.

Double Function Drug Eluting Stent

According to an aspect of the invention, there is provided a double function drug eluting stent (df-DES) to be deployed in an occluded vessel at the site of occlusion following balloon angioplasty. The double function drug eluting stent is configured to enable slow release of anti-proliferative drug into the wall of a vessel to enable slow release of leptin antagonist into the lumen, to be carried by the blood stream and be uptaken by cells that sustained ischemia and reperfusion injury.

The double function dug eluting stent comprises an expandable structural framework configured to be deployed in a blood vessel. The stent may be a self-expandable stent or a balloon-expandable stent and may comprise a network of elongated struts.

Figure 30:
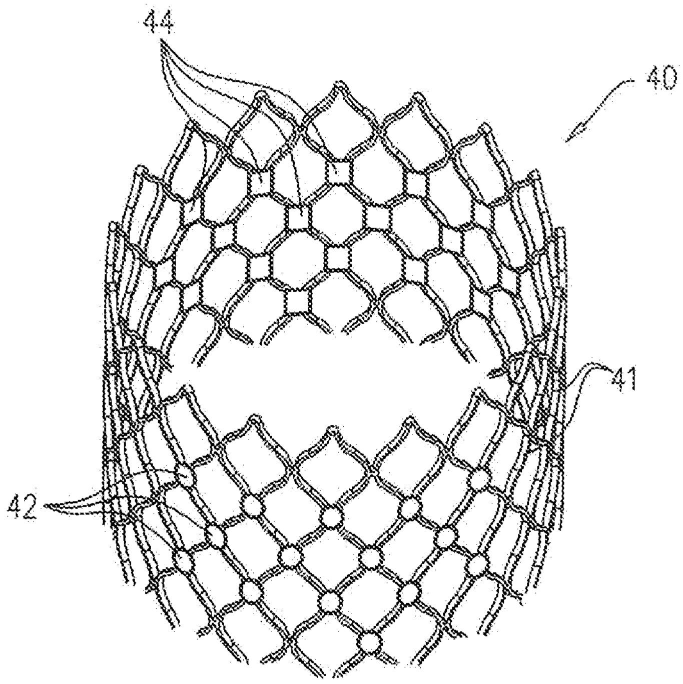
FIG. 30 schematically depicts an embodiment of a double-function drug eluting stent in accordance with the teachings herein.

FIG. 30 schematically depicts a drug eluting stent 40 according to the teachings herein. Stent 40 is an elongated, tubular, radially-expandable stent comprising a network of struts 41. Struts 41 comprise outer surface reservoirs 42 and inner surface reservoirs 44, which are located, for example, at the junctions between the struts. Outer surface reservoirs 42 that abut the vessel wall when stent 40 is deployed within a vessel, contain a sustained release composition of an anti-proliferative drug. Inner surface reservoirs 44, which are in contact with the fluid flowing through the lumen, contain a sustained release composition of leptin antagonist. Reservoirs 42 and 44 can be configured, for example, as pits embedded in the junctions points between struts 41. FIG. 30 illustrates reservoirs 42 and 44 as circular and square pits, respectively, by way of example only. It will be easily realized that the pits may assume any other shape. Stent 40 may be a self-expandable or a self-expanding stent. Struts 41 may be made of metal, alloy or biodegradable polymer, as described above in association with FIG. 29.

Figure 31A:
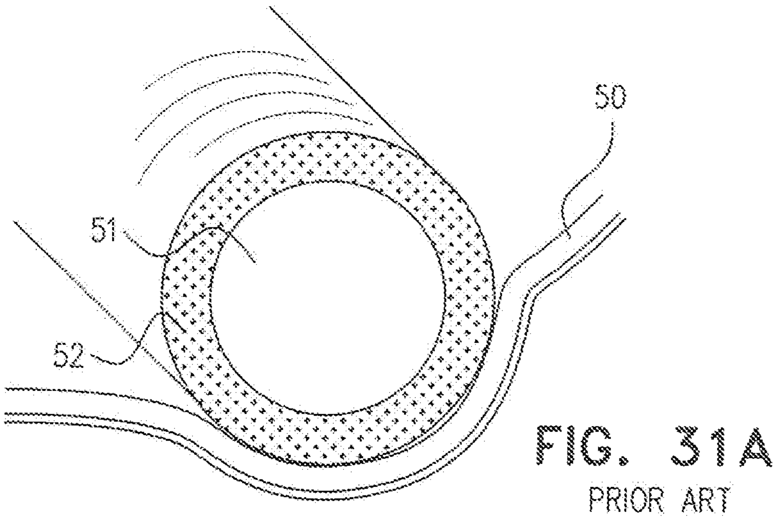
FIG. 31*a* is partial cross sectional perspective view of a prior art stent.
Figure 31B:
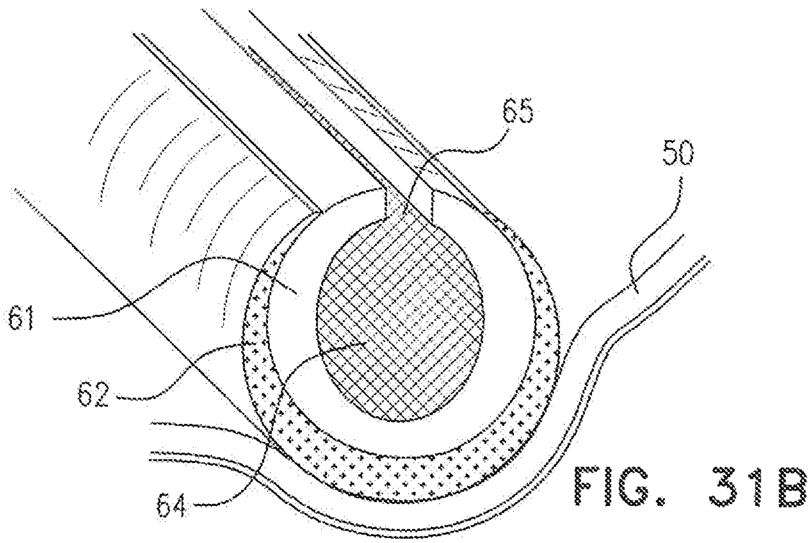
FIGS. 31*b* and 31*c* are partial cross sectional perspective views of further embodiments of a double-function drug eluting stent in accordance with the teachings herein.
Figure 31C:
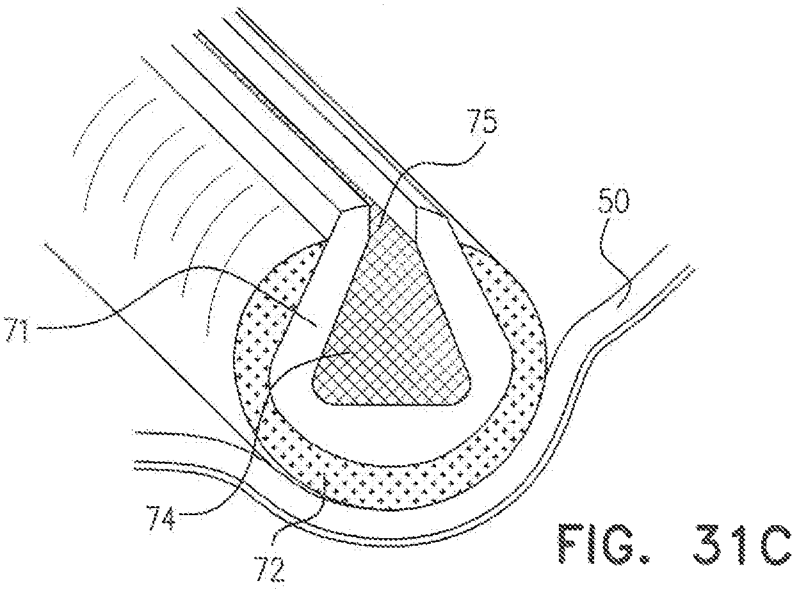

FIGS. 31*b* and 31*c* illustrate another embodiment of a double function drug eluting stent, depicting cross sectional views of one of the struts that constitute the stent, abutting vessel wall 50. According to this embodiment, the outer surface of struts 61 and 71 is partially coated by layer, 62 and 72, respectively, of a polymer containing the anti-proliferative drug. Layers 62, 72 cover about 75% of the strut's circumference. The inner surface of the strut, facing the lumen, is provided with a long recessed slit, 64, 74, which serves as a reservoir for containing the sustained release composition of the leptin antagonist for slow release into the lumen. Slits 64 and 74 that extend along the length of the strut have circular and triangular cross sections, respectively, but may assume other cross sectional shapes as well. Preferably, the slit opening, 65, 75, at the luminal aspect of the struts leads to a wider reservoir. This design prevents early detachment of the sustained release matrix. The size of opening 65, 75 can also be selected as one of the parameters that control the release rate. According to some embodiments of the invention, layers 62, 72 and slits 64,74 extend continuously along the length of the stent. According to other embodiments, layers 54, 62 and slits 52 and 64 may be discontinuous. Similarly, all or only part of the struts constituting the stent may be loaded with the leptin antagonist and the anti antiproliferative drug. By way of comparison, FIG. 31*a* depicts a strut 51 of a prior art drug eluting stent coated by a layer 52 of antiproliferative drug to prevent in-stent stenosis (restonosis). It is noted that prior art drug eluting stents do not provide for selective release of one active agent into the wall of a vessel and a second different active agent into the lumen to be carried by the flow of blood and to be uptaken by the cells to which the vessel supplies blood.

Suitable Leptin Antagonists

Any suitable leptin antagonist may be used in implementing any specific aspect or embodiment of the teachings herein. In some embodiments, a single leptin antagonist is used. In some embodiments, two or more leptin antagonists are used simultaneously or concurrently.

Various leptin antagonists suitable for implementing the teachings herein have been described in detail hereinabove.

In some embodiments, the leptin antagonist comprises a polypeptide portion.

In some embodiments, the leptin antagonist is a polypeptide.

Preferred leptin antagonists include all of the leptin antagonists listed and taught in U.S. Pat. No. 7,307,142 (SEQ ID NOs 3-35) and U.S. Pat. No. 8,969,292 (SEQ ID NOs 36-47), which are both included by reference as if fully set-forth herein. In some embodiments, the leptin antagonist is selected from the group consisting of:

a leptin antagonist consisting of: (a) a mammalian leptin polypeptide in which the LDFI (SEQ ID NO:33 in U.S. Pat. No. 7,307,142 or SEQ ID NO 35 in the present application) hydrophobic binding site at the positions corresponding to positions 39-42 of the wild-type human leptin, is modified such that from two to four amino acid residues of the hydrophobic binding site are substituted with different amino acid residues such that the site becomes less hydrophobic, the modified, mammalian leptin polypeptide being a leptin antagonist; (b) a fragment of the modified mammalian leptin polypeptide of (a) comprising the altered hydrophobic binding site, wherein the fragment is itself a leptin antagonist; (c) a fragment of (b)

a synthetic leptin antagonist comprising: (d) a full length modified mammalian leptin polypeptide in which: (i) the LDFI hydrophobic binding site at the position corresponding to positions 39-42 of the wild-type human leptin is modified such that from two to four amino acid residues of the hydrophobic binding site are substituted with different amino acid residues such that the site becomes less hydrophobic; and (ii) the aspartic acid at the position corresponding to position 23 of the wild-type human leptin (D23) is substituted with an amino acid residue selected from the group consisting of glycine, alanine, leucine, lysine, arginine, phenylalanine, tryptophan and histidine, or the threonine at the position corresponding to position 12 of the wild-type human leptin (T12) is substituted with a different amino acid residue that is hydrophobic;

(e) a synthetic leptin antagonist consisting of a polypeptide having the amino acid sequence of SEQ ID NO: 1 of U.S. Pat. No. 8,969,292 or SEQ ID NO 36 of the present application;

(f) a modified mammalian leptin polypeptide in which: (i) the LDFI hydrophobic binding site at the position corresponding to 5 positions 39-42 of the wild-type human leptin is modified such that from two to four amino acid residues of the hydrophobic binding site are substituted with different amino acid residues such that the site becomes less hydrophobic, the modified mammalian leptin polypeptide being a leptin antagonist; and (ii) the aspartic acid at the position corresponding to position 23 of the wild-0 type human leptin (D23) is substituted with a different amino acid residue that is not negatively charged or the threonine at the position corresponding to position 12 of the wild-type human leptin (T12) is substituted with a different amino acid residue that is hydrophobic;

(g) a fragment of the modified mammalian leptin polypeptide of (f), in which D235 is substituted with a different amino acid residue that is not negatively charged or T12 is substituted with a different amino acid residue that is hydrophobic, wherein the fragment is itself a leptin antagonist;

a synthetic leptin agonist comprising: (h) a modified mammalian leptin polypeptide in which D23 is substituted with a different amino acid residue that is not negatively charged or T12 is substituted with a different amino acid residue that is hydrophobic;

(j) a fragment of the modified mammalian leptin polypeptide of (h), in which D23 is substituted with a different amino acid residue that is not negatively charged or T12 is substituted with a different amino acid residue that is hydrophobic, wherein the fragment is itself a leptin agonist;

(k) any one of the above wherein the mammalian leptin is selected from the group consisting of human, ovine and murine;

(l) any one of (a), (b), (c), (d), (e), (f), (g), (h), (j) and (k) in pegylated form; and a pharmaceutically acceptable salt of any one of (a)-(l).

Unless otherwise defined, all technical and scientific terms used herein have the same meaning as commonly understood by one of ordinary skill in the art to which the invention pertains. In case of conflict, the specification, including definitions, will take precedence.

As used herein, intracavitary relates to within an organ or body cavity.

Art that provides enabling support for the teachings herein, and that may also be useful in understanding the background and the inventive aspects of the teachings herein includes U.S. Pat. Nos. 7,307,142; 8,969,292; "leptin Locally Synthesized in Carotid Atherosclerotic Plaques Could Be Associated With Lesion Instability and Cerebral Emboli" by Schneiderman J et al in J Am Heart Assoc. 2012, 1:e001727 doi: 10.1161/JAHA.112.001727 and "Locally Applied leptin Induces Regional Aortic Wall Degeneration Preceding Aneurysm Formation in Apolipoprotein E-Deficient Mice" by Tao M et al in Arterioscler Thromb Vasc Biol. 2013; 33:311-320, all four which are included by reference (together with any published supplemental materials) as if fully set-forth herein.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Example 1

Localized Leptin Synthesis in a Mouse Model

A novel mouse model was used to simulate local leptin synthesis in the ascending aorta in order to assess the effect of leptin on aortic remodeling and heart structure and function.

Materials and Methods

Figure 4:
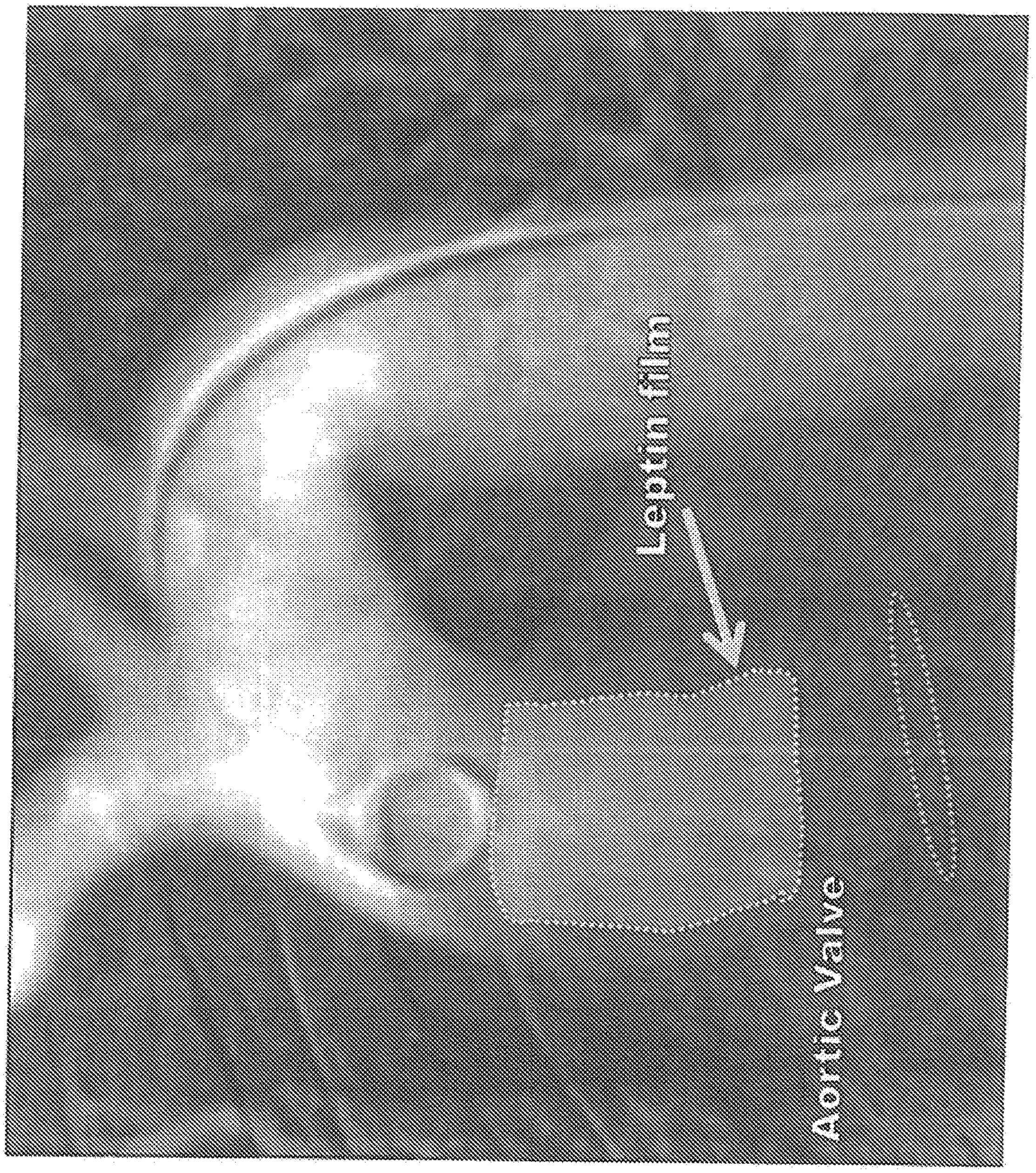
FIG. 4 illustrates the location of leptin film application on the anterior outer surface of the ascending aorta. Human arch angiogram depicts mouse anatomy.

A slow release leptin film (FIG. 1*b*) made of polylactic co-glycolic acid (PLGA) matrix (1×1.5 mm), and containing either 2 μg leptin or no protein (control) was applied to the anterior surface of the proximal ascending aorta (FIG. 4).

The leptin slow-release film was manufactured by impregnating a poly lactic-co-glycolic acid (PLGA) film with leptin. One gram of PLGA 6535 polymer (D,L-lactide: glycolide: 65:35, Mw=45,000-75,000 Da; Lakeshore. Biomaterials, Birmingham, Ala., USA) was dissolved in 10 mL $MgCl_2$ (Fisher Scientific, Loughborough, UK). Sodium chloride (10 mg in 0.2 mL distilled water) and 25 μL ethylene glycol (Sigma-Aldrich, St. Louis, Mo., USA) were added to the polymeric solution and sonicated for 20 seconds. Mouse leptin powder (1 mg; #L3772; Sigma-Aldrich, St. Louis, Mo., USA) was suspended in 2 mL of the polymeric solution, followed by casting on a flat surface of Teflon molds to create a flat film. Films were dried in a hood for 48 hours, and then subjected to high vacuum for 12 hours to extract any residual solvent. Control (placebo) films were fabricated in the same way without the addition of leptin. The calculated amount of leptin per 1×1.5-mm film used currently for implantation in each mouse was 2 μg.

Another option of leptin application for local slow-release has been a gel composed of two liquid materials which gel (solidify) upon mixing at the time of injection. These are a modified carboxymethyl cellulose with adipic dihydrazide (CMC-ADH) and an oxidized dextrane in DDW (DX-COH). Methylene blue dye (0.5%) was also added to the DX-COH solution to make the resulting gel more visible. Leptin (Sigma, L3772, St. Louis, Mo., USA) was added to the gel by an emulsion technique.

Figure 5:
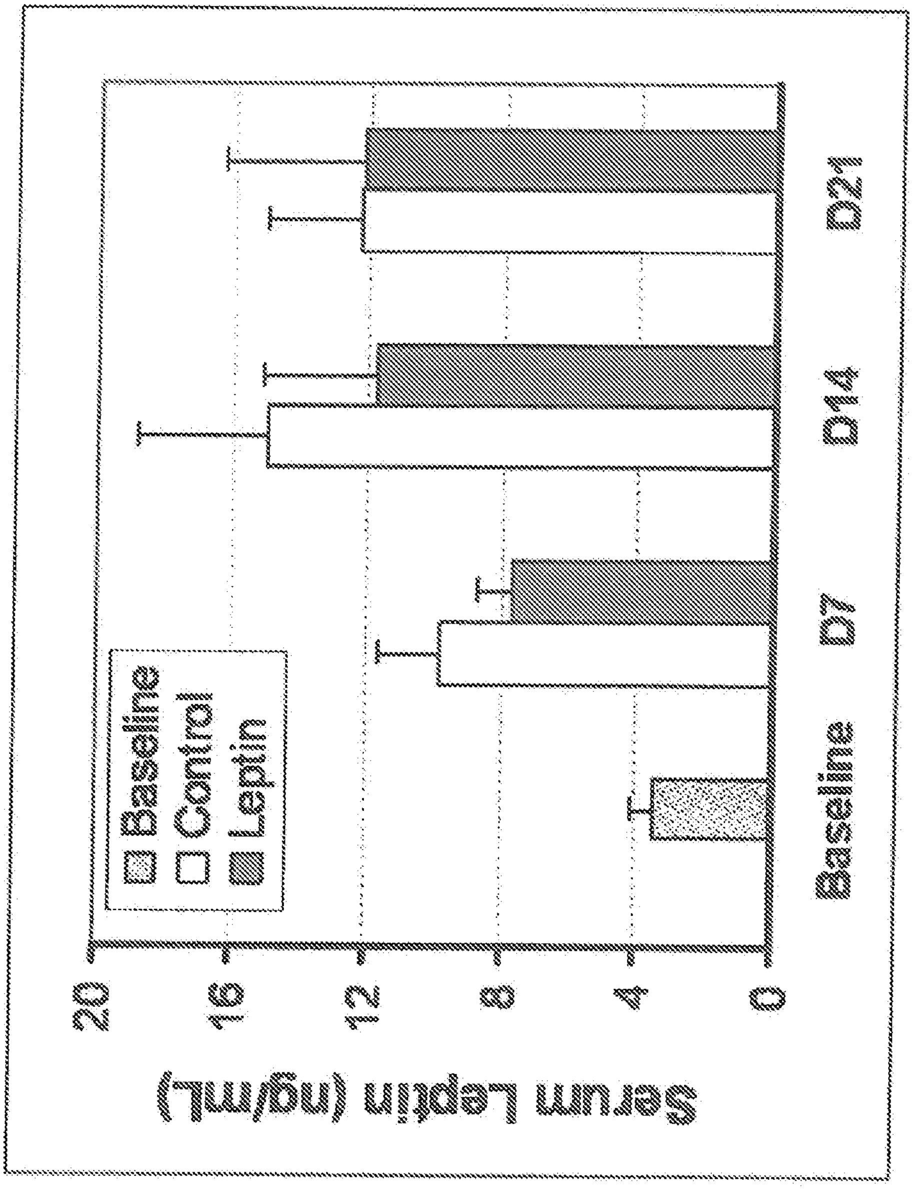
FIG. 5 illustrates a time course analysis of serum leptin level in $ApoE^{-/-}$ mice that underwent peri-aortic application of leptin film (20 μg).

Serum leptin levels were determined in $ApoE^{-/-}$ mice after receiving 20 μg mouse leptin via peri-aortic application (in another experiment, Tao et al. ATVB 2013). Blood was samples on days 0, 7, 14, and 21, and leptinanalyzeded by ELISA assay (Quantikine Mouse Lep Kit, R&D Systems, Minneapolis, Minn., USA): Day 0-3.5 ng/mL; day 7—leptin 8.0 ng/mL, placebo 9.2 ng/mL; day 14—leptin 12.0 ng/mL, placebo 14.5 ng/mL; and day 21-leptin 12.25 ng/mL, placebo 12.5 ng/mL (FIG. 5). Notably, these values fell within the normal range of plasma leptin in ApoE−/− mice receiving Western diet (mean 5.1±1.4 to 17±3.4 ng/mL). It should also be emphasized that circulating leptin levels are known to increase with age, as also observed in our series.

This unique mouse model was utilized to perform two experiments: Mice in experiment 1 were fed postoperatively with high fat diet (HFD), and were followed up for 45 days. In experiment 2 mice received normal chow for 30 or 60 days. Mouse weight and blood pressure (BP) were assessed weekly. All mice recovered from surgery uneventfully.

Results

In both mouse model experiments, leptin or control treated mice gained weight equally during the follow up period, suggesting no systemic leptin effect. Systolic BP measured weekly in mice of experiment 2 was 100 mmHg throughout the first 4 weeks, and increased to 120 mmHg by week 6 in both leptin treated and control mice. Based on two separate experiments, both HFD and normal chow feeding yielded in general similar results.

The following data report the results of experiment 2 (normal chow feeding).

Figure 6:
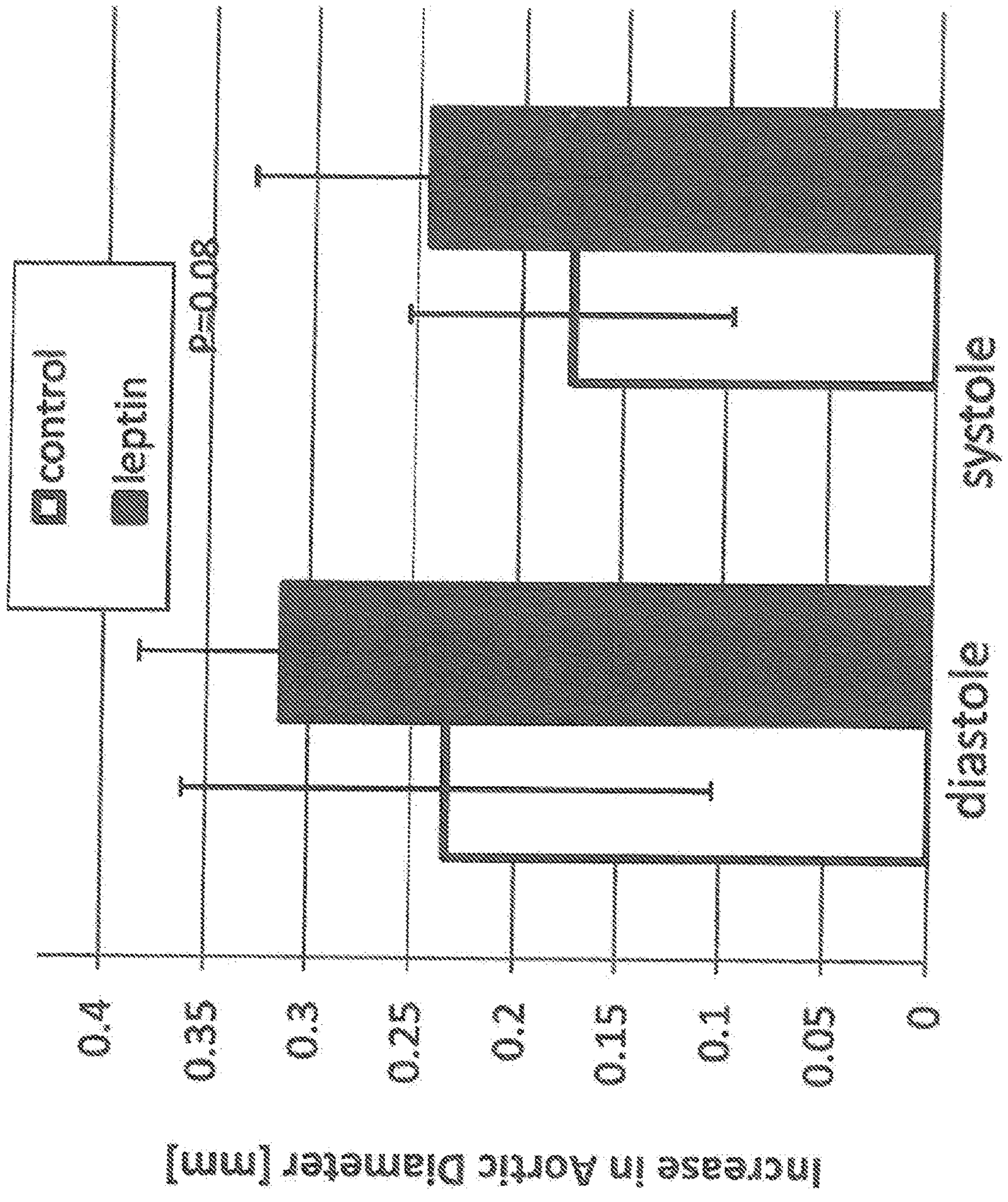
FIG. 6 illustrates increased ascending aortic diameter at the location of leptin film application versus controls.
Figure 7:
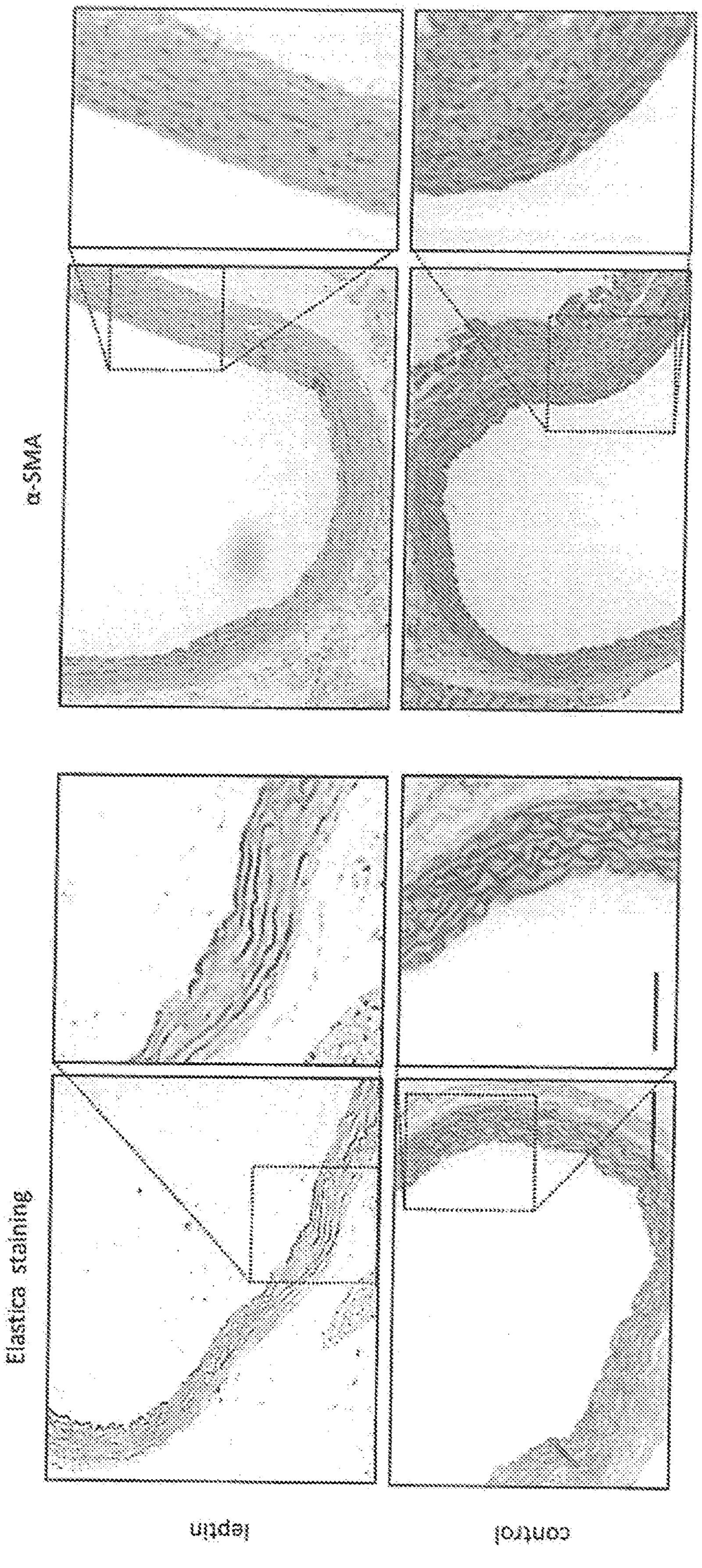
FIG. 7 illustrates elastica staining and αSMA IHC analysis of ascending aortic cross sections of mice locally treated with leptin versus controls.

Echocardiography of the ascending aorta at 2 mm distal to the aortic valve level revealed an increase in aortic diameter at peak systole in leptin treated mice vs controls (p=0.08, FIG. 6; Exp. 1 using HFD yielded P<0.003). That same aortic location exhibited decreased elasticity, which was defined as the percent increase in aortic diameter in systole vs. diastole, in leptin compared to control treated mice. There was no significant difference in diameter further distally on the ascending aorta. Notably, the aortic valve annulus did not dilate in response to local leptin application. Histological analysis of the ascending aorta revealed features of medial degeneration at the site of leptin application, including fragmentation of the elastic lamellas, as demonstrated by elastica van Giesen staining, and depletion of αSMA in the media (FIG. 7). These structural changes likely underlie local stiffening and dilatation in the proximal ascending aorta.

Figure 8:
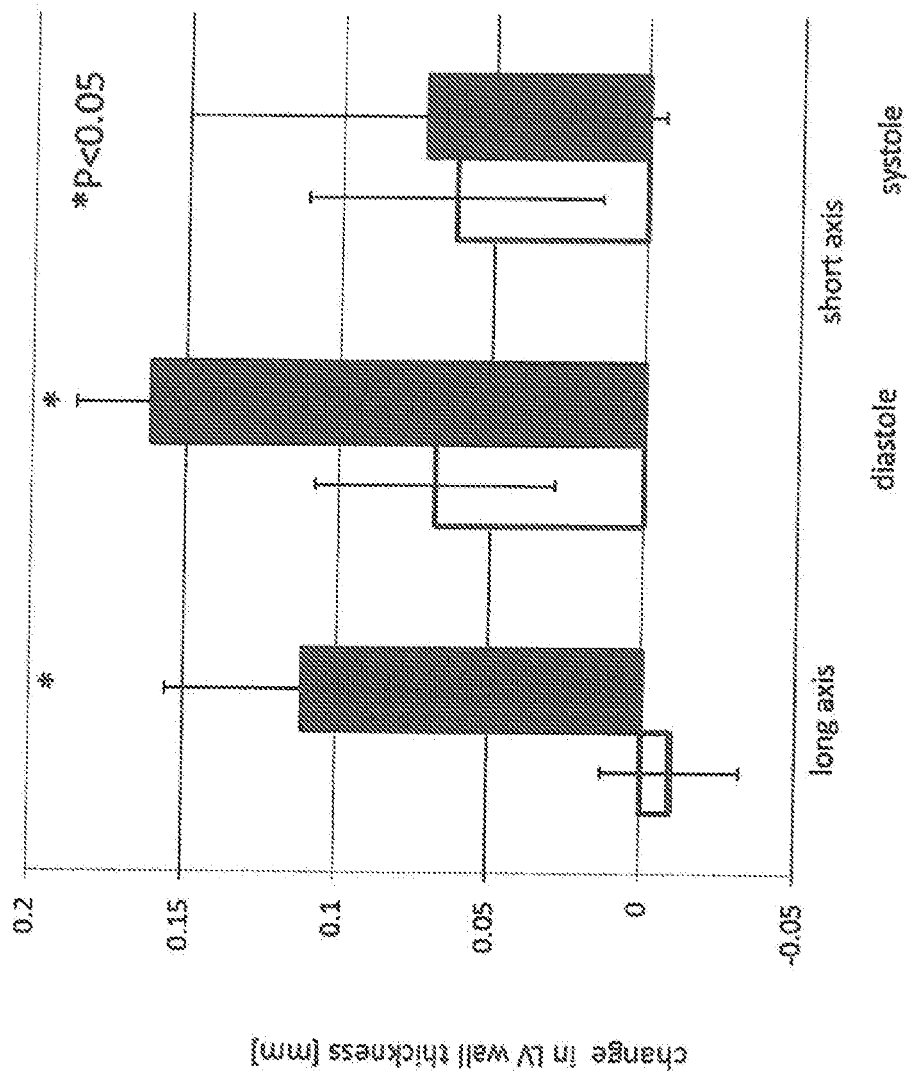
FIG. 8 illustrates change in left ventricle (LV) wall thickness in leptin-treated (filled columns) versus control (open columns) mice.
Figure 9:
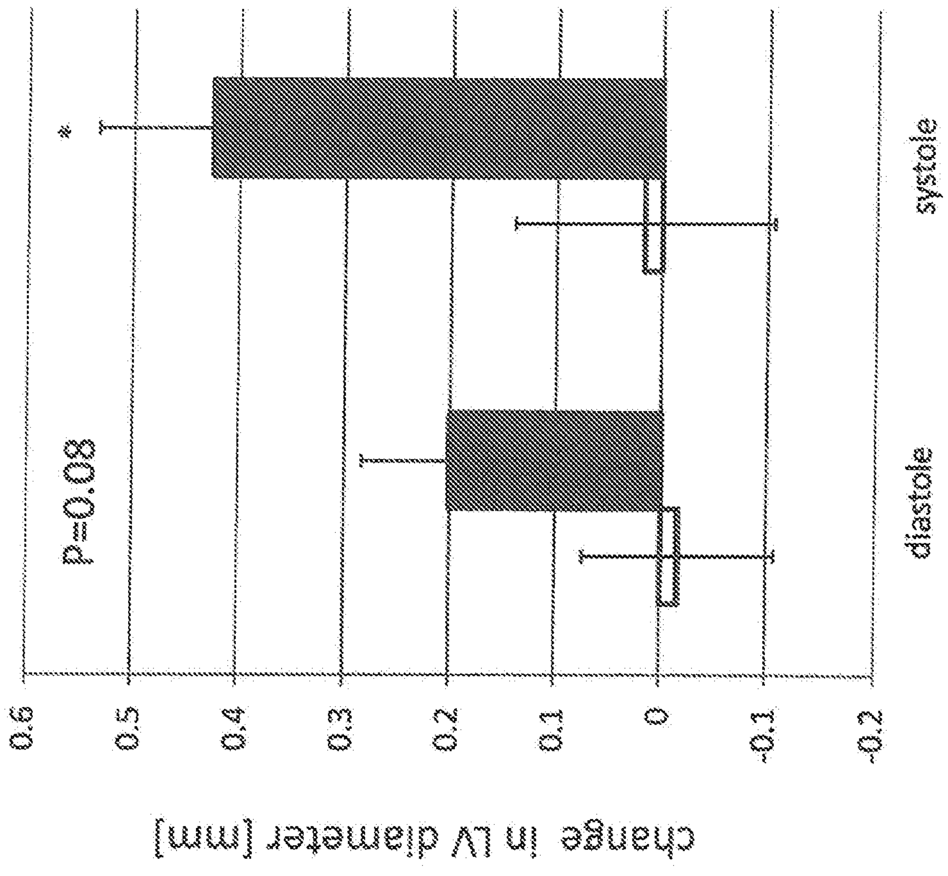
FIG. 9 illustrates LV diameter in systole and diastole in leptin-treated (filled columns) and control (open columns) mice.
Figure 10:
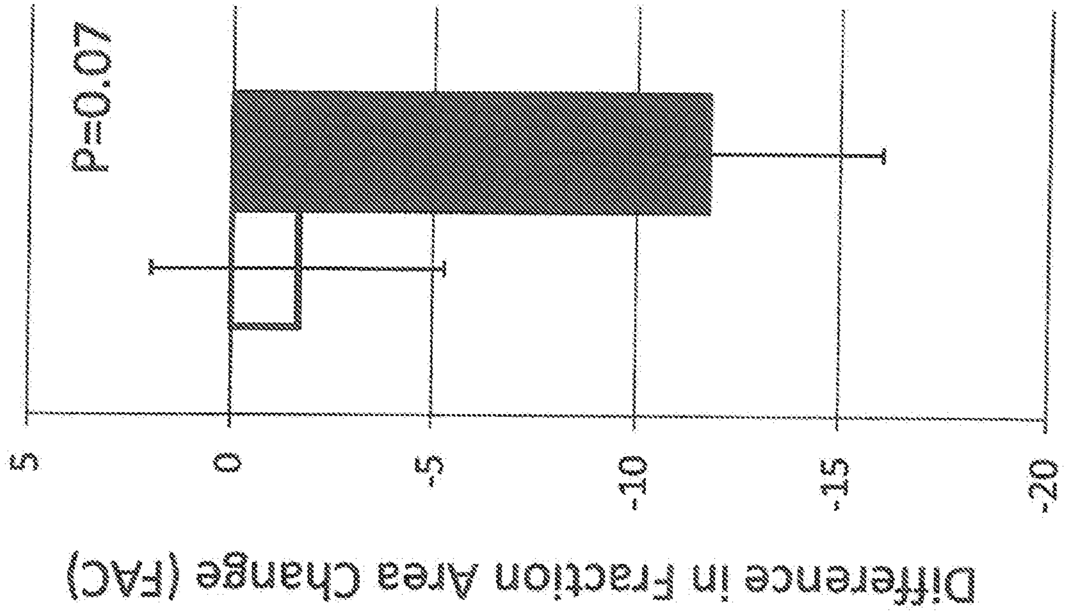
FIG. 10 illustrates LV fractional area change in leptin-treated (filled columns) versus control (open columns) mice.

Echocardiography (final vs. pre-operative) revealed a concentric remodeling of the left ventricle, with hypertrophy of all LV walls (p<0.001). Wall thickening was most pronounced in diastole (p=0.002, FIG. 8). Left ventricular diameter was increased in both systole and diastole (p=0.08, p=0.02, respectively, FIG. 9), leading to a reduction in the LV fractional area change (FAC, p=0.07, FIG. 10).

Figure 11:
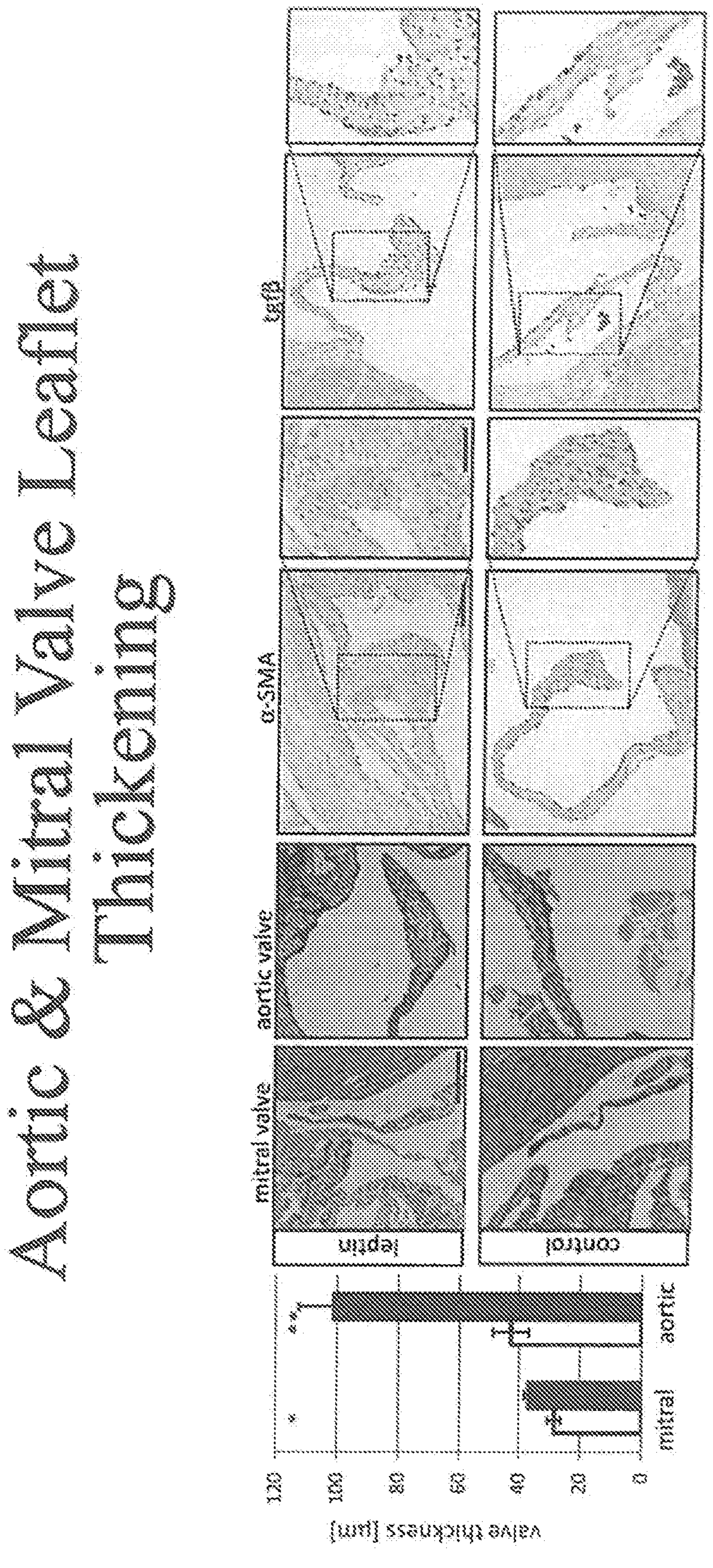
FIG. 11 illustrates aortic and mitral valve leaflet thickness in leptin-treated and control mice.

Local leptin application at the proximal ascending aorta promoted thickening of the mitral and aortic valve leaflets (p=0.01, p<0.001 accordingly, FIG. 11). Mitral leaflets were diffusely thickened, while aortic valve leaflets displayed thickening in their free edge, composed mostly of ECM and stromal cells. These proliferating cells are assumed analogous to human valvular interstitial cells (VICs). A few stromal cells within these lesions were positive for αSMA and TGFβ as shown by IHC staining (in analyzed aortic valve leaflets), suggesting VICs activation (FIG. 11). A trend was observed for increased VIC proliferation through Ki67 IHC in leptin treated mice. However, the lack of statistical significance implies that most leaflet hyperplasia took place at an earlier time.

Increased peak systolic velocity (PSV), as measured at the aortic valve in leptin treated vs control mice was short of statistical significance. However, PSV was significantly augmented in postoperative HFD fed animals.

These experiments reveal that available leptin in the proximal ascending aorta induces local aortic stiffening and dilatation. The resulting changes in local hemodynamics likely drive remodeling of the left ventricle, including LV wall hypertrophy and valve thickening through the aorto-ventricular coupling axis.

Example 2

Local Leptin Antagonism in an Ang II Mouse Model

Angiotensin II (AngII) is the key hormone of the renin-angiotensin system, underlying hypertension and cardiovascular remodeling (Renna et al. Pathophysiology of vascular remodeling in hypertension. Int J Hypertens. 2013; 2013: 808353). The phenotypes induced by local leptin application described in Example 1 are reminiscent of AngII induced aortic-ventricular (coupling) remodeling, suggesting that leptin mediates these processes. As such, a leptin antagonist was delivered locally to the ascending aorta in order to assess the effects of leptin down-regulation on AngII induced local aortic remodeling, and aortic-ventricular remodeling in mice.

Materials and Methods

Figure 12:
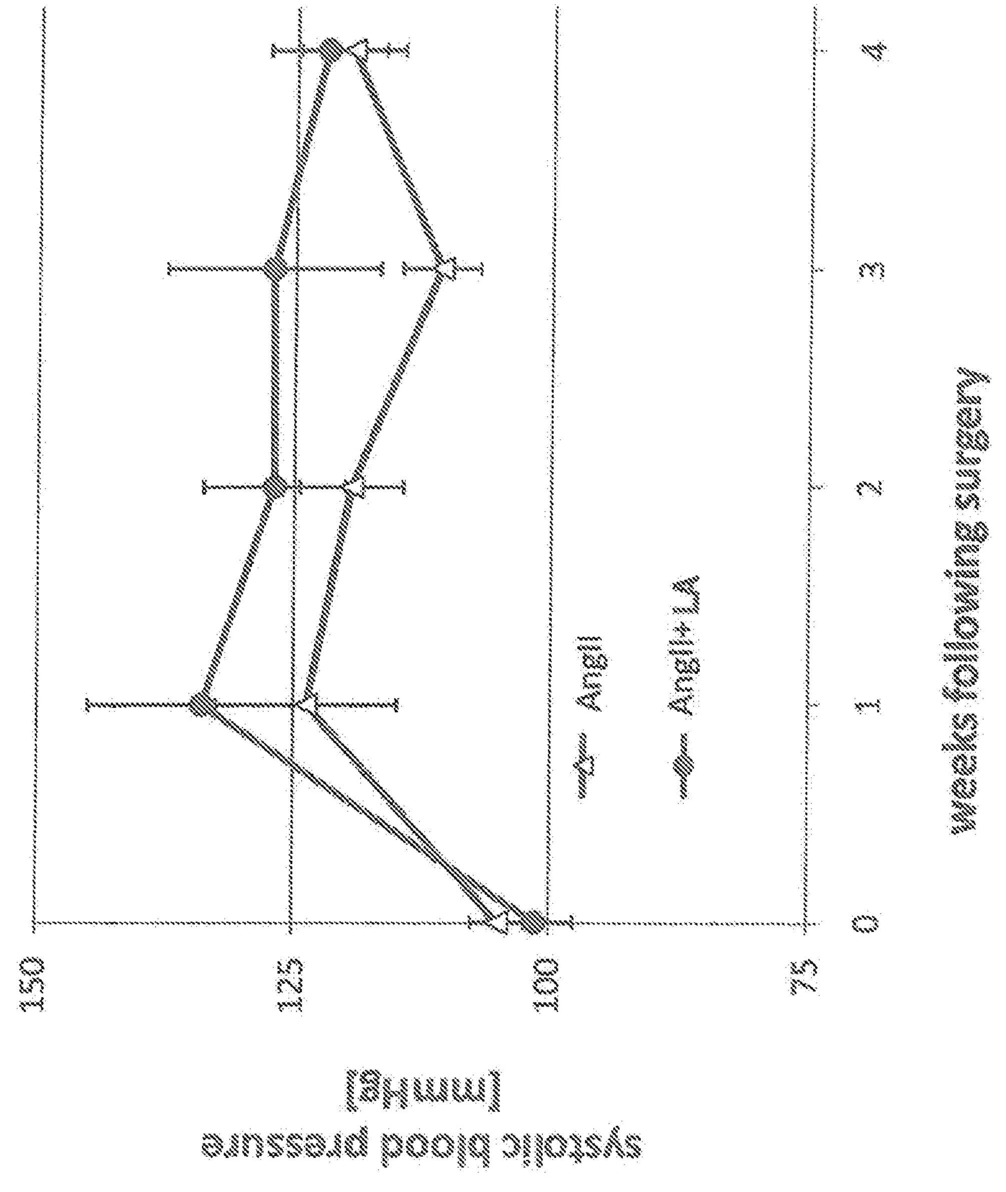
FIG. 12 illustrates mean systolic blood pressure in angiotensin II treated mice.
Figure 13:
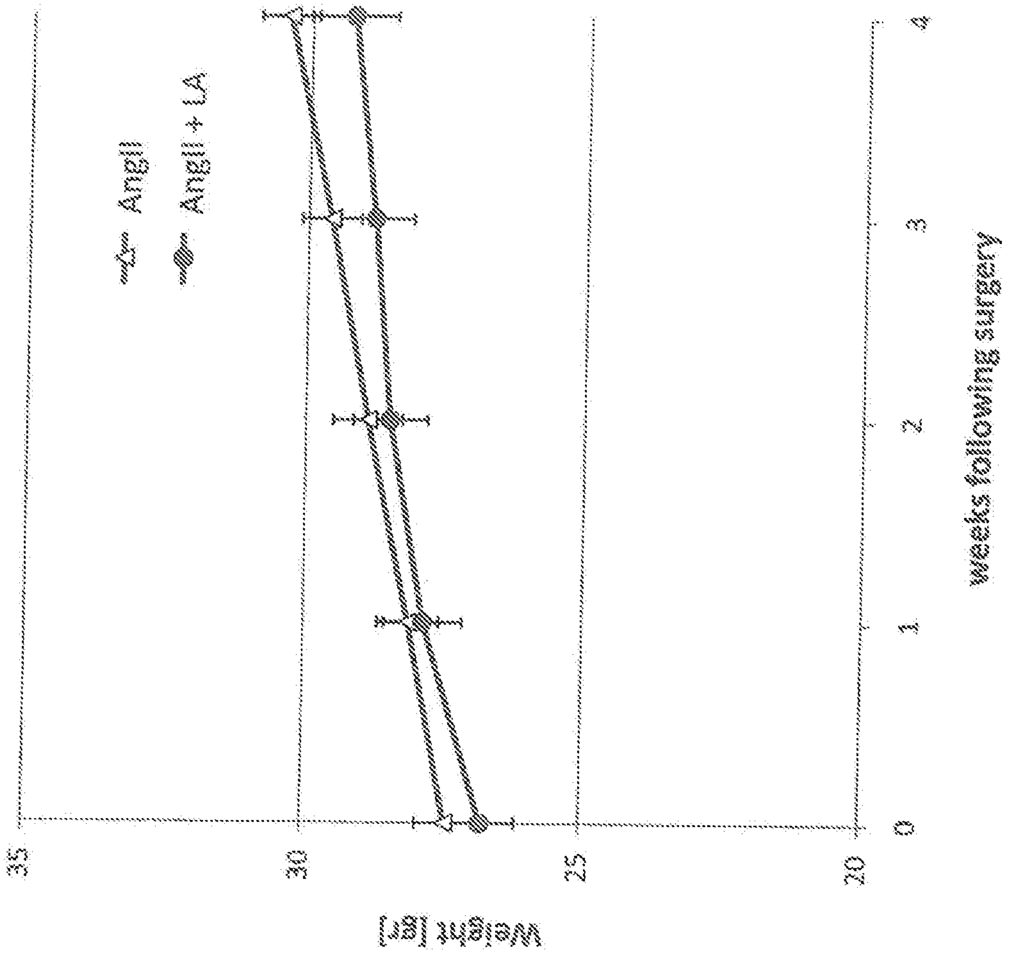
FIG. 13 illustrates a time course analysis presenting weight of angiotensin II treated mice (open triangles), and mice receiving both, angiotensin II and leptin antagonist (LA).

An osmotic mini-pump, delivering AngII at a rate of 1000 ng/kg/min was implanted subcutaneously in the back of the neck of 14 week old $ApoE^{-/-}$ mice. Each mouse also underwent left mini-thoracotomy for application of a slow release miniature PLGA film (1×1.5 mm) containing either 5 μg leptin antagonist (LA), or PLGA matrix devoid of protein (control). The slow release film was deployed on the surface of the proximal ascending aorta at the position described in Experiment 1. Mice were euthanized 4 weeks following surgery. As expected, blood pressure assessed in both Ang II treated groups after one week was increased by approximately 20% (125 mmHg mean systolic), and was sustained throughout the follow up (FIG. 12). Weight gain pattern was similar in both groups, indicating no systemic effects related to the leptin antagonist (FIG. 13).

Results

Figure 14:
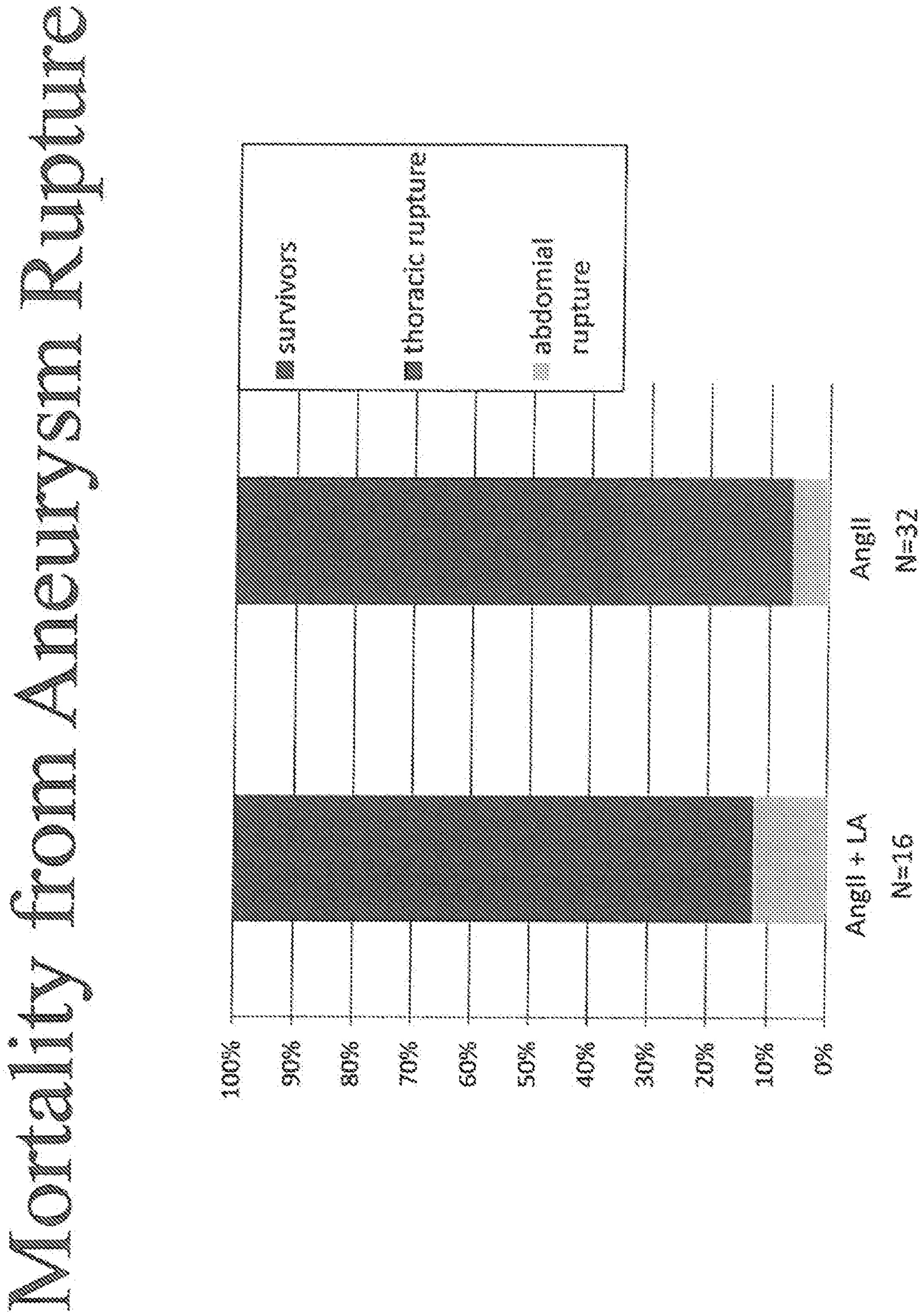
FIG. 14 illustrates number of mice that succumbed due to ruptured abdominal and thoracic aneurysms in angiotensin II treated mice versus mice receiving angiotensin II and leptin antagonist (LA).

To assess the impact of AngII alone versus AngII plus leptin antagonist on mouse longevity, mortality data from the present experiment were combined with data from a previous experiment, which included a similar cohort of $ApoE^{-/-}$ mice exposed to AngII, in same dose and duration (Tao M, et al. ATVB 2013). Collectively, a 34% mortality (referred to premature death, prior to the completion of the experiment) was observed in mice treated with AngII (either Ang II alone or Ang II with control film applied on the ascending aorta). Death was related to thoracic (28%) or abdominal (6%) aortic aneurysm rupture. Notably, mice treated with AngII that received also LA were protected from thoracic aneurysm rupture (p=0.04, FIG. 14). Death rate in mice receiving LA was only 13%, related exclusively to rupture of abdominal aortic aneurysms.

Figure 15:
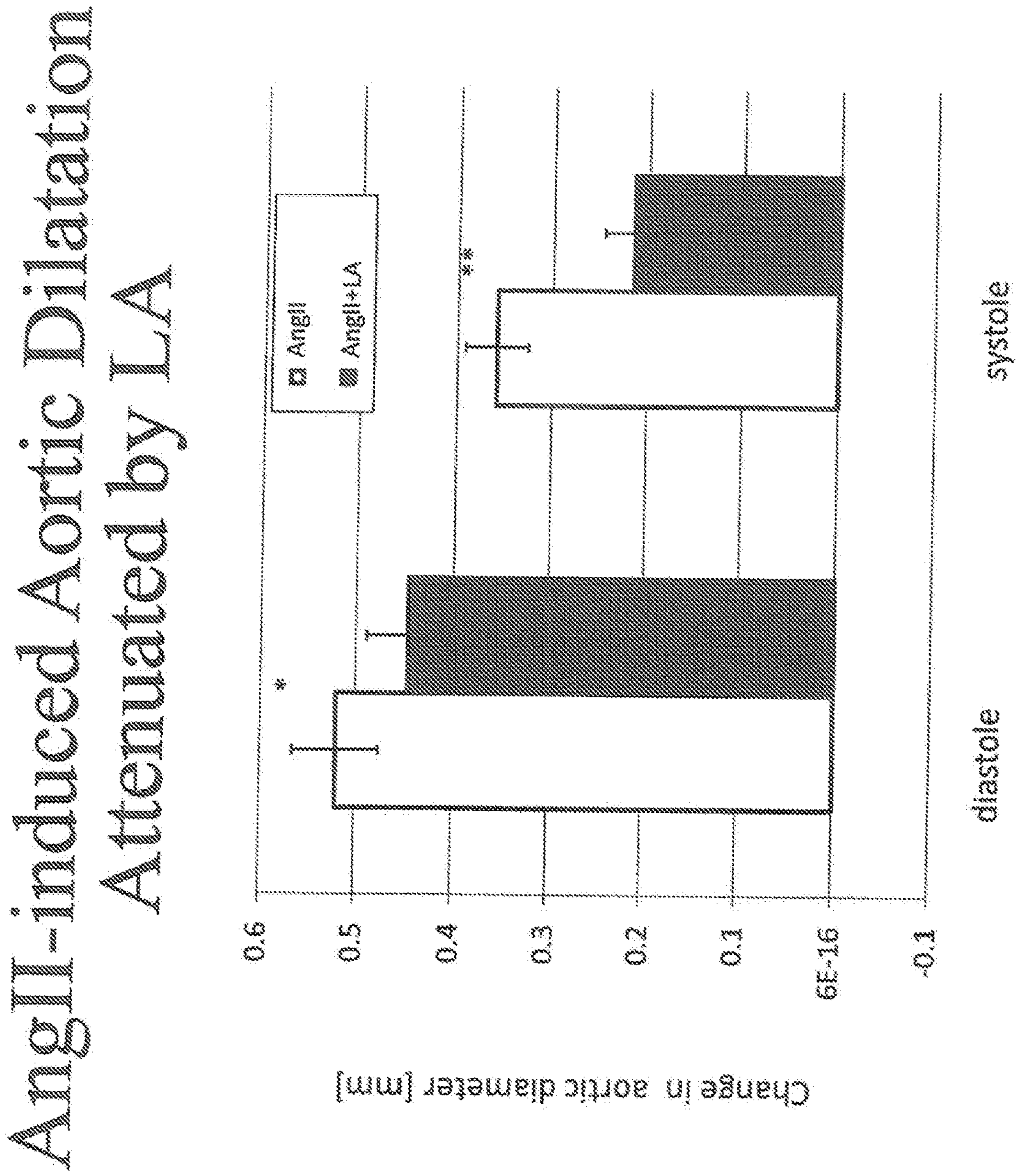
FIG. 15 illustrates ascending aortic dilatation in angiotensin II treated mice versus mice receiving angiotensin II and leptin antagonist (LA).

Echocardiograpic imaging of the ascending aorta demonstrated that local LA application in AngII treated mice significantly attenuated dilatation of the ascending aorta compared to AngII alone when measured 2 mm from the valve, at both diastole and systole (p=0.03, p=0.005, respectively, FIG. 15). However, these data did not suggest moderation of increased aortic stiffness by LA application.

Figure 16:
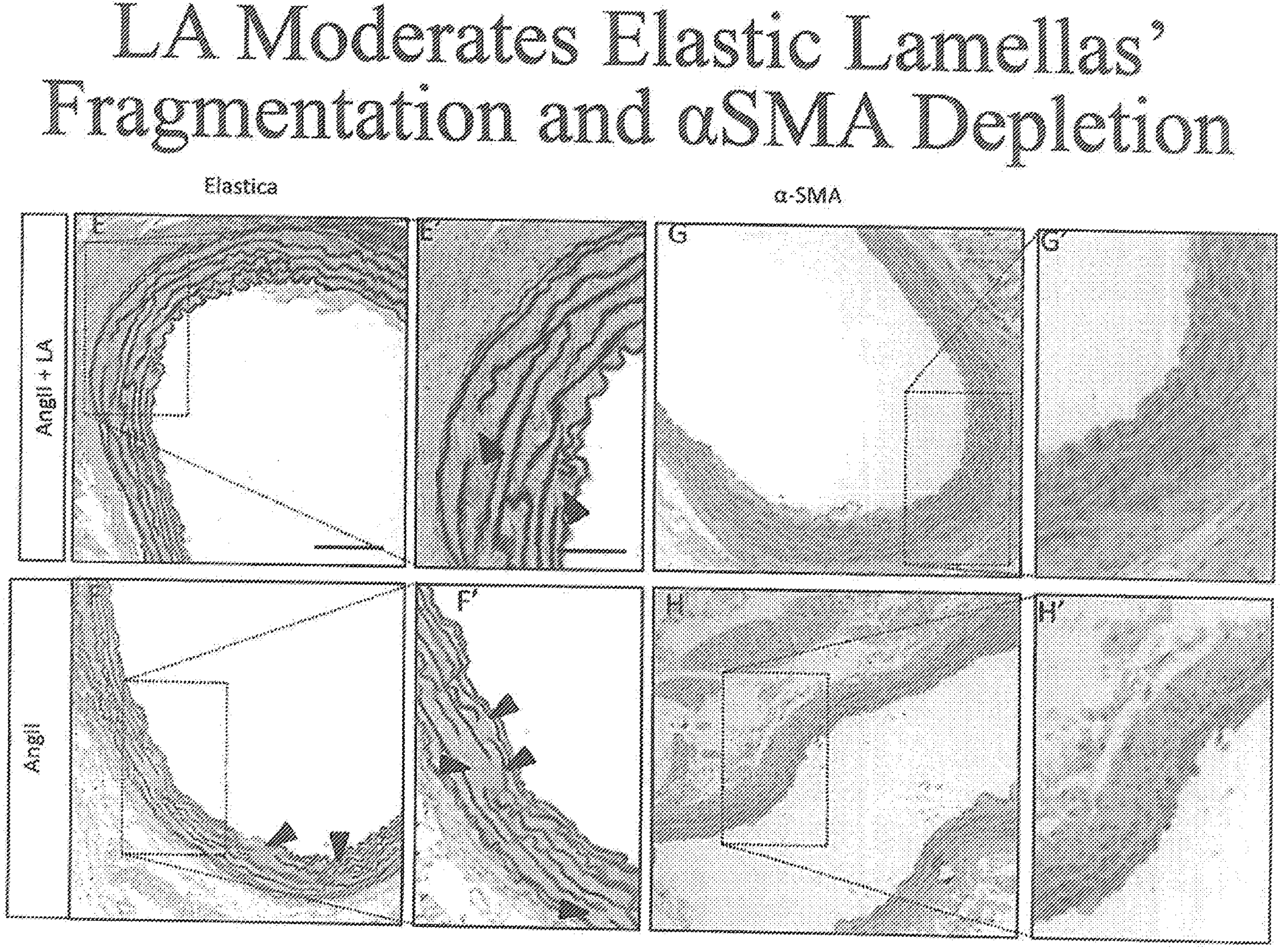
FIG. 16 illustrates elastic lamella fragmentation and αSMA depletion in angiotensin II treated mice versus mice receiving angiotensin II and leptin antagonist (LA).

Histological analysis revealed medial degeneration in both groups that were treated with AngII. Nevertheless, additional LA application resulted in less fragmentation of the elastic lamellas and fewer sites of αSMA depletion in the aortic media (FIG. 16). Notably, amongst mice receiving AngII, medial degeneration was rather diffused throughout the aorta. This was in sharp contrast to the effects of local leptin application, which exhibited medial degeneration within the segment in contact with the leptin film alone.

Figure 17:
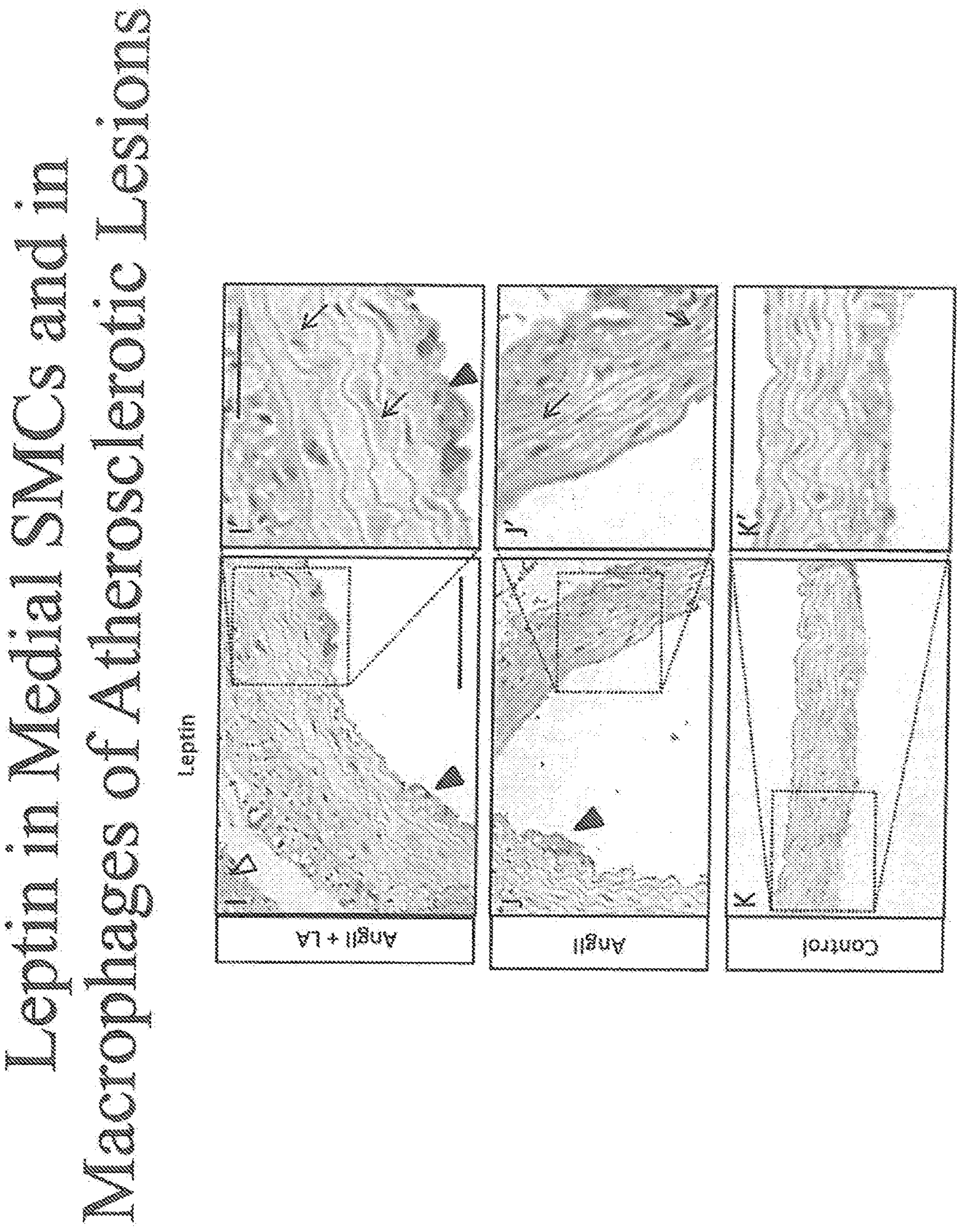
FIG. 17 illustrates leptin expression in medial SMCs (arrows) and macrophages of atherosclerotic lesions (filled arrowheads) in angiotensin II treated, angiotensin II and leptin antagonist (LA) treated, and control mice.

Immunohistochemical analysis for leptin antigen revealed a weak expression in medial SMCs, and a strong signal within foam cells of aortic luminal atherosclerotic plaques (FIG. 17).

Figure 18:
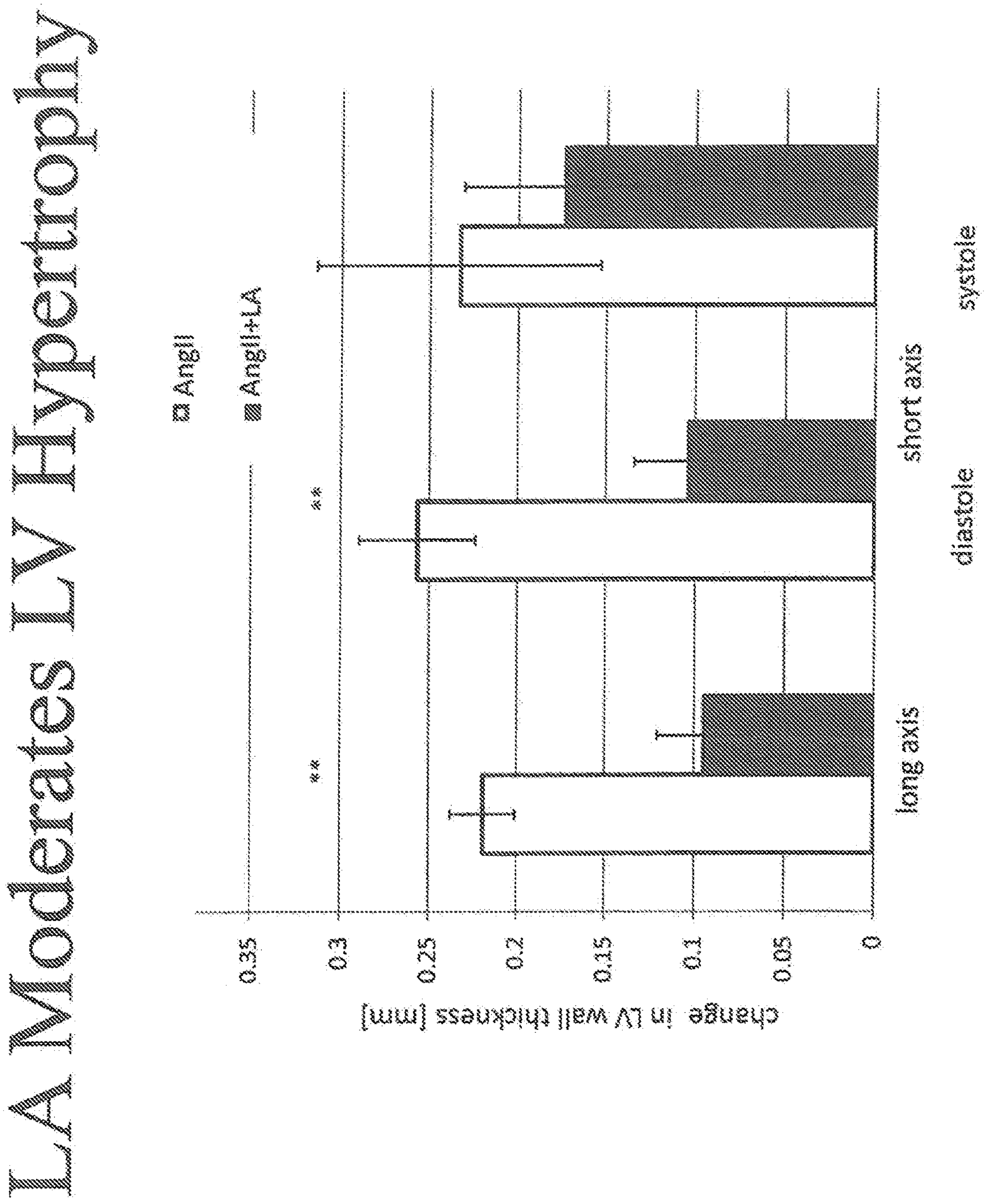
FIG. 18 illustrates LV hypertrophy in angiotensin II treated mice versus mice receiving angiotensin II and leptin antagonist (LA).
Figure 19:
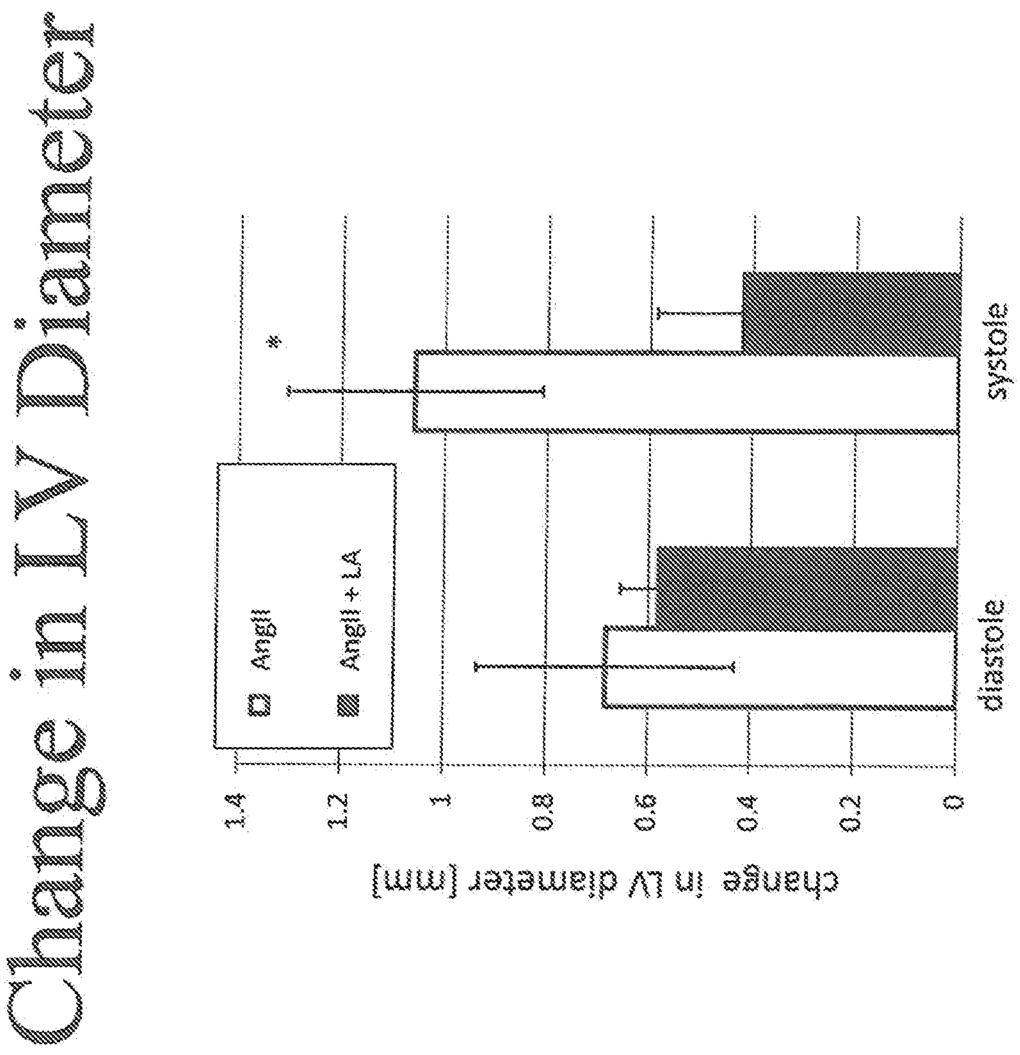
FIG. 19 illustrates changes in LV diameter in angiotensin II treated mice versus mice receiving angiotensin II and leptin antagonist (LA).
Figure 20:
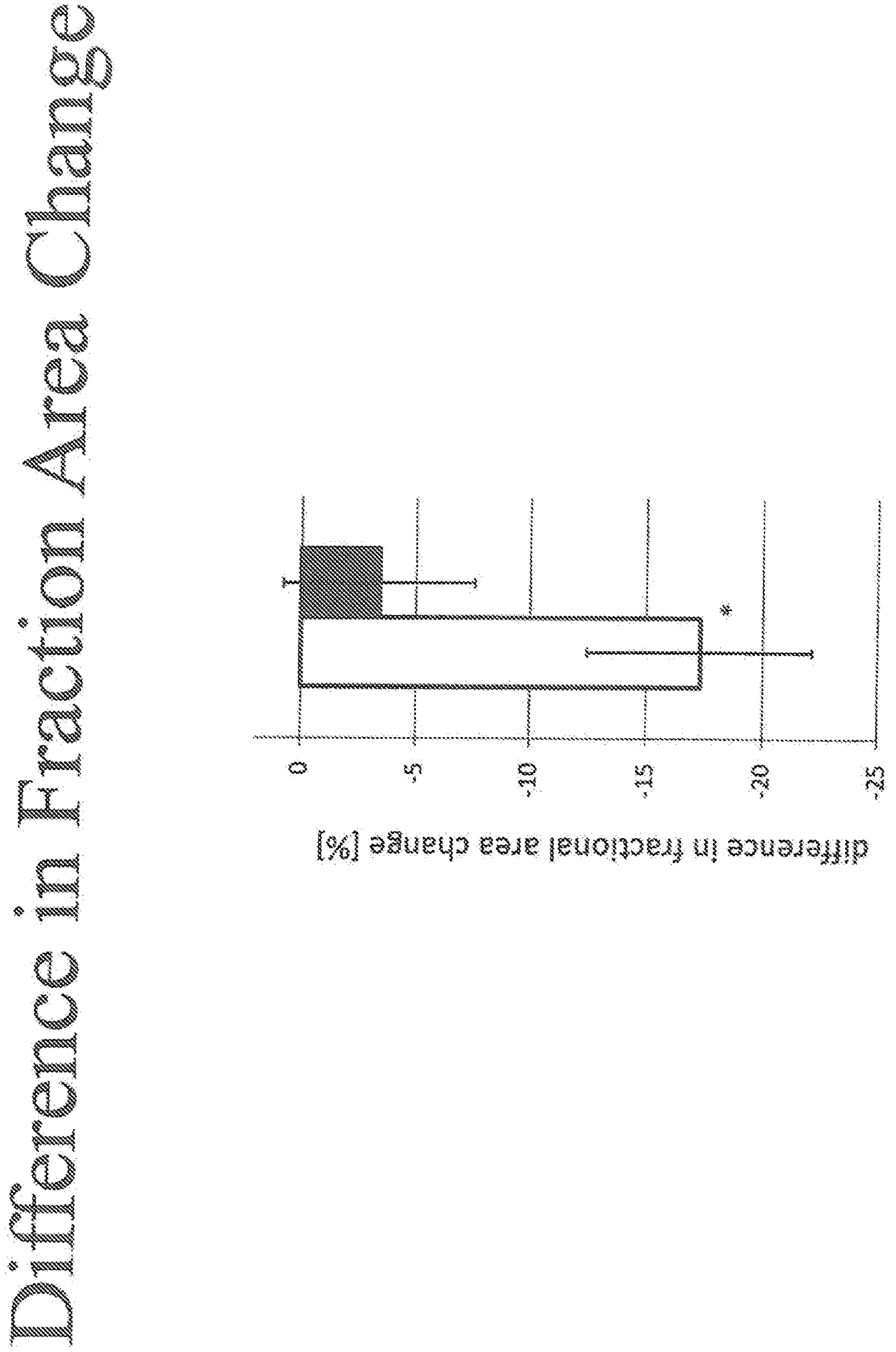
FIG. 20 illustrates LV fractional area change in angiotensin II treated mice (open column) versus mice receiving angiotensin II and leptin antagonist (LA) (filled column).

Mice treated with LA presented less thickening of the left ventricular wall, particularly in diastole (p<0.01, FIG. 18). Left ventricular diameter increased similarly in both groups in diastole however, LA treatment attenuated the increase in LV diameter during systole (p=0.05, FIG. 19). As anticipated, and corresponding to these results, a decrease in FAC in mice co-treated with AngII and LA, was observed, while mice treated by AngII alone exhibited a decrease in fractional area change by over 15% ($p=0.03$, FIG. 20). Moreover, LV diameter which increased in response to AngII treatment, was preserved within the baseline (pre-AngII treatment) range in the LA treated mice ($P<0.05$).

Figure 21:
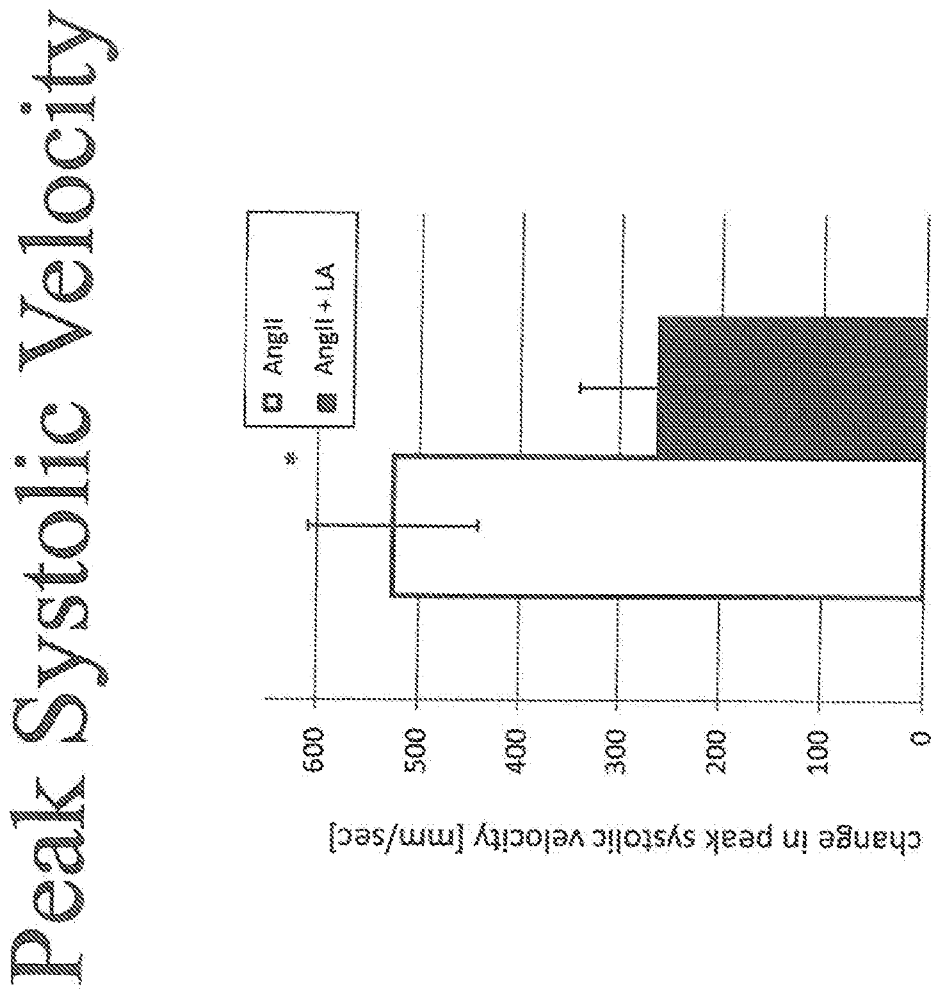
FIG. 21 illustrates peak systolic velocity at the aortic valve in angiotensin II treated mice versus mice receiving angiotensin II and leptin antagonist (LA).

Peak systolic velocity was decreased in AngII treated mice that also received LA application, vs. AngII alone ($p=0.03$, FIG. 21). Notably, since no aortic valve obstruction or changes in its annulus diameter were detected, the PSV parameter is likely reflecting the interaction between proximal aortic hemodynamics, and left ventricular systolic contraction. Thus, PSV moderation by LA may represent attenuation of both aortic and LV remodeling.

Figure 22:
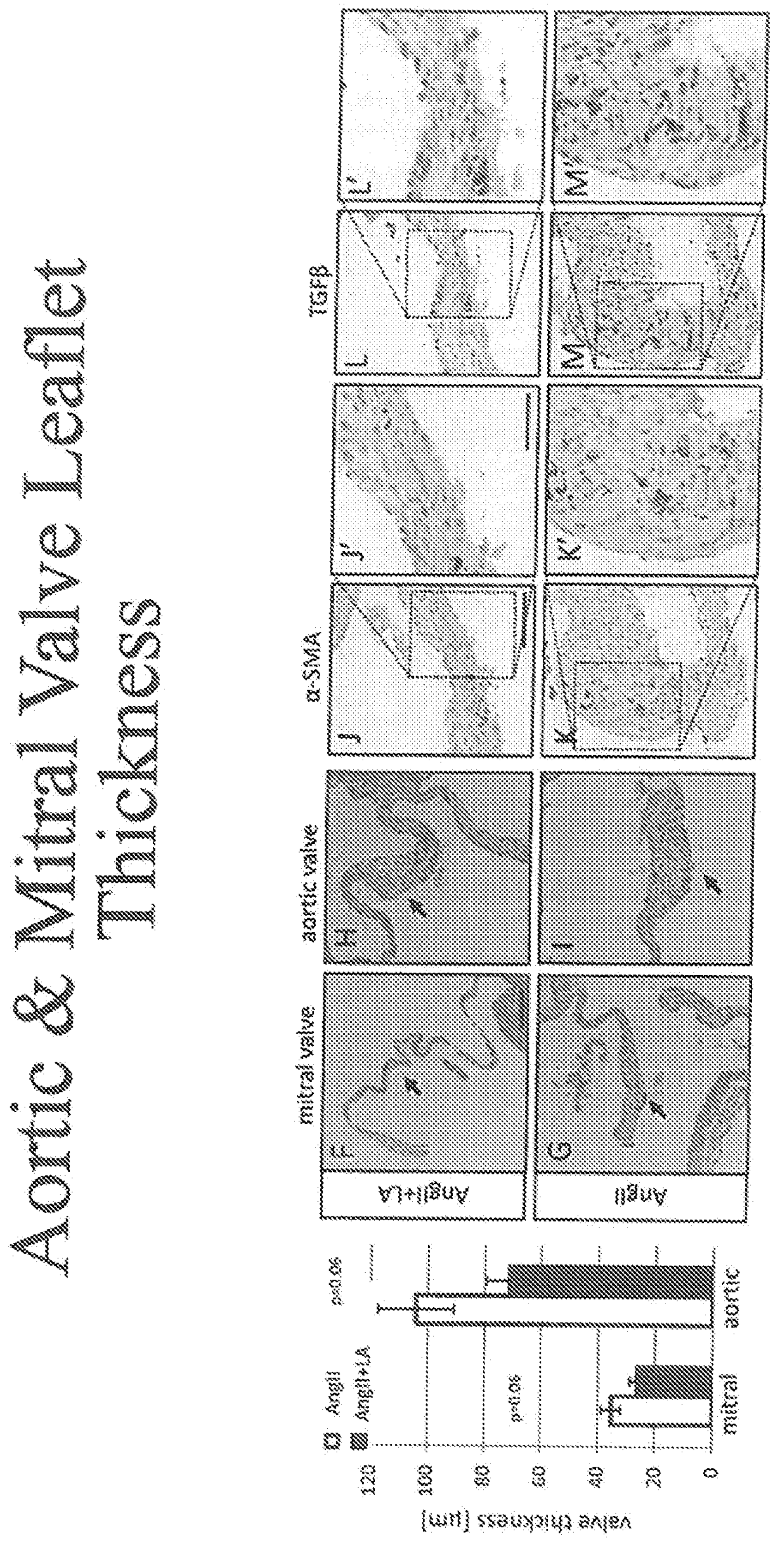
FIG. 22 illustrates aortic and mitral valve thickness (graph on left), and staining of valve leaflets with H&E (panels F-I). αSMA and TGFβ (panels J-M', staining for aortic valves) in mice receiving angiotensin II versus mice treated with angiotensin II and leptin antagonist (LA).

LA also attenuated remodeling of the LV valve. AngII-induced thickening of aortic and mitral valve leaflets was reduced by LA application in both valves ($p=0.06$ in both valves, FIG. 22 left panels F-I).

The αSMA and TGFβ antigens were observed in aortic valve leaflet stromal cells in all AngII treated mice (FIG. 22 panels J-M'); decreased proliferation of stromal cells in LA treated mice was demonstrated through Ki67 staining ($p=0.26$).

Thus, the present findings show that application of a leptin antagonist at the pivotal location on the proximal ascending aortic surface prevents rupture of thoracic aneurysms induced by systemic infusion of Ang II. Local inhibition of leptin activity reduces the degenerative effects of Ang II on the proximal aorta, which underlie aortic wall destabilization. Thus, moderation of Ang II induced aortic dilatation and attenuates left heart remodeling, presumably via the aorto-ventricular coupling.

These results highlight the role of leptin as a key mediator of Ang II signaling and indicate that leptin which underlie left ventricular hypertrophy also drives the formation of early aortic valve hyperplastic lesions, which may progress to aortic valve stenosis (AVS).

Example 3

The Role of Leptin in AVS

Materials and Methods

Human AVS and normal arterial valve (AV) samples were collected for analysis, including autopsy samples, freshly collected AVS specimens from patients undergoing aortic valve replacement surgery, and normal aortic valves from explanted hearts. Formalin fixed valve samples were analyzed by immunohistochemistry for leptin, leptin receptor, CD68 and αSMA. Fresh samples of AVS valves and normal aortic valves underwent total RNA extraction and analyzed by qPCR and Nanostring technique to assess leptin and leptin receptor mRNA levels. Retroperitoneal fat was used as a positive control in both assays.

Results

Figure 23:
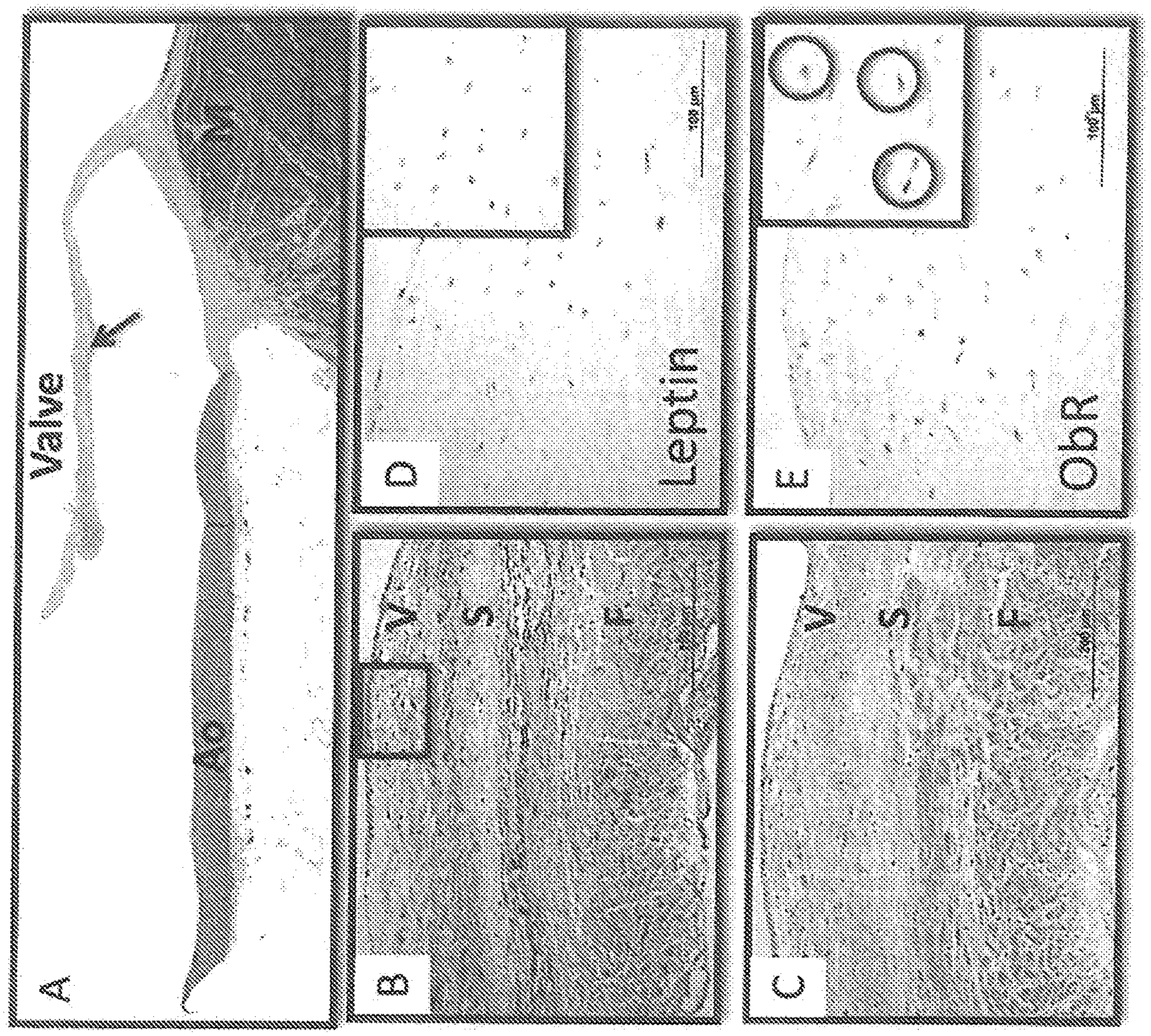
FIG. 23 illustrates expression of leptin (D), and leptin receptor (E) in normal human aortic valve leaflet tissue.
Figure 24:
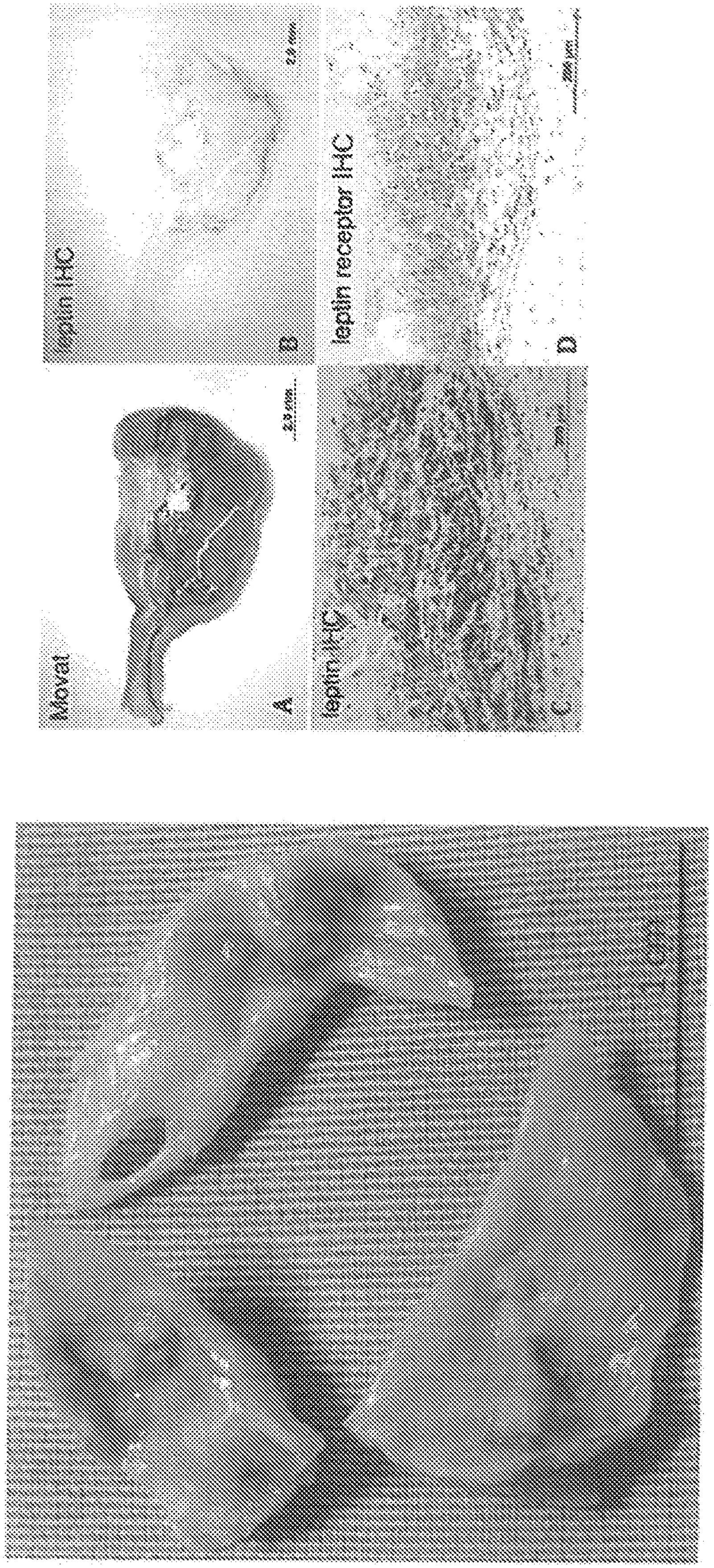
FIG. 24 illustrates leptin and leptin receptor antigen prevalent in severe aortic valve stenosis, evident in SMC-like cells, and infiltrating macrophages.
Figure 25:
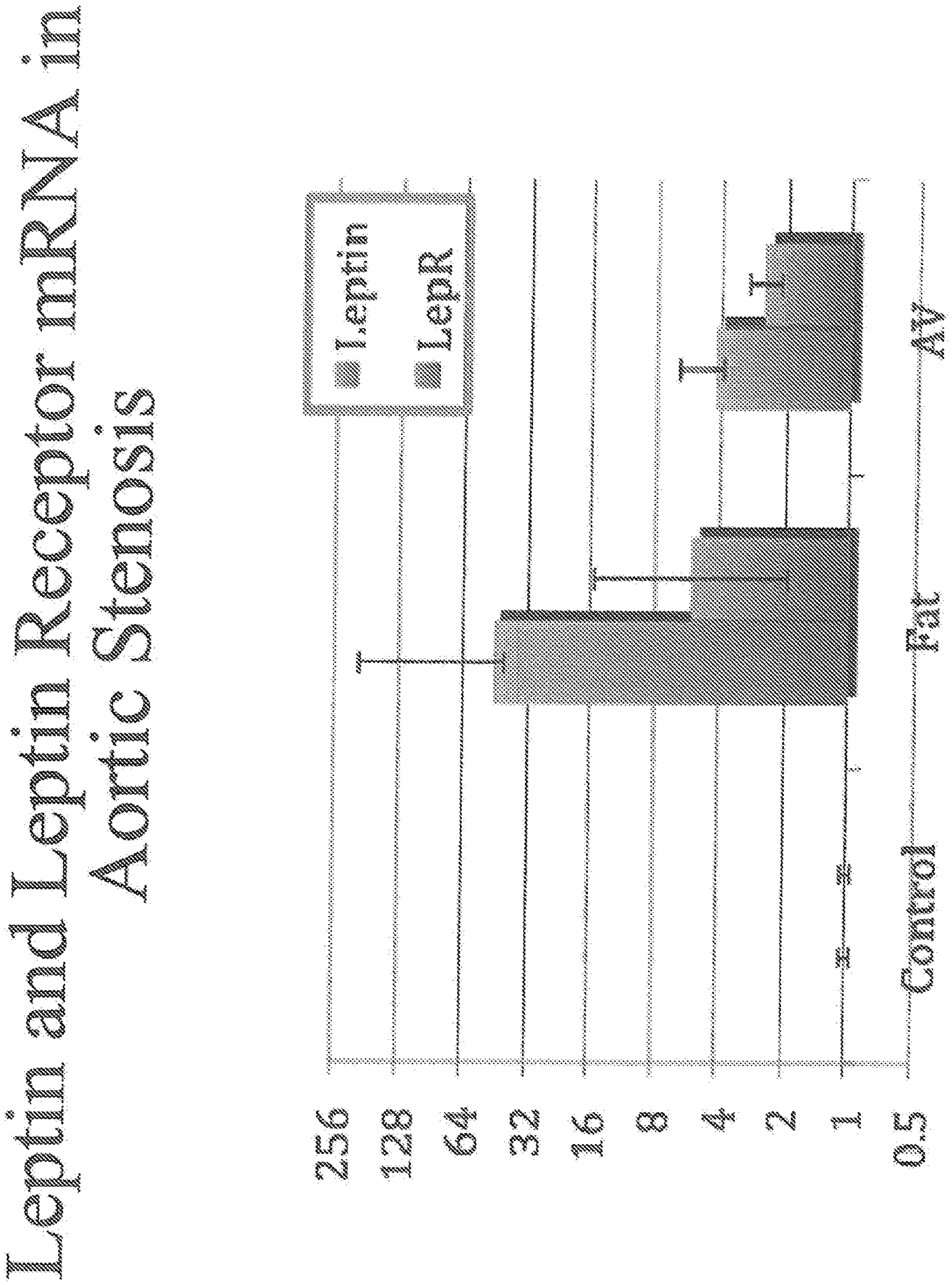
FIG. 25 illustrates leptin and leptin receptor mRNA levels in leaflets of stenosed aortic valve versus normal aortic valve controls, and fat tissue (as positive control)

Normal aortic valve leaflets lack leptin (Ob) antigen, and show very few leptin receptor (ObR) positive cells (FIG. 23). Advanced AVS disease was characterized by extensive ossification and infiltration of inflammatory macrophages in the non-calcified rim of cellular tissue (FIG. 24). Leptin was demonstrated mostly in two cell types, SMC-like elongated cells, and macrophage-like round cells, and its prevalence was proportional to the severity of AVS disease. In situ hybridization analysis performed on AVS samples demonstrated leptin mRNA expression, suggesting de novo synthesis (not shown) leptin and leptin receptor mRNA levels were assessed by qPCR and Nanostrings hybridization, using total RNA extracted from freshly collected AVS. AVS were compared to normal AV leaflets (FIG. 25), revealing increased leptin and leptin receptor mRNA in AVS samples.

Figure 26:
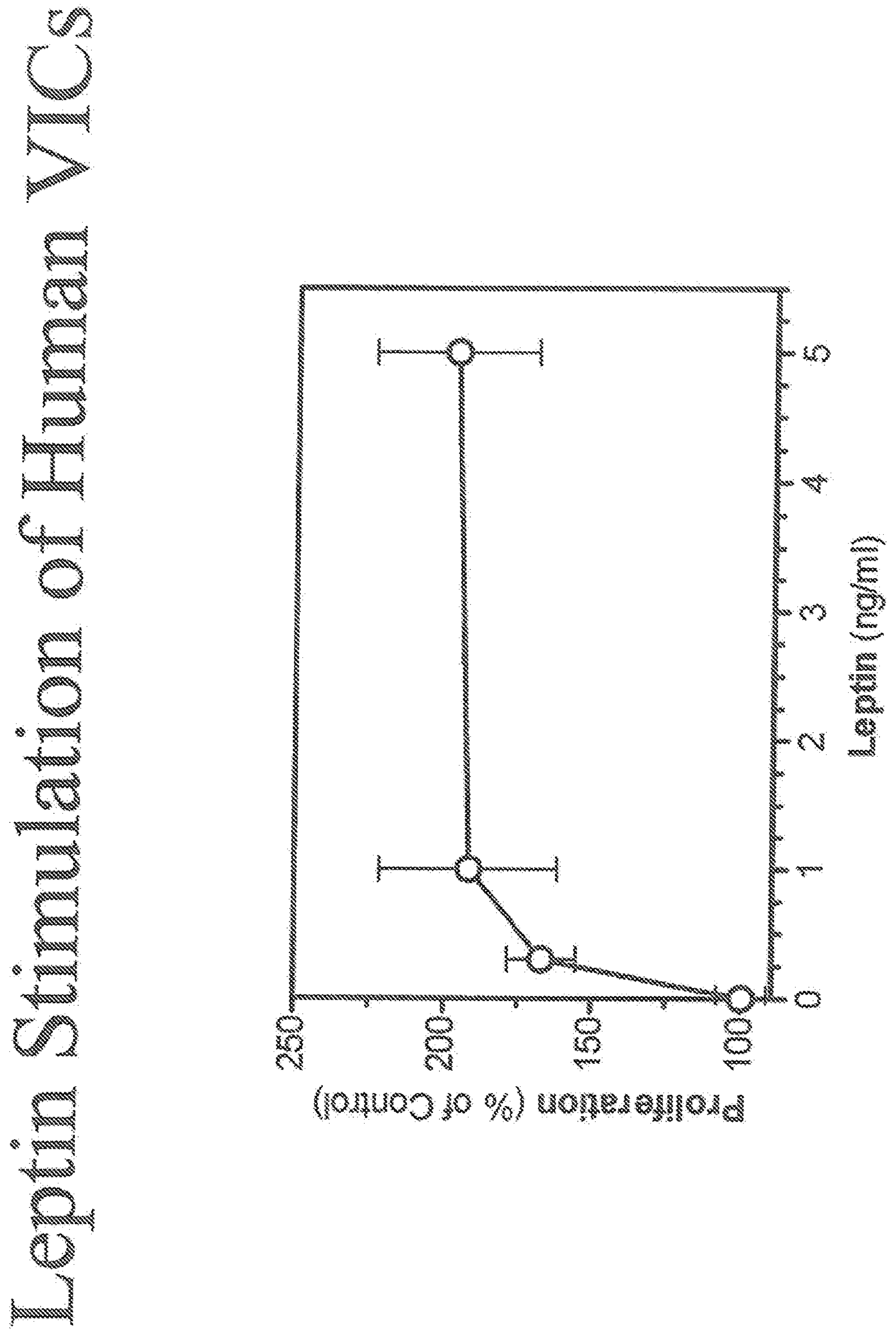
FIG. 26 illustrates proliferation of valve interstitial cells (VICs) in response to leptin stimulation.

To investigate the potential impact of AngII and leptin on human valve cells, in vitro analysis revealed that AngII-mediated proliferation of human valve interstitial cells (VICs) is leptin mediated (leptin-induced proliferation of VICs in FIG. 26). This suggests that leptin synthesized in aortic valve leaflets by VICs and inflammatory macrophages may elicit VIC proliferation and subsequent ossification via a paracrine/autocrine pathways.

Example 4

Preparation of Sustained-Release Film

Poly lactic-co-glycolic acid (PLGA) films containing a leptin antagonist (e.g., a leptin antagonist described in U.S. Pat. No. 8,969,292) is produced in a manner analogous to the described in Webber W L et al "Characterization of soluble, salt-loaded degradable PLGA films and their release of tetracycline" J Biomed Mater Res 1998, 41, 18-29.

Specifically, 1 g PLGA 6535 polymer (D,L-lactide:glycolide: 65:35, Mw=45,000-75,000 Da; Lakeshore. Biomaterials, Birmingham, Ala., USA) is dissolved in 10 mL $MeCl_2$ (Fisher Scientific, Loughborough, UK). Sodium chloride (10 mg in 0.2 ml distilled water) and 25 μL ethylene glycol (Sigma-Aldrich, St. Louis, Mo., USA) are added to the PLGA solution and sonicated for 20 seconds. 1 mg of the leptin antagonist is suspended in 2 mL of the PLGA solution, followed by casting on the flat surface of a Teflon mold to create a film comprising a leptin antagonist.

Example 5S

Evaluation of Sustained-Release Properties of Film

A 2×2.5-mm patch of PLGA film of Example 4 is maintained in 5 mL sterile PBS at 37° C. for 28 days. Every 7 days the PBS medium is sampled before being aspirated and replaced by 5 mL of fresh PBS. The medium samples are analyzed by ELISA (RayBiotech, Norcross, Ga., USA) for leptin antagonist levels. The in vitro measurement of leptin discharged from the slow-release PLGA film yields substantial release of leptin antagonist for at least two weeks.

Example 6

Preparation of Two-Component Gelling Sustained-Release Gel Composition

A first component of the composition is an aqueous solution of modified carboxymethyl cellulose with adipic dihydrazide (CMC-ADH). Dried and finely ground sustained-release gel with leptin antagonist as described in Example 1 is added to the CMC-ADH solution and vortexed to yield a suspension.

A second component of the composition is oxidized dextrane in DDW (DX-COH). A dye such as methylene blue (0.5%) is optionally added to the DX-COH solution to make the resulting gel more visible.

For use the two components are mixed together to form a viscous fluid that is immediately administered by injection. In a short time, the viscous fluid gels.

Example 7

Covered Stents

A stent cover is fashioned from the PLGA film of Example 4.

The stent cover is used to cover the balloon expandable stents of a MULTI-LINK 8 LL coronary stent system, a MULTI-LINK ULTRA coronary stent system and a MULTI-LINK MINI VISION coronary stent system (all of Abbot Laboratories, Abbot Park, Ill., USA).

The graft (stent cover) portion of an Endurant II AAA Stent Graft System (Medtronic, Dublin, Ireland) is impregnated with a leptin antagonist. In one example, impregnation is by immersion in a first component of the composition of Example 3, followed by contact with contact with the second component thereof.

The stent cover is used as an external cover for a self-expanding WallFlex Stent (Boston Scientific Corporation, Natick, Mass., USA).

The covered stents are deployed in the usual way inside the lumen of a blood vessel of a living subject in need thereof. Once implanted, the leptin antagonist elutes from the stent cover through the blood vessel endothelium into the blood vessel to exert a desired pharmaceutical effect.

Example 8

Drug-Elating Stent

An XIENCE Alpine coronary stent system (Abbot Laboratories, Abbot Park, Ill., USA) is prepared in the usual way, but impregnated with a leptin antagonist as an active pharmaceutical ingredient instead of Everolimus.

The resulting drug-eluting stent is deployed in the usual way inside the lumen of a blood vessel of a living subject in need thereof. Once implanted, the leptin antagonist elutes from the stent through the blood vessel endothelium into the blood vessel to exert a desired pharmaceutical effect.

Example 9

Bioresorbable Stent

A bioresorbable balloon-expandable stent is fashioned of bioresorbable polylactide (PLA) comprising a leptin antagonist, substantially as done to fashion a bioresorbable stent by Arterial Remodeling Technologies (Paris, France).

A bioresorbable balloon-expandable stent is fashioned of bioresorbable poly (L-lactide) (PLLA) comprising a leptin antagonist and also comprises a bioresorbable coating of PLLA including a leptin antagonist, substantially as done to fashion an Absorb GT1 vascular scaffold stent.

The resulting bioresorbable stents are deployed in the usual way inside the lumen of a blood vessel of a living subject in need thereof. Once implanted, the leptin antagonist elutes from the stents as these resorb, to pass through the blood vessel endothelium into the blood vessel to exert a desired pharmaceutical effect.

Example 10

Spike or Rod

An implantable spike or rod (bioresorbable or not) is made as known in the art, for example as described above with reference to the stents and includes leptin antagonist integrated into the material of the spike or rod, or adsorbed, absorbed or coated onto the spike or rod.

The resulting spike or rod is implanted in the usual way inside an organ, for example by piercing the organ. Once implanted, the leptin antagonist elutes from the spike or rod, to exert a desired pharmaceutical effect on the organ.

Example 11

Injectable Gel

The two components of the composition of Example 3 are provided. The components are mixed together and implanted in the body of the subject by injection into or onto an organ to form a gelled mass in or on the organ.

Once implanted, the leptin antagonist elutes from the gelled mass, to exert a desired pharmaceutical effect on the organ.

Example 12

Sheet

A sheet of the film of Example 1 is provided. The sheet is placed against the outer surface of an organ (e.g., aorta, for example, ascending aorta, aortic arch, descending aorta, abdominal aorta) and optionally held in place by sutures and/or biological glue (e.g., Evicel® by Ethicon of Johnson and Johnson).

Once implanted, the leptin antagonist elutes from the film, to exert a desired pharmaceutical effect on the organ.

Example 13

Treatment of AAA

A human subject is diagnosed with an abdominal aortic aneurysm (AAA).

A composition according to the teachings herein in the form of a long sheet such as described in Example 12 (a ribbon) comprising leptin antagonist is provided. The abdominal aorta of the subject is surgically accessed from the outside (e.g., using keyhole surgery) and the composition administered by winding the long sheet around the abdominal aorta to wrap the entire aneurysm as well as a portion of the aorta above and below the aneurysm, and held in place with a biological glue and/or sutures. Optionally, a stent graft (e.g., an Endurant® II AAA Stent Graft System (Medtronic, Dublin, Ireland)) is deployed in the aneurysm in the usual way, before or after administration of the composition. Subsequently, leptin antagonist from the composition passes through the tunica externa to provide a beneficial effect to the subject, Alternatively or additionally, an AAA stent graft is provided that is similar to known AAA stent grafts (e.g., similar to an Endurant® II AAA Stent Graft System (Medtronic, Dublin, Ireland)) where at least one of: the graft and/or anchoring stents are a composition of the teachings herein and comprises a leptin antagonist; at least the anchoring portions of the graft and/or anchoring stents are impregnated with a composition of the teachings herein that comprises a leptin antagonist; and at least the anchoring portions of the graft and/or anchoring stents are coated with a composition of the teachings herein that comprises a leptin antagonist. The stent-graft is deployed in the usual way in the abdominal aneurysm, that is to say, where the anchoring stents are expanded against healthy portions of tunica intima above and below the aneurysm. Subsequently, leptin antagonist from the composition passes through the tunica intima to provide a beneficial effect to the subject, for example, preventing or reducing the extent that the aneurysm spreads to portions of tissue in proximity of the anchoring stents, thereby preventing loosening of the anchoring stents.

Alternatively or additionally, a drug-eluting balloon similar to the In.Pact Admiral® DCB drug-coated balloon by Medtronic (Dublin, Ireland) that is coated with a composition comprising leptin antagonist according to the teachings herein is introduced through the femoral arteries and advanced to areas of the abdominal and iliac arteries that are just above and just below the aneurysm (for example, "landing zones" where anchoring stents of a stent-graft would be deployed. The balloon is expanded to contact the aorta and iliac walls, thereby administering composition to the healthy tissue and preventing advancement of the aneurysm. In some such embodiments, the administration of leptin antagonist is repeated periodically, e.g., with a frequency that is less than once a month, less than once every two months and even less than once every 3 months. In some such embodiments, the administration of the leptin antagonist leads to stabilization of the wall tissue, halting the processes of aneurysm formation at the portions of the blood vessels above and below the aneurysm and at the portions of the blood vessel in contact with the deployed stent graft.

Example 14

Treatment of Thoracic Aortic Aneurysm

A human subject is diagnosed with an aneurysm in the thoracic aorta, including one or more of the ascending aorta, aortic arch and descending aorta. It is known that segmental increased stiffness and aortic dilatation cause local aneurysm formation. These structural changes underlie hemodynamic perturbation, which increases left ventricular afterload. This results in left ventricular remodeling, including left ventricular hypertrophy, and thickening of the aortic and mitral valve leaflets. Left ventricular hypertrophy may lead to heart failure, and aortic valve remodeling may progress to the full clinical presentation of aortic valve stenosis.

A composition according to the teachings herein in the form of a patch such as described in Example 12 comprising leptin antagonist is provided. The thoracic aorta of the subject is surgically accessed from the outside (e.g., using thorascopy) and the composition administered by contacting the outer surface of the affected portions of the aorta with the patch, and optionally holding the patch in place with a biological glue and/or sutures.) aortic valve annulus diameter) a drug eluting stent graft impregnated with leptin antagonist is deployed in the aneurysm in the usual way, without oversizing.

Another shape of intra-vascular device that may be deployed within an aortic aneurysm is a tubular self-expandable biodegradable (or non-degradable, like bare metal) leptin antagonist slow release mesh or stent. Such a device may self-expand upon deployment, and gently adhere to the luminal surface of the aortic aneurysm (applying minimal radial force to the luminal surface). Leptin antagonist that is associated with, e.g., incorporated within the biodegradable or non-degradable struts of the mesh or stent or covered or coated onto the mesh or stent, will access the aortic wall at the aneurysm by local diffusion. Yet another shape of a device for proximity and local slow release of leptin antagonist at the luminal surface of aortic or peripheral aneurysm will be a single wire (biodegradable or bare metal) possessing the memory of spiral expansion within the aneurysm cavity. The leptin antagonist incorporated within this wire will diffuse into the arterial wall. Subsequently, leptin antagonist from the composition passes into the tissue to provide a beneficial effect to the subject, in some embodiments one or more of attenuate aneurysm progression, stabilize the vessel wall and prevent rupture or dissection of the aneurysm. In some embodiments of treatment of the ascending aorta, the administration of the leptin antagonist also leads to reducing the rate of development, or stopping the development and in some embodiments, reversing the remodeling of parts of the heart.

Example 15

Angioplasty

A human subject is diagnosed with arterial stenosis that is treatable by angioplasty.

A drug-eluting balloon similar to the In.Pact Admiral® DCB drug-coated balloon by Medtronic (Dublin, Ireland) that is coated with a composition comprising leptin antagonist according to the teachings herein is used in the usual way to perform the angioplasty procedure, for example, at sites of arterial bifurcations and in-stent stenoses. At least some of the composition according to the teachings herein that coats the balloon is administered to the surface of the treated blood vessel, thereby administering a composition according to the teachings herein. In some such embodiments, the administration of leptin antagonist is repeated periodically, e.g., with a frequency that is less than once a month, less than once every two months and even less than once every 3 months, even when there is no express need for repeated angioplasty. Subsequently, leptin antagonist from the composition passes into and/or through the lesion and/or tunica intima to provide a beneficial effect to the subject.

Alternatively or additionally, at least one of:

a composition according to the teachings herein in the form of a stent;

a stent impregnated with a composition according to the teachings herein;

a stent coated with a composition according to the teachings herein;

a composition according to the teachings herein in the form of a stent cover;

a stent cover impregnated with a composition according to the teachings herein; and a stent cover coated with a composition according to the teachings herein;

is deployed in the usual way, e.g., during performance of an angioplasty procedure, thereby administering a composition according to the teachings herein. Subsequently, leptin antagonist from the administered composition passes into and/or through the lesion and/or tunica intima to provide a beneficial effect to the subject.

Example 16

Myocardial Infarction

Myocardial infarction causes left ventricular remodeling, leading to progressive impairment of cardiac function. A human subject is diagnosed with an acute myocardial infarction and is treated in the usual way, for example coronary catheterization for primary revascularization and myocardial salvage. A treating health-care professional identifies that the subject has an elevated risk of developing cardiac dysfunction.

A composition comprising leptin antagonist is administered to the ascending aorta as described in the preceding examples using one or more of a drug-eluting balloon, a stent, a covered stent and a stent graft. Subsequently, leptin antagonist from the administered composition passes into and/or through the tunica intima of the aorta to provide a beneficial effect to the subject. In some embodiments, the beneficial effect is prophylactic, preventing development of or reducing the rate of development of an thoracic aortic aneurysm, and/or remodeling of the heart (in particular the left ventricle and associated valves) and/or a recurring infarction. Without wishing to be held to any one theory, it is currently believed that such administration of a leptin antagonist in the ascending aorta reduces angiotensin II synthesis in the left ventricle, thereby moderating the hypertrophy response to the ischemic insult associated with the acute myocardial infarction suffered by the subject.

Example 16-A

Post Myocardial Ischemia (MI) Therapy

In order to minimize the extent of post MI left ventricular remodeling, a bolus of leptin antagonist in aqueous solution may be administered into the involved coronary artery. The following strategy may be exercised for acute MI patients: Patients who sustain acute MI are most frequently admitted through the catheterization lab, to undergo coronary catheterization and primary PTCA (Percutaneous Transarterial Coronary Angioplasty) for primary revascularization. Once blood-flow is re-established in the coronary artery involved, a bolus of leptin antagonist in an aqueous solution is to be injected into the coronary artery through the catheter, after which the catheter will be withdrawn. This new strategy should achieve local distribution of leptin antagonist within the left ventricular heart muscle cells (cardiomyocytes) that were exposed to the ischemic as well as reperfusion insult. Inhibition of cardiomyocyte leptin activity is anticipated to mitigate left ventricular remodeling, and reduce the damage to left ventricular function.

Induction of myocardial ischemia in experimental animals may be achieved by temporary balloon inflation within the proximal left anterior descending (LAD) coronary artery. Leptin antagonist aqueous solution may be injected into the LAD after balloon deflation. Control group may receive intracoronary bolus of saline injection. An intravascular injection of leptin antagonist may be provided into the treated coronary artery after it has been reopened and blood flow to the ischemic myocardium is restored, in order to prevent post MI left ventricular remodeling. Leptin antagonist may be administered by intravascular injection into a vascular territory that sustained ischemia and reperfusion injury. This injection is a localized injection to a specific section of the left ventricle and does not constitute a systemic treatment.

Example 17

Myointimal Hyperplasia (MIH)

It is known that trauma to a blood vessel may lead to myointimal hyperplasia (MIH), where medial smooth muscle cells undergo uncontrolled proliferation that may lead to stenosis or restenosis of the blood vessel in the area of the trauma. Such trauma include vascular injury caused by expansion of a blood vessel during angioplasty, stent deployment, stent-graft deployment, as a result of surgical anastomosis and associated suturing, clamping of blood vessels, and as a result of blunt and/or penetrating vascular injury.

A health-care professional identifies that a subject has an elevated risk of developing myointimal hyperplasia due to some vascular trauma, administers a composition comprising leptin antagonist according to the teachings herein to the site of the trauma. The administered leptin antagonist reduces the rate or stops the uncontrolled proliferation of cells, reducing the rate of development or preventing MIH. Administration includes the use of any of the compositions according to the teachings herein, including localized administration of a leptin antagonist composition on the outer surface of the blood vessel at the site of injury during surgery (e.g., application of a film of Example 4 as a patch), peri-vascular injection of leptin antagonist in solution or within a slow release gel, Intravascular administration using a drug eluting balloon, or by administration of a composition that impregnates or coats a medical device, or a composition that is in the shape of a medical device by deploying the medical device. In some embodiments, specific suitable medical devices include intracavitary devices such as a stent cover, a stent, a graft assembly, a ring, a suture and a prosthetic cardiac valve as well as extraluminal devices such as sheets, all such comprising leptin antagonist according to the teachings herein,

Example 18

Treatment of Aneurysm

A human subject is diagnosed with a peripheral or venous aneurysm, e.g., a visceral artery aneurysm, a cerebral aneurysm, especially a saccular or pseudo-fusiform aneurysm.

A composition according to the teachings herein associated with a covered stent is provided, e.g., one or more of coating the stent, coating the stent cover, impregnating the stent, impregnating the stent cover, constituting the stent and constituting the stent cover. The covered stent is deployed in the usual way, where the stent cover covers the mouth of the stent. Subsequently, leptin antagonist from the composition passes into and/or through the tissue in proximity to the aneurysm to provide a beneficial effect to the subject.

Alternatively or additionally, a composition according to the teachings herein is placed inside the cavity of the aneurysm through the mouth thereof, e.g., as a fluid composition (e.g., Example 6) or as an aneurysm coil that is impregnated with leptin antagonist, coated with leptin antagonist or is made of a composition according to the teachings herein. A person having ordinary skill in the art is able to implement coating an aneurysm coil with an active pharmaceutical ingredient with reference to, for example, Cerecyte® (Codman Neuro, a division of DePuySynthes, part of Johnson & Johnson, New Brunswick, N.J., USA), Nexus® (Micro Therapeutics, Inc., Irvine, Calif., USA), and HydroCoil®, HydroSoft® (Terumo Corporation, Tokyo, Japan). Subsequently, leptin antagonist from the composition passes into the cavity of the aneurysm, and subsequently to affected tissue to provide a beneficial effect to the subject.

Example 19

Treatment of Aneurysm

A human subject is diagnosed with an aneurysm, e.g., aortic aneurysms, which are typically related to a variety of diseases associated with angiotensin II hormonal activity. Also peripheral arterial aneurysms, which affect visceral, carotid, peripheral, and cerebral arteries, as well as venous aneurysms, including pulmonary artery (which carries venous blood) may be diagnosed.

A leptin antagonist eluting stent or scaffold may be provided, e.g., intravascular stent or scaffold device (which may or may not be biodegradable) covered or coated with leptin antagonist, available for slow release into the vessel wall locally, thereby attenuating aortic aneurysm progression. A stent-graft destined for treatment of aortic aneurysm may be provided, covered or coated with leptin antagonist available for slow release into the vessel wall at the specific sites of stent-graft attachment to non-dilated (normal) proximal and distal vessel (landing zones). In some embodiments, a stent-like prosthetic heart valve for intravascular application, covered with leptin antagonist may be provided, to prevent local dilation of the hosting tissue ring.

Example 20

Treatment of Vascular Injury

A human subject may be exposed to localized vascular injury which may occur as a result of vascular surgery, local balloon angioplasty. This may cause local arterial narrowing due to smooth muscle cell proliferation, namely myointimal hyperplasia (MIH). This proliferative response may also occur at arterio-venous anastomosis or graft-arterial anastomosis, and in leptin-induced inflammatory and cellular proliferative arterial disease (e.g., Takayasu disease). In order to prevent local arterial narrowing due to cellular proliferation at the sites of vascular injury, and circumstances as described above, an intravascular stent or scaffold device may be provided, (which may or may not be biodegradable) which may be associated with, e.g., covered or coated with leptin antagonist that is available for slow release into the vessel wall. Also, peri-vascular injection of leptin antagonist slow release gel can attenuate the MIH response.

Example 21

Treatment of Atherosclerotic Plaques

A human subject is diagnosed with atherosclerotic plaques. These lesions frequently undergo transformation from a stable plaque into an unstable rupture-prone lesion. An intravascular stent or scaffold device (which may or may not be biodegradable) covered with leptin antagonist that is available for slow release into the vessel wall may be provided, in order to provide vessel stabilization. Deployment of such a stent or scaffold device may apply to any arterial site. Also, peri-vascular injection of leptin antagonist slow release gel can pacify the atherosclerotic plaque and prevent its transformation into an unstable lesion.

Example 22

Treatment of Left Heart Failure and Aortic Valve Disease

Patients who are diagnosed as hypertensive and hypercholestrolemic and exhibit initial dilation of the ascending aorta may be treated by positioning an intravascular stent or scaffold device at the ascending aorta. The stent or scaffold device may or may not be biodegradable. The device, may be associated with, e.g., covered or coated with leptin antagonist that is available for slow release into the vessel wall. Subsequently, slowing down the progression of the aortic aneurysm by intraluminal, locally applied leptin antagonist will prevent the development of left heart failure, and remodeling of aortic and mitral valve leaflets.

The intravascular stent or scaffold device carrying or covered with leptin antagonist, may be positioned intraluminally at the ascending aorta. Such a stent or scaffold device may attenuate local dilation and stiffening thereby prevent local hemodynamic perturbation, which activate the aorto-ventricular coupling. This coupling, when turned on promotes the production and release of angiotensin II from left ventricular cells (cardiomyocytes). Angiotensin II drives intracellular synthesis of leptin in cardiomyocytes and in aortic valve interstitial cells (VICs). Leptin synthesis in cardiomyocytes and VICs contributes to left ventricular hypertrophy, and aortic/mitral valve thickening, respectively. Therefore, de-activation of the aorto-ventricular coupling will control both left ventricular hypertrophy (heart failure) and also attenuate the progression of aortic/mitral valve disease.

Example 23

Effect of Excessive Endogenous Leptin Expression on Post-MI Heart Failure

Post-MI heart failure involves complex mechanisms. One of these mechanisms is the over-expression of leptin in cardiomyocytes after ischemia and reperfusion injury (IRI). Leptin activity in cardiomyocytes promotes left ventricular hypertrophy and fibrosis, both of which contribute to cardiac dysfunction. Post-MI therapies in rats, aimed at blocking leptin activity via systemic (Purham et al., Am. J Physiol. Heart Circ. Physio. 2008: 295:H441-H446) or local (Moro et al., J Cell Mol. Med. 2011; 15:1688-1694) approaches mitigated post-MI cardiac damage. Patients that suffer from systemic inflammatory disease and exhibit hyperleptinemia have been found to be at an increased risk of heart failure following acute MI. Therefore, to assess the role of increased endogenous leptin synthesis in the context of IRI, we intentionally induced leptin expression in an ischemia and reperfusion mouse model. A single IP injection of high dose leptin antagonist (LepA) with a short half-life transiently disrupted the availability of leptin receptors, and induced endogenous over expression of the leptin gene in multiple tissues, including the heart.

Activated renin-angiotensin aldosterone system (RAAS) acts via angiotensin II (AngII) in IRI, contributing to tissue damage through various pathways. In the myocardium AngII induces cardiac cell hypertrophy leading to left ventricular dysfunction through the induction of leptin in cardiomyocytes. Past experimental data have provided evidence that both, cardiomyocyte hypertrophy and the resulting heart failure can be mitigated by inhibiting leptin synthesis and activity. In the kidney (which is an end organ that is solely supplied in most cases by a single artery, mechanisms related to angiotensin II cause cell injury through constriction of renal vessels, enhancement of vascular sensitivity to sympathetic nerve stimulation, increased oxidative stress and induced apoptosis. Also recruitment of macrophages and neutrophil activation in the injured kidney may be driven by angiotensin II and its mediator, leptin. Studies have demonstrated that angiotensin converting enzyme inhibitors (ACEIs) and angiotensin receptor blockers have protective effects on IRI in the kidney.

In the current experiment, a clinical scenario of myocardial ischemia and reperfusion injury (IRI) has been simulated in C57BL6 mice in order to examine the effects of excessive endogenous leptin on post-MI heart failure. Myocardial IRI was achieved by ligating the anterior descending coronary artery for 45 minutes. Thereafter, the artery was re-opened to restore perfusion. Excessive endogenous leptin expression was induced by intraperitoneal (IP) injection of 250 μg of superactive mouse leptin antagonist (SMLA) that was administered sequentially following the induced myocardial IRI, upon reperfusion. Control mice received intraperitoneal injection of saline solution upon perfusion. It is emphasized that the intraperitoneal injection of SMLA, namely a systemic administration of leptin antagonist, is used as a trigger to disrupt the systemic leptin pathway, stimulating augmented leptin synthesis.

Figure 32A:
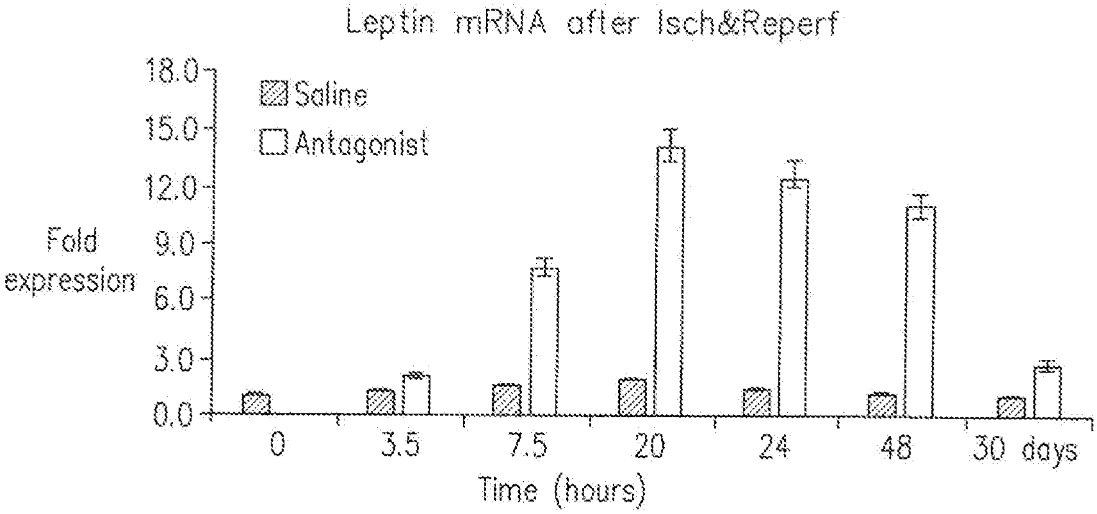
FIGS. 32*a* and 32*b* illustrate a time course of leptin mRNA expression and leptin receptor mRNA expression, respectively, in the heart of mice that underwent myocardial IRI and systemic administration of leptin antagonist to stimulate endogenous leptin synthesis, or saline, upon reperfusion.
Figure 32B:
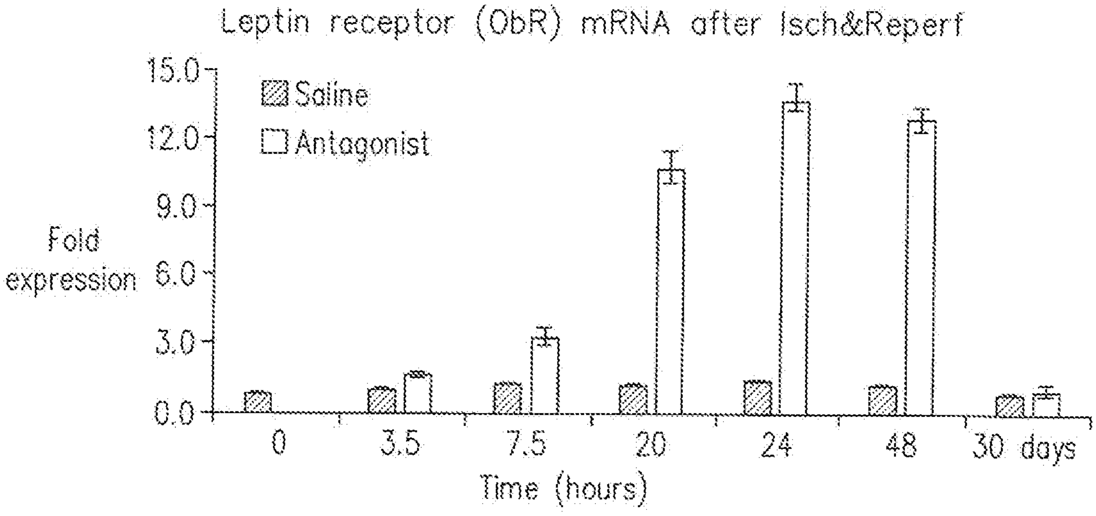

Leptin mRNA was increased significantly in different tissues throughout the first 48 hours, including adipose tissue and heart. Leptin receptor mRNA presented a similar pattern. Levels of leptin mRNA and leptin receptor mRNA were measured in the heart over a period of 30 days (FIG. 32). Interestingly, the heart exhibited maximal leptin mRNA upregulation 20 hours post IRI. There was also a long-term increase in leptin transcript by 3-6 fold on post operative day (POD) 30, compared to saline controls.

Figure 33:
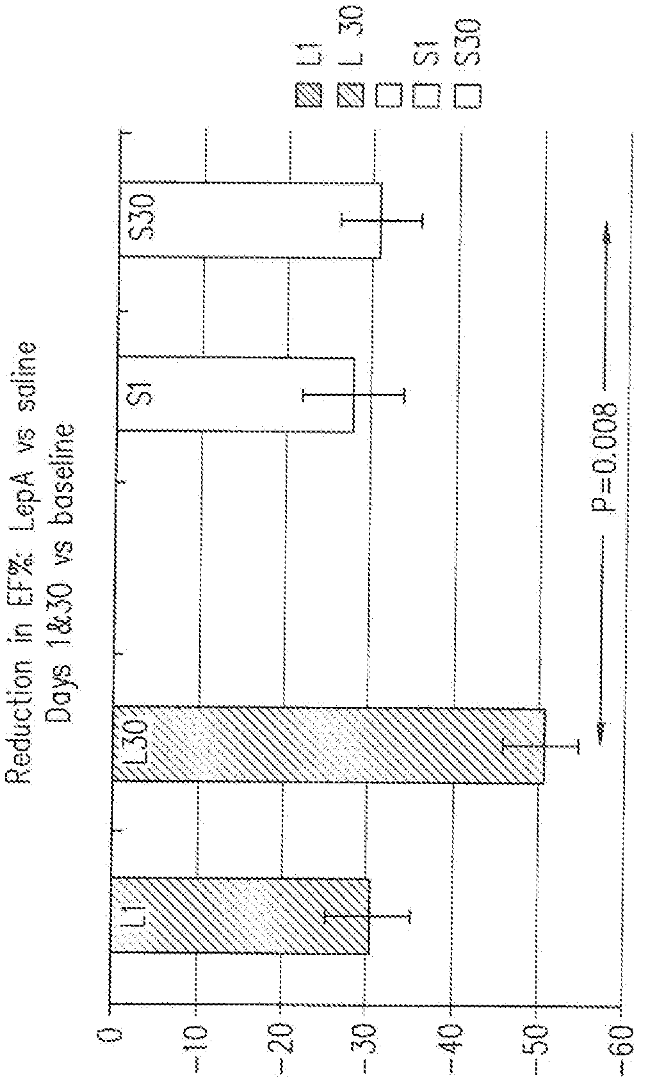
FIG. 33 illustrates percent of ejection fraction (EF %) of mice at 1 and 30 days after undergoing IRI and systemic administration of leptin antagonist or saline upon reperfusion.

Echocardiography performed 24 hours and 30 day following IRI in LepA versus saline injected mice revealed a significant reduction in cardiac function in LepA receivers, on post-IRI day 30 (FIG. 33).

As can be clearly seen, IRI mice injected with leptin antagonist exhibited more extensive post-MI cardiac dysfunction compared to IRI control mice. These results imply that the extent of post-MI cardiac dysfunction correlates directly with local leptin expression. Notably, the capability to block local leptin activity when using local application of leptin antagonist in angiotensin II-induced leptin mediated aortic aneurysm mouse model has been previously demonstrated experimentally by the current inventor. Collectively, based on multiple data, it is therefore hypothesized that the local inhibition of leptin activity in LV cardiomycytes would attenuate post-MI cardiac tissue damage. It should be emphasized that the strategy of local administration of leptin antagonist selectively into the infarcted territory, should prevent systemic hormonal perturbation. A previous key experiment demonstrated effective mitigation of post-MI heart failure by disrupting leptin synthesis, via, antisense oligodesoxynucleotide against leptin mRNA that was injected directly into the infarcted zone in rats undergoing cardiac IRI. It is therefore conceivable that direct intracoronary injection of LepA, aimed exclusively at the infarct-related myocardial territory, could be a viable therapeutic option for cardiomyocytes that sustained sub-critical injury, to diminish the extent of post-MI heart failure (HF).

The mRNA and histological analyses suggest that most left ventricular cellular/tissue damage takes place within the first 24 hours. Therefore, a single bolus injection of leptin antagonist that will be administered into the infarct-related coronary artery may be sufficient to inhibit leptin activity during the critical period of leptin synthesis in cardiomyocytes. However, in order to address cases of extended period of increased leptin expression as synthesized by injured cardiomyocytes, it is suggested to supplement the bolus therapy by deploying a df-DES within the involved coronary artery. This approach will achieve extended period of sustained leptin antagonist release over additional 7-14 days. This may specifically apply to patients that suffer from an inflammatory comorbidity that have intrinsic stimulation for leptin synthesis. It is emphasized that according to the present invention the administration of leptin antagonist is made directly and exclusively into the infarcted myocardium.

Example 24

Treatment of Brain Ischemia and Reperfusion Injury by Local Injection of LepA into the Revascularized Artery A clinical scenario of major brain ischemia and reperfusion injury has been simulated in mice to examine the effects of selective intra-arterial leptin antagonist (LepA) on global brain ischemia and reperfusion injury in mice.

Figure 34A:
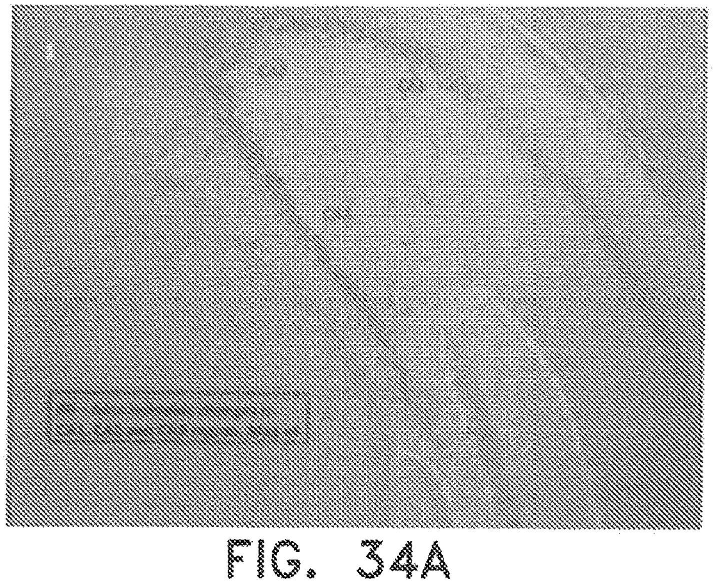
FIGS. 34 (*a-c*) illustrate coronal sections of a mouse brain that underwent IRI (a-c)
Figure 34B:
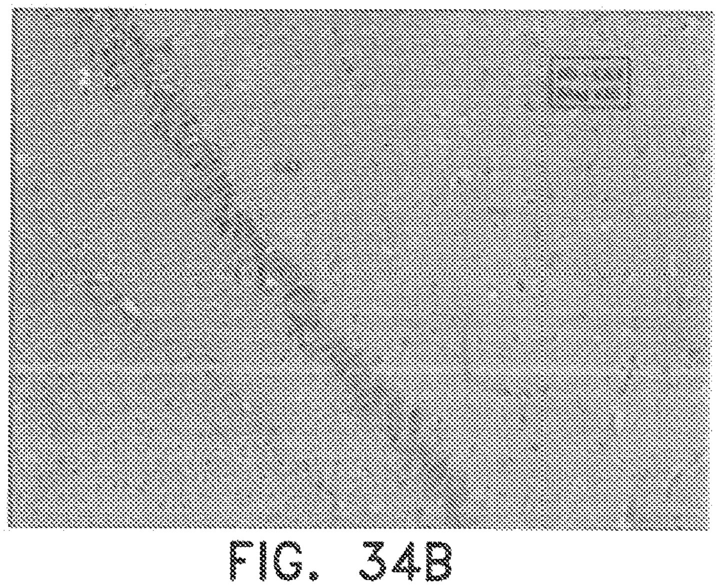
Figure 34C:
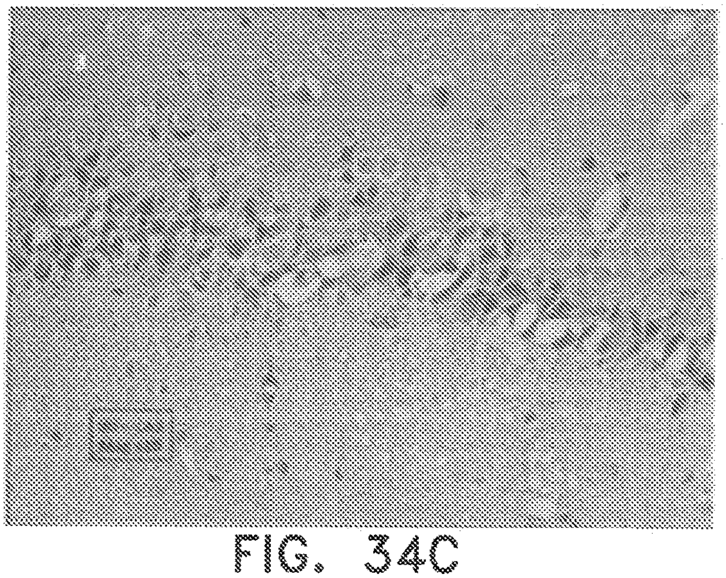
Figure 35A:
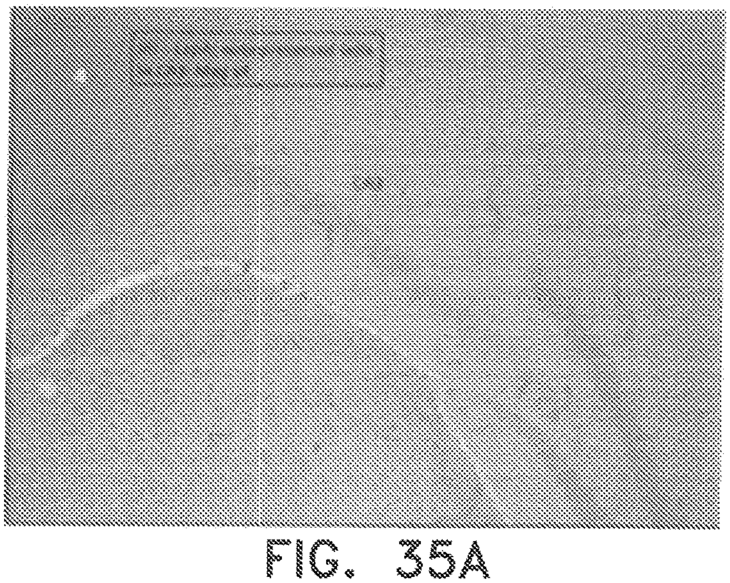
FIGS. 35 (*a-c*) illustrate coronal sections of a mouse brain that underwent IRI plus selective administration of leptin antagonist upon reperfusion.
Figure 35B:
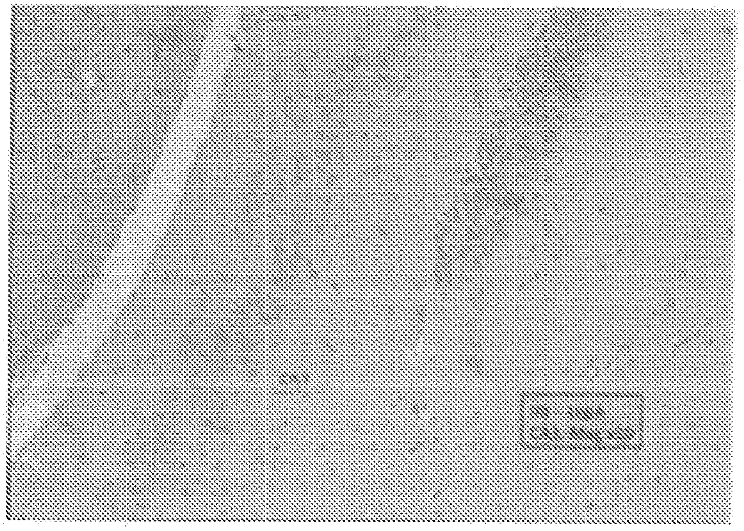
Figure 35C:
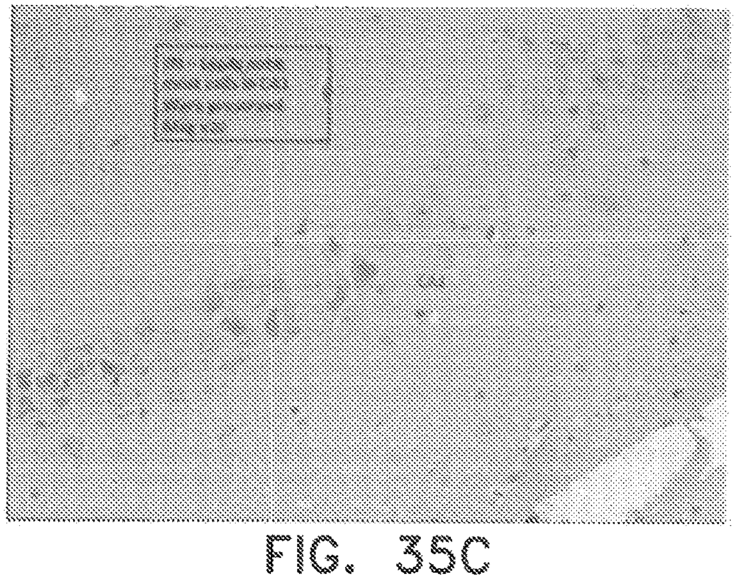
Figure 36A:
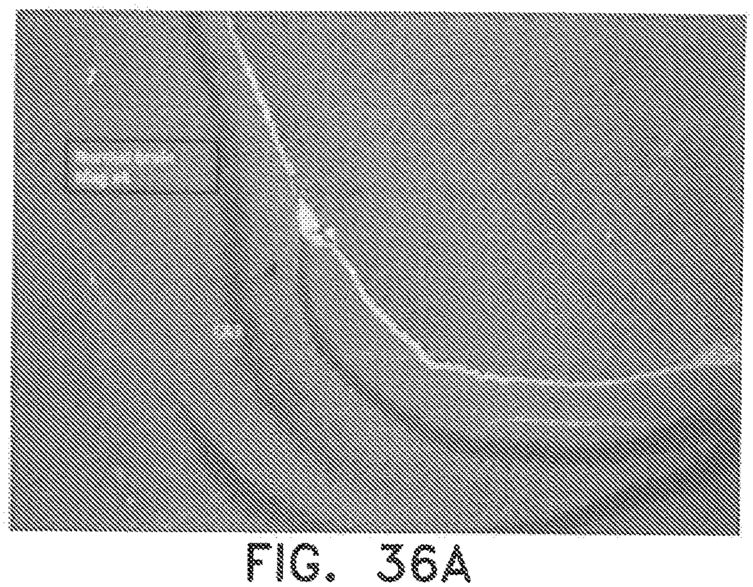
FIGS. 36 (*a-c*) illustrate coronal sections of a normal mouse brain.
Figure 36B:
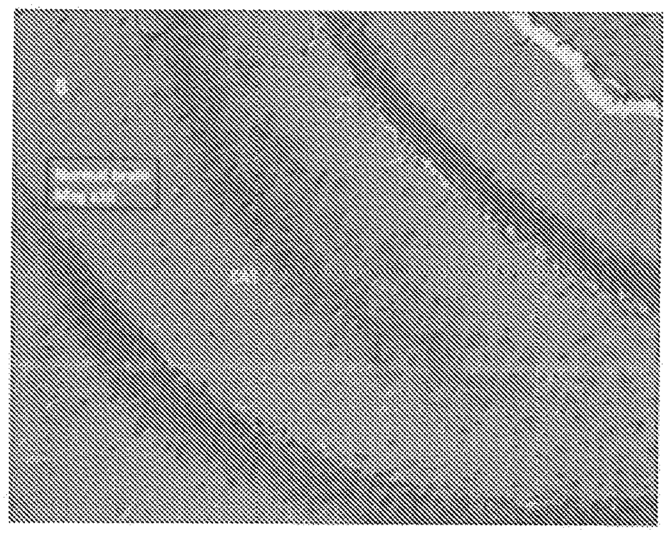
Figure 36C:
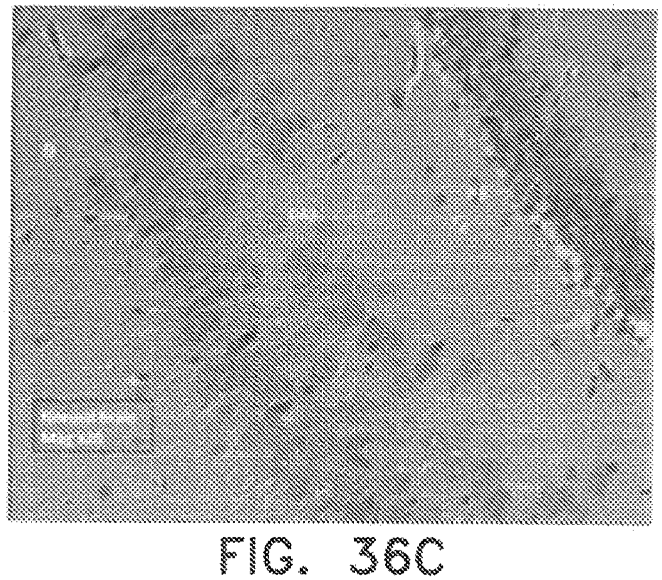

Eight weeks old C57BL6 male mice underwent bilateral ligation of the common carotid arteries (CCA). After a period of 10 min ischemia, the right CCA was re-perfused. Leptin antagonist (SMLA), 20 μg dissolved in 50 μl saline, was immediately bolus injected selectively into the right ECA, to be delivered to the brain through the right ICA. Twenty four hours later mice were euthanized, and brains were perfused with 4% paraformaldehyde. The brains were removed and additionally fixed in 10% paraformaldehyde over night at 4° C. and embedded in paraffin. The brain was cut into coronal sections, and 5p slides were stained with H&E (FIG. 34). As can be seen, while pyramidal cells in regions CA1, CA2 and CA3 of the hypocampus in the brain that underwent IRI are severely damaged, most of the pyramidal cells in the same regions of the brain that underwent IRI plus selective administration of leptin antagonist are intact.

These experimental results demonstrate the neuroprotective effects of leptin antagonist when administered locally into the brain immediately after reperfusion, implying that local inhibition of leptin activity in a brain that sustained IRI will attenuate cellular damage, and most likely will preserve cerebral function. It An extended selective local administration of leptin antagonist into the ischemic and re-perfused region may provide additional benefits in regard to brain cell preservation. It is therefore suggested that both routs of administration, including leptin antagonist bolus injection and/or slow release of leptin antagonist by the double function drug eluting stent (df-DES) of the invention may be used to alleviate brain IRI damage. Furthermore, brain neurodegenerative diseases, like Alzheimer's disease are associated with ischemia and inflammation affecting the brain microcirculation (Kalaria R N; Neurol Res. 2000; 21:321-330). It is therefore suggested that selective intra-arterial administration of leptin antagonist into the cerebral circulation, through bolus injection or slow release via df-DES may attenuate pathological changes in the brain and mitigate symptoms related to different neurodegenerative disorders, like Alzheimer's disease.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. Section headings are used herein to ease understanding of the specification and should not be construed as necessarily limiting.

TABLE 1

Sequence listing

| SEQ ID NOs | Name | Organism |
|---|---|---|
| 1 | leptin precursor | *Homo sapiens* |
| 2 | leptin mRNA | *Homo sapiens* |
| 3 | U.S Pat. No. 7,307,142 seq1 | Artificial Sequence |
| 4 | U.S Pat. No. 7,307,142 seq2 | Artificial Sequence |
| 5 | U.S Pat. No. 7,307,142 seq3 | Artificial Sequence |
| 6 | U.S Pat. No. 7,307,142 seq4 | Artificial Sequence |
| 7 | U.S Pat. No. 7,307,142 seq5 | Artificial Sequence |
| 8 | U.S Pat. No. 7,307,142 seq6 | Artificial Sequence |
| 9 | U.S Pat. No. 7,307,142 seq7 | Artificial Sequence |
| 10 | U.S Pat. No. 7,307,142 seq8 | Artificial Sequence |
| 11 | U.S Pat. No. 7,307,142 seq9 | Artificial Sequence |
| 12 | U.S Pat. No. 7,307,142 seq10 | Artificial Sequence |
| 13 | U.S Pat. No. 7,307,142 seq11 | Artificial Sequence |
| 14 | U.S Pat. No. 7,307,142 seq12 | Artificial Sequence |
| 15 | U.S Pat. No. 7,307,142 seq13 | Artificial Sequence |
| 16 | U.S Pat. No. 7,307,142 seq14 | Artificial Sequence |
| 17 | U.S Pat. No. 7,307,142 seq15 | Artificial Sequence |
| 18 | U.S Pat. No. 7,307,142 seq16 | Artificial Sequence |
| 19 | U.S Pat. No. 7,307,142 seq17 | Artificial Sequence |
| 20 | U.S Pat. No. 7,307,142 seq18 | Artificial Sequence |
| 21 | U.S Pat. No. 7,307,142 seq19 | Artificial Sequence |
| 22 | U.S Pat. No. 7,307,142 seq20 | Artificial Sequence |
| 23 | U.S Pat. No. 7,307,142 seq21 | Artificial Sequence |
| 24 | U.S Pat. No. 7,307,142 seq22 | Artificial Sequence |
| 25 | U.S Pat. No. 7,307,142 5eq23 | Artificial Sequence |
| 26 | U.S Pat. No. 7,307,142 seq24 | Artificial Sequence |
| 27 | U.S Pat. No. 7,307,142 seq25 | Artificial Sequence |
| 28 | U.S Pat. No. 7,307,142 seq26 | Artificial Sequence |
| 29 | U.S Pat. No. 7,307,142 seq27 | Artificial Sequence |
| 30 | U.S Pat. No. 7,307,142 seq28 | Artificial Sequence |
| 31 | U.S Pat. No. 7,307,142 seq29 | Artificial Sequence |
| 32 | U.S Pat. No. 7,307,142 seq30 | Artificial Sequence |
| 33 | U.S Pat. No. 7,307,142 seq31 | Artificial Sequence |
| 34 | U.S Pat. No. 7,307,142 seq32 | Artificial Sequence |
| 35 | U.S Pat. No. 7,307,142 seq33 | Artificial Sequence |
| 36 | U.S Pat. No. 8,969,292 seq1 | Artificial Sequence |
| 37 | U.S Pat. No. 8,969,292 seq2 | *Homo sapiens* |
| 38 | U.S Pat. No. 8,969,292 seq3 | Artificial Sequence |
| 39 | U.S Pat. No. 8,969,292 seq4 | Artificial Sequence |
| 40 | U.S Pat. No. 8,969,292 seq5 | Artificial Sequence |
| 41 | U.S Pat. No. 8,969,292 seq6 | Artificial Sequence |
| 42 | U.S Pat. No. 8,969,292 seq7 | Artificial Sequence |
| 43 | U.S Pat. No. 8,969,292 seq8 | Artificial Sequence |
| 44 | U.S Pat. No. 8,969,292 seq9 | Artificial Sequence |
| 45 | U.S Pat. No. 8,969,292 seq10 | Artificial Sequence |
| 46 | U.S Pat. No. 8,969,292 seq11 | Artificial Sequence |
| 47 | U.S Pat. No. 8,969,292 seq12 | Artificial Sequence |
| 48 | leptin precursor Rat | *Rattus norvegicus* |
| 49 | US20070104708 seq1 | *Mus musculus* |
| 50 | US20070104708 seq2 | *Mus musculus* |
| 51 | US20070104708 seq3 | *Homo sapiens* |
| 52 | US20070104708 seq4 | *Homo sapiens* |
| 53 | US20070104708 seq5 | *Homo sapiens* |
| 54 | US20070104708 seq6 | *Homo sapiens* |
| 55 | US20070104708 seq7 | Artificial Sequence |
| 56 | pcDNA3 | Artificial Sequence |
| 57 | pcDNA3.1(+) | Artificial Sequence |
| 58 | pcDNA3.1(−) | Artificial Sequence |
| 59 | pGL3 | Artificial Sequence |
| 60 | pZeoSV2(+) | Artificial Sequence |
| 61 | pSecTag2 | Artificial Sequence |
| 62 | pDisplay | Artificial Sequence |
| 63 | pEF/myc/cyto | Artificial Sequence |
| 64 | pCMV/myc/cyto | Artificial Sequence |
| 65 | pCR3.1 | Artificial Sequence |
| 66 | pSinRep5 | Artificial Sequence |
| 67 | pCI | Artificial Sequence |
| 68 | pMbac | Artificial Sequence |
| 69 | pPbac | Artificial Sequence |
| 70 | pBK-RSV | Artificial Sequence |
| 71 | pBK-CMV | Artificial Sequence |
| 72 | pMT2 | Artificial Sequence |

What is claimed is:

1. A method of treating a tissue injured by an ischemia and reperfusion injury (IRI) for moderating cellular damage in said tissue, the method comprising administering a composition comprising a leptin antagonist into a re-opened blood vessel which supplies blood to said tissue, said administration being configured to deliver leptin antagonist primarily into the flow of blood in the vessel with minimal sustained delivery of leptin antagonist into the wall of said blood vessel, thereby delivering the leptin antagonist by blood flowing through said blood vessel to said tissue, said leptin antagonist being a modified mammalian leptin polypeptide capable of binding a leptin receptor.

2. The method according to claim 1, wherein said administering is effected by an intra-arterial bolus injection.

3. The method according to claim 1, wherein said blood vessel is a coronary artery and said tissue is a cardiac tissue that was subjected to ischemia and reperfusion injury.

4. The method according to claim 1, wherein said tissue is an isolated tissue section that functions as an end organ.

5. The method according to claim 4, wherein said end organ is selected from the group consisting of a kidney, an intestine and a brain.

6. The method according to claim 1, wherein said leptin antagonist is selected from the group consisting of (a) a modified mammalian leptin polypeptide in which the LDFI hydrophobic binding site at the positions corresponding to positions 39-42 of the wild-type human leptin (SEQ ID NO:1) is modified such that from two to four amino acid residues of said hydrophobic binding site are substituted with different amino acid residues such that the site becomes less hydrophobic, said modified mammalian leptin polypeptide being a leptin antagonist; (b) the modified mammalian leptin according to (a) in which the aspartic acid at the position corresponding to position 23 of the wild-type human leptin (D23) is substituted with an amino acid residue selected from the group consisting of glycine, alanine, leucine, lysine, arginine, phenylalanine, tryptophan and histidine, or in which the threonine at the position corresponding to position 12 of the wild-type human leptin (T12) is substituted with a different amino acid residue that is hydrophobic; (c) a fragment of (a) comprising the modified hydrophobic binding site, wherein the fragment is itself a leptin antagonist; and (d) a fragment of (b), in which D23 is substituted with a different amino acid residue that is not negatively charged or T12 is substituted with a different amino acid residue that is hydrophobic, wherein the fragment is itself a leptin antagonist; and (e) a pharmaceutically acceptable salt of (a), (b), (c) or (d).

7. The method according to claim 1, wherein said composition comprises aqueous solution.

8. The method of claim 1, wherein said administering is effected by means of a drug eluting stent configured to enable sustained release of leptin antagonist into the lumen of said blood vessel, with minimal sustained delivery of leptin antagonist into the wall of said blood vessel.

9. The method according to claim 8, wherein said drug eluting stent is a double function drug eluting stent configured to further enable sustained release of anti-proliferative drug into a wall of said blood vessel.

* * * * *